United States Patent
Rudd et al.

(10) Patent No.: US 10,239,849 B2
(45) Date of Patent: Mar. 26, 2019

(54) CYANOPYRIDINE DERIVATIVES AS LIVER X RECEPTOR BETA AGONISTS, COMPOSITIONS, AND THEIR USE

(71) Applicants: Merck Sharp & Dohme Corp., Rahway, NJ (US); Michael T. Rudd, Collegeville, PA (US); Edward J. Brnardic, Lansdale, PA (US); Yuntae Kim, Yongin-Si (KR); Robert S. Meissner, Newton, MA (US); Vanessa L. Rada, Hatfield, PA (US); Shawn J. Stachel, Perkasie, PA (US); Celina V. Zerbinatti, Hamburg (DE)

(72) Inventors: Michael T. Rudd, Collegeville, PA (US); Edward J. Brnardic, Lansdale, PA (US); Yuntae Kim, Yongin-Si (KR); Robert S. Meissner, Newton, MA (US); Vanessa L. Rada, Hatfield, PA (US); Shawn J. Stachel, Perkasie, PA (US); Celina V. Zerbinatti, Hamburg (DE)

(73) Assignee: Merck Sharp & Dohme Corp.

( * ) Notice: Subject to any disclaimer, the term of this patent is extended or adjusted under 35 U.S.C. 154(b) by 0 days.

(21) Appl. No.: 15/774,157

(22) PCT Filed: Nov. 7, 2016

(86) PCT No.: PCT/US2016/060765
§ 371 (c)(1),
(2) Date: May 7, 2018

(87) PCT Pub. No.: WO2017/083216
PCT Pub. Date: May 18, 2017

(65) Prior Publication Data
US 2018/0327374 A1 Nov. 15, 2018

Related U.S. Application Data
(60) Provisional application No. 62/254,478, filed on Nov. 12, 2015.

(51) Int. Cl.
*C07D 243/08* (2006.01)
*C07D 295/16* (2006.01)
(Continued)

(52) U.S. Cl.
CPC .............. *C07D 295/16* (2013.01); *A61P 3/10* (2018.01); *A61P 25/16* (2018.01); *A61P 25/18* (2018.01);
(Continued)

(58) Field of Classification Search
None
See application file for complete search history.

(56) References Cited

U.S. PATENT DOCUMENTS

| 5,780,472 A | 7/1998 | Cho et al. |
| 2008/0242677 A1 | 10/2008 | Dehmlow et al. |

(Continued)

FOREIGN PATENT DOCUMENTS

| WO | 2017083219 A1 | 5/2017 |
| WO | 2017095758 A1 | 6/2017 |

(Continued)

OTHER PUBLICATIONS
International Search Report for PCT/US2016/060765 dated, Jan. 9, 2017, 8 pages.

*Primary Examiner* — Alicia L Otton
(74) *Attorney, Agent, or Firm* — Keith D. MacMillan; Catherine D. Fitch

(57) ABSTRACT

In its many embodiments, the present invention provides substituted cyanopyridine containing compounds of the Formula (I): and acceptable salts thereof, wherein $R^1$, $R^2$, $R^3$, $R^4$, $R^5$, X, Y, Q, and the moiety are as defined herein. The novel compounds of the invention, and pharmaceutically acceptable compositions comprising a compound thereof, are useful as Liver X-β receptor (LXRβ) agonists, and may be useful for treating or preventing pathologies related thereto. Such pathologies include, but are not limited to, inflammatory diseases and diseases characterized by defects in cholesterol and lipid metabolism, such as Alzheimer's disease.

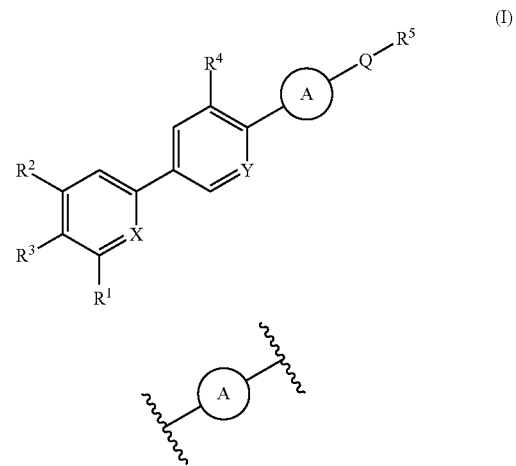

13 Claims, No Drawings

(51) Int. Cl.

| | |
|---|---|
| *C07D 401/04* | (2006.01) |
| *C07D 401/14* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 471/08* | (2006.01) |
| *C07D 487/08* | (2006.01) |
| *C07D 513/04* | (2006.01) |
| *A61P 25/18* | (2006.01) |
| *A61P 25/16* | (2006.01) |
| *A61P 25/28* | (2006.01) |
| *A61P 3/10* | (2006.01) |

(52) U.S. Cl.
CPC ......... *C07D 243/08* (2013.01); *C07D 401/04* (2013.01); *C07D 401/14* (2013.01); *C07D 405/14* (2013.01); *C07D 409/14* (2013.01); *C07D 413/14* (2013.01); *C07D 417/14* (2013.01); *C07D 471/08* (2013.01); *C07D 487/08* (2013.01); *C07D 513/04* (2013.01)

(56) References Cited

U.S. PATENT DOCUMENTS

| | | | |
|---|---|---|---|
| 2010/0280013 A1 | 11/2010 | Koura et al. | |
| 2012/0196849 A1 | 8/2012 | Gao et al. | |
| 2012/0302524 A1* | 11/2012 | Asai | ............... C07D 413/04 514/63 |
| 2015/0065515 A1 | 3/2015 | Dong et al. | |

FOREIGN PATENT DOCUMENTS

| | | |
|---|---|---|
| WO | 2018071313 A1 | 4/2018 |
| WO | 2018071317 A1 | 4/2018 |
| WO | 2918071315 A2 | 4/2018 |

\* cited by examiner

CYANOPYRIDINE DERIVATIVES AS LIVER X RECEPTOR BETA AGONISTS, COMPOSITIONS, AND THEIR USE

FIELD OF THE INVENTION

The present invention provides certain cyanopyridine compounds of formula (I), and compositions comprising these compounds, as Liver X-β receptor (LXRβ) agonists, which may be useful for treating or preventing pathologies related thereto. Such pathologies include, but are not limited to, inflammatory diseases and diseases characterized by defects in cholesterol and lipid metabolism, such as Alzheimer's disease.

BACKGROUND OF THE INVENTION

Alzheimer's disease is a common neurodegenerative disease affecting the elderly, resulting in progressive memory impairment, loss of language and visuospatial skills, and behavior deficits. Clinical, genetic, epidemiological and biochemical evidence suggest that dysfunctional cholesterol metabolism is implicated in the pathogenesis of Alzheimer's Disease. Hypercholesterolemia and low levels of high density lipoprotein are well-established risk factors for Alzheimer's Disease. It has been suggested that vascular, genetic and amyloid factors, in combination with diet and lifestyle, contribute to the cause and progression of Alzheimer's Disease. Hooijmans et al, *Eur J Pharmacol* 585 (2008), 176-196.

The liver X receptor (LXR) is a member of the nuclear receptor family of transcription factors, and is a part of the cholesterol regulation pathway. There are two identified isoforms of LXRs. LXRu is found in liver, intestine and in macrophages, while LXR3 is widely expressed in many tissues and is considered a ubiquitous receptor. Typically, the activity of nuclear receptors is controlled by small lipophilic moieties, such as hormones, fatty acids, bile acids, cholesterol precursors and oxysterols. Lala, *Curr Opinions Invest Drugs* 2005, 6:934-943. Cholesterol precursors such as desmosterol and oxysterols are known to bind and activate LXRs.

LXRs have demonstrated a role in the physiological metabolism of lipid and cholesterol, and thus are believed to have an important role in metabolic disorders such as hyperlipidemia and atherosclerosis. Activation of LXRs reduces cholesterol absorption, thereby reducing the ability of the body to take up cholesterol. Consistently, deletion of LXRs in mice leads to impaired cholesterol and bile acid metabolism. See Peet et al, *Cell* 1998, 93(5): 693-704. Activation of LXRs also increase peripheral cholesterol efflux systems, and impact the elimination of cholesterol by regulating cholesterol excretion into bile. See Cao et al, *Drug News Perspect* 20004, 17(1), 35-41.

LXRs also regulate lipid homeostasis in the brain. The connection between metabolic disorders and Alzheimer's Disease suggests that LXRs may have a role in the Alzheimer's disease pathway. Activation of LXRs also inhibit inflammation and pro-inflammatory expression in the body. Zelcer et al, *J Clin Invest* 2006, 116:3 (607-614). Thus, LXRs may serve as targets for the treatment of inflammatory diseases. However, activation of hepatic LXRα is believed to be the underlying cause of liver steatosis and hyperlipidemia associated with dual LXRα/β small agonist molecules developed to date.

LXRs have also been proposed as possible therapeutics to treat a number of cancers e.g. prostate, breast, ovarian, melanoma, pancreas, lung, colon and hematological malignancy (Lin, C-Y and Gustafsson, J-A, (2015) Nature Reviews Cancer 15, 216-224).

LXRβ is the predominant brain isoform. See Song et al, *Ann NY Acad Sci* 195, 761:38-49. LXRβ knockout male mice demonstrated adult-onset motor neuron degeneration. (Andersson et al, *Proc Nat'l Acad Sci USA* 2005, 8; 1902(1)): 3857-3862), and the LXRα and LXRβ double knockout mice develop neurodegenerative changes in brain tissue. (Wang et al, Proc Natl Acad Sci USA. 2002, 99(21):13878-83). Therefore development of selective LXRβ agonists could be a therapeutic approach to neurodegenerative diseases such as AD and avoid the peripheral adverse lipid effects that have been linked to LXRα.

Applicants have now discovered a series of LXRβ selective agonists. Thus, the compounds of the invention, which are selective LXRβ agonists, may be useful in the treatment of Alzheimer's disease, inflammatory diseases, and diseases characterized by defects in cholesterol and lipid metabolism.

SUMMARY OF THE INVENTION

The present invention provides certain compounds, which are collectively or individually referred to herein as "compound(s) of the invention", as described herein. The compounds of the invention are selective agonists of LXRβ, and may be useful for treating or preventing diseases or pathologies related thereto.

In one embodiment, the compounds of the invention have the structural Formula (I):

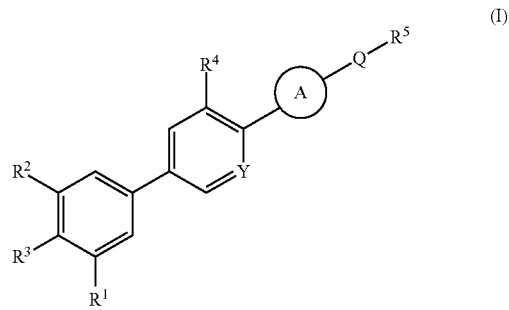

or a pharmaceutically acceptable salt thereof, wherein: the moiety

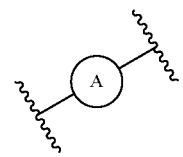

is a divalent moiety selected from the group consisting of

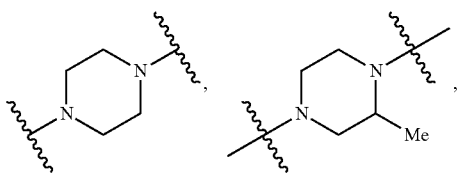

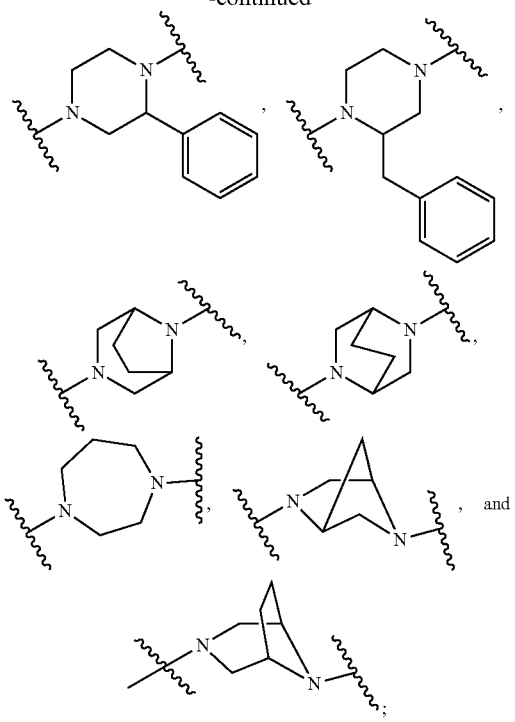

Y is selected from the group consisting of C(H), C(F), C(Cl), and N, $R^1$ is selected from the group consisting of halogen, CN, OH, —($C_3$-$C_6$)cycloalkyl, —($C_1$-$C_4$)alkyl, —($C_1$-$C_4$)haloalkyl, and —($C_1$-$C_4$)alkoxy;

$R^2$ is selected from the group consisting of H and halogen;

$R^3$ is a moiety selected from the group consisting of:
—C(O)N($R^{N1}$)($R^{N2}$),
  wherein $R^{N1}$ and $R^{N2}$ are each independently selected from the group consisting of H, —NH2, —NH($C_1$-$C_4$alkyl), —N($C_1$-$C_4$alkyl)$_2$, —($C_1$-$C_4$)alkyl, —($C_2$-$C_6$)alkenyl, —($C_1$-$C_4$)alkoxy, —($C_3$-$C_6$)cycloalkyl, —CH$_2$($C_3$-$C_6$)cycloalkyl, phenyl, —($C_1$-$C_4$)alkylphenyl, heterocycloalkyl, —($C_1$-$C_4$)alkylheterocycloalkyl, heteroaryl, and —($C_1$-$C_4$)alkylheteroaryl, wherein said —($C_1$-$C_4$)alkyl, —($C_1$-$C_4$)alkoxy, phenyl, —($C_3$-$C_6$)cycloalkyl, heterocycloalkyl, and heteroaryl portions of said $R^{N1}$ and $R^{N2}$ are unsubstituted or substituted with one, two, or three groups independently selected from the group consisting of OH, CN, halogen, —NH$_2$, —N($C_1$-$C_4$alkyl)$_2$, —NH($C_1$-$C_4$alkyl), —($C_1$-$C_4$)alkoxy, optionally substituted phenyl, and optionally substituted heteroaryl, wherein said optional substituents on said phenyl are 1 to 3 groups independently selected from OH, CN, —($C_1$-$C_4$)alkyl, —($C_1$-$C_4$)alkoxy, and wherein said optional substituents on said heteroaryl are 1 to 3 groups independently selected from —($C_1$-$C_4$)alkyl, and —($C_1$-$C_4$)alkoxyl, or, alternatively, $R^{N1}$ and $R^{N2}$, together with the nitrogen atom to which they are shown attached, form a 4-, 5-, or 6-membered heteroaryl or partially unsaturated or fully saturated heterocyclic ring comprising (including said nitrogen atom) 1, 2, or 3 ring heteroatoms independently selected from the group consisting of N, O, and S, wherein said heterocyclic ring is unsubstituted or substituted with one, two, or three substituents independently selected from the group consisting of halo, OH, CN, —($C_1$-$C_4$)alkyl, amino-substituted —($C_1$-$C_4$)alkyl, wherein said amino is one, two, or three groups independently selected from the group consisting of —NH$_2$, —N($C_1$-$C_4$alkyl)$_2$, and —NH($C_1$-$C_4$alkyl), —($C_1$-$C_4$)haloalkyl, —($C_1$-$C_4$)alkyl-OH, phenyl, benzyl, heteroaryl, and —($C_1$-$C_4$)alkylheteroaryl;

$R^4$ is selected from the group consisting of H, —CN, halogen, —($C_1$-$C_4$)alkyl, —($C_2$-$C_4$)alkenyl, and —($C_2$-$C_4$)alkynyl, wherein said —($C_1$-$C_4$)alkyl is optionally substituted with hydroxyl;

Q is selected from the group consisting of —S(O)$_2$—, —C(O)—, —C(O)O—, and —C(O)C(O)—; and $R^5$ is selected from the group consisting of
—($C_1$-$C_8$)alkyl, —($C_1$-$C_8$)haloalkyl, —C(OH)($R^{5A}$)$_2$, —C(OCH$_3$)($R^{5A}$)$_2$, phenyl, —($C_1$-$C_4$)alkyl-phenyl, cycloalkyl, —($C_1$-$C_4$)alkyl-cycloalkyl, heterocycloalkyl, —($C_1$-$C_4$)alkylheterocycloalkyl, heteroaryl, and —($C_1$-$C_4$)alkyl-heteroaryl,
wherein each said phenyl, cycloalkyl, and heteroaryl portion of $R^5$ is unsubstituted or substituted with one, two, or three groups independently selected from the group consisting of halogen, CN, —($C_1$-$C_6$)alkyl, —($C_1$-$C_4$)haloalkyl, —O($C_1$-$C_6$)alkyl, —O($C_1$-$C_4$)haloalkyl, phenyl, and
wherein each $R^{5A}$ is independently selected from the group consisting of —($C_1$-$C_8$)alkyl, —($C_1$-$C_5$)haloalkyl, phenyl, —($C_1$-$C_4$)alkyl-phenyl, and cycloalkyl, wherein said phenyl and said cycloalkyl portion of $R^{5A}$ is unsubstituted or substituted with one, two, or three groups independently selected from the group consisting of halogen, CN, —($C_1$-$C_6$)alkyl, —($C_1$-$C_4$)haloalkyl, —O($C_1$-$C_6$)alkyl, and —O($C_1$-$C_4$)haloalkyl.

In other embodiments, the invention provides compositions, including pharmaceutical compositions, comprising one or more compounds of the invention (e.g., one compound of the invention) or a pharmaceutically acceptable salt thereof, optionally together with one or more additional therapeutic agents, optionally in an acceptable (e.g., pharmaceutically acceptable) carrier or diluent.

In another embodiment, the invention is directed to methods of treating an inflammatory diseases or a disease characterized by defects in cholesterol or lipid metabolism, in a patient in need thereof by administering to the patient a compound of the invention or a pharmaceutically acceptable salt thereof. Non-limiting examples of such inflammatory diseases and diseases characterized by defects in cholesterol or lipid metabolism are described below.

In another embodiment, the invention provides for the use of a compound of the invention in the manufacture of a medicament for treating an inflammatory disease or a disease characterized by defects in cholesterol or lipid metabolism in a patient in need thereof. Non-limiting examples of such inflammatory diseases and diseases characterized by defects in cholesterol or lipid metabolism are described below.

In another embodiment, the invention is directed to a method of treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of a compound of the invention in the manufacture of a medicament for treating cancer in a patient in need thereof comprising administering to the patient a compound of the invention or a pharmaceutically acceptable salt thereof. Such cancers include prostate, breast, ovarian, melanoma, pancreas, lung, colon and hematological malignancy.

In another embodiment, the invention provides for the use of any of the compounds of the invention for use as a medicament, or in medicine, or in therapy.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I). In each of the embodiments described herein, each variable is selected independently of the other unless otherwise noted.

In one embodiment, the compounds of the invention have the structural Formula (I) as described above, and pharmaceutically acceptable salts thereof.

The following alternative embodiments of Y apply to each of the embodiments and alternative embodiments described hereinabove.

In one alternative embodiment, in Formula (I), Y is selected from the group consisting of CH, C(Cl), and N.

In another embodiment, in Formula (I), Y is selected from the group consisting of CH and C(Cl).

In another embodiment, in Formula (I), Y is N.

The following alternative embodiments of $R^4$ apply to each of the embodiments and alternative embodiments described hereinabove.

In one alternative embodiment, in Formula (I), $R^4$ is selected from the group consisting of H, CN, Cl, —($C_1$-$C_4$) alkyl, —C≡CH, —C≡C—$CH_3$, —$CH_2OH$, and —CH=$CH_2$.

In another embodiment, in Formula (I), $R^4$ is selected from the group consisting of H, CN, Cl, —C≡CH, —C≡C—$CH_3$, —$CH_2OH$, and —CH=$CH_2$.

In another embodiment, in Formula (I), $R^4$ is selected from the group consisting of H, CN, and Cl.

The following alternative embodiments of the moiety

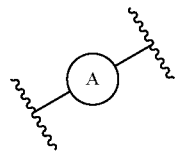

apply to each of the embodiments and alternative embodiments described hereinabove.

In one alternative embodiment, in Formula (I), the moiety

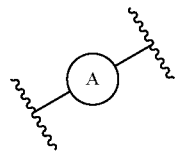

is selected from the group consisting of

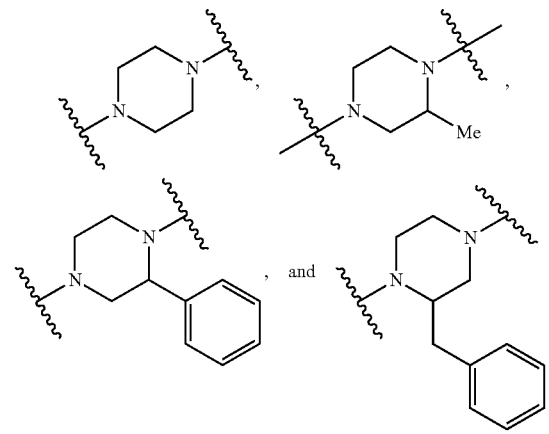

In another embodiment, in Formula (I), the moiety

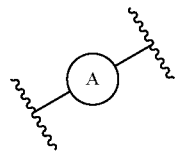

is selected from the group consisting of

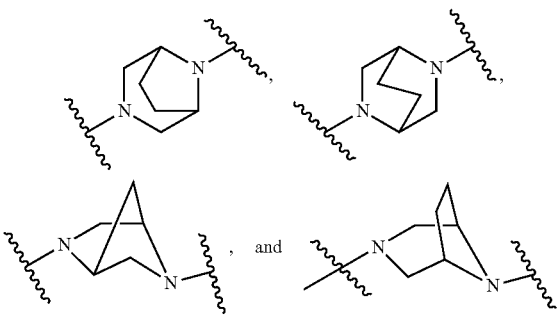

In another embodiment, in Formula (I), the moiety

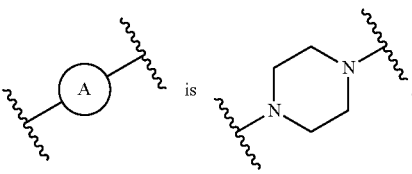

In another embodiment, in Formula (I), the moiety is

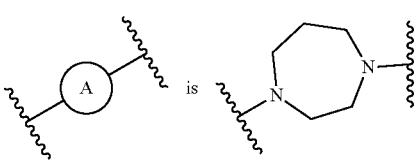

In another embodiment, in Formula (I), Y is selected from the group consisting of CH, C(F), C(Cl); and
the moiety

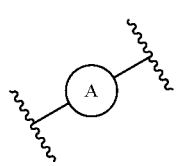

is selected from the group consisting of

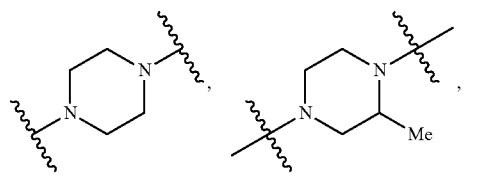

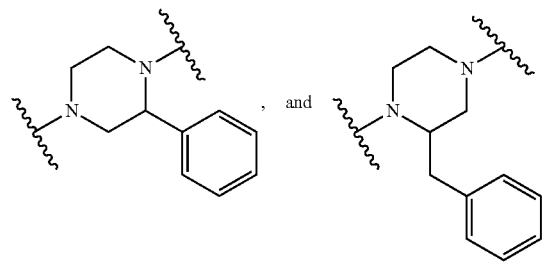

In another embodiment, in Formula (I), Y is selected from the group consisting of CH, C(F), C(Cl); and
the moiety

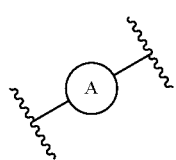

is selected from the group consisting of

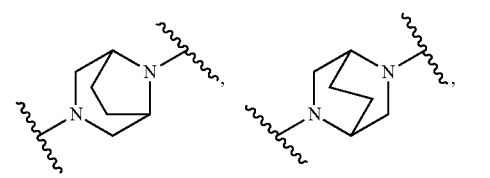

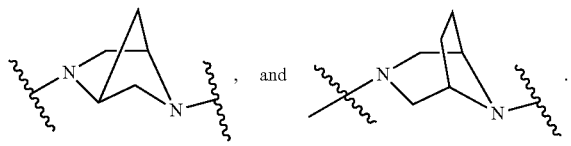

In another embodiment, in Formula (I), Y is selected from the group consisting of CH, C(F), C(Cl); and
the moiety

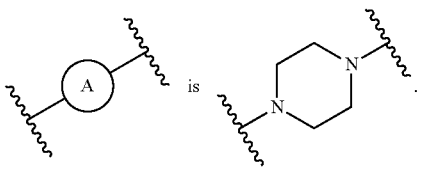

is

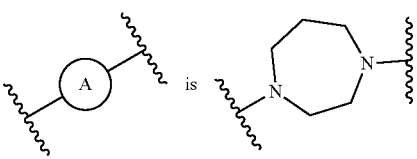

In another embodiment, in Formula (I), Y is selected from the group consisting of CH, C(F), C(Cl); and
the moiety

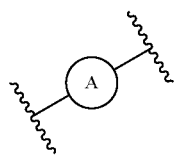

is

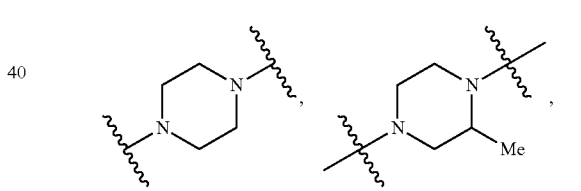

In another embodiment, in Formula (I), Y is N; and
the moiety

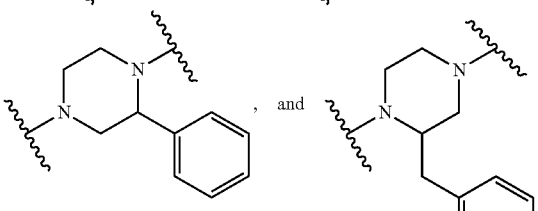

is selected from the group consisting of

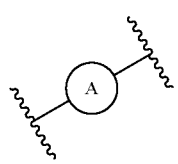

In another embodiment, in Formula (I), Y is N; and
the moiety is selected from the group consisting of

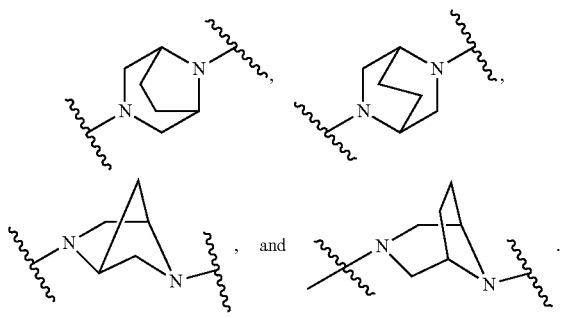

In another embodiment, in Formula (I), Y is N; and the moiety

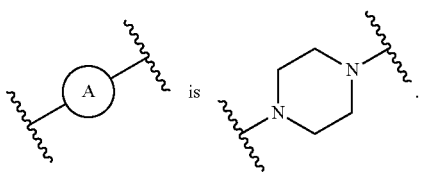

In another embodiment, in Formula (I), Y is N; and the moiety

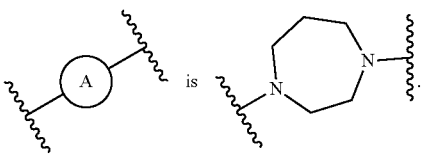

The following alternative embodiments of $R^1$ apply to each of the embodiments and alternative embodiments described hereinabove.

In one alternative embodiment, in Formula (I), $R^1$ is selected from the group consisting of halogen, cyclopropyl methyl, ethyl, —$CF_3$, and —OMe.

In another embodiment, in Formula (I), $R^1$ is selected from the group consisting of F, Cl, cyclopropyl methyl, ethyl, —$CF_3$, and —OMe.

The following alternative embodiments of $R^2$ apply to each of the embodiments and alternative embodiments described hereinabove.

In one alternative embodiment, in Formula (I), $R^2$ is selected from the group consisting of H and Cl.

In another embodiment, in Formula (I), $R^2$ is H.

In another embodiment, in Formula (I), $R^2$ is Cl.

As noted in Formula (I), $R^3$ is —C(O)N($R^{N1}$)($R^{N2}$). The following alternative embodiments of $R^{N1}$ and $R^{N2}$ in the context of $R^3$ apply to each of the embodiments and alternative embodiments described hereinabove.

In one alternative embodiment, in Formula (I), $R^{N1}$ is selected from the group consisting of H, $CH_3$, and cyclopropyl.

In another embodiment, in Formula (I), $R^{N2}$ is selected from the group consisting of —NH2, —NH($C_1$-$C_4$alkyl), —N($C_1$-$C_4$alkyl)$_2$, —($C_1$-$C_4$)alkyl, —($C_1$-$C_4$)alkenyl, —($C_1$-$C_4$)alkoxyl, and heterocycloalkyl, wherein said —($C_1$-$C_4$)alkyl of $R^{N2}$ is unsubstituted or substituted with from 1 to 3 groups independently selected from CN, OH, optionally substituted phenyl, and optionally substituted heteroaryl, wherein said optional substituents on said phenyl are 1 to 3 groups independently selected from OH, CN, —($C_1$-$C_4$)alkyl, —($C_1$-$C_4$)alkoxyl, and wherein said optional substituents on said heteroaryl are 1 to 3 groups independently selected from —($C_1$-$C_4$)alkyl, and —($C_1$-$C_4$)alkoxyl.

In another embodiment, in Formula (I), $R^{N1}$ is selected from the group consisting of H, $CH_3$, and cyclopropyl; and $R^{N2}$ is selected from the group consisting of —NH2, —NH($C_1$-$C_4$alkyl), —N($C_1$-$C_4$alkyl)$_2$, —($C_1$-$C_4$)alkyl, —($C_1$-$C_4$)alkenyl, —($C_1$-$C_4$)alkoxyl, and heterocycloalkyl, wherein said —($C_1$-$C_4$)alkyl of $R^{N2}$ is unsubstituted or substituted with from 1 to 3 groups independently selected from CN, OH, optionally substituted phenyl, and optionally substituted heteroaryl, wherein said optional substituents on said phenyl are 1 to 3 groups independently selected from OH, CN, —($C_1$-$C_4$)alkyl, —($C_1$-$C_4$)alkoxyl, and wherein said optional substituents on said heteroaryl are 1 to 3 groups independently selected from —($C_1$-$C_4$)alkyl, and —($C_1$-$C_4$)alkoxyl.

In another embodiment, in Formula (I), $R^{N1}$ and $R^{N2}$ are each independently selected from the group consisting of H, —($C_1$-$C_4$)alkyl, —($C_1$-$C_4$)alkyl-OH, and —($C_1$-$C_4$)alkyl-CN.

In another embodiment, in Formula (I), $R^{N1}$ and $R^{N2}$ are each H.

In another embodiment, in Formula (I), $R^{N1}$ and $R^{N2}$ are each —($C_1$-$C_4$)alkyl.

In another embodiment, in Formula (I), $R^{N1}$ and $R^{N2}$ are each $CH_3$.

In another embodiment, in Formula (I), $R^{N1}$ and $R^{N2}$, together with the nitrogen atom to which they are shown attached, form a 4-, 5-, or 6-membered heteroaryl or partially unsaturated or fully saturated heterocyclic ring comprising (including said nitrogen atom) 1, 2 or 3 ring heteroatoms independently selected from the group consisting of N, O, and S, wherein said heteroaryl and said heterocyclic ring is unsubstituted or substituted with one, two, or three substitutents independently selected from the group consisting of halo, OH, CN, —($C_1$-$C_4$)alkyl, amino-substituted —($C_1$-$C_4$)alkyl, wherein said amino is one, two, or three groups independently selected from the group consisting of —$NH_2$, —N($C_1$-$C_4$alkyl)$_2$, and —NH($C_1$-$C_4$alkyl), —($C_1$-$C_4$)haloalkyl, —($C_1$-$C_4$)alkyl-OH, phenyl, benzyl, heteroaryl, and —($C_1$-$C_4$)alkylheteroaryl. Non-limiting examples of such heteroaryl and heterocyclic rings include those shown in the corresponding position of each of the example compounds.

The following alternative embodiment of $R^4$ applies to each of the embodiments described above.

In one alternative embodiment, in Formula (I), $R^4$ is selected from the group consisting of H, —CN, halogen, —$CH_2OH$, —CH=$CH_2$, —C≡CH, and —C≡C—$CH_3$.

The following alternative embodiments of Q apply to each of the embodiments and alternative embodiments described hereinabove.

In one alternative embodiment, in Formula (I), Q is —S(O)$_2$—.

In another embodiment, in Formula (I), Q is —C(O)—.

In another embodiment, in Formula (I), Q is —C(O)O—.

In another embodiment, in Formula (I), Q is —C(O)C(O)—.

The following alternative embodiments of $R^5$ apply to each of the embodiments and alternative embodiments described hereinabove.

In one alternative embodiment, in Formula (I), $R^5$ is selected from the group consisting of the corresponding moiety in each of the example compounds of the invention.

Specific non-limiting examples of compounds of the invention are shown in the examples below. Where both the structures and the IUPAC names of the example compounds are provided, if there are any discrepancies between the structure and the name provided, the structure shall control unless otherwise apparent in context.

In another embodiment, 1 to 3 carbon atoms of the compounds of the invention may be replaced with 1 to 3 silicon atoms so long as all valence requirements are satisfied.

In another embodiment, there is provided a composition comprising a compound of the invention and a pharmaceutically acceptable carrier or diluent.

In one embodiment, the invention is directed to methods of treating a patient (preferably a human) for inflammatory diseases and diseases characterized by defects in cholesterol or lipid metabolism, by administering to the patient a compound of the invention or a pharmaceutically acceptable salt thereof.

The invention is also directed to the use of a compound of the invention for treating inflammatory diseases and diseases characterized by defects in cholesterol or lipid metabolism, by administering to a patient (preferably a human) a compound of the invention or a pharmaceutically acceptable salt thereof.

The invention is also directed to medicaments or pharmaceutical compositions for treating inflammatory diseases and diseases characterized by defects in cholesterol or lipid metabolism, by administering to a patient (preferably a human) a compound of the invention, or a pharmaceutically acceptable salt thereof, and a pharmaceutically acceptable carrier.

The invention is further directed to a the manufacture of a medicament or a composition for inflammatory diseases and diseases characterized by defects in cholesterol or lipid metabolism, by administering to a patient (preferably a human) a compound of the invention or a pharmaceutically acceptable salt thereof, with one or more pharmaceutically acceptable carriers.

Exemplary inflammatory diseases and diseases characterized by defects in cholesterol or lipid metabolism for which the compounds of the invention are useful include neurodegenerative and neurological diseases, such as Alzheimer's Disease, Neimann-Pick disease type $C_1$, Parkinson's Disease, amyotrophic lateral sclerosis, stroke, age-related macular degeneration, psychiatric disorders such as schizophrenia and depression, and metabolic disorders such as cardiovascular disease, obesity and diabetes.

The present invention is directed to the use of the compounds of the invention as LXRβ agonists in a patient or subject such as a mammal in need of such activity, comprising the administration of an effective amount of the compound. In addition to humans, a variety of other mammals can be treated according to the method of the present invention.

The compounds of the invention may have utility in treating or ameliorating Alzheimer's disease. The compounds may also be useful in treating or ameliorating other inflammatory diseases and diseases characterized by defects in cholesterol and lipid metabolism, such as Neimann-Pick disease type $C_1$, Parkinson's Disease, amyotrophic lateral sclerosis, stroke, age-related macular degeneration, psychiatric disorders such as schizophrenia and depression, and metabolic disorders such as cardiovascular disease, obesity and diabetes.

For example, the compounds of the invention may be useful for the prevention of dementia of the Alzheimer's type, as well as for the treatment of early stage, intermediate stage or late stage dementia of the Alzheimer's type.

Potential cardiovascular conditions or disorders for which the compounds of the invention may be useful include atherosclerosis, hypertension, hyperlipidemia, coronary heart disease, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, vascular complications of diabetes, obesity (including abdominal obesity) and endotoxemia.

The compounds of the invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

The compounds of the invention may also be useful for the treatment of Type 2 diabetes, and conditions and disorders related to Type 2 diabetes, such as (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

The compounds of the invention may also have utility in treating certain kinds of cancers which are affected by the LXR mechanism. Such cancers include, but are not limited to, prostate, breast, ovarian, melanoma, pancreas, lung, colon and hematological malignancy. (Lin, C-Y and Gustafsson, J-A, (2015) Nature Reviews Cancer 15, 216-224).

The compounds of the invention may be used in combination with one or more other drugs in the treatment of diseases or conditions for which the compounds of the invention have utility, where the combination of the drugs together are safer or more effective than either drug alone. Additionally, the compounds of the invention may be used in combination with one or more other drugs that treat, prevent, control, ameliorate, or reduce the risk of side effects or toxicity of the compounds of the invention. Such other drugs may be administered, by a route and in an amount commonly used contemporaneously or sequentially with the compounds of the invention. Accordingly, the pharmaceutical compositions of the present invention include those that contain one or more other active ingredients, in addition to the compounds of the invention. The combinations may be administered as part of a unit dosage form combination product, or as a kit or treatment protocol wherein one or more additional drugs are administered in separate dosage forms as part of a treatment regimen.

Examples of combinations of the compounds of the invention include combinations with anti-Alzheimer's Disease agents, for example other LXRβ agonists; beta-secretase inhibitors including verubecestat (N-[3-[(5R)-3-amino-2,5-dimethyl-1,1-dioxo-6H-1,2,4-thiadiazin-5-yl]-4-fluorophenyl]-5-fluoropyridine-2-carboxamide); alpha 7 nicotinic agonists; ADAM 10 ligands or activators; gamma-secretase inhibitors, such as LY450139 and TAK 070; gamma secretase modulators; tau phosphorylation inhibitors; glycine transport inhibitors; ApoE4 conformational modulators; NR2B antagonists; androgen receptor modulators; blockers of Aβ 13orticotr formation; 5-HT4 agonists, such as PRX-03140; 5-HT6 antagonists, such as xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as I-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine and ladostigil; growth hormone secretagogues such as ibutamoren, ibutamoren mesylate, and capromorelin; histamine H3 receptor antagonists; AMPA agonists or AMPA modulators; PDE IV inhibitors; GABAA inverse agonists; GSK30 inhibitors; neuronal nicotinic agonists; selective M1 agonists; HDAC inhibitors; and microtubule affinity regulating kinase (MARK) ligands; dimebon; or other drugs that affect receptors or enzymes that either increase the efficacy, safety, convenience, or reduce unwanted side effects or toxicity of the compounds of the invention.

Other examples of combinations of the compounds of the invention include combinations with anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, $\beta_3$ adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y antagonists (e.g., NPY Y5 receptor antagonists) thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™, available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like.

Other examples of combinations of the compounds of the invention include combinations with antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone and olanzapine); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide™, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, A-4166; glitazones: ciglitazone, pioglitazone, englitazone, troglitazone, darglitazone, Avandia™; fatty acid oxidation inhibitors: clomoxir, etomoxir; alpha-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386,398; lipid-lowering agents: benfluorex: fenfluramine; vanadate and vanadium complexes (e.g., Naglivan™) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-CoA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. Non-limiting examples of HMG-CoA reductase inhibitors include statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; cerivastatin, particularly the sodium salt thereof, and nisvastatin.

The compounds of the invention may also be administered in combination with a naturally occurring compound that acts to lower plasma cholesterol levels. Such naturally occurring compounds are commonly called nutraceuticals and include, for example, garlic extract, Hoodia plant extracts, and niacin.

Other examples of combinations of the compounds of the invention include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, corticotrophi, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be used in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the compounds of the invention may be used in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Other examples of combinations of the compounds of the invention include combinations with agents for the treatment of stroke or stroke recovery. Examples of such second agents for treatment of stroke include, but are not limited to, aspirin, intercellular adhesion molecule (ICAM)-I and LFA-I antagonists including antibodies such as enlimomab (an anti-ICAM-1 monoclonal antibody), and anti-CD18 and anti-CD 1Ia antibodies, human anti-leukocytic antibodies such as Hu23F2G, glycoprotein lib IIia antagonists such as eptifibatide (INTEGRELIN™), direct thrombin inhibitors, external or local ultrasound, mechanical clot retrieval or inaceration, fibrinolytic agents, neuronal wound healing agents such as basic fibroblast growth factor (e.g., FIBLAST™), neuroprotective agents such as citicoline, magnesium, nalmefene, dizocilpine, nimodipine, lamotrigine, sipatrigine, lubeluzole, mexiletine, clomethiazole, calcium and sodium channel blocking agents, beta-amino-3-hydroxy-5-methylisoxazole-4-proprionic acid antagonist, a serotonin agonist, a transmembrane potassium channel modulator, agents that inhibit astrocyte activation (e.g., ONO 2506), antioxidants (e.g., MCI-186), anti-adhesion monoclonal antibodies and antagonists and antibodies inhibiting platelet aggregation such as argatroban and abciximab (REOPRO™), phenytoin, nitrogen oxides, CNS-protective therapies, free-radical scavengers such as tirilazad, reactive oxygen metabolites, and antioxidants, and other thrombolytic agents than tenecteplase, as defined below, such as, for example, acylated plasminogen-streptokinase activator complex (APSAC), single-chain urokinase-plasminogen activator (scu-PA), thrombin-like enzymes from snake venoms such as ancrod, streptokinase (e.g., SAKSTAR™), urokinase, anistreplase, alteplase, saruplase, reteplase, lanoteplase (SUN-9216; Genetics Institute Inc.), plasmin, a truncated form of plasmin (microplasmin; ThromboGenics Ltd), a direct-acting thrombolytic with non-thrombolytic-related neuroprotective activities, recombinant *desmodus rotundus* salivary plasminogen activator (rDSPA) alpha-1 (Schering/Teijin Pharmaceuticals), a mutant fibrin-activated human plasminogen (BB 101 53; British Biotech Inc.), staphylokinase, fibrolase, prourokinase (intra-arterial administration directly into M1 or M2 arterial thrombus), monteplase (modified rtPA), pamiteplase, tisokinase, and vampire bat plasminogen activator, a spin-trap agent such as NXY-059 (cerovive), clopidogrel, n-methyl-dextro-aspartic acid receptor blocking agent, an anticonvulsive agent, a caspase 3 inhibitor, ((tert butylimino)methyl) 1,3 (benzenedisulfonate disodium n oxide), ebselen, glutathione peroxidase, norphenazone, rovelizumab, lactacystin beta-lactone, tsukubaenolide, 4 phosphonomethylpipecolic acid, eliprodil, antibodies to ganglioside GMI; and thrombolytic agents, including streptokinase, acylated plasminogen-streptokinase activator complex (APSAC), urokinase, single-chain urokinase-plasminogen activator (scu-PA), thrombin-like enzymes from snake venoms such as ancrod (Bell, W. "Defibrinogenating enzymes" In Colman et al (eds), Hemostasis and Thrombosis Lippincott, Philadelphia (1987) p. 886), tPA, and biologically active variants of each of the above.

Other examples of combinations of the compounds of the invention include combinations with agents for the treatment of depression or anxiety, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), alpha-adrenoreceptor antagonists, atypical anti-depressants, benzodiazepines, 5-HT$_{1A}$ agonists or antagonists, especially 5-HT$_{1A}$ partial agonists, 18orticotrophin releasing factor (CRF) antagonists, and pharmaceutically acceptable salts thereof.

Other examples of combinations of the compounds of the invention include combinations with agents for the treatment of diabetes or diabetes conditions, including dipeptidyl peptidase IV (DPP-IV) inhibitors (including isoleucine thiazolidide vildagliptin and saxagliptin); insulin sensitizers, including (i) PPARγ agonists, such as the glitazones (e.g. troglitazone, pioglitazone, englitazone, MCC-555, rosiglitazone, balaglitazone, and the like) and other PPAR ligands, including PPARα or γ dual agonists, such as KRP-297, muraglitazar, naveglitazar, tesaglitazar, TAK-559, PPARα agonists, such as fenofibric acid derivatives (gemfibrozil, clofibrate, fenofibrate and bezafibrate), and selective PPAR gamma modulators (SPPARγM's); (ii) biguanides such as metformin and phenformin, and (iii) protein tyrosine phosphatase-1B (PTP-1B) inhibitors; insulin or insulin mimetics; sulfonylureas and other insulin secretagogues, such as tolbutamide, glyburide, glipizide, glimepiride, and meglitinides, such as nateglinide and repaglinide; α-glucosidase inhibitors (such as acarbose and miglitol); glucagon receptor antagonists; GLP-1, GLP-1 analogues or mimetics, and GLP-1 receptor agonists, such as exendin-4 (exenatide), liraglutide; GIP and GIP mimetics and GIP receptor agonists; PACAP, PACAP mimetics, and PACAP receptor agonists; cholesterol lowering agents; PPAR delta agonists; antiobesity agents; ileal bile acid transporter inhibitors; agents intended for use in inflammatory conditions such as aspirin, non-steroidal anti-inflammatory drugs (NSAIDs), glucocorticoids, azulfidine, and selective cyclooxygenase-2 (COX-2) inhibitors; antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers; glucokinase activators (GKAs); inhibitors of 11-β-hydroxysteroid dehydrogenase type 1; inhibitors of cholesteryl ester transfer protein (CETP), such as torcetrapib; and inhibitors of fructose 1,6-bisphosphatase.

The subject or patient to whom the compounds of the invention is administered is generally a human being, male or female, in whom LXRβ agonism is desired, but may also encompass other mammals, such as dogs, cats, mice, rats, cattle, horses, sheep, rabbits, monkeys, chimpanzees or other apes or primates, for which treatment of the above noted disorders is desired.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen. "Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, and they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to about 4 carbon atoms. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Alkenyl" means an aliphatic hydrocarbon group containing at least one carbon-carbon double bond and which may be straight or branched and comprising about 2 to about 10 carbon atoms in the straight or branched chain. Branched means that one or more lower alkyl groups such as methyl, ethyl propyl, ethenyl or propenyl are attached to a linear or branched alkenyl chain. "Lower alkenyl" means about 2 to about 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means about 2 to about 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moieties include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising about 3 to about 10 carbon atoms, preferably about 3 to about 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

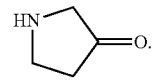

As used herein, the term "monocyclic heterocycloalkyl" refers monocyclic versions of the heterocycloalkyl moities decribed herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

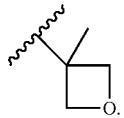

It should be noted that in hetero-atom containing ring systems of this invention, there are no hydroxyl groups on carbon atoms adjacent to a N, O or S, as well as there are no N or S groups on carbon adjacent to another heteroatom.

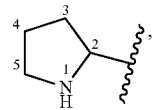

there is no —OH attached directly to carbons marked 2 and 5.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Alkoxy" means an —O-alkyl group in which the alkyl group is as previously described. Non-limiting examples of alkoxy groups include methoxy, ethoxy, n-propoxy, iso-propoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —$N(R^6)_2$, or a variable appears more than once in a structure presented herein, the variables can be the same or different.

The line ———, as a bond generally indicates a mixture of, or either of, the possible isomers, e.g., containing (R)- and (S)-stereochemistry. For example:

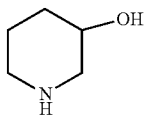

means containing both

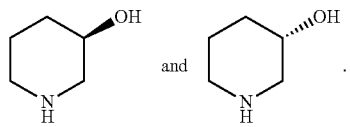

The wavy line ⌇⌇⌇, as used herein, indicates a point of attachment to the rest of the compound. Lines drawn into the ring systems, such as, for example:

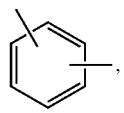

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

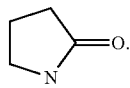

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

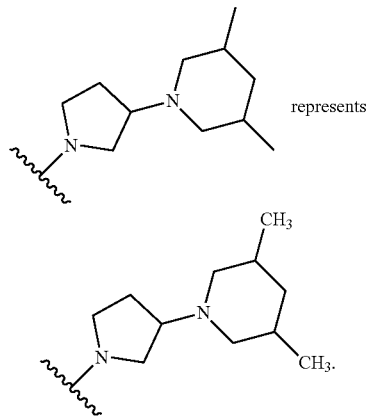

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible*

*Carriers in Drug Design*, (1987) Edward B. Roche, ed., American Pharmaceutical Association and Pergamon Press. The term "prodrug" means a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comprising one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

General Schemes

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

General Scheme A outlines a method for preparing compounds that have a cyanopyridyl with an appropriately substituted piperazine (A-1) such as a sulfonamide, amide or carbamate. In this method mono-boc protected piperazine is coupled in an SnAr reaction with 5-bromo-2-chloropyridine-3-carbonitrile to provide aminopyridine A-3. A-3 is then subjected to a palladium catalyzed cross-coupling reaction with 3-chloro-4-(dimethylcarbamoyl)phenyl boronic acid to produce biaryl amide A-4 which is deprotected in methanolic HCl to yield intermediate A-5. Intermediate A-5 can then be acylated or sulfonylated to produce the desired products (A-6, A-7, A-8).

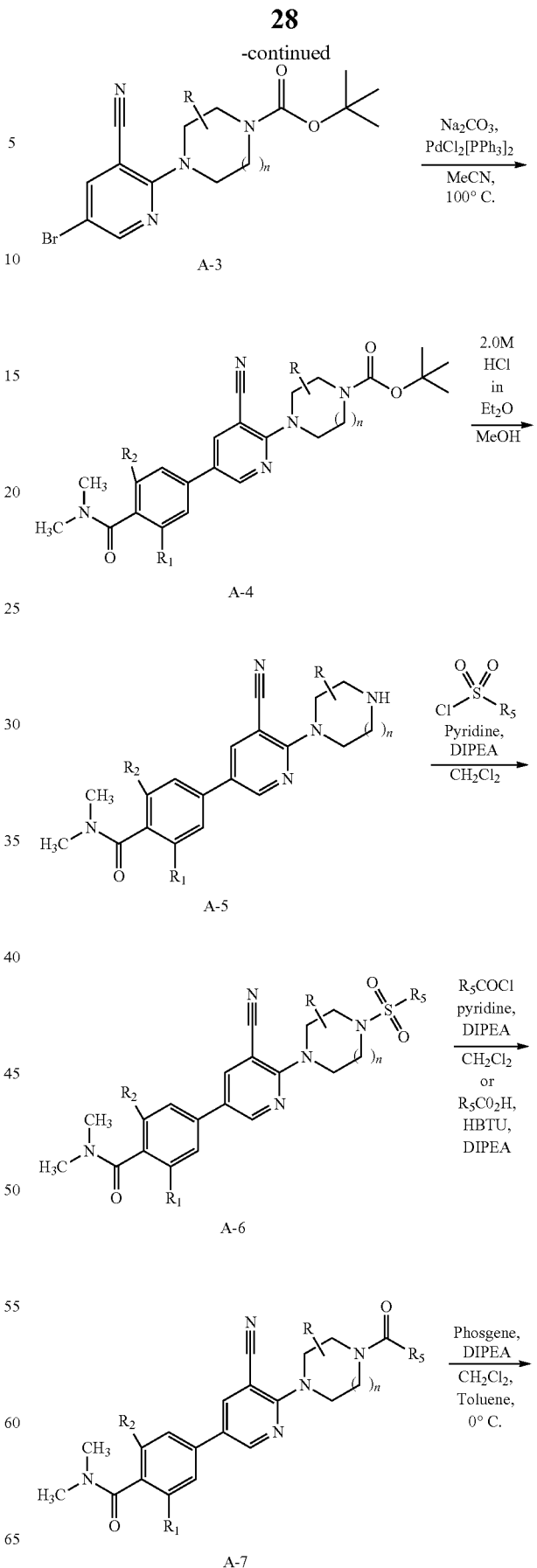

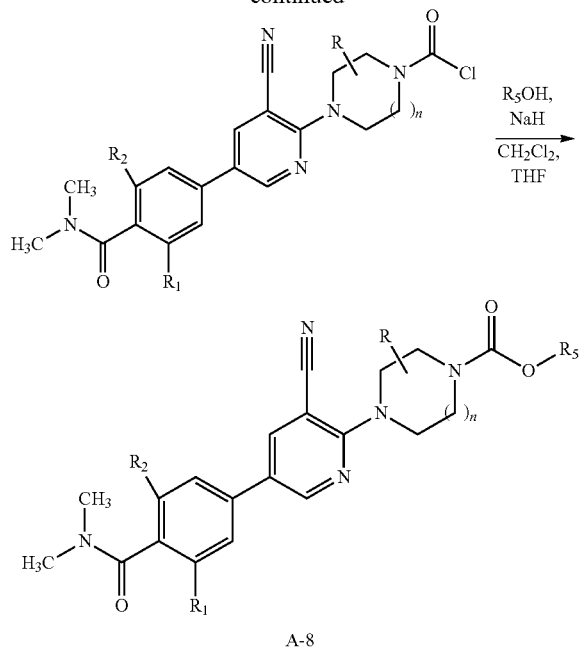

A-8

General Scheme B outlines a method for preparing aryl substituted piperazines. In this method 4-bromo-2-chlorobenzoic acid is coupled with an appropriate primary or secondary amine to produce the corresponding amide B-2. Bromide B-2 is then subjected to palladium catalyzed cross-coupling conditions with dioxazaborolane B-3 to yield the bis-aryl piperazine B-4. Deprotection in methanolic HCl followed by acylation produces acylated piperazine B-6. Chlorination using N-chlorosuccinimide yields a mixture of mono and bis-chlorinated products B-7 and B-8

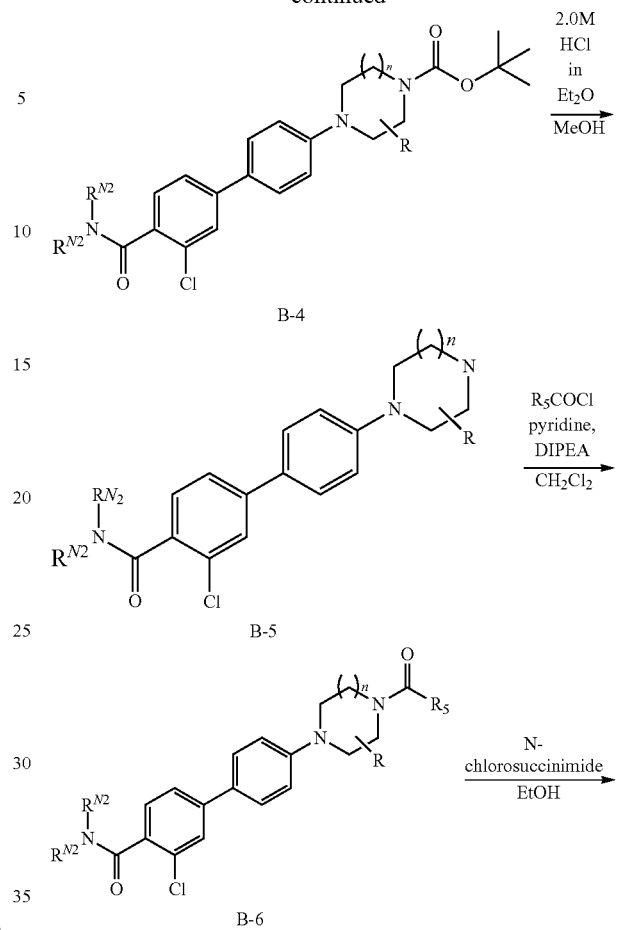

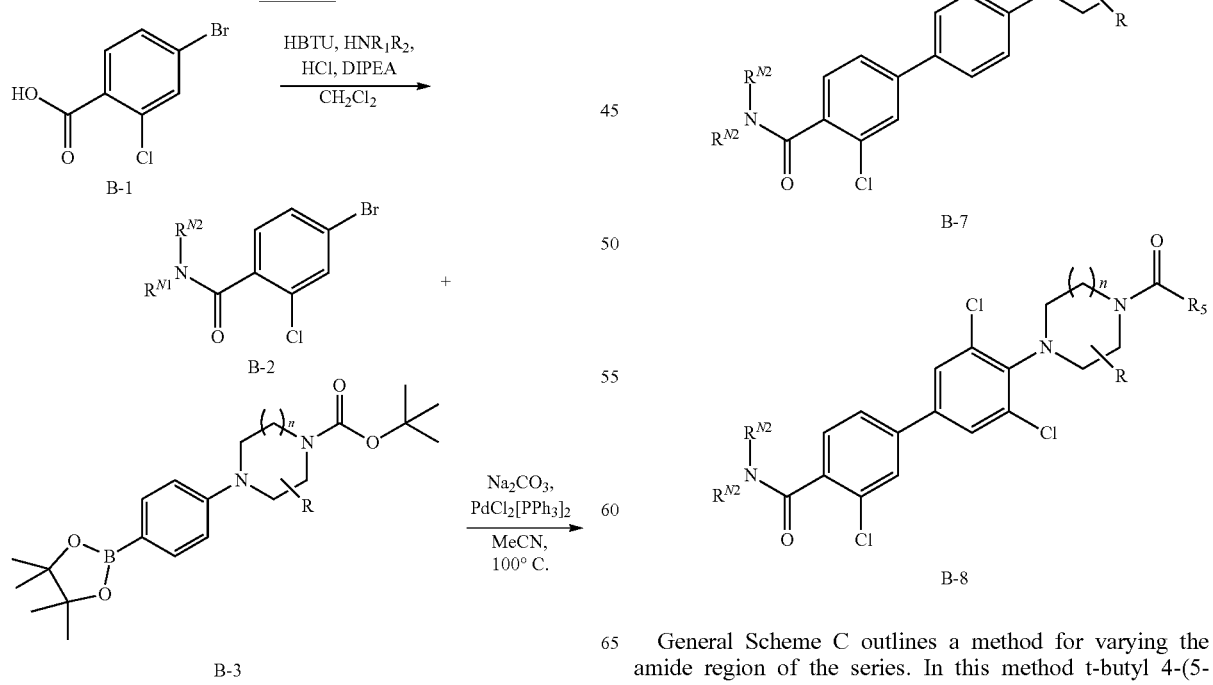

General Scheme C outlines a method for varying the amide region of the series. In this method t-butyl 4-(5-bromo-3-cyanopyridin-2-yl)piperazine-1-carboxylate (A-3)

is subjected to palladium catalyzed cross-coupling with 3-chloro-4-(methoxycarbonyl)phenyl boronic acid to produce the methyl ester C-1. C-1 is hydrolyzed to the corresponding carboxylic acid C-2 and coupled with appropriate amine using standard peptide coupling conditions to produce amides C-3. These compounds can subsequently be deprotected and acylated or sulfonylated in a similar manner to Scheme A.

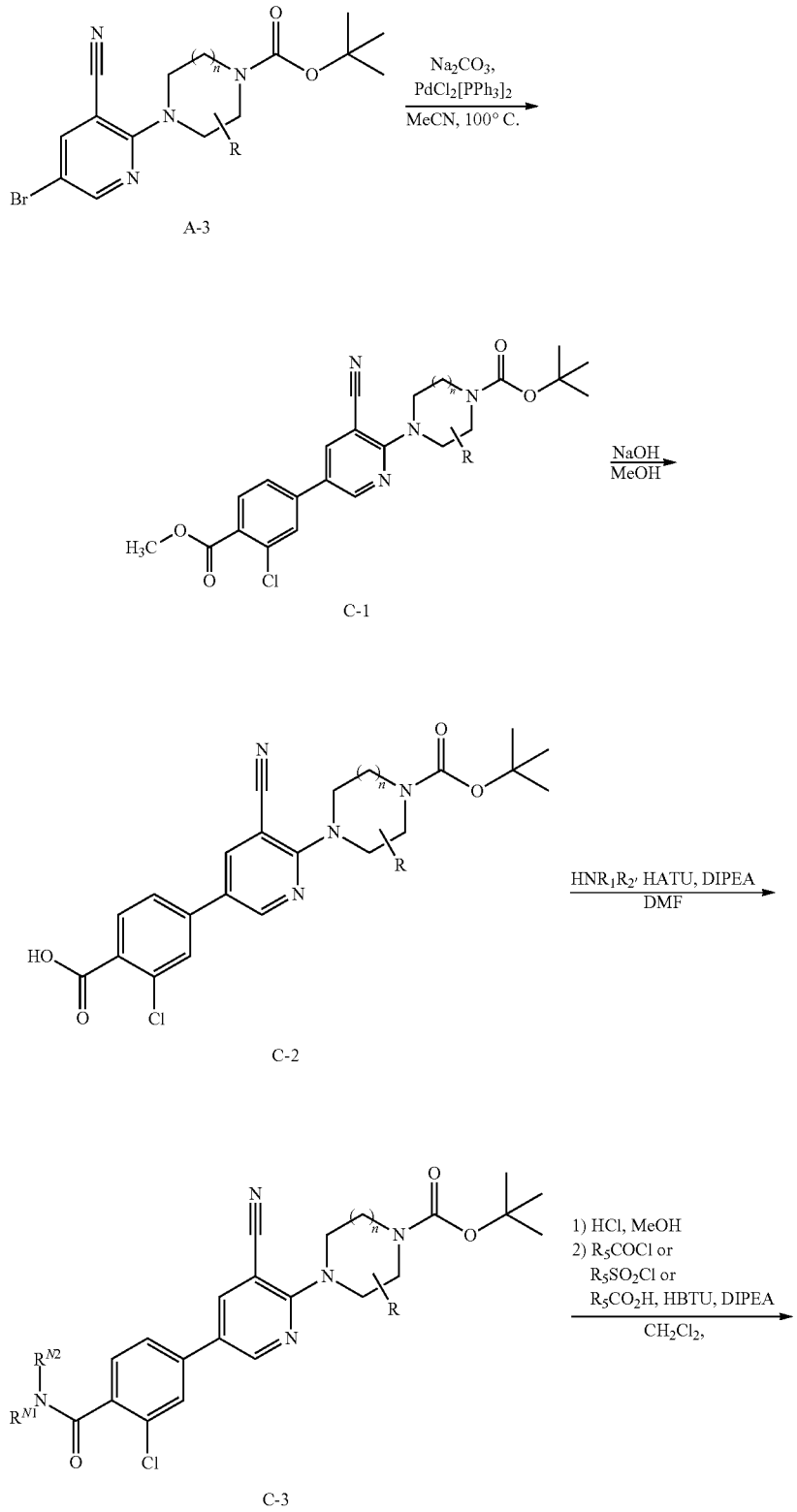

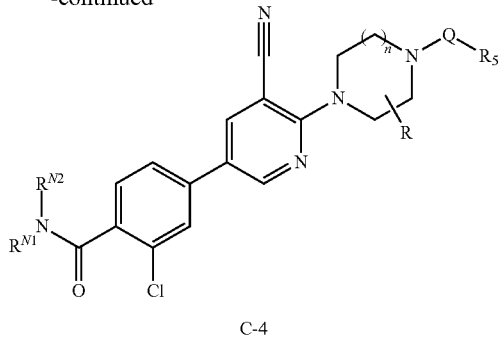

C-4

General Scheme D outlines a method for the preparation of the bis-chloro substituted cyanopyridyl biaryl system. In this method 4-bromo-2,6-dichlorobenzoic acid is coupled with the appropriate amine using standard peptide coupling conditions. The amide is then coupled with boronic acid D-3 using palladium catalysis conditions to produce the pyridyl substituted aromatic system D-4. Deprotection in methanolic HCl followed by acylation produced the target compound D-6.

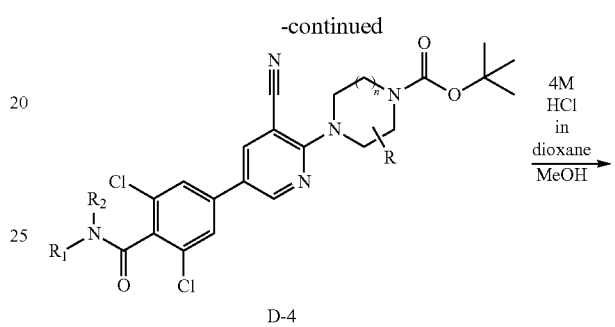

D-4

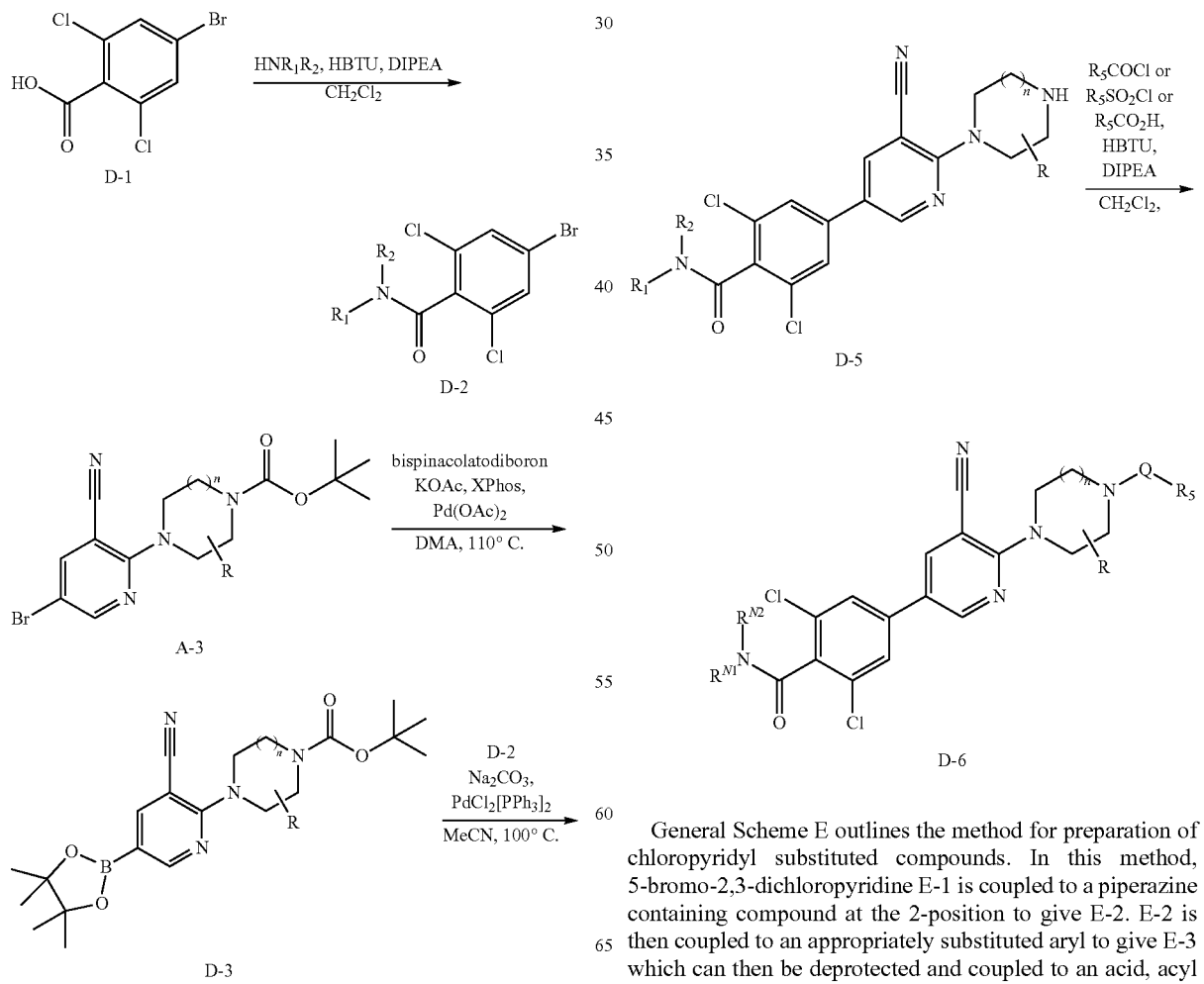

General Scheme E outlines the method for preparation of chloropyridyl substituted compounds. In this method, 5-bromo-2,3-dichloropyridine E-1 is coupled to a piperazine containing compound at the 2-position to give E-2. E-2 is then coupled to an appropriately substituted aryl to give E-3 which can then be deprotected and coupled to an acid, acyl chloride, or sulfonyl chloride to give E-5.

Scheme E

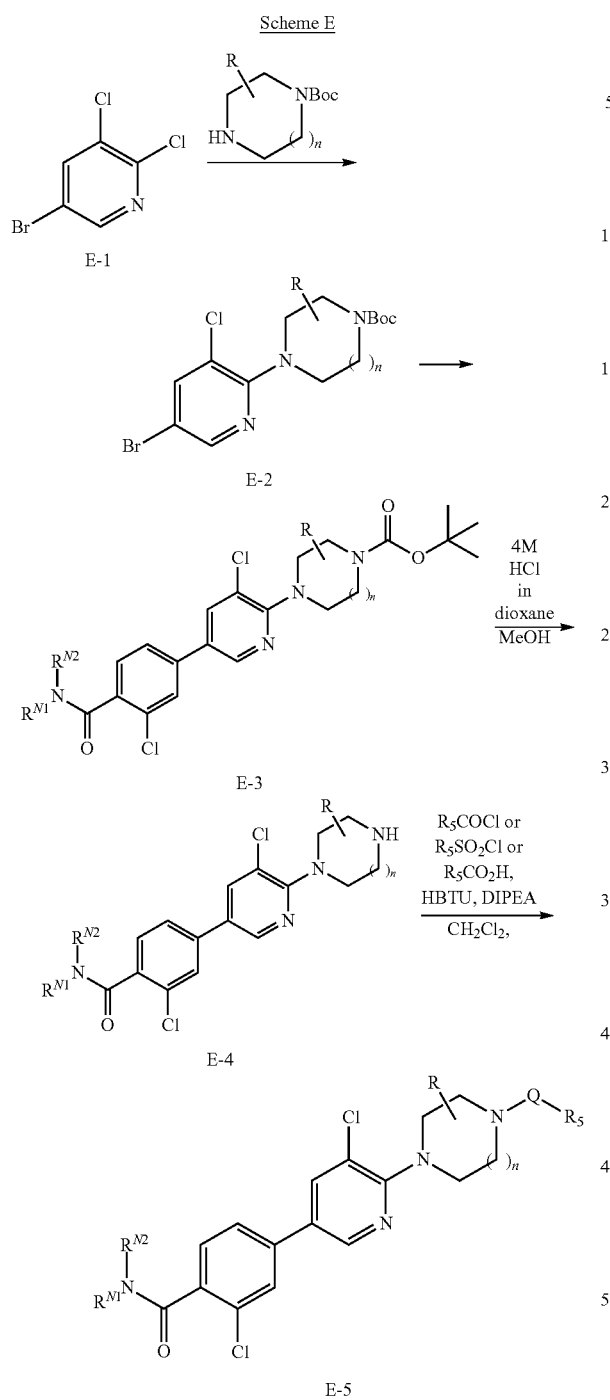

SCHEME F

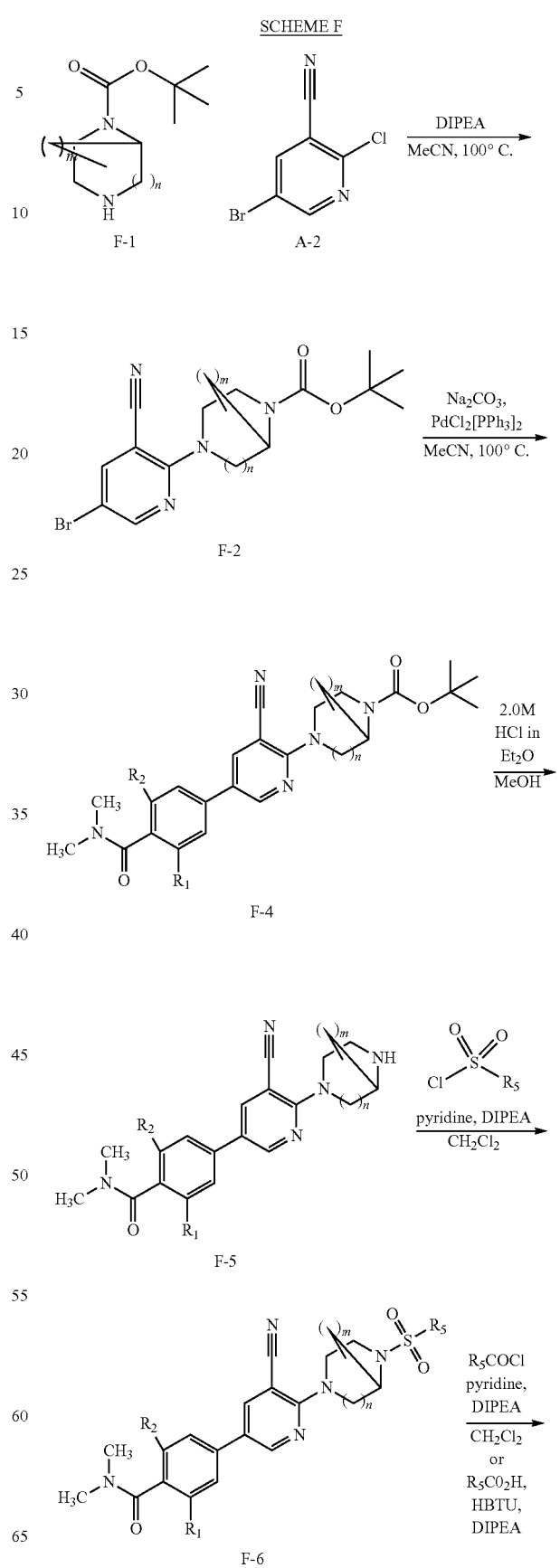

General Scheme F outlines a method for preparing compounds that have a cyanopyridyl with an appropriately bridged bicyclic piperazine (F-1) such as a sulfonamide, amide or carbamate. In this method mono-boc protected piperazine is coupled in an SnAr reaction with 5-bromo-2-chloropyridine-3-carbonitrile to provide aminopyridine F-3. F-3 is then subjected to a palladium catalyzed cross-coupling reaction with 3-chloro-4-(dimethylcarbamoyl)phenyl boronic acid to produce biaryl amide F-4 which is deprotected in methanolic HCl to yield intermediate F-5. Intermediate F-5 can then be acylated or sulfonylated to produce the desired products (F-6, F-7, F-8).

37
-continued

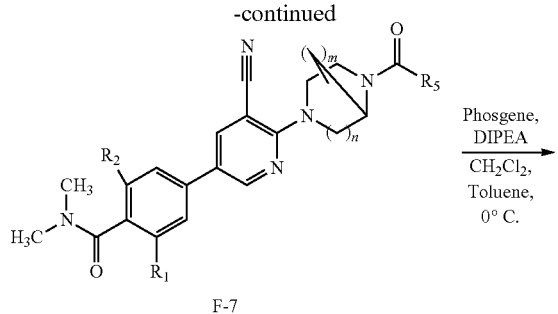

F-7

Phosgene,
DIPEA
CH₂Cl₂,
Toluene,
0° C.

38
-continued

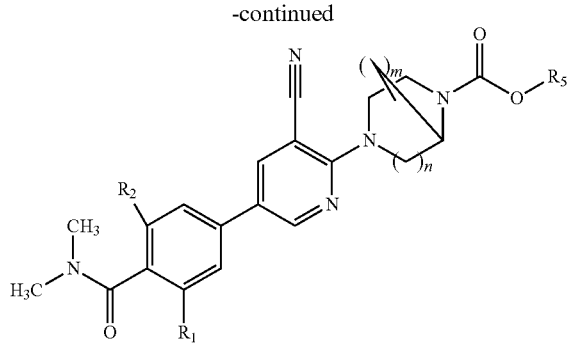

F-8

General Scheme G outlines a method for preparing aryl substituted piperazines. In this method bridged bicyclic piperizine G-1 is coupled to 1-bromo-4-iodobenzene using copper and base. The resulting mixture of G-2a and G-2b is subjected to palladium catalyzed cross-coupling conditions with 3-chloro-4-dimethylcarbamoylphenylboronic acid to yield the piperazine G-4. Deprotection in methanolic HCl followed by acylation produces acylated piperazine G-6. Chlorination using N-chlorosuccinimide yields a mixture of mono and bis-chlorinated products G-7 and G-8. Alternatively, G-3 can be directly chlorinated to G-8 and G-9.

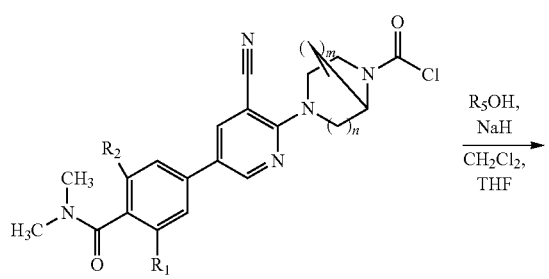

R₅OH,
NaH
CH₂Cl₂,
THF

Scheme G

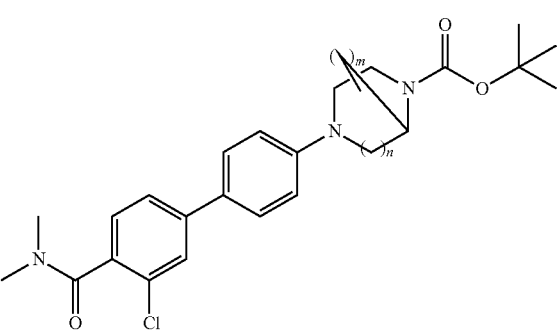

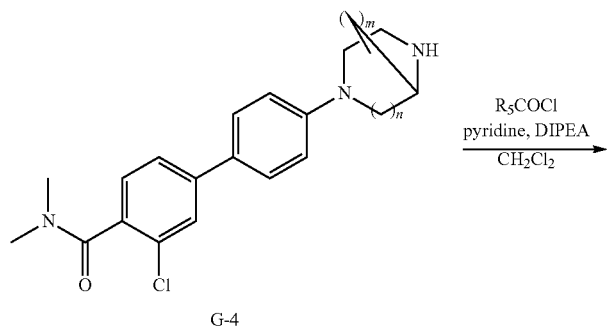
G-4
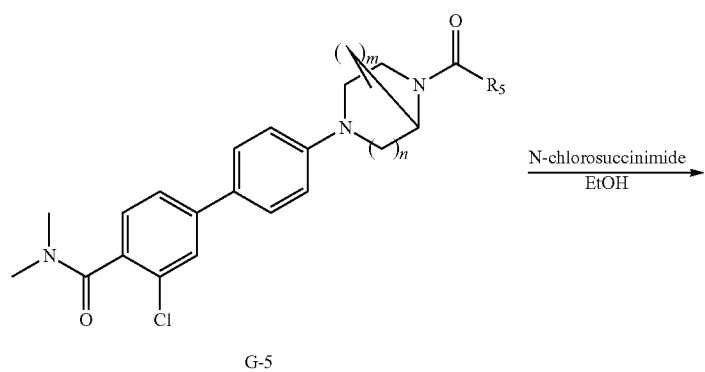
G-5
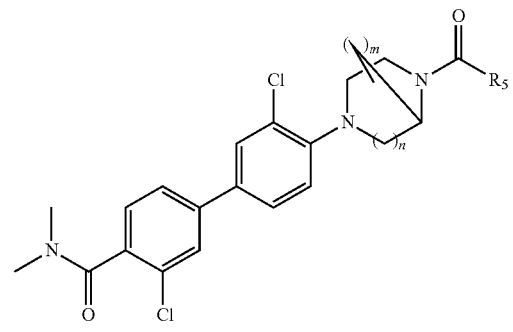
G-6
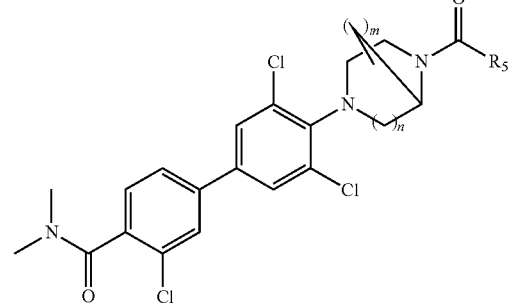
G-7

G-3 →<sup>NCS</sup>

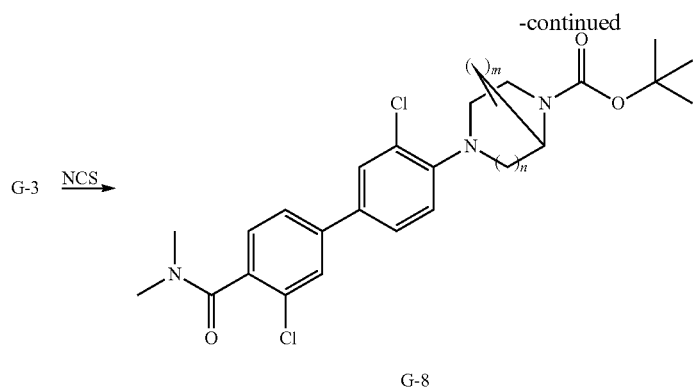

G-8

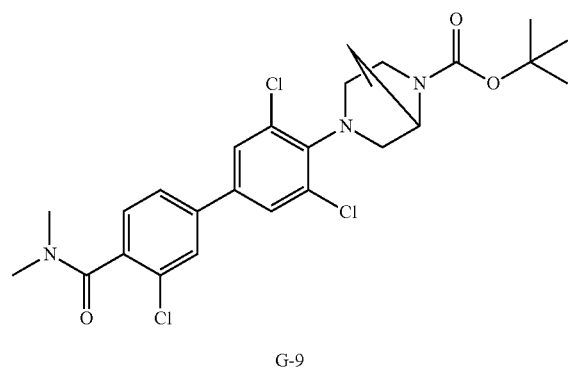

G-9

List of Abbreviations

BOP (benzotriazol-1-yloxy)tris(dimethylamino)phosphonium hexafluorophosphate
Br$_2$BH-SMe$_2$ dibromoborane-methylsulfide complex
CDI N,N'-carbonyldiimidazole
Cs$_2$CO$_3$ cesium carbonate
DCC N,N'-dicyclohexylcarbodiimide
DCE dichloroethane
DCM dichloromethane
DIAD diisopropyl azodicarboxylate
DIBAL-H diisobutylaluminum hydride
DIEA diisopropylethylamine (N,N-diisopropylethylamine)
DMF dimethylformamide
DMSO dimethyl sulfoxide
Dppf diphenylphosphinoferrocene
EDC N-(3-dimethylaminopropyl)-N'-ethylcarbodiimide
Et$_2$O diethyl ether
Et$_3$N triethylamine
EtOAc ethyl acetate
EtOH ethanol
HATU O-(7-azabenzotriazol-1-yl)-N,N,N',N'-tetramethyluronium hexafluorophosphate
HBTU N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate
HCl hydrochloric acid
(HF)$_3$-Et$_3$N triethylamine trihydrofluoride
IPA isopropanol
K$_2$CO$_3$ potassium carbonate
KHSO$_4$ potassium bisulfate
KOAc potassium acetate
LiOH lithium hydroxide
MeCN acetonitrile
MeOH methanol
MgSO$_4$ magnesium sulfate
MIDA N-methyliminodiacetic acid
Na$_2$SO$_4$ sodium sulfate
NaHCO$_3$ sodium bicarbonate
NaH sodium hydride
NaOH sodium hydroxide
n-BuLi n-butyl lithium
NIS N-iodosuccinimide
Pd(Ph$_3$P)$_4$ tetrakis(triphenylphosphine) palladium (0)
Pd/C palladium on carbon
PdCl$_2$(dppf)-CH$_2$Cl$_2$ adduct dichloro[1,1'-bis(diphenylphosphino)ferrocene]palladium (II) dichloromethane adduct
PdCl$_2$(PPh$_3$)$_2$ palladium dichloride bis-triphenylphosphine
PE Petroleum ether
POCl$_3$ phosphorous oxychloride
PPh$_3$ triphenylphosphine
RT, r.t., rt room temperature
TBTU O-benzotriazol-1-yl-N,N,N',N'-tetramethyluronium tetrafluoroborate
Tf$_2$O triflic anhydride
TFA trifluoroacetatic acid
TfOH trifluoromethanesulfonic acid
THF tetrahydofuran
Xphos 2-Dicyclohexylphosphino-2',4',6'-triisopropylbiphenyl

Intermediates A-3 tert-butyl 4-(5-bromo-3-cyanopyridin-2-yl)piperazine-1-carboxylate (A-3.1)

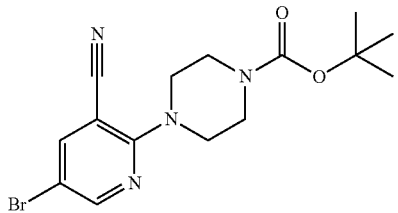 [SMILES: CC(C)(C)OC(=O)N1CCN(c2ncc(Br)cc2C#N)CC1]

To a solution of tert-butyl piperazine-1-carboxylate (9.4 g, 51 mmol, 1.1 eq) and 5-bromo-2-chloropyridine-3-carbonitrile (10 g, 46 mmol, 1.0 eq) in acetonitrile (200 mL) was added and N,N-diisopropylethylamine (9.6 mL, 55 mmol, 1.2 eq) and the resulting solution was heated at reflux for 16 hours. The reaction mixture was concentrated and the residue was dissolved in dichloromethane (200 mL). The organic layer was washed with 1 N aqueous HCl solution (50 mL) followed by 10% aqueous sodium bicarbonate solution (50 mL) then dried over sodium sulfate and concentrated to yield tert-butyl 4-(5-bromo-3-cyanopyridin-2-yl)piperazine-1-carboxylate. $^1$H NMR (400 MHz, CDCl$_3$): δ 8.35 (d, J=2.5 Hz, 1H); 7.85 (d, J=2.5 Hz, 1H); 3.71-3.65 (m, 4H); 3.59-3.54 (m, 4H); 1.48 (s, 9H). LRMS m/z (M+H) 367.1 found, 367.1 required.

tert-butyl 3-(5-bromo-3-cyanopyridin-2-yl)-3,8-diazabicyclo[3.2.1]octane-8-carboxylate (A-3.2)

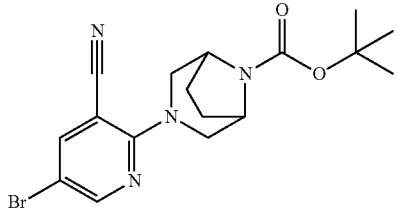 [SMILES: CC(C)(C)OC(=O)N1C2CCC1CN(c1ncc(Br)cc1C#N)C2]

tert-butyl 3-(5-bromo-3-cyanopyridin-2-yl)-3,8-diazabicyclo[3.2.1]octane-8-carboxylate was prepared according to the procedure described for tert-butyl 4-(5-bromo-3-cyanopyridin-2-yl)piperazine-1-carboxylate, but using commercially available tert-butyl 3,8-diazabicyclo[3.2.1]octane-8-carboxylate in place of tert-butyl piperazine-1-carboxylate. LRMS m/z (M+H) 393.1 found, 393.1 required.

tert-butyl 5-(5-bromo-3-cyanopyridin-2-yl)-2,5-diazabicyclo[2.2.2]octane-2-carboxylate (A-3.3)

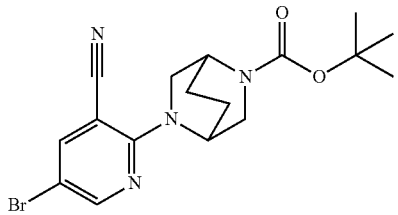 [SMILES: CC(C)(C)OC(=O)N1CC2CCC1CN2c1ncc(Br)cc1C#N]

tert-butyl 5-(5-bromo-3-cyanopyridin-2-yl)-2,5-diazabicyclo[2.2.2]octane-2-carboxylate was prepared according to the procedure described for tert-butyl 4-(5-bromo-3-cyanopyridin-2-yl)piperazine-1-carboxylate, but using commercially available tert-butyl 2,5-diazabicyclo[2.2.2]octane-2-carboxylate in place of tert-butyl piperazine-1-carboxylate. LRMS m/z (M+H) 393.1 found, 393.1 required.

tert-butyl (1R)-5-(5-bromo-3-cyanopyridin-2-yl)-2,5-diazabicyclo[2.2.1]heptane-2-carboxylate (A-3.4)

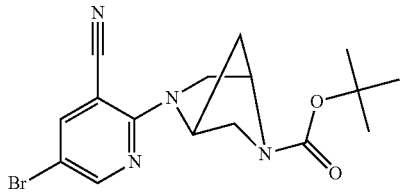 [SMILES: CC(C)(C)OC(=O)N1CC2CC1CN2c1ncc(Br)cc1C#N]

tert-butyl (1R)-5-(5-bromo-3-cyanopyridin-2-yl)-2,5-diazabicyclo[2.2.1]heptane-2-carboxylate was prepared according to the procedure described for tert-butyl 4-(5-bromo-3-cyanopyridin-2-yl)piperazine-1-carboxylate, but using commercially available tert-butyl 2,5-diazabicyclo[2.2.1]heptane-2-carboxylate in place of tert-butyl piperazine-1-carboxylate. LRMS m/z (M-Boc+H) 278.1 found, 278.1 required.

tert-butyl 4-(5-bromo-3-cyanopyridin-2-yl)-2-methylpiperazine-1-carboxylate (A-3.5)

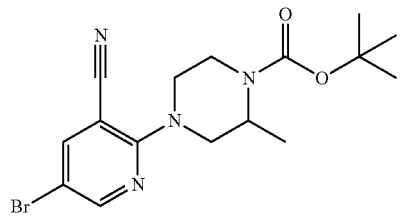 [SMILES: CC1CN(c2ncc(Br)cc2C#N)CCN1C(=O)OC(C)(C)C]

tert-butyl 4-(5-bromo-3-cyanopyridin-2-yl)-2-methylpiperazine-1-carboxylate was prepared according to the procedure described for tert-butyl 4-(5-bromo-3-cyanopyridin-2-yl)piperazine-1-carboxylate, but using commercially available tert-butyl 2-methylpiperazine-1-carboxylate in place of tert-butyl piperazine-1-carboxylate. LRMS m/z (M-Boc+H) 281.2 found, 281.1 required.

tert-butyl 10-(5-bromo-3-cyanopyridin-2-yl)-9,10-diazatricyclo[4.2.1.1$^{2,5}$]decane-9-carboxylate (A-3.6)

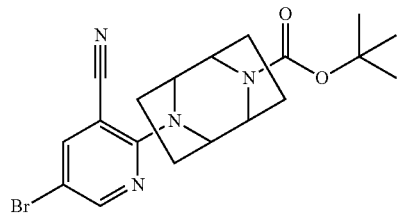 [SMILES: CC(C)(C)OC(=O)N1C2CCC1C1CCC2N1c1ncc(Br)cc1C#N]

tert-butyl 10-(5-bromo-3-cyanopyridin-2-yl)-9,10-diazatricyclo[4.2.1.12,5]decane-9-carboxylate was prepared according to the procedure described for tert-butyl 4-(5-bromo-3-cyanopyridin-2-yl)piperazine-1-carboxylate, but using tert-butyl 9,10-diazatricyclo[4.2.1.12,5]decane-9-carboxylate which was prepared according to WO 2013066714 A1 in place of tert-butyl piperazine-1-carboxylate. LRMS m/z (M-t-Bu+H) 363.2 found, 363.0 required.

tert-butyl 4-(5-bromo-3-cyanopyridin-2-yl)-2-phenylpiperazine-1-carboxylate (A-3.7)

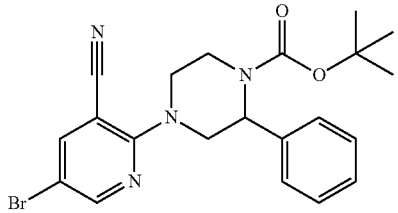 [SMILES: CC(C)(C)OC(=O)N1CCN(c2ncc(Br)cc2C#N)CC1c1ccccc1]

tert-butyl 4-(5-bromo-3-cyanopyridin-2-yl)-2-phenylpiperazine-1-carboxylate was prepared according to the procedure described for tert-butyl 4-(5-bromo-3-cyanopyridin-2-yl)piperazine-1-carboxylate, but using commercially available tert-butyl 2-phenylpiperazine-1-carboxylate in place of tert-butyl piperazine-1-carboxylate. LRMS m/z (M-Boc+H) 343.2 found, 343.1 required.

tert-butyl 3-benzyl-4-(5-bromo-3-cyanopyridin-2-yl)piperazine-1-carboxylate (A-3.8)

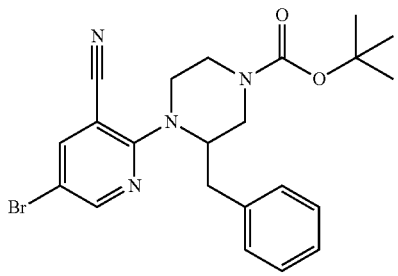 [SMILES: CC(C)(C)OC(=O)N1CCN(c2ncc(Br)cc2C#N)C(Cc2ccccc2)C1]

tert-butyl 3-benzyl-4-(5-bromo-3-cyanopyridin-2-yl)piperazine-1-carboxylate was prepared according to the procedure described for tert-butyl 4-(5-bromo-3-cyanopyridin-2-yl)piperazine-1-carboxylate, but using commercially available tert-butyl 3-benzylpiperazine-1-carboxylate in place of tert-butyl piperazine-1-carboxylate. LRMS m/z (M-Boc+H) 357.2 found, 357.1 required.

Example 1-1

2-chloro-4-(5-cyano-6-{4-[(2,6-dichlorophenyl)sulfonyl]piperazin-1-yl}pyridin-3-yl)-N,N-dimethylbenzamide

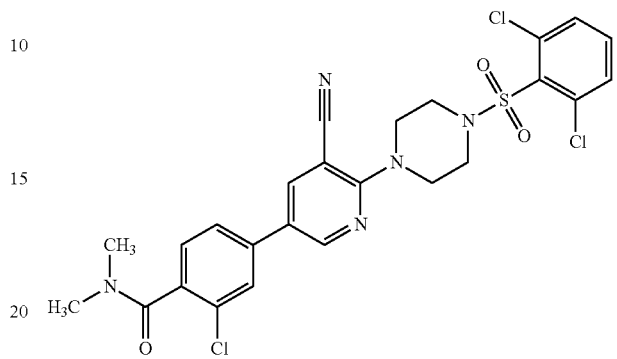

A mixture of tert-butyl 4-(5-bromo-3-cyanopyridin-2-yl)piperazine-1-carboxylate (intermediate A-3.1) (8.0 g, 22 mmol, 1.0 eq), 3-chloro-4-(dimethylcarbamoyl)phenyl boronic acid (6.0 g, 26 mmol, 1.2 eq) and 2M sodium carbonate solution (11 mL, 22 mmol, 1.0 eq) in acetonitrile (100 mL) was degassed with nitrogen for 15 minutes prior to the addition of bis(triphenylphosphine) palladium (II) chloride (0.76 g, 1.1 mmol, 0.050 eq). The resulting reaction mixture was heated at reflux under nitrogen for 16 hours. The reaction mixture was concentrated and the residue was partitioned between dichloromethane (200 mL) and water (100 ml). The organic layer was separated, dried over sodium sulfate and concentrated and the resulting residue was purified by silica gel chromatography (0-100% ethyl acetate/hexanes) to yield tert-butyl 4-{5-[3-chloro-4-(dimethylcarbamoyl)phenyl]-3-cyanopyridin-2-yl}piperazine-1-carboxylate. $^1$H NMR (400 MHz, CDCl$_3$): δ 8.52 (d, J=2.6 Hz, 1H); 7.93 (d, J=2.6 Hz, 1H); 7.49 (s, 1H); 7.41-7.35 (m, 2H); 3.78-3.72 (m, 4H); 3.61-3.55 (m, 4H); 3.13 (s, 3H); 2.89 (s, 3H); 1.46 (s, 9H).
LRMS m/z (M+H) 470.2 found, 470.2 required.

2-chloro-4-[5-cyano-6-(piperazin-1-yl)pyridin-3-yl]-N,N-dimethylbenzamide

To a solution of tert-butyl 4-{5-[3-chloro-4-(dimethylcarbamoyl)phenyl]-3-cyanopyridin-2-yl}piperazine-1-carboxylate (6.3 g, 13 mmol, 1.0 eq) in methanol (100 mL) was added 2 M hydrochloric acid in diethyl ether (100 mL, 100 mmol, 7.5 eq) and the resulting reaction mixture was stirred at 23° C. for 16 hours. The reaction mixture was concentrated under reduced pressure to give the bis HCl salt of 2-chloro-4-[5-cyano-6-(piperazin-1-yl)pyridin-3-yl]-N,N-dimethylbenzamide. $^1$H NMR (400 MHz, D$_2$O): δ 8.51 (d, J=2.5 Hz, 1H); 8.22 (d, J=2.5 Hz, 1H); 7.64 (s, 1H); 7.50 (d, J=8.0 Hz, 1H); 7.33-7.31 (m, 1H); 3.78-3.73 (m, 4H); 3.33-3.28 (m, 4H); 2.99 (s, 3H); 2.80 (s, 3H). LRMS m/z (M+H) 370.1 found, 370.1 required.

To a solution of the bis hydrochloride salt of 2-chloro-4-[5-cyano-6-(piperazin-1-yl)pyridin-3-yl]-N,N-dimethylbenzamide (48 mg, 0.11 mmol, 1.0 eq) and N,N-diisopropylethylamine (38 μL, 0.22 mmol, 2.0 eq) in dichloromethane (3.0 mL) was added pyridine (44 μL, 0.54 mmol, 5.0 eq) followed by 2,6-dichlorobenzenesulfonyl chloride (32 mg, 0.13 mmol, 1.2 eq) and the resulting reaction was stirred at 23° C. for 16 hours. The reaction mixture was concentrated and the residue was dissolved in DMSO and purified by reverse phase liquid chromatography (Gemini-NX C18, 5 μm, 30×100 mm column; 0-100% CH$_3$CN/H$_2$O gradient w/0.10% TFA present) to yield 2-chloro-4-(5-cyano-6-{4-[(2,6-dichlorophenyl)sulfonyl]piperazin-1-yl}pyridin-3-yl)-N,N-dimethylbenzamide. $^1$H NMR (400 MHz, CDCl$_3$): δ 8.57 (d, J=2.5 Hz, 1H); 8.07-7.93 (m, 1H); 7.54-7.34 (m, 6H); 3.86 (t, J=4.8 Hz, 4H); 3.61 (t, J=4.8 Hz, 4H); 3.21 (s, 3H); 2.96 (s, 3H). LRMS m/z (M+H) 578.1 found, 578.1 required.

The following examples were prepared according to the procedure in example 1-1 using the appropriate sulfonyl chloride.

TABLE 1

| Example | Structure | IUPAC Name | Exact Mass [M + H]+ |
|---|---|---|---|
| 1-2 | 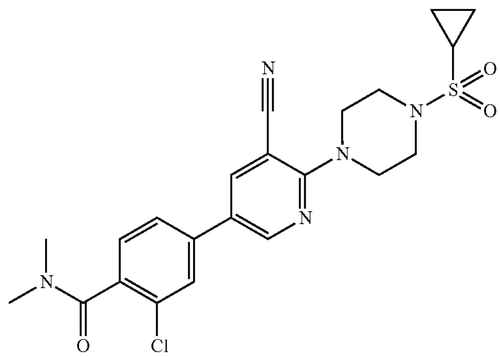 [SMILES: CN(C)C(=O)c1ccc(-c2cnc(N3CCN(S(=O)(=O)C4CC4)CC3)c(C#N)c2)cc1Cl] | 2-chloro-4-{5-cyano-6-[4-(cyclopropylsulfonyl)piperazin-1-yl]pyridin-3-yl}-N,N-dimethylbenzamide | Calc'd 474.1, found 474.1 |
| 1-3 | 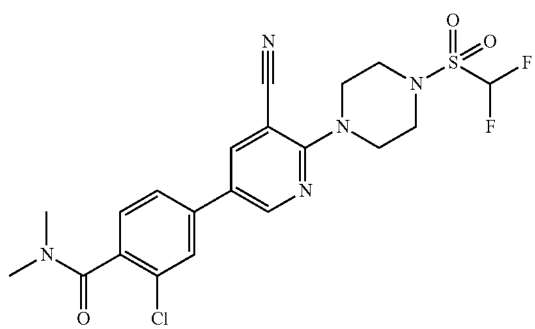 [SMILES: CN(C)C(=O)c1ccc(-c2cnc(N3CCN(S(=O)(=O)C(F)F)CC3)c(C#N)c2)cc1Cl] | 2-chloro-4-(5-cyano-6-{4-[(difluoromethyl)sulfonyl]piperazin-1-yl}pyridin-3-yl)-N,N-dimethylbenzamide | Calc'd 484.1, found 484.0 |
| 1-4 | 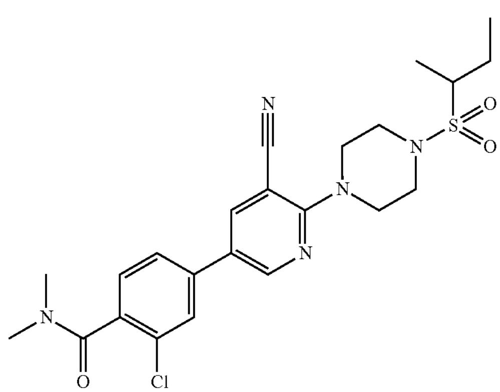 [SMILES: CCC(C)S(=O)(=O)N1CCN(c2ncc(-c3ccc(C(=O)N(C)C)c(Cl)c3)cc2C#N)CC1] | 2-chloro-4-(5-cyano-6-{4-[(1-methylpropyl)sulfonyl]piperazin-1-yl}pyridin-3-yl)-N,N-dimethylbenzamide | Calc'd 490.2, found 490.1 |

TABLE 1-continued

| Example | Structure | IUPAC Name | Exact Mass [M + H]+ |
|---|---|---|---|
| 1-5 | 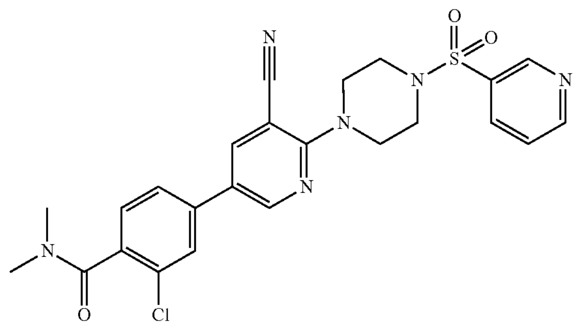 [SMILES: CN(C)C(=O)c1ccc(-c2cnc(N3CCN(S(=O)(=O)c4cccnc4)CC3)c(C#N)c2)cc1Cl] | 2-chloro-4-{5-cyano-6-[4-(pyridin-3-ylsulfonyl)piperazin-1-yl]pyridin-3-yl}-N,N-dimethylbenzamide | Calc'd 511.1, found 511.1 |
| 1-6 | 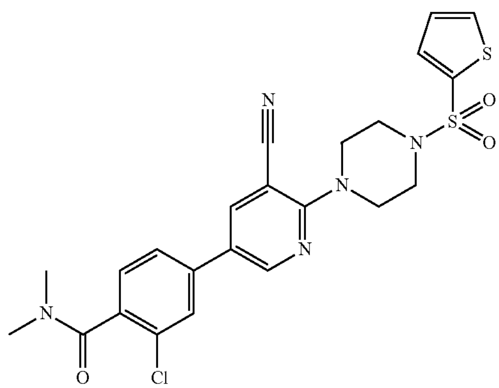 [SMILES: CN(C)C(=O)c1ccc(-c2cnc(N3CCN(S(=O)(=O)c4cccs4)CC3)c(C#N)c2)cc1Cl] | 2-chloro-4-{5-cyano-6-[4-(thiophen-2-ylsulfonyl)piperazin-1-yl]pyridin-3-yl}-N,N-dimethylbenzamide | Calc'd 516.1, found 516.0 |
| 1-7 | 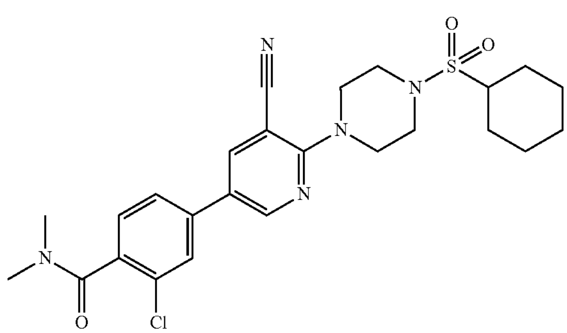 [SMILES: CN(C)C(=O)c1ccc(-c2cnc(N3CCN(S(=O)(=O)C4CCCCC4)CC3)c(C#N)c2)cc1Cl] | 2-chloro-4-{5-cyano-6-[4-(cyclohexylsulfonyl)piperazin-1-yl]pyridin-3-yl}-N,N-dimethylbenzamide | Calc'd 516.2, found 516.1 |
| 1-8 | 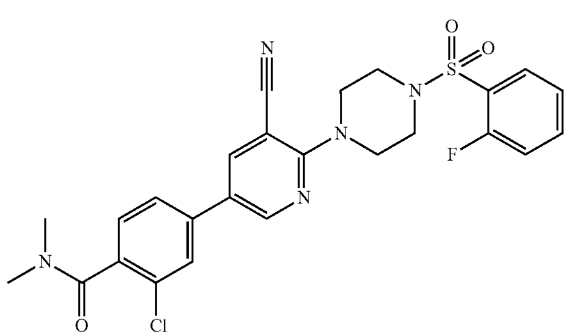 [SMILES: CN(C)C(=O)c1ccc(-c2cnc(N3CCN(S(=O)(=O)c4ccccc4F)CC3)c(C#N)c2)cc1Cl] | 2-chloro-4-(5-cyano-6-{4-[(2-fluorophenyl)sulfonyl]piperazin-1-yl}pyridin-3-yl)-N,N-dimethylbenzamide | Calc'd 528.1, found 528.0 |

TABLE 1-continued

| Example | Structure | IUPAC Name | Exact Mass [M + H]+ |
|---|---|---|---|
| 1-9 | 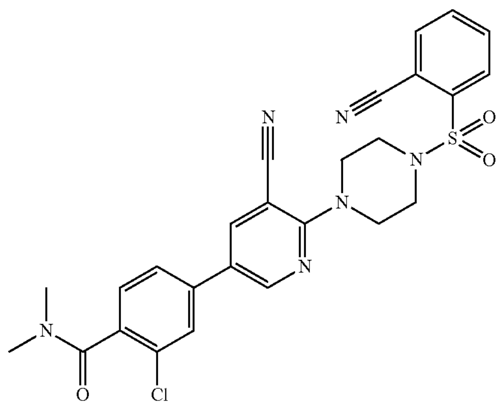 [SMILES: CN(C)C(=O)c1ccc(-c2cnc(N3CCN(S(=O)(=O)c4ccccc4C#N)CC3)c(C#N)c2)cc1Cl] | 2-chloro-4-(5-cyano-6-{4-[(2-cyanophenyl)sulfonyl]piperazin-1-yl}pyridin-3-yl)-N,N-dimethylbenzamide | Calc'd 535.1, found 535.0 |
| 1-10 | 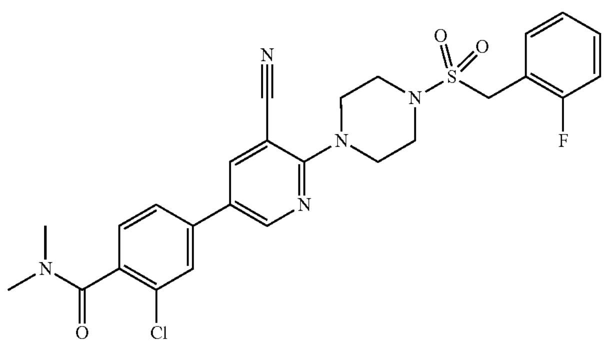 [SMILES: CN(C)C(=O)c1ccc(-c2cnc(N3CCN(S(=O)(=O)Cc4ccccc4F)CC3)c(C#N)c2)cc1Cl] | 2-chloro-4-(5-cyano-6-{4-[(2-fluorobenzyl)sulfonyl]piperazin-1-yl}pyridin-3-yl)-N,N-dimethylbenzamide | Calc'd 542.1, found 542.1 |
| 1-11 | 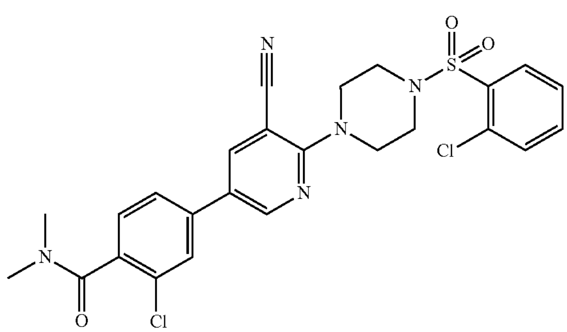 [SMILES: CN(C)C(=O)c1ccc(-c2cnc(N3CCN(S(=O)(=O)c4ccccc4Cl)CC3)c(C#N)c2)cc1Cl] | 2-chloro-4-(6-{4-[(2-chlorophenyl)sulfonyl]piperazin-1-yl}-5-cyanopyridin-3-yl)-N,N-dimethylbenzamide | Calc'd 544.1, found 544.0 |
| 1-12 | 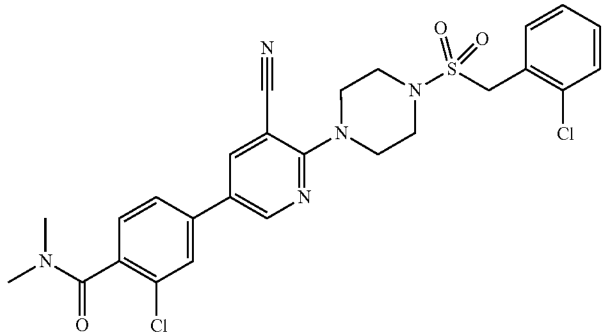 [SMILES: CN(C)C(=O)c1ccc(-c2cnc(N3CCN(S(=O)(=O)Cc4ccccc4Cl)CC3)c(C#N)c2)cc1Cl] | 2-chloro-4-(6-{4-[(2-chlorobenzyl)sulfonyl]piperazin-1-yl}-5-cyanopyridin-3-yl)-N,N-dimethylbenzamide | Calc'd 558.1, found 558.0 |

TABLE 1-continued

| Example | Structure | IUPAC Name | Exact Mass [M + H]+ |
|---|---|---|---|
| 1-13 | 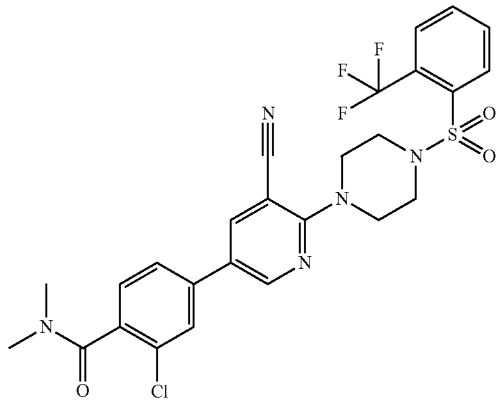 [SMILES: CN(C)C(=O)c1ccc(-c2cnc(N3CCN(S(=O)(=O)c4ccccc4C(F)(F)F)CC3)c(C#N)c2)cc1Cl] | 2-chloro-4-[5-cyano-6-(4-{[2-(trifluoromethyl)phenyl]sulfonyl}piperazin-1-yl)pyridin-3-yl]-N,N-dimethylbenzamide | Calc'd 578.1, found 578.1 |
| 1-14 | 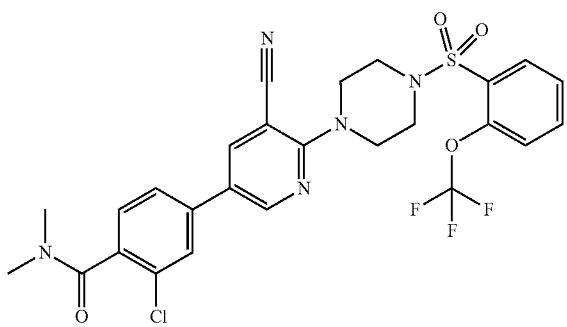 [SMILES: CN(C)C(=O)c1ccc(-c2cnc(N3CCN(S(=O)(=O)c4ccccc4OC(F)(F)F)CC3)c(C#N)c2)cc1Cl] | 2-chloro-4-[5-cyano-6-(4-{[2-(trifluoromethoxy)phenyl]sulfonyl}piperazin-1-yl)pyridin-3-yl]-N,N-dimethylbenzamide | Calc'd 594.1, found 594.0 |
| 1-15 | 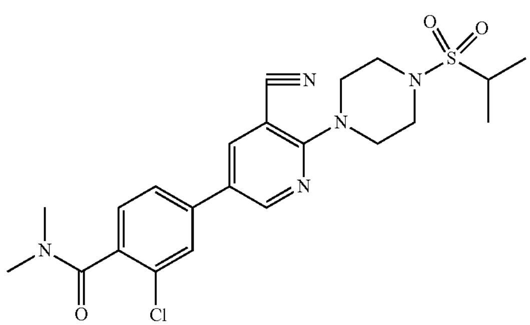 [SMILES: CC(C)S(=O)(=O)N1CCN(c2ncc(-c3ccc(C(=O)N(C)C)c(Cl)c3)cc2C#N)CC1] | 2-chloro-4-(5-cyano-6-{4-[(1-methylethyl)sulfonyl]piperazin-1-yl}pyridin-3-yl)-N,N-dimethylbenzamide | Calc'd 476.2, found 476.1 |
| 1-16 | 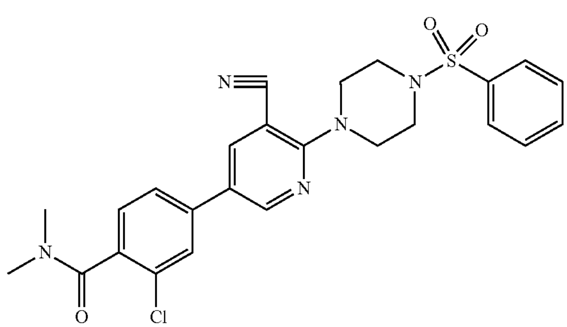 [SMILES: CN(C)C(=O)c1ccc(-c2cnc(N3CCN(S(=O)(=O)c4ccccc4)CC3)c(C#N)c2)cc1Cl] | 2-chloro-4-{5-cyano-6-[4-(phenylsulfonyl)piperazin-1-yl]pyridin-3-yl}-N,N-dimethylbenzamide | Calc'd 510.1, found 509.9 |

TABLE 1-continued

| Example | Structure | IUPAC Name | Exact Mass [M + H]+ |
|---|---|---|---|
| 1-17 | 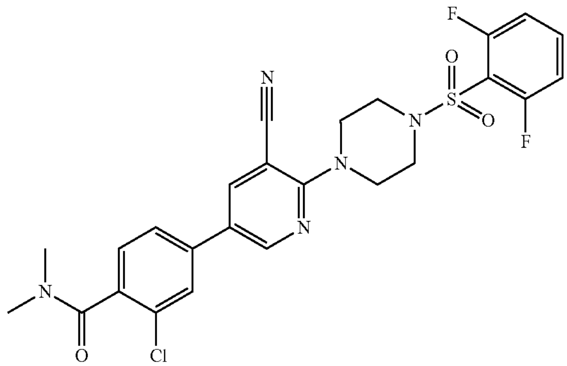 [SMILES: CN(C)C(=O)c1ccc(-c2cnc(N3CCN(S(=O)(=O)c4c(F)cccc4F)CC3)c(C#N)c2)cc1Cl] | 2-chloro-4-(5-cyano-6-{4-[(2,6-difluorophenyl)sulfonyl]piperazin-1-yl}pyridin-3-yl)-N,N-dimethylbenzamide | Calc'd 546.1, found 546.2 |
| 1-18 | 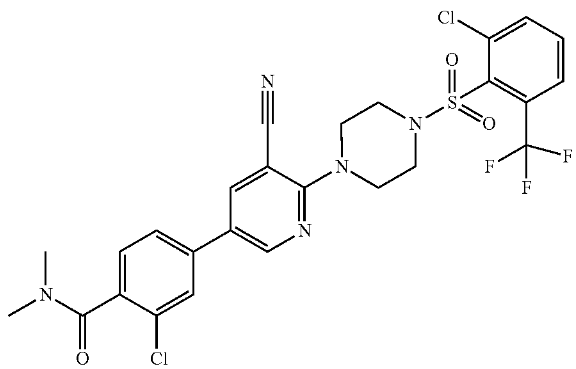 [SMILES: CN(C)C(=O)c1ccc(-c2cnc(N3CCN(S(=O)(=O)c4c(Cl)cccc4C(F)(F)F)CC3)c(C#N)c2)cc1Cl] | 2-chloro-4-[6-(4-{[2-chloro-6-(trifluoromethyl)phenyl]sulfonyl}piperazin-1-yl)-5-cyanopyridin-3-yl]-N,N-dimethylbenzamide | Calc'd 612.1, found 612.2 |

Example 2-1

2-chloro-4-(5-cyano-6-{4-[(2,6-difluorophenyl)carbonyl]piperazin-1-yl}pyridin-3-yl)-N,N-dimethylbenzamide

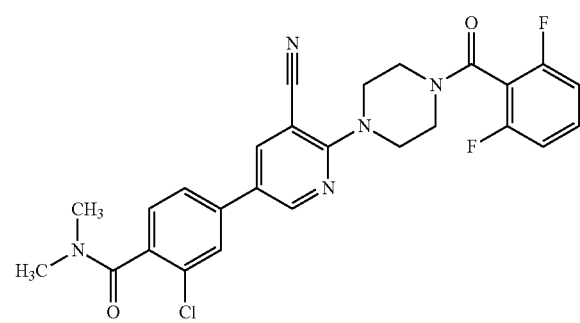 [SMILES: CN(C)C(=O)c1ccc(-c2cnc(N3CCN(C(=O)c4c(F)cccc4F)CC3)c(C#N)c2)cc1Cl]

To a solution of the bis hydrochloride salt of 2-chloro-4-[5-cyano-6-(piperazin-1-yl)pyridin-3-yl]-N,N-dimethylbenzamide (50 mg, 0.11 mmol, 1.0 eq) and N,N-diisopropylethylamine (39 μL, 0.23 mmol, 2.0 eq) in dichloromethane (3.0 mL) was added pyridine (46 μL, 0.56 mmol, 5.0 eq) followed by 2,6-difluorobenzoyl chloride (20 mg, 0.11 mmol, 1.0 eq) and the resulting reaction was stirred at 23° C. for 16 hours. The reaction mixture was concentrated and the residue was dissolved in DMSO and purified by reverse phase liquid chromatography (Gemini-NX C18, 5 μm, 30×100 mm column; 0-100% CH₃CN/H₂O gradient w/0.10% TFA present) to yield 2-chloro-4-(5-cyano-6-{4-[(2,6-difluorophenyl)carbonyl]piperazin-1-yl}pyridin-3-yl)-N,N-dimethylbenzamide (2-1). $^1$H NMR (400 MHz, CDCl₃): δ 8.58 (d, J=2.5 Hz, 1H); 8.00 (d, J=2.5 Hz, 1H); 7.55 (d, J=1.6 Hz, 1H); 7.47-7.39 (m, 2H); 7.07-6.90 (m, 3H); 4.05-4.00 (m, 2H); 3.94-3.89 (m, 2H); 3.82 (t, J=4.9 Hz, 2H); 3.55 (t, J=4.8 Hz, 2H); 3.20 (s, 3H); 2.96 (s, 3H). LRMS m/z (M+H) 510.1 found, 510.1 required.

Example 2-2

2-chloro-4-(5-cyano-6-{4-[(2R)-3,3,3-trifluoro-2-hydroxy-2-phenylpropanoyl]piperazin-1-yl}pyridin-3-yl)-N,N-dimethylbenzamide To a solution of the bis hydrochloride salt of 2-chloro-4-[5-cyano-6-(piperazin-1-yl)pyridin-3-yl]-N,N-dimethylbenzamide (1.7 g, 3.8 mmol, 1.0 eq) and N,N-diisopropylethylamine (2.7 mL, 15 mmol, 4.0 eq) in dichloromethane (30 mL) was added (2R)-3,3,3-trifluoro-2-hydroxy-2-phenylpropanoic acid (0.93 g, 4.2 mmol, 1.1 eq) followed by HBTU (2.2 g, 5.7 mmol, 1.5 eq) and the resulting reaction was stirred at 23° C. for 16 hours. The reaction mixture was purified by silica gel chromatography (0-100% ethyl acetate/hexanes) to yield 2-chloro-4-(5-cyano-6-{4-[(2R)-3,3,3-trifluoro-2-hydroxy-2-phenylpropanoyl]piperazin-1-yl}pyridin-3-yl)-N,N-dimethylbenzamide. $^1$H NMR (400 MHz, DMSO): δ 8.74 (d, J=2.5 Hz, 1H); 8.47 (d, J=2.5 Hz, 1H); 8.16 (s, 1H); 7.87 (d, J=1.7 Hz, 1H); 7.71 (dd, J=8.0, 1.8 Hz, 1H); 7.53-7.35 (m, 5H); 3.75-3.41 (m, 8H); 2.98 (s, 3H); 2.76 (s, 3H). LRMS m/z (M+H) 572.3 found, 572.2 required.

The following examples were prepared according to the procedure in examples 2-1 and 2-2 using the appropriate acid or acid chloride.

TABLE 2

| Example | Structure | IUPAC Name | Exact Mass [M + H]+ |
|---|---|---|---|
| 2-3 | 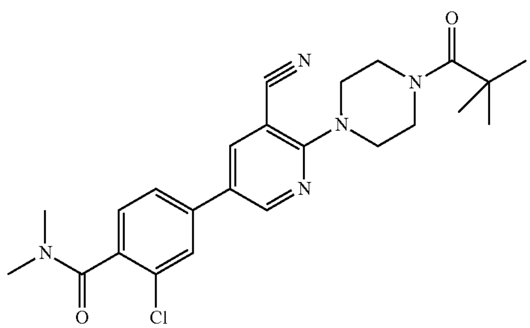 [SMILES: CN(C)C(=O)c1ccc(-c2cnc(N3CCN(C(=O)C(C)(C)C)CC3)c(C#N)c2)cc1Cl] | 2-chloro-4-{5-cyano-6-[4-(2,2-dimethylpropanoyl)piperazin-1-yl]pyridin-3-yl}-N,N-dimethylbenzamide | Calc'd 454.2, found 454.2 |
| 2-4 | 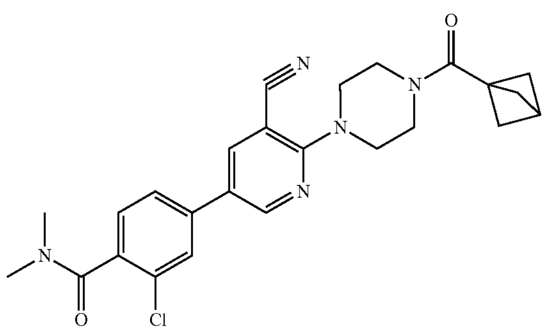 [SMILES: CN(C)C(=O)c1ccc(-c2cnc(N3CCN(C(=O)C45CC(C4)C5)CC3)c(C#N)c2)cc1Cl] | 4-{6-[4-(bicyclo[1.1.1]pent-1-ylcarbonyl)piperazin-1-yl]-5-cyanopyridin-3-yl}-2-chloro-N,N-dimethylbenzamide | Calc'd 464.2, found 463.94 |
| 2-5 | 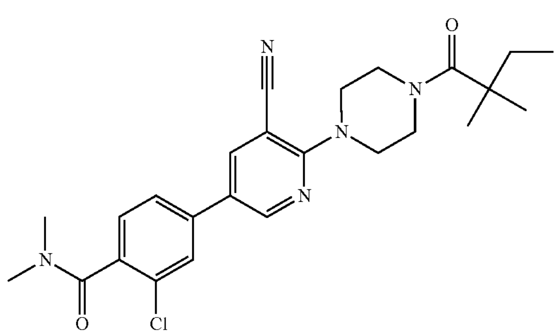 [SMILES: CCC(C)(C)C(=O)N1CCN(c2ncc(-c3ccc(C(=O)N(C)C)c(Cl)c3)cc2C#N)CC1] | 2-chloro-4-{5-cyano-6-[4-(2,2-dimethylbutanoyl)piperazin-1-yl]pyridin-3-yl}-N,N-dimethylbenzamide | Calc'd 468.2, found 468.2 |

TABLE 2-continued

| Example | Structure | IUPAC Name | Exact Mass [M + H]+ |
|---|---|---|---|
| 2-6 | 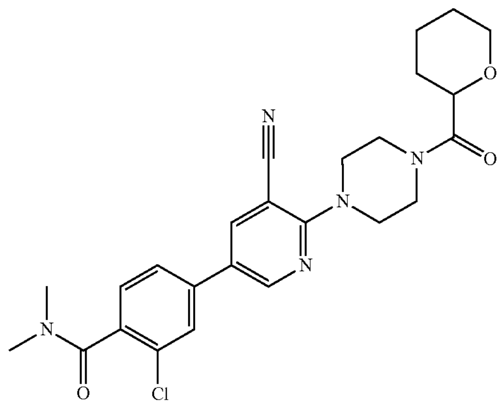 [SMILES: CN(C)C(=O)c1ccc(-c2cnc(N3CCN(C(=O)C4CCCCO4)CC3)c(C#N)c2)cc1Cl] | 2-chloro-4-{5-cyano-6-[4-(tetrahydro-2H-pyran-2-ylcarbonyl)piperazin-1-yl]pyridin-3-yl}-N,N-dimethylbenzamide | Calc'd 482.2, found 482.1 |
| 2-7 | 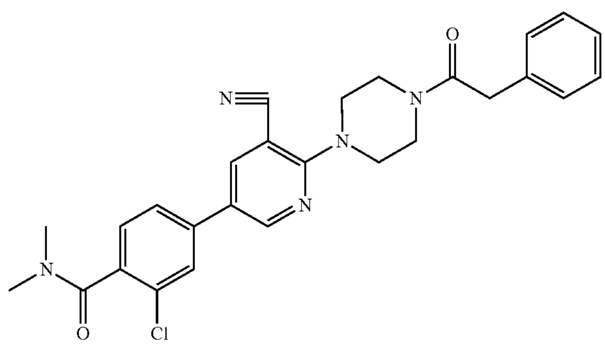 [SMILES: CN(C)C(=O)c1ccc(-c2cnc(N3CCN(C(=O)Cc4ccccc4)CC3)c(C#N)c2)cc1Cl] | 2-chloro-4-{5-cyano-6-[4-(phenylacetyl)piperazin-1-yl]pyridin-3-yl}-N,N-dimethylbenzamide | Calc'd 488.2, found 487.9 |
| 2-8 | 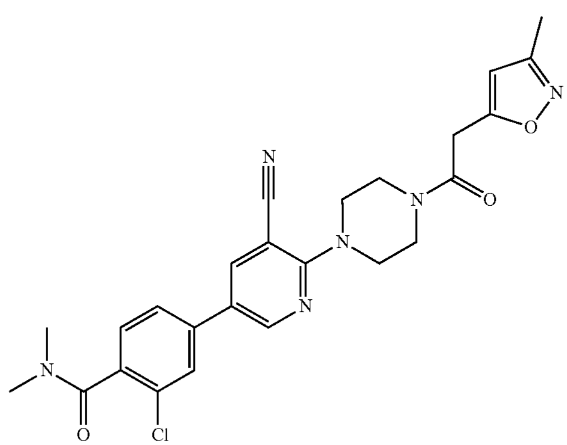 [SMILES: Cc1cc(CC(=O)N2CCN(c3ncc(-c4ccc(C(=O)N(C)C)c(Cl)c4)cc3C#N)CC2)on1] | 2-chloro-4-(5-cyano-6-{4-[(3-methylisoxazol-5-yl)acetyl]piperazin-1-yl}pyridin-3-yl)-N,N-dimethylbenzamide | Calc'd 493.2, found 493.1 |
| 2-9 | 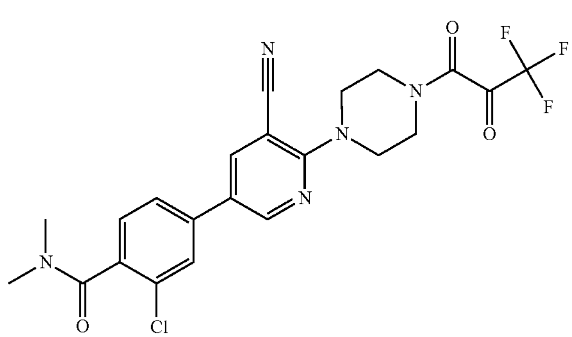 [SMILES: CN(C)C(=O)c1ccc(-c2cnc(N3CCN(C(=O)C(=O)C(F)(F)F)CC3)c(C#N)c2)cc1Cl] | 2-chloro-4-{5-cyano-6-[4-(3,3,3-trifluoro-2-oxopropanoyl)piperazin-1-yl]pyridin-3-yl}-N,N-dimethylbenzamide | Calc'd 494.1, found 494.2 |

TABLE 2-continued

| Example | Structure | IUPAC Name | Exact Mass [M + H]+ |
|---|---|---|---|
| 2-10 | 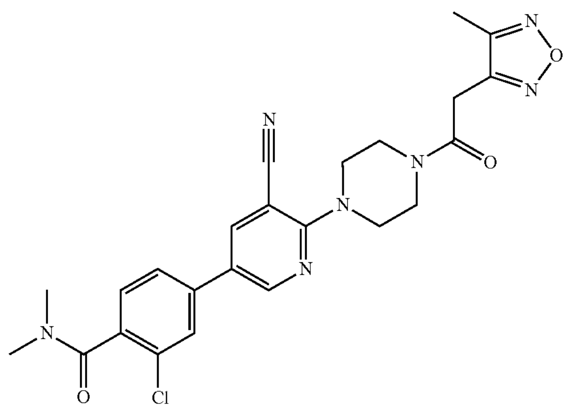 [SMILES: Cc1nonc1CC(=O)N1CCN(c2ncc(-c3ccc(C(=O)N(C)C)c(Cl)c3)cc2C#N)CC1] | 2-chloro-4-(5-cyano-6-{4-[(4-methyl-1,2,5-oxadiazol-3-yl)acetyl]piperazin-1-yl}pyridin-3-yl)-N,N-dimethylbenzamide | Calc'd 494.2, found 494.1 |
| 2-11 | 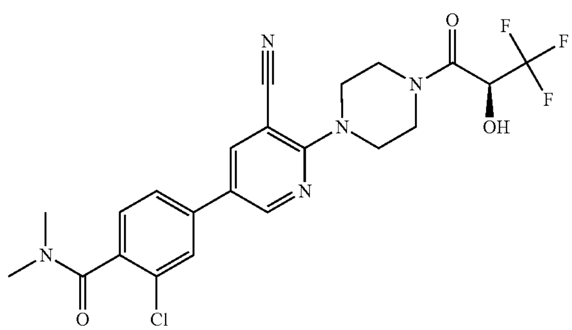 [SMILES: CN(C)C(=O)c1ccc(-c2cnc(N3CCN(C(=O)[C@H](O)C(F)(F)F)CC3)c(C#N)c2)cc1Cl] | 2-chloro-4-(5-cyano-6-{4-[(2S)-3,3,3-trifluoro-2-hydroxypropanoyl]piperazin-1-yl}pyridin-3-yl)-N,N-dimethylbenzamide | Calc'd 496.1, found 496.1 |
| 2-12 | 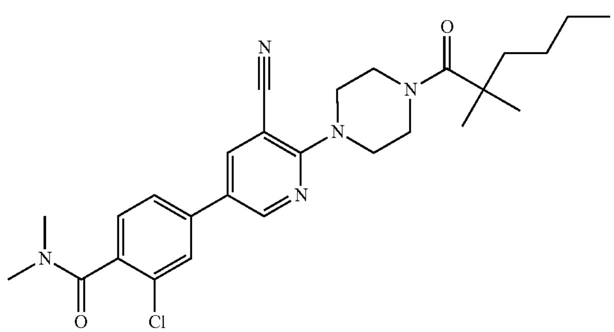 [SMILES: CCCCC(C)(C)C(=O)N1CCN(c2ncc(-c3ccc(C(=O)N(C)C)c(Cl)c3)cc2C#N)CC1] | 2-chloro-4-{5-cyano-6-[4-(2,2-dimethylhexanoyl)piperazin-1-yl]pyridin-3-yl}-N,N-dimethylbenzamide | Calc'd 496.2, found 496.2 |
| 2-13 | 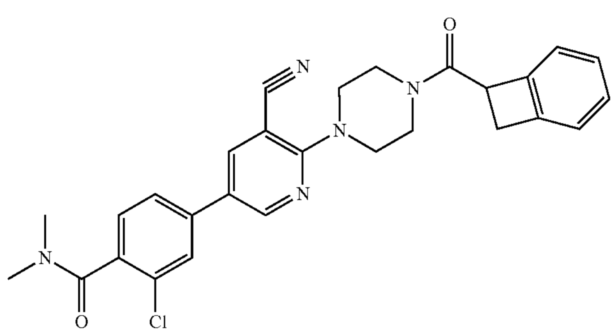 [SMILES: CN(C)C(=O)c1ccc(-c2cnc(N3CCN(C(=O)C4Cc5ccccc54)CC3)c(C#N)c2)cc1Cl] | 4-{6-[4-(bicyclo[4.2.0]octa-1,3,5-trien-7-ylcarbonyl)piperazin-1-yl]-5-cyanopyridin-3-yl}-2-chloro-N,N-dimethylbenzamide | Calc'd 500.2, found 499.9 |

TABLE 2-continued

| Example | Structure | IUPAC Name | Exact Mass [M + H]+ |
|---|---|---|---|
| 2-14 | 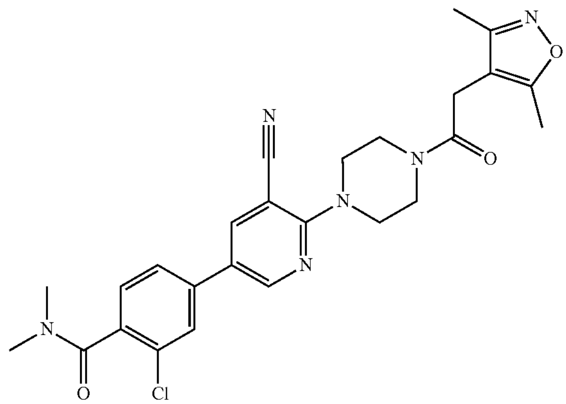 [SMILES: Cc1noc(C)c1CC(=O)N1CCN(c2ncc(-c3ccc(C(=O)N(C)C)c(Cl)c3)cc2C#N)CC1] | 2-chloro-4-(5-cyano-6-{4-[(3,5-dimethylisoxazol-4-yl)acetyl]piperazin-1-yl}pyridin-3-yl)-N,N-dimethylbenzamide | Calc'd 507.2, found 507.1 |
| 2-15 | 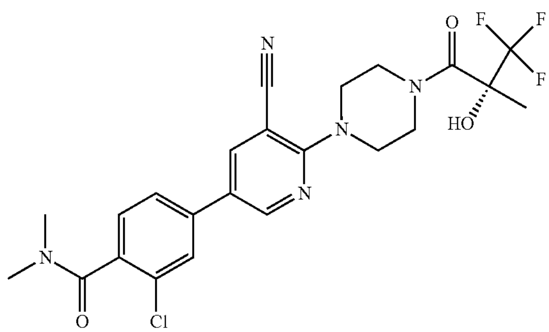 [SMILES: CN(C)C(=O)c1ccc(-c2cnc(N3CCN(C(=O)[C@@](C)(O)C(F)(F)F)CC3)c(C#N)c2)cc1Cl] | 2-chloro-4-(5-cyano-6-{4-[(2R)-3,3,3-trifluoro-2-hydroxy-2-methylpropanoyl]piperazin-1-yl}pyridin-3-yl)-N,N-dimethylbenzamide | Calc'd 510.2, found 510.2 |
| 2-16 | 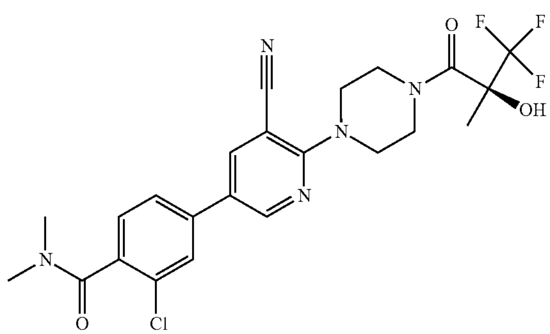 [SMILES: CN(C)C(=O)c1ccc(-c2cnc(N3CCN(C(=O)[C@](C)(O)C(F)(F)F)CC3)c(C#N)c2)cc1Cl] | 2-chloro-4-(5-cyano-6-{4-[(2S)-3,3,3-trifluoro-2-hydroxy-2-methylpropanoyl]piperazin-1-yl}pyridin-3-yl)-N,N-dimethylbenzamide | Calc'd 510.2, found 510.2 |
| 2-17 | 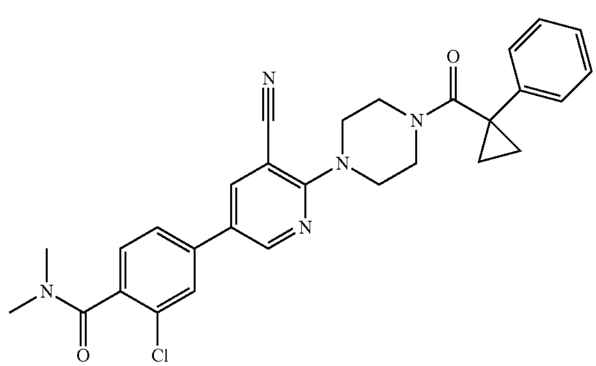 [SMILES: CN(C)C(=O)c1ccc(-c2cnc(N3CCN(C(=O)C4(c5ccccc5)CC4)CC3)c(C#N)c2)cc1Cl] | 2-chloro-4-(5-cyano-6-{4-[(1-phenylcyclopropyl)carbonyl]piperazin-1-yl}pyridin-3-yl)-N,N-dimethylbenzamide | Calc'd 514.2, found 514.2 |

TABLE 2-continued

| Example | Structure | IUPAC Name | Exact Mass [M + H]+ |
|---|---|---|---|
| 2-18 | 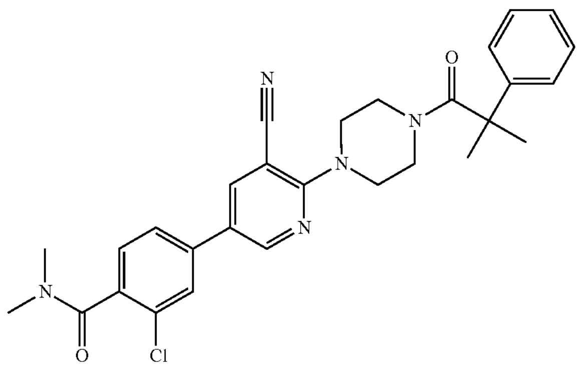 [SMILES: CN(C)C(=O)c1ccc(-c2cnc(N3CCN(C(=O)C(C)(C)c4ccccc4)CC3)c(C#N)c2)cc1Cl] | 2-chloro-4-{5-cyano-6-[4-(2-methyl-2-phenylpropanoyl)piperazin-1-yl]pyridin-3-yl}-N,N-dimethylbenzamide | Calc'd 516.2, found 516.2 |
| 2-19 | 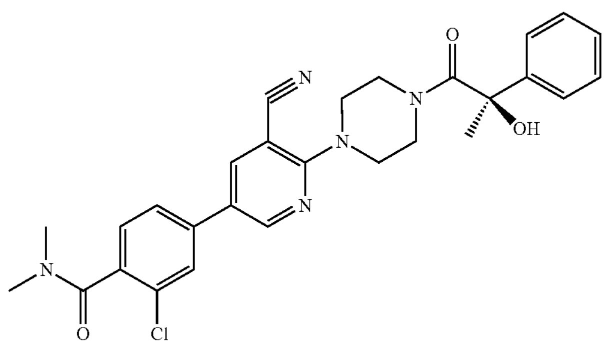 [SMILES: CN(C)C(=O)c1ccc(-c2cnc(N3CCN(C(=O)[C@](C)(O)c4ccccc4)CC3)c(C#N)c2)cc1Cl] | 2-chloro-4-(5-cyano-6-{4-[(2R)-2-hydroxy-2-phenylpropanoyl]piperazin-1-yl}pyridin-3-yl)-N,N-dimethylbenzamide | Calc'd 518.2, found 518.4 |
| 2-20 | 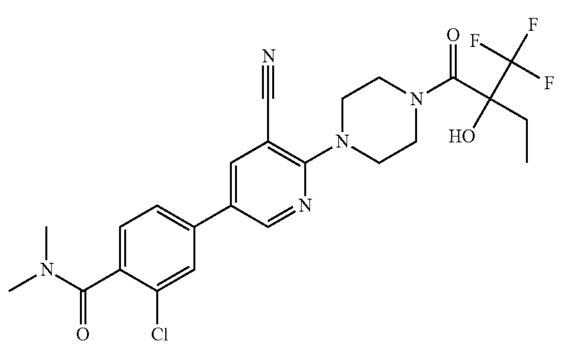 [SMILES: CCC(O)(C(=O)N1CCN(c2ncc(-c3ccc(C(=O)N(C)C)c(Cl)c3)cc2C#N)CC1)C(F)(F)F] | 2-chloro-4-(5-cyano-6-{4-[2-hydroxy-2-(trifluoromethyl)butanoyl]piperazin-1-yl}pyridin-3-yl)-N,N-dimethylbenzamide | Calc'd 524.2, found 524.2 |
| 2-21 | 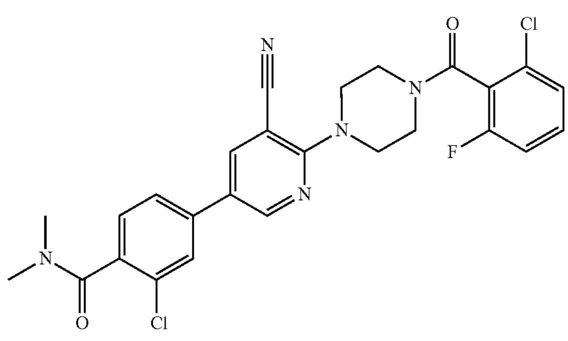 [SMILES: CN(C)C(=O)c1ccc(-c2cnc(N3CCN(C(=O)c4c(F)cccc4Cl)CC3)c(C#N)c2)cc1Cl] | 2-chloro-4-(6-{4-[(2-chloro-6-fluorophenyl)carbonyl]piperazin-1-yl}-5-cyanopyridin-3-yl)-N,N-dimethylbenzamide | Calc'd 526.1, found 526.0 |

TABLE 2-continued

| Example | Structure | IUPAC Name | Exact Mass [M + H]+ |
|---|---|---|---|
| 2-22 | 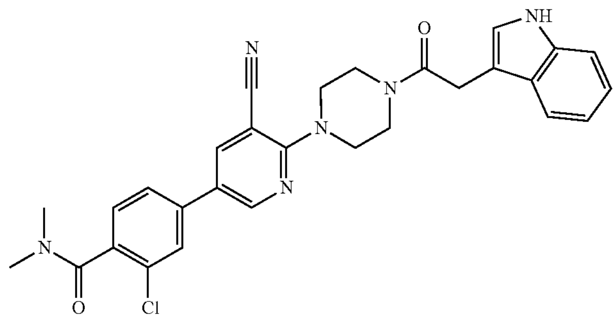 [SMILES: CN(C)C(=O)c1ccc(-c2cnc(N3CCN(C(=O)Cc4c[nH]c5ccccc45)CC3)c(C#N)c2)cc1Cl] | 2-chloro-4-{5-cyano-6-[4-(1H-indol-3-ylacetyl)piperazin-1-yl]pyridin-3-yl}-N,N-dimethylbenzamide | Calc'd 527.2, found 527.1 |
| 2-23 | 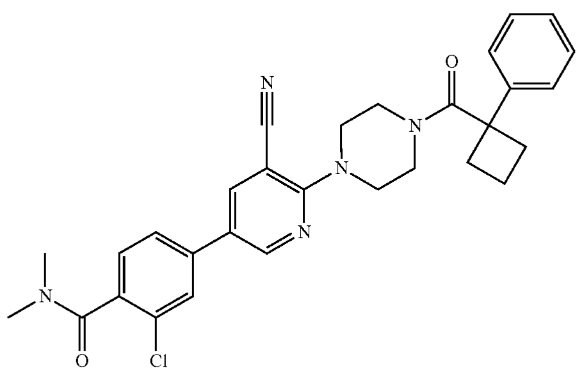 [SMILES: CN(C)C(=O)c1ccc(-c2cnc(N3CCN(C(=O)C4(c5ccccc5)CCC4)CC3)c(C#N)c2)cc1Cl] | 2-chloro-4-(5-cyano-6-{4-[(1-phenylcyclobutyl)carbonyl]piperazin-1-yl}pyridin-3-yl)-N,N-dimethylbenzamide | Calc'd 528.2, found 528.2 |
| 2-24 | 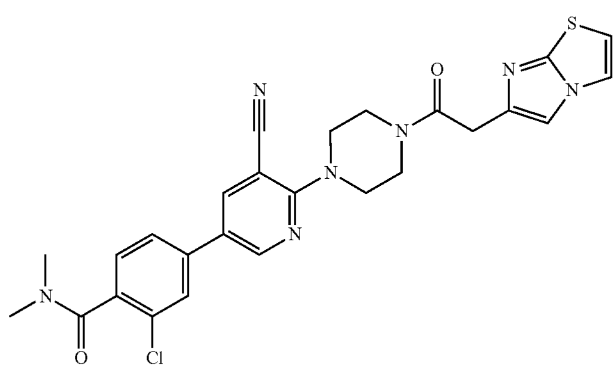 [SMILES: CN(C)C(=O)c1ccc(-c2cnc(N3CCN(C(=O)Cc4cn5ccsc5n4)CC3)c(C#N)c2)cc1Cl] | 2-chloro-4-{5-cyano-6-[4-(imidazo[2,1-b][1,3]thiazol-6-ylacetyl)piperazin-1-yl]pyridin-3-yl}-N,N-dimethylbenzamide | Calc'd 534.1, found 534.1 |
| 2-25 | 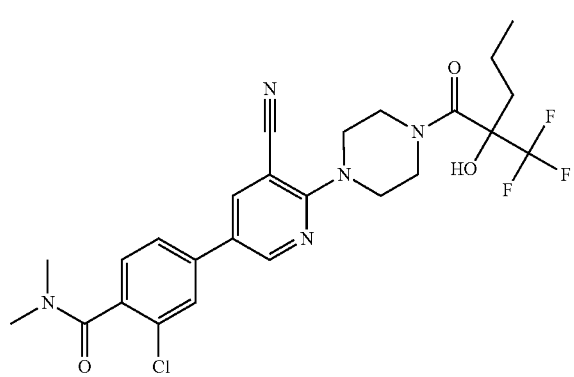 [SMILES: CCCC(O)(C(=O)N1CCN(c2ncc(-c3ccc(C(=O)N(C)C)c(Cl)c3)cc2C#N)CC1)C(F)(F)F] | 2-chloro-4-(5-cyano-6-{4-[2-hydroxy-2-(trifluoromethyl)pentanoyl]piperazin-1-yl}pyridin-3-yl)-N,N-dimethylbenzamide | Calc'd 538.2, found 538.2 |

TABLE 2-continued

| Example | Structure | IUPAC Name | Exact Mass [M + H]+ |
|---|---|---|---|
| 2-26 | 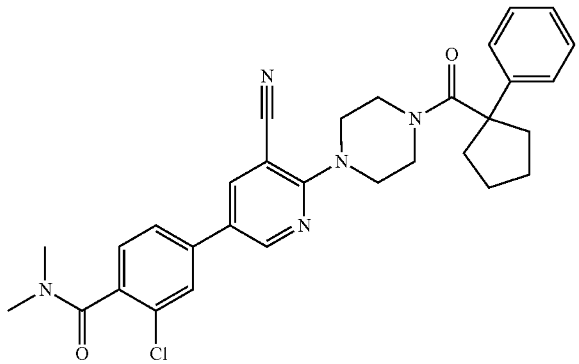 [SMILES: CN(C)C(=O)c1ccc(-c2cnc(N3CCN(C(=O)C4(c5ccccc5)CCCC4)CC3)c(C#N)c2)cc1Cl] | 2-chloro-4-(5-cyano-6-{4-[(1-phenylcyclopentyl)carbonyl]piperazin-1-yl}pyridin-3-yl)-N,N-dimethylbenzamide | Calc'd 542.2, found 542.2 |
| 2-28 | 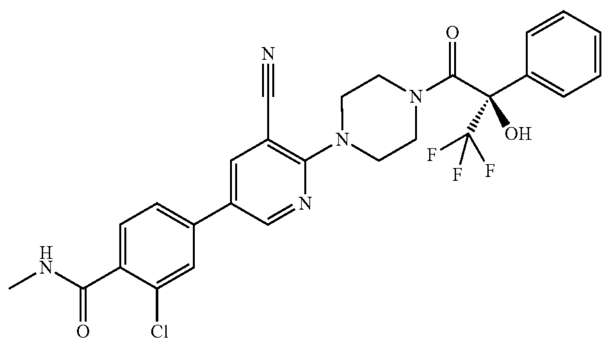 [SMILES: CNC(=O)c1ccc(-c2cnc(N3CCN(C(=O)[C@](O)(c4ccccc4)C(F)(F)F)CC3)c(C#N)c2)cc1Cl] | 2-chloro-4-(5-cyano-6-{4-[(2R)-3,3,3-trifluoro-2-hydroxy-2-phenylpropanoyl]piperazin-1-yl}pyridin-3-yl)-N-methylbenzamide | Calc'd 558.2, found 558.3 |
| 2-29 | 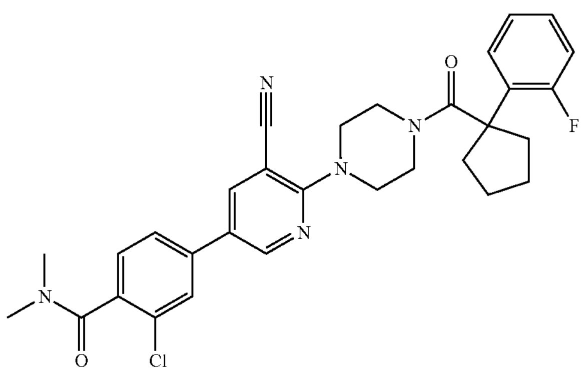 [SMILES: CN(C)C(=O)c1ccc(-c2cnc(N3CCN(C(=O)C4(c5ccccc5F)CCCC4)CC3)c(C#N)c2)cc1Cl] | 2-chloro-4-[5-cyano-6-(4-{[1-(2-fluorophenyl)cyclopentyl]carbonyl}piperazin-1-yl)pyridin-3-yl]-N,N-dimethylbenzamide | Calc'd 560.2, found 560.2 |
| 2-30 | 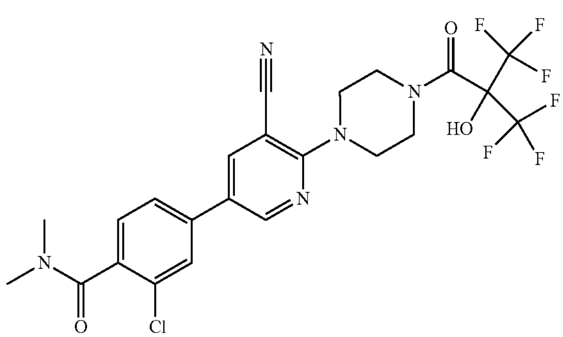 [SMILES: CN(C)C(=O)c1ccc(-c2cnc(N3CCN(C(=O)C(O)(C(F)(F)F)C(F)(F)F)CC3)c(C#N)c2)cc1Cl] | 2-chloro-4-(5-cyano-6-{4-[3,3,3-trifluoro-2-hydroxy-2-(trifluoromethyl)propanoyl]piperazin-1-yl}pyridin-3-yl)-N,N-dimethylbenzamide | Calc'd 564.1, found 564.1 |

TABLE 2-continued

| Example | Structure | IUPAC Name | Exact Mass [M + H]+ |
|---|---|---|---|
| 2-31 | 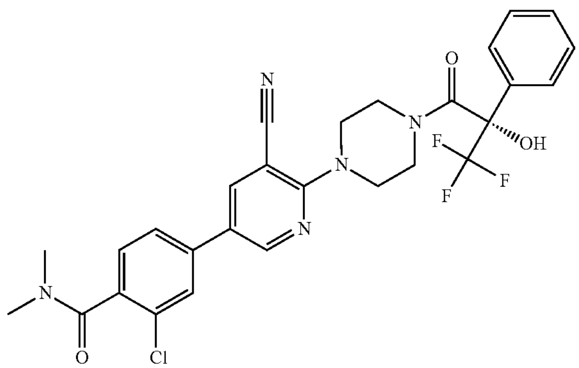 [SMILES: CN(C)C(=O)c1ccc(-c2cnc(N3CCN(C(=O)[C@@](O)(c4ccccc4)C(F)(F)F)CC3)c(C#N)c2)cc1Cl] | 2-chloro-4-(5-cyano-6-{4-[(2S)-3,3,3-trifluoro-2-hydroxy-2-phenylpropanoyl]piperazin-1-yl}pyridin-3-yl)-N,N-dimethylbenzamide | Calc'd 572.2, found 572.2 |
| 2-32 | 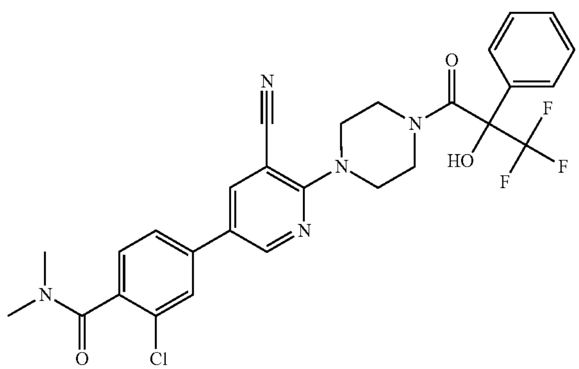 [SMILES: CN(C)C(=O)c1ccc(-c2cnc(N3CCN(C(=O)C(O)(c4ccccc4)C(F)(F)F)CC3)c(C#N)c2)cc1Cl] | 2-chloro-4-{5-cyano-6-[4-(3,3,3-trifluoro-2-hydroxy-2-phenylpropanoyl)piperazin-1-yl]pyridin-3-yl}-N,N-dimethylbenzamide | Calc'd 572.2, found 572.2 |
| 2-33 | 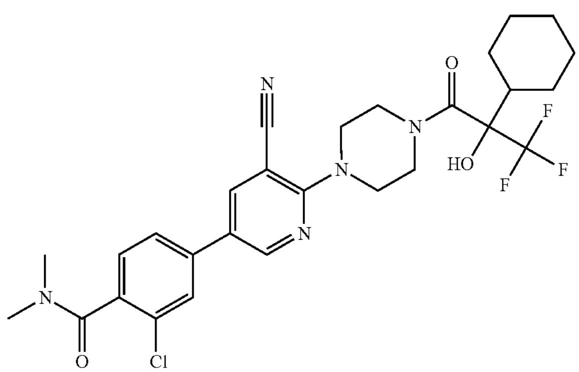 [SMILES: CN(C)C(=O)c1ccc(-c2cnc(N3CCN(C(=O)C(O)(C4CCCCC4)C(F)(F)F)CC3)c(C#N)c2)cc1Cl] | 2-chloro-4-{5-cyano-6-[4-(2-cyclohexyl-3,3,3-trifluoro-2-hydroxypropanoyl)piperazin-1-yl]pyridin-3-yl}-N,N-dimethylbenzamide | Calc'd 578.2, found 578.2 |
| 2-34 | 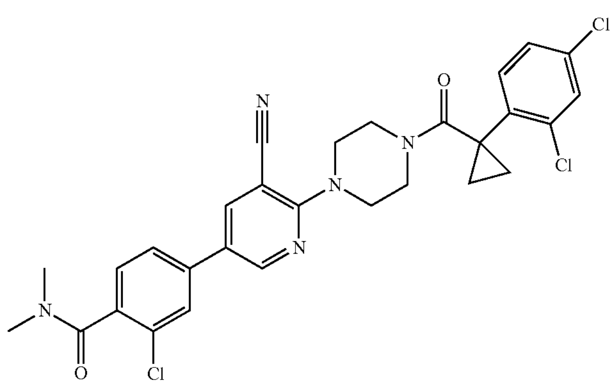 [SMILES: CN(C)C(=O)c1ccc(-c2cnc(N3CCN(C(=O)C4(c5ccc(Cl)cc5Cl)CC4)CC3)c(C#N)c2)cc1Cl] | 2-chloro-4-[5-cyano-6-(4-{[1-(2,4-dichlorophenyl)cyclopropyl]carbonyl}piperazin-1-yl)pyridin-3-yl]-N,N-dimethylbenzamide | Calc'd 582.1, found 582.1 |

TABLE 2-continued

| Example | Structure | IUPAC Name | Exact Mass [M + H]+ |
|---|---|---|---|
| 2-35 | 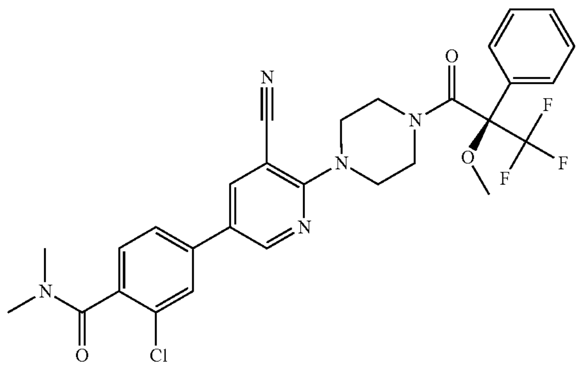 [SMILES: CO[C@@](C(=O)N1CCN(c2ncc(-c3ccc(C(=O)N(C)C)c(Cl)c3)cc2C#N)CC1)(c1ccccc1)C(F)(F)F] | 2-chloro-4-(5-cyano-6-{4-[(2R)-3,3,3-trifluoro-2-methoxy-2-phenylpropanoyl]piperazin-1-yl}pyridin-3-yl)-N,N-dimethylbenzamide | Calc'd 586.2, found 586.2 |
| 2-36 | 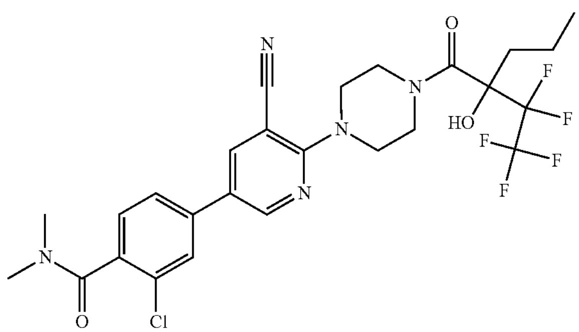 [SMILES: CCCC(O)(C(=O)N1CCN(c2ncc(-c3ccc(C(=O)N(C)C)c(Cl)c3)cc2C#N)CC1)C(F)(F)C(F)(F)F] | 2-chloro-4-(5-cyano-6-{4-[2-hydroxy-2-(pentafluoroethyl)pentanoyl]piperazin-1-yl}pyridin-3-yl)-N,N-dimethylbenzamide | Calc'd 588.2, found 588.2 |
| 2-37 | 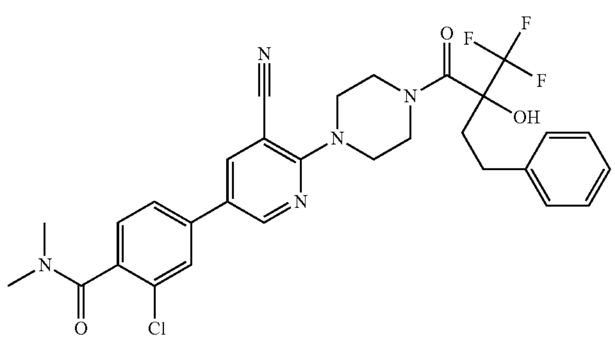 [SMILES: CN(C)C(=O)c1ccc(-c2cnc(N3CCN(C(=O)C(O)(CCc4ccccc4)C(F)(F)F)CC3)c(C#N)c2)cc1Cl] | 2-chloro-4-(5-cyano-6-{4-[2-hydroxy-4-phenyl-2-(trifluoromethyl)butanoyl]piperazin-1-yl}pyridin-3-yl)-N,N-dimethylbenzamide | Calc'd 600.2, found 600.2 |
| 2-38 | 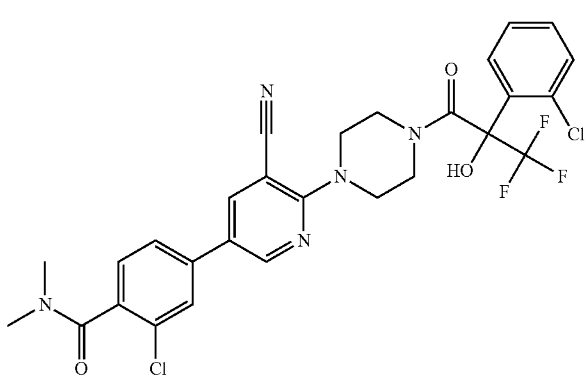 [SMILES: CN(C)C(=O)c1ccc(-c2cnc(N3CCN(C(=O)C(O)(c4ccccc4Cl)C(F)(F)F)CC3)c(C#N)c2)cc1Cl] | 2-chloro-4-(6-{4-[2-(2-chlorophenyl)-3,3,3-trifluoro-2-hydroxypropanoyl]piperazin-1-yl}-5-cyanopyridin-3-yl)-N,N-dimethylbenzamide | Calc'd 606.1, found 606.1 |

Example 3-1

2,6-dichlorobenzyl 4-{5-[3-chloro-4-(dimethylcarbamoyl)phenyl]-3-cyanopyridin-2-yl}piperazine-1-carboxylate

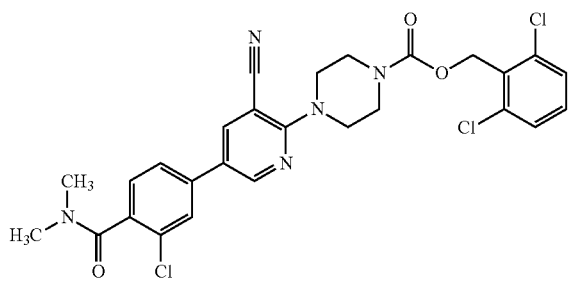 [SMILES: CN(C)C(=O)c1ccc(-c2cnc(N3CCN(C(=O)OCc4c(Cl)cccc4Cl)CC3)c(C#N)c2)cc1Cl]

To a solution of the bis hydrochloride salt of 2-chloro-4-[5-cyano-6-(piperazin-1-yl)pyridin-3-yl]-N,N-dimethylbenzamide (5.3 g, 12 mmol, 1.0 eq) and N,N-diisopropylethylamine (10 mL, 57 mmol, 4.8 eq) in dichloromethane (100 mL) at 0° C. was added a solution of 20% phosgene in toluene (7.7 g, 16 mmol, 1.3 eq) and the reaction was stirred to 23° C. over 16 hours. The reaction solution was washed with saturated aqueous sodium bicarbonate solution (100 mL), dried over sodium sulfate and concentrated to yield 4-{5-[3-chloro-4-(dimethylcarbamoyl)phenyl]-3-cyanopyridin-2-yl}piperazine-1-carbonyl chloride. LRMS m/z (M+H) 432.2 found, 432.1 required.

To a solution of 2,6-dichlorobenzyl alcohol (22 mg, 0.13 mmol, 1.0 eq) in tetrahydrofuran (1.5 mL) was added sodium hydride (25 mg, 0.99 mmol, 7.8 eq) and the resulting reaction mixture was stirred at 23° C. After 10 minutes a solution of 4-{5-[3-chloro-4-(dimethylcarbamoyl)phenyl]-3-cyanopyridin-2-yl}piperazine-1-carbonyl chloride (55 mg, 0.13 mmol, 1.0 eq) in dichloromethane (1.5 mL) was added and the reaction mixture was stirred at 23° C. for 16 hours. The excess sodium hydride was quenched with the dropwise addition of water (0.15 mL), the mixture was concentrated and the residue was dissolved in DMSO and purified by reverse phase liquid chromatography (Gemini-NX $C_{18}$, 5 μm, 30×100 mm column; 0-100% $CH_3CN/H_2O$ gradient w/0.10% TFA present) to yield 2,6-dichlorobenzyl 4-{5-[3-chloro-4-(dimethylcarbamoyl)phenyl]-3-cyanopyridin-2-yl}piperazine-1-carboxylate. $^1$H NMR (400 MHz, $CD_3OD$): δ 8.69 (d, J=2.5 Hz, 1H); 8.29 (d, J=2.5 Hz, 1H); 7.79 (d, J=1.7 Hz, 1H); 7.67 (dd, J=8.0, 1.7 Hz, 1H); 7.48-7.33 (m, 4H); 5.44 (s, 2H); 3.85-3.58 (m, 8H); 3.13 (s, 3H); 2.92 (s, 3H). LRMS m/z (M+H) 572.2 found, 572.1 required.

The following examples were prepared according to the procedure in example 3-1 using the appropriate alcohol.

TABLE 3

| Example | Structure | IUPAC Name | Exact Mass [M + H]+ |
|---|---|---|---|
| 3-2 | 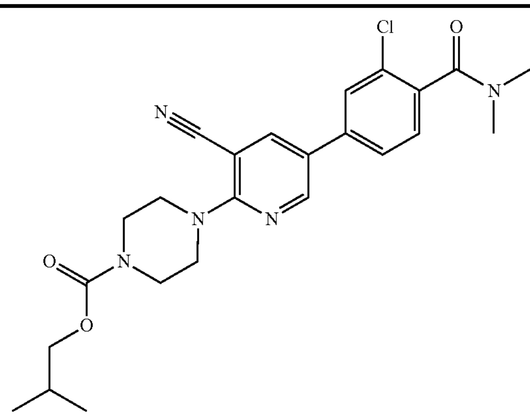 | 2-methylpropyl 4-{5-[3-chloro-4-(dimethylcarbamoyl)phenyl]-3-cyanopyridin-2-yl}piperazine-1-carboxylate | Calc'd 470.2, found 470.1 |
| 3-3 | 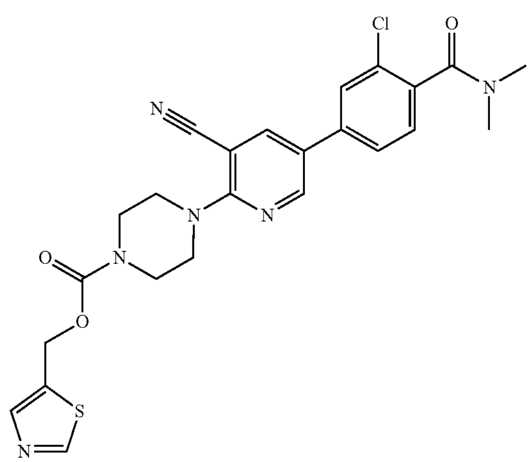 [SMILES: CN(C)C(=O)c1ccc(-c2cnc(N3CCN(C(=O)OCc4cncs4)CC3)c(C#N)c2)cc1Cl] | 1,3-thiazol-5-ylmethyl 4-{5-[3-chloro-4-(dimethylcarbamoyl)phenyl]-3-cyanopyridin-2-yl}piperazine-1-carboxylate | Calc'd 511.1, found 511.1 |

TABLE 3-continued

| Example | Structure | IUPAC Name | Exact Mass [M + H]+ |
|---------|-----------|------------|---------------------|
| 3-4 | 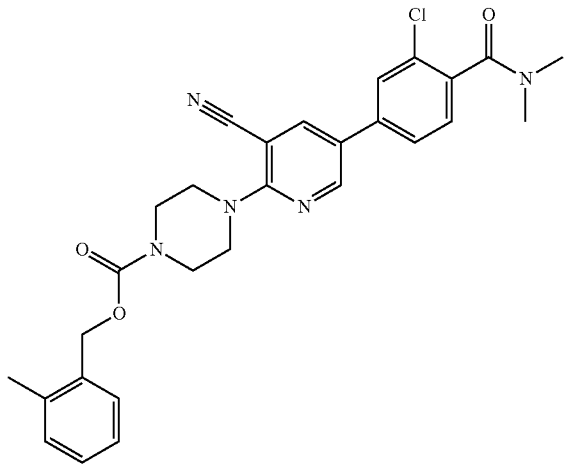 | 2-methylbenzyl 4-{5-[3-chloro-4-(dimethylcarbamoyl)phenyl]-3-cyanopyridin-2-yl}piperazine-1-carboxylate | Calc'd 518.2, found 518.1 |
| 3-5 | 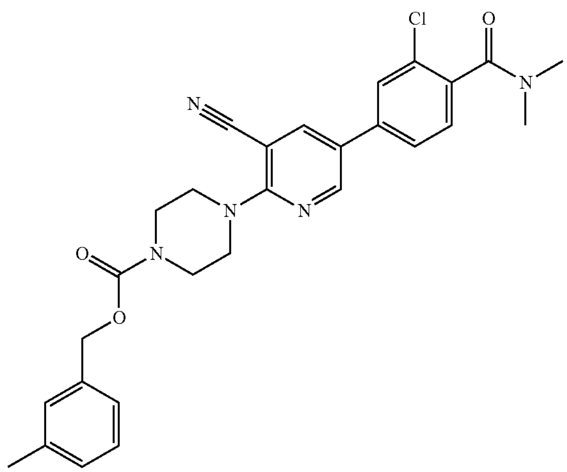 | 3-methylbenzyl 4-{5-[3-chloro-4-(dimethylcarbamoyl)phenyl]-3-cyanopyridin-2-yl}piperazine-1-carboxylate | Calc'd 518.2, found 518.1 |
| 3-6 | 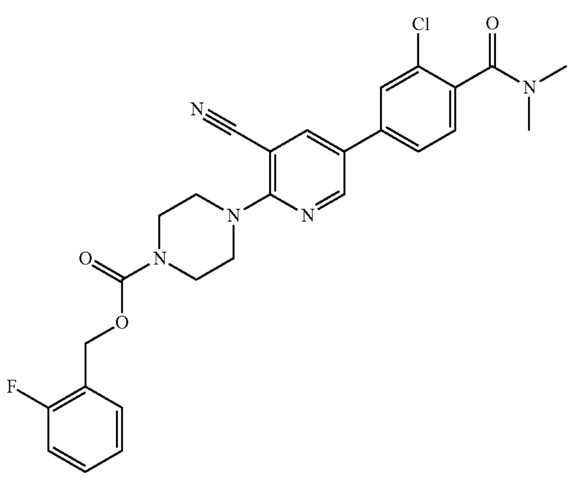 [SMILES: CN(C)C(=O)c1ccc(-c2cnc(N3CCN(C(=O)OCc4ccccc4F)CC3)c(C#N)c2)cc1Cl] | 2-fluorobenzyl 4-{5-[3-chloro-4-(dimethylcarbamoyl)phenyl]-3-cyanopyridin-2-yl}piperazine-1-carboxylate | Calc'd 522.2, found 522.1 |

TABLE 3-continued

| Example | Structure | IUPAC Name | Exact Mass [M + H]+ |
|---|---|---|---|
| 3-7 | 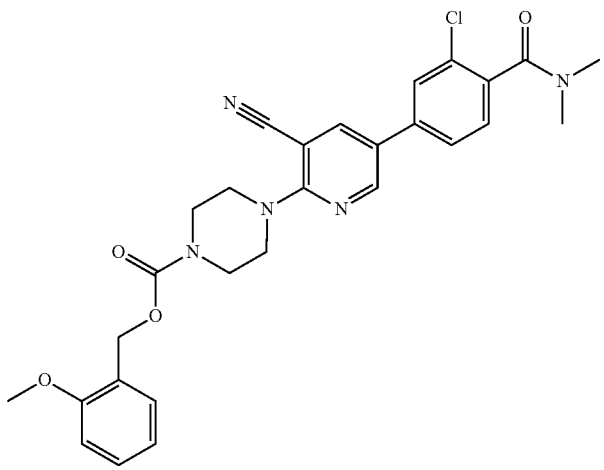 | 2-methoxybenzyl 4-{5-[3-chloro-4-(dimethylcarbamoyl)phenyl]-3-cyanopyridin-2-yl}piperazine-1-carboxylate | Calc'd 534.2, found 534.1 |
| 3-8 | 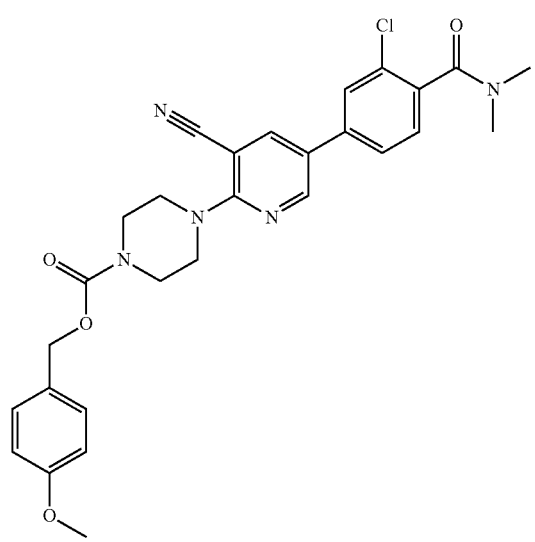 [SMILES: COc1ccc(COC(=O)N2CCN(c3ncc(-c4ccc(C(=O)N(C)C)c(Cl)c4)cc3C#N)CC2)cc1] | 4-methoxybenzyl 4-{5-[3-chloro-4-(dimethylcarbamoyl)phenyl]-3-cyanopyridin-2-yl}piperazine-1-carboxylate | Calc'd 534.2, found 534.1 |
| 3-9 | 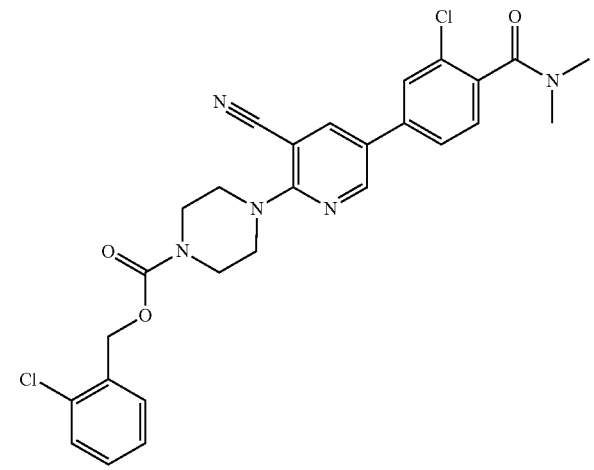 [SMILES: CN(C)C(=O)c1ccc(-c2cnc(N3CCN(C(=O)OCc4ccccc4Cl)CC3)c(C#N)c2)cc1Cl] | 2-chlorobenzyl 4-{5-[3-chloro-4-(dimethylcarbamoyl)phenyl]-3-cyanopyridin-2-yl}piperazine-1-carboxylate | Calc'd 538.1, found 538.0 |

TABLE 3-continued

| Example | Structure | IUPAC Name | Exact Mass [M + H]+ |
|---|---|---|---|
| 3-10 | 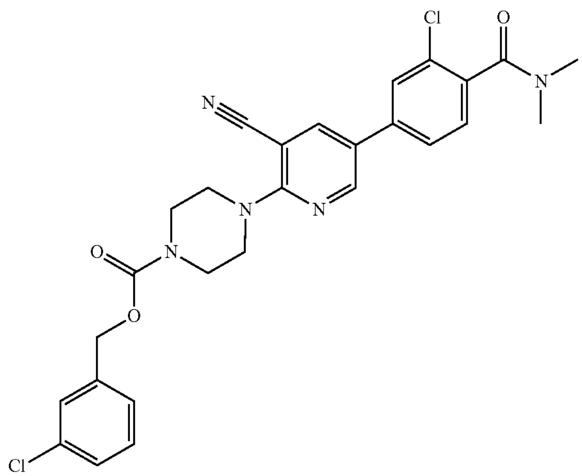 [SMILES: CN(C)C(=O)c1ccc(-c2cnc(N3CCN(C(=O)OCc4cccc(Cl)c4)CC3)c(C#N)c2)cc1Cl] | 3-chlorobenzyl 4-{5-[3-chloro-4-(dimethylcarbamoyl)phenyl]-3-cyanopyridin-2-yl}piperazine-1-carboxylate | Calc'd 538.1, found 538.1 |
| 3-11 | 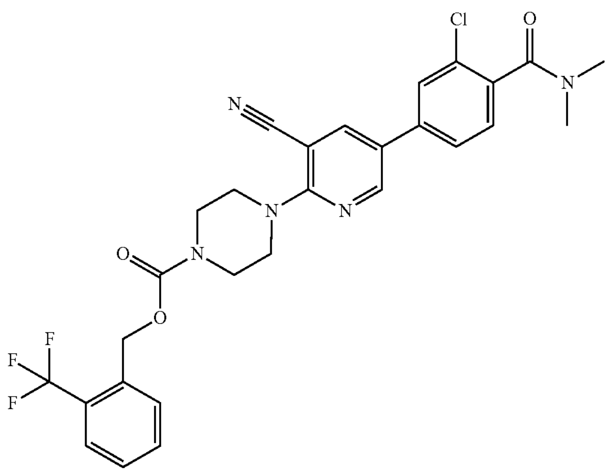 [SMILES: CN(C)C(=O)c1ccc(-c2cnc(N3CCN(C(=O)OCc4ccccc4C(F)(F)F)CC3)c(C#N)c2)cc1Cl] | 2-(trifluoromethyl)benzyl 4-{5-[3-chloro-4-(dimethylcarbamoyl)phenyl]-3-cyanopyridin-2-yl}piperazine-1-carboxylate | Calc'd 572.2, found 572.1 |
| 3-12 | 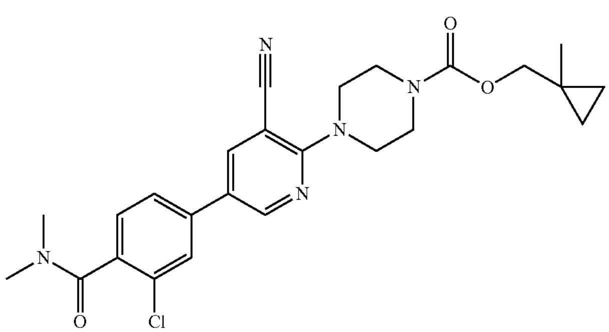 [SMILES: CN(C)C(=O)c1ccc(-c2cnc(N3CCN(C(=O)OCC4(C)CC4)CC3)c(C#N)c2)cc1Cl] | (1-methylcyclopropyl)methyl 4-{5-[3-chloro-4-(dimethylcarbamoyl)phenyl]-3-cyanopyridin-2-yl}piperazine-1-carboxylate | Calc'd 482.2, found 482.4 |
| 3-13 | 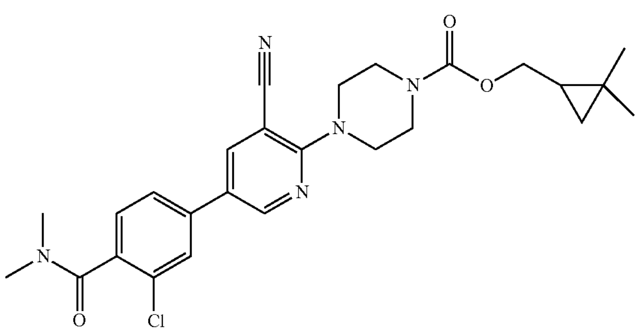 | (2,2-dimethylcyclopropyl)methyl 4-{5-[3-chloro-4-(dimethylcarbamoyl)phenyl]-3-cyanopyridin-2-yl}piperazine-1-carboxylate | Calc'd 496.2, found 496.4 |

TABLE 3-continued

| Example | Structure | IUPAC Name | Exact Mass [M + H]+ |
|---|---|---|---|
| 3-14 | 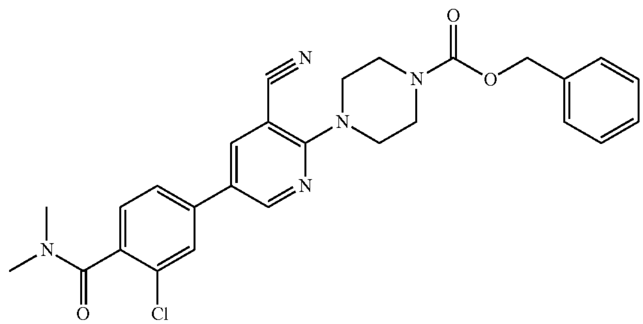 [SMILES: CN(C)C(=O)c1ccc(-c2cnc(N3CCN(C(=O)OCc4ccccc4)CC3)c(C#N)c2)cc1Cl] | benzyl 4-{5-[3-chloro-4-(dimethylcarbamoyl)phenyl]-3-cyanopyridin-2-yl}piperazine-1-carboxylate | Calc'd 504.2, found 504.2 |

Example 4-1

3,3'-dichloro-4'-{4-[(2,6-difluorophenyl)carbonyl]piperazin-1-yl}-N,N-dimethylbiphenyl-4-carboxamide

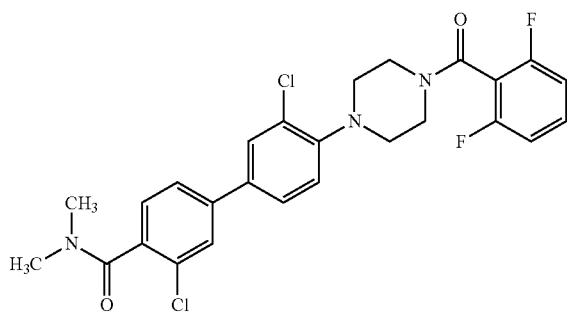 [SMILES: CN(C)C(=O)c1ccc(-c2ccc(N3CCN(C(=O)c4c(F)cccc4F)CC3)c(Cl)c2)cc1Cl]

To a solution of 4-bromo-2-chlorobenzoic acid (4.2 g, 18 mmol, 1.0 eq) and N,N-diisopropylethyl amine (13 mL, 72 mmol, 4.0 eq) in dichloromethane (30 mL) was added dimethylamine hydrochloride (2.2 g, 27 mmol, 1.5 eq) followed by HBTU (10 g, 27 mmol, 1.5 eq) and the resulting reaction was stirred at 23° C. for 16 hours. The reaction mixture was purified by silica gel chromatography (0-100% ethyl acetate/hexanes) to yield 4-bromo-2-chloro-N,N-dimethylbenzamide. $^1$H NMR (400 MHz, CDCl$_3$): δ 7.57 (d, J=1.9 Hz, 1H); 7.45 (dd, J=8.1, 1.9 Hz, 1H); 7.17 (d, J=8.1 Hz, 1H); 3.12 (s, 3H); 2.85 (s, 3H). LRMS m/z (M+H) 262.0 found, 262.0 required.

A mixture of tert-butyl 4-[4-(4,4,5,5-tetramethyl-1,3,2-dioxaborolan-2-yl)phenyl]piperazine-1-carboxylate (2.5 g, 6.6 mmol, 1.0 eq), 4-bromo-2-chloro-N,N-dimethylbenzamide (1.7 g, 6.6 mmol, 1.0 eq) and 2 M aqueous sodium carbonate solution (6.6 mL, 13.1 mmol, 2.0 eq) in acetonitrile (75 mL) was degassed with nitrogen for 15 minutes prior to the addition of bis(triphenylphosphine) palladium (II) chloride (0.24 g, 0.33 mmol, 0.050 eq). The resulting reaction mixture was heated at reflux under nitrogen for 16 hours. The reaction mixture was concentrated and the residue was partitioned between dichloromethane (200 mL) and water (100 ml). The organic layer was separated, dried over sodium sulfate and concentrated. The residue was purified by silica gel chromatography (0-100% ethyl acetate/hexanes) to yield tert-butyl 4-[3'-chloro-4'-(dimethylcarbamoyl)biphenyl-4-yl]piperazine-1-carboxylate. $^1$H NMR (400 MHz, DMSO): δ 7.69 (d, J=1.8 Hz, 1H); 7.58 (d, J=8.7 Hz, 3H); 7.32 (d, J=8.0 Hz, 1H); 6.99 (d, J=8.5 Hz, 2H); 3.45-3.39 (m, 4H); 3.17-3.11 (m, 4H); 2.97 (s, 3H); 2.77 (s, 3H); 1.38 (s, 9H). LRMS m/z (M+H) 444.3 found, 444.2 required.

To a solution of tert-butyl 4-[3'-chloro-4'-(dimethylcarbamoyl)biphenyl-4-yl]piperazine-1-carboxylate (1.9 g, 4.3 mmol, 1.0 eq) in methanol (35 mL) was added 4 M hydrochloric acid in dioxanes (20 mL, 80 mmol, 19 eq) and the resulting reaction was stirred at 23° C. for 16 hours. The reaction mixture was concentrated under reduced pressure to give the bis HCl salt of 3-chloro-N,N-dimethyl-4'-(piperazin-1-yl)biphenyl-4-carboxamide. $^1$H NMR (400 MHz, CD$_3$OD): δ 7.68 (d, J=1.7 Hz, 1H); 7.64-7.58 (m, 3H); 7.36 (d, J=8.0 Hz, 1H); 7.12 (d, J=8.6 Hz, 2H); 3.49-3.46 (m, 4H); 3.39-3.35 (m, 4H); 3.12 (s, 3H); 2.91 (s, 3H). LRMS m/z (M+H) 344.3 found, 344.1 required.

To a solution of the bis hydrochloride salt of 3-chloro-N,N-dimethyl-4'-(piperazin-1-yl)biphenyl-4-carboxamide (50 mg, 0.12 mmol, 1.0 eq) and N,N-diisopropylethylamine (69 μL, 0.40 mmol, 3.3 eq) in dichloromethane (3.0 mL) was added 2,6-difluorobenzoyl chloride (25 mg, 0.14 mmol, 1.2 eq) and the resulting reaction was stirred at 23° C. for 16 hours. The reaction mixture was concentrated and the residue was dissolved in DMSO and purified by reverse phase liquid chromatography (Gemini-NX C18, 5 μm, 30×100 mm column; 0-100% CH$_3$CN/H$_2$O gradient w/0.10% TFA present) to yield 3-chloro-4'-{4-[(2,6-difluorophenyl)carbonyl]piperazin-1-yl}-N,N-dimethylbiphenyl-4-carboxamide. $^1$H NMR (400 MHz, CDCl$_3$): δ 7.58 (d, J=1.6 Hz, 1H); 7.54-7.45 (m, 3H); 7.44-7.32 (m, 2H); 7.07-6.94 (m, 4H); 4.07-4.01 (m, 2H); 3.58-3.52 (m, 2H); 3.41-3.35 (m, 2H); 3.30-3.24 (m, 2H); 3.18 (s, 3H); 2.94 (s, 3H). LRMS m/z (M+H) 484.1 found, 484.2 required.

To a solution of 3-chloro-4'-{4-[(2,6-difluorophenyl)carbonyl]piperazin-1-yl}-N,N-dimethylbiphenyl-4-carboxamide (8 mg, 0.02 mmol, 1 eq) in ethanol (1 ml) was added N-chlorosuccinimide (4 mg, 0.03 mmol, 2 eq) and the reaction mixture was heated at 60° C. for 1 hour. The reaction mixture was concentrated and the residue was dissolved in DMSO and purified by reverse phase liquid chromatography (Gemini-NX C18, 5 μm, 30×100 mm column; 0-100% CH$_3$CN/H$_2$O gradient w/0.10% TFA present) to yield 3,3'-dichloro-4'-{4-[(2,6-difluorophenyl)carbonyl]piperazin-1-yl}-N,N-dimethylbiphenyl-4-carboxamide [$^1$H NMR (400 MHz, CD$_3$OD): δ 7.73-7.71 (m, 2H); 7.64 (dd, J=8.0, 1.7 Hz, 1H); 7.59 (dd, J=8.4, 2.3 Hz, 1H); 7.57-7.50 (m, 1H); 7.40 (d, J=8.0 Hz, 1H); 7.25 (d, J=8.4 Hz, 1H); 7.16-7.08 (m, 2H); 4.03-3.98 (m, 2H); 3.58-3.53 (m, 2H); 3.23-3.17 (m, 2H); 3.13 (s, 3H); 3.13-3.07 (m, 2H); 2.92 (s, 3H). LRMS m/z (M+H) 518.2 found, 518.1 required] and 3,3',5'-trichloro-4'-{4-[(2,6-difluorophenyl)carbonyl]piperazin-1-yl}-N,N-dimethylbiphenyl-4-carboxamide [$^1$H NMR (400 MHz, CD$_3$OD): δ 7.76 (d, J=1.7 Hz, 1H); 7.70 (s, 2H); 7.65 (dd, J=8.0, 1.7 Hz, 1H); 7.56-7.49 (m, 1H); 7.42 (d, J=8.0 Hz, 1H); 7.12 (t, J=8.0 Hz, 2H); 4.02-3.97 (m, 2H); 3.57-3.52 (m, 2H); 3.39-3.34 (m, 2H); 3.29-3.25 (m, 2H); 3.13 (s, 3H); 2.92 (s, 3H). LRMS m/z (M+H) 552.1 found, 552.1 required.]

Example 4-3 tert-butyl 5-[3,3'-dichloro-4'-(dimethylcarbamoyl)biphenyl-4-yl]-2,5-diazabicyclo[2.2.2]octane-2-carboxylate

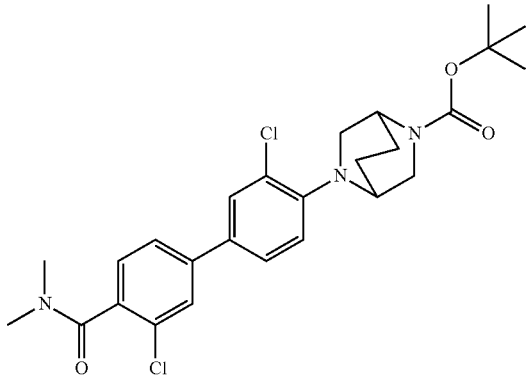 [SMILES: CN(C)C(=O)c1ccc(-c2ccc(N3CC4CCC3CN4C(=O)OC(C)(C)C)c(Cl)c2)cc1Cl]

A mixture of tert-butyl 2,5-diazabicyclo[2.2.2]octane-2-carboxylate (1.29 g, 6.08 mmol), p-bromoiodobenzene (1.89 g, 6.68 mmol), CuI (1.16 g, 6.08 mmol), Cesium Carbonate (7.9 g, 24.3 mmol), and 2-(2-methyl-1-oxopropyl)cyclohexanone (2.03 mL, 12.15 mmol) was stirred in DMF (20.3 mL) at 100° C. overnight. The mixture was then extracted with EtOAc and water, the organic layer was dried over magnesium sulfate, and the solvents were removed in vacuo to give crude product which was purified by silica gel chromatography (0-30% EtOAc/hexanes) and reverse phase chromatography (20-95% ACN/water with 0.1% TFA) to yield an inseparable mixture of tert-butyl 5-(4-bromophenyl)-2,5-diazabicyclo[2.2.2]octane-2-carboxylate [LRMS m/z (M+H) 367.2 found, 367.1 required.]
with tert-butyl 5-(4-iodophenyl)-2,5-diazabicyclo[2.2.2]octane-2-carboxylate [LRMS m/z (M+H) 415.2 found, 415.1 required.](283 mg).

A mixture of products from step 1 (tert-butyl 5-(4-bromophenyl)-2,5-diazabicyclo[2.2.2]octane-2-carboxylate and tert-butyl 5-(4-iodophenyl)-2,5-diazabicyclo[2.2.2]octane-2-carboxylate) (283 mg), 3-chloro-4-dimethylcarbamoylphenylboronic acid (210 mg, 0.925 mmol), sodium carbonate (2M, 0.96 mL, 1.9 mmol) in ACN (3.8 mL) was degassed by bubbling N$_2$ for 15 min. Bis(triphenylphosphine)palladium(II) chloride (21.6 mg, 0.03 mmol) was added and the mixture was stirred at 70° C. overnight. The mixture was then extracted with EtOAc and 5% aq. KHSO$_4$, the organic layer was dried over magnesium sulfate, and the solvents were removed in vacuo to give crude product which was purified by silica gel chromatography (0-100% EtOAc/hexanes) and reverse phase chromatography (25-95% ACN/water with 0.1% TFA) to yield tert-butyl 5-(3'-chloro-4'-(dimethylcarbamoyl)-[1,1'-biphenyl]-4-yl)-2,5-diazabicyclo[2.2.2]octane-2-carboxylate (44 mg). LRMS m/z (M+H) 470.3 found, 470.2 required.

NCS (10.4 mg, 0.078 mmol) was added to a solution of tert-butyl 5-(3'-chloro-4'-(dimethylcarbamoyl)-[1,1'-biphenyl]-4-yl)-2,5-diazabicyclo[2.2.2]octane-2-carboxylate (35 mg, 0.074 mmol) in EtOH (1.5 mL) and the mixture was heated to 75° C. for 3 h. The solvent was then removed in vacuo and crude material was purified by reverse phase liquid chromatography (Gemini-NX C18, 5 μm, 30×100 mm column; 25-95% CH$_3$CN/H$_2$O gradient w/0.10% TFA present) to yield tert-butyl 5-[3,3'-dichloro-4'-(dimethylcarbamoyl)biphenyl-4-yl]-2,5-diazabicyclo[2.2.2]octane-2-carboxylate (25 mg). HRMS m/z (M+H) 504.1803 found, 504.1815 required.

The following examples were prepared according to the procedure in example 4-1 using the appropriate intermediates and acid chlorides or appropriate carboxylic acids or sulfonyl chloride using the coupling procedure described in examples 1-1 and 2-2.

TABLE 4

| Example | Structure | IUPAC Name | Exact Mass [M + H]+ |
|---|---|---|---|
| 4-2 | 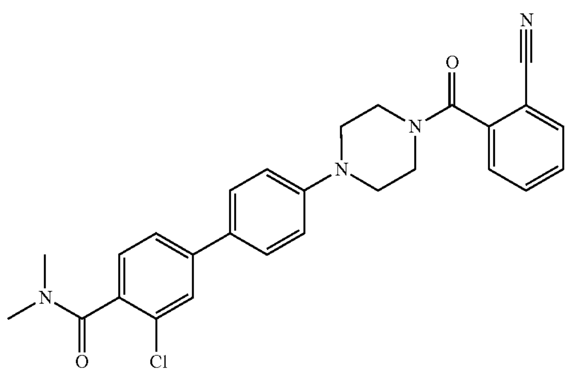 [SMILES: CN(C)C(=O)c1ccc(-c2ccc(N3CCN(C(=O)c4ccccc4C#N)CC3)cc2)cc1Cl] | 3-chloro-4'-{4-[(2-cyanophenyl)carbonyl]piperazin-1-yl}-N,N-dimethylbiphenyl-4-carboxamide | Calc'd 473.2, found 473.3 |

TABLE 4-continued

| Example | Structure | IUPAC Name | Exact Mass [M + H]+ |
|---|---|---|---|
| 4-4 | 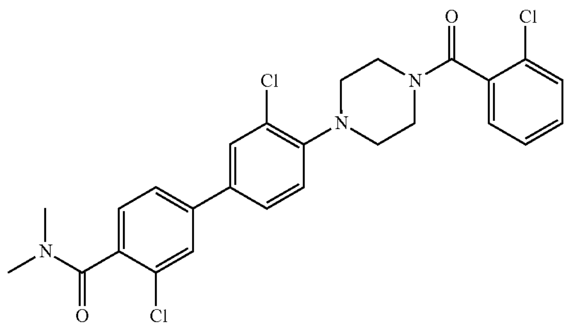 [SMILES: CN(C)C(=O)c1ccc(-c2ccc(N3CCN(C(=O)c4ccccc4Cl)CC3)c(Cl)c2)cc1Cl] | 3,3'-dichloro-4'-{4-[(2-chlorophenyl)carbonyl]piperazin-1-yl}-N,N-dimethylbiphenyl-4-carboxamide | Calc'd 516.1, found 516.2 |
| 4-5 | 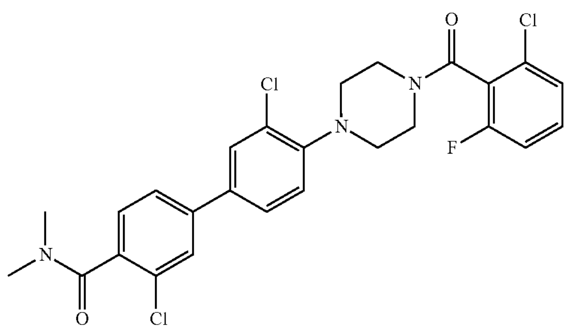 [SMILES: CN(C)C(=O)c1ccc(-c2ccc(N3CCN(C(=O)c4c(F)cccc4Cl)CC3)c(Cl)c2)cc1Cl] | 3,3'-dichloro-4'-{4-[(2-chloro-6-fluorophenyl)carbonyl]piperazin-1-yl}-N,N-dimethylbiphenyl-4-carboxamide | Calc'd 534.1, found 534.2 |
| 4-6 | 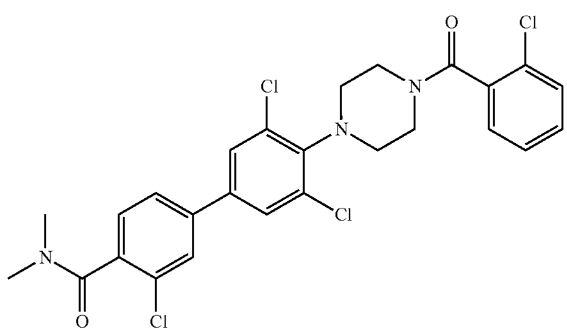 [SMILES: CN(C)C(=O)c1ccc(-c2cc(Cl)c(N3CCN(C(=O)c4ccccc4Cl)CC3)c(Cl)c2)cc1Cl] | 3,3',5'-trichloro-4'-{4-[(2-chlorophenyl)carbonyl]piperazin-1-yl}-N,N-dimethylbiphenyl-4-carboxamide | Calc'd 550.1, found 550.2 |
| 4-7 | 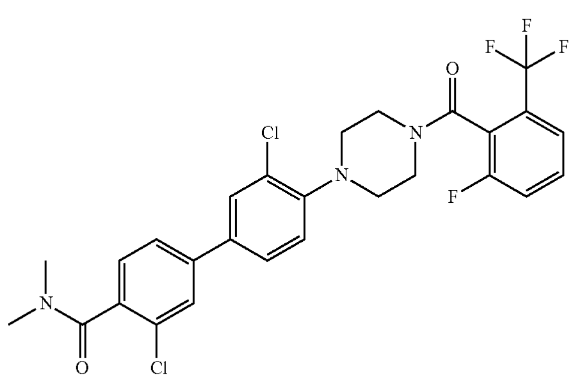 [SMILES: CN(C)C(=O)c1ccc(-c2ccc(N3CCN(C(=O)c4c(F)cccc4C(F)(F)F)CC3)c(Cl)c2)cc1Cl] | 3,3'-dichloro-4'-(4-{[2-fluoro-6-(trifluoromethyl)phenyl]carbonyl}piperazin-1-yl)-N,N-dimethylbiphenyl-4-carboxamide | Calc'd 568.1, found 568.2 |

TABLE 4-continued

| Example | Structure | IUPAC Name | Exact Mass [M + H]+ |
|---|---|---|---|
| 4-8 | 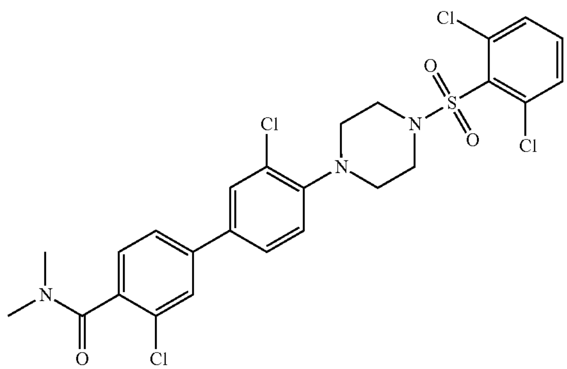 [SMILES: CN(C)C(=O)c1ccc(-c2ccc(N3CCN(S(=O)(=O)c4c(Cl)cccc4Cl)CC3)c(Cl)c2)cc1Cl] | 3,3'-dichloro-4'-{4-[(2,6-dichlorophenyl)sulfonyl]piperazin-1-yl}-N,N-dimethylbiphenyl-4-carboxamide | Calc'd 586.0, found 585.9 |
| 4-9 | 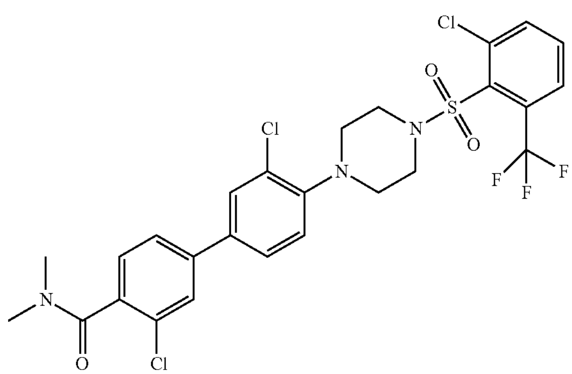 [SMILES: CN(C)C(=O)c1ccc(-c2ccc(N3CCN(S(=O)(=O)c4c(Cl)cccc4C(F)(F)F)CC3)c(Cl)c2)cc1Cl] | 3,3'-dichloro-4'-(4-{[2-chloro-6-(trifluoromethyl)phenyl]sulfonyl}piperazin-1-yl)-N,N-dimethylbiphenyl-4-carboxamide | Calc'd 620.1, found 620.0 |
| 4-10 | 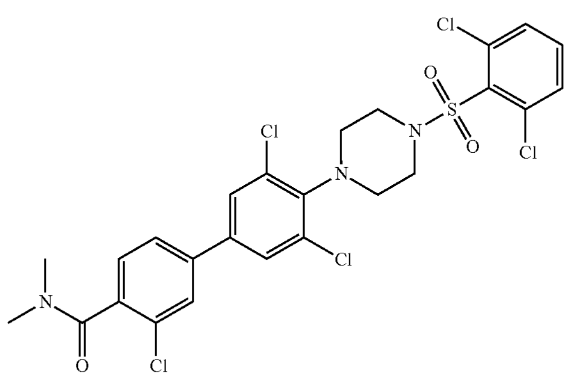 [SMILES: CN(C)C(=O)c1ccc(-c2cc(Cl)c(N3CCN(S(=O)(=O)c4c(Cl)cccc4Cl)CC3)c(Cl)c2)cc1Cl] | 3,3',5'-trichloro-4'-{4-[(2,6-dichlorophenyl)sulfonyl]piperazin-1-yl}-N,N-dimethylbiphenyl-4-carboxamide | Calc'd 620.0, found 620.1 |
| 4-11 | 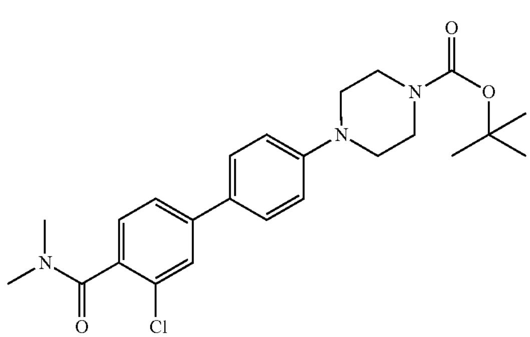 [SMILES: CN(C)C(=O)c1ccc(-c2ccc(N3CCN(C(=O)OC(C)(C)C)CC3)cc2)cc1Cl] | tert-butyl 4-[3'-chloro-4'-(dimethylcarbamoyl)biphenyl-4-yl]piperazine-1-carboxylate | Calc'd 444.2, found 444.3 |

TABLE 4-continued

| Example | Structure | IUPAC Name | Exact Mass [M + H]+ |
|---|---|---|---|
| 4-12 | 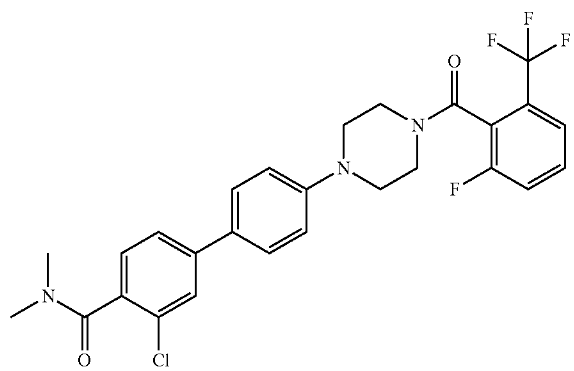 [SMILES: CN(C)C(=O)c1ccc(-c2ccc(N3CCN(C(=O)c4c(F)cccc4C(F)(F)F)CC3)cc2)cc1Cl] | 3-chloro-4'-(4-{[2-fluoro-6-(trifluoromethyl)phenyl]carbonyl}piperazin-1-yl)-N,N-dimethylbiphenyl-4-carboxamide | Calc'd 534.2, found 534.1 |
| 4-13 | 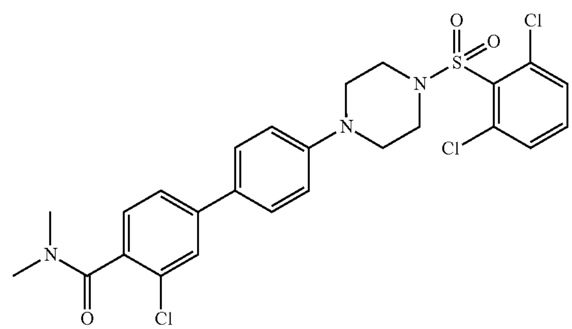 [SMILES: CN(C)C(=O)c1ccc(-c2ccc(N3CCN(S(=O)(=O)c4c(Cl)cccc4Cl)CC3)cc2)cc1Cl] | 3-chloro-4'-{4-[(2,6-dichlorophenyl)sulfonyl]piperazin-1-yl}-N,N-dimethylbiphenyl-4-carboxamide | Calc'd 552.1, found 552.2 |
| 4-14 | 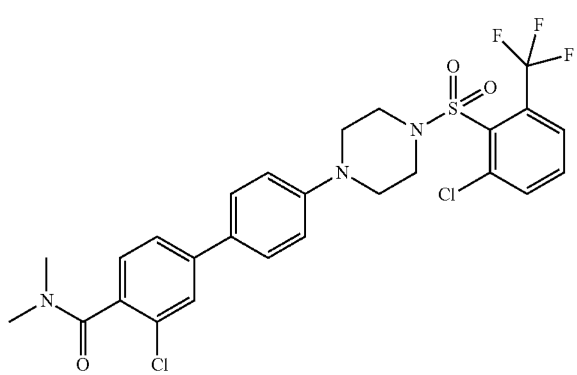 [SMILES: CN(C)C(=O)c1ccc(-c2ccc(N3CCN(S(=O)(=O)c4c(Cl)cccc4C(F)(F)F)CC3)cc2)cc1Cl] | 3-chloro-4'-(4-{[2-chloro-6-(trifluoromethyl)phenyl]sulfonyl}piperazin-1-yl)-N,N-dimethylbiphenyl-4-carboxamide | Calc'd 586.1, found 586.3 |
| 4-15 | 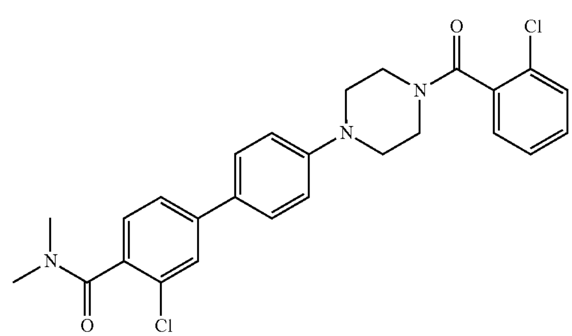 [SMILES: CN(C)C(=O)c1ccc(-c2ccc(N3CCN(C(=O)c4ccccc4Cl)CC3)cc2)cc1Cl] | 3-chloro-4'-{4-[(2-chlorophenyl)carbonyl]piperazin-1-yl}-N,N-dimethylbiphenyl-4-carboxamide | Calc'd 482.1, found 482.1 |

TABLE 4-continued

| Example | Structure | IUPAC Name | Exact Mass [M + H]+ |
|---|---|---|---|
| 4-16 | 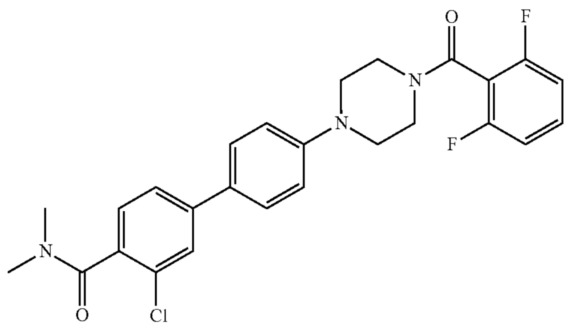 [SMILES: CN(C)C(=O)c1ccc(-c2ccc(N3CCN(C(=O)c4c(F)cccc4F)CC3)cc2)cc1Cl] | 3-chloro-4'-{4-[(2,6-difluorophenyl)carbonyl]piperazin-1-yl}-N,N-dimethylbiphenyl-4-carboxamide | Calc'd 484.2, found 484.1 |
| 4-17 | 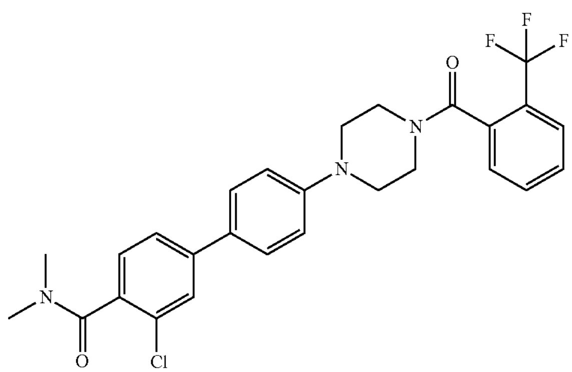 [SMILES: CN(C)C(=O)c1ccc(-c2ccc(N3CCN(C(=O)c4ccccc4C(F)(F)F)CC3)cc2)cc1Cl] | 3-chloro-N,N-dimethyl-4'-(4-{[2-(trifluoromethyl)phenyl]carbonyl}piperazin-1-yl)biphenyl-4-carboxamide | Calc'd 516.2, found 516.1 |
| 4-18 | 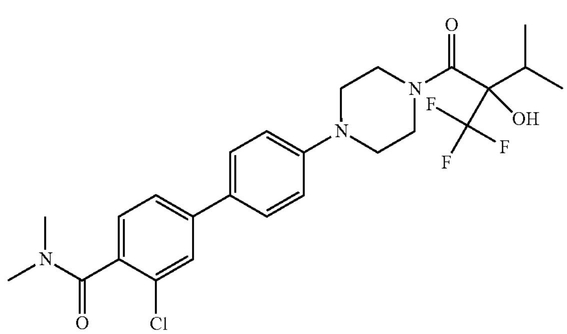 [SMILES: CC(C)C(O)(C(=O)N1CCN(c2ccc(-c3ccc(C(=O)N(C)C)c(Cl)c3)cc2)CC1)C(F)(F)F] | 3-chloro-4'-{4-[2-hydroxy-3-methyl-2-(trifluoromethyl)butanoyl]piperazin-1-yl}-N,N-dimethylbiphenyl-4-carboxamide | Calc'd 512.2, found 512.1 |
| 4-19 | 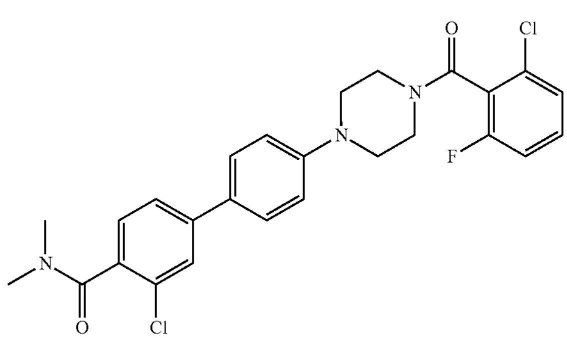 | 3-chloro-4'-{4-[(2-chloro-6-fluorophenyl)carbonyl]piperazin-1-yl}-N,N-dimethylbiphenyl-4-carboxamide | Calc'd 500.1, found 500.1 |

TABLE 4-continued

| Example | Structure | IUPAC Name | Exact Mass [M + H]+ |
|---|---|---|---|
| 2-27 | 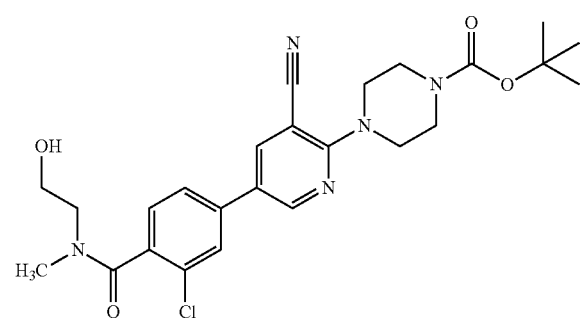 [SMILES: CN(CCO)C(=O)c1ccc(-c2cnc(N3CCN(C(=O)OC(C)(C)C)CC3)c(C#N)c2)cc1Cl] | 3-chloro-N,N-dimethyl-4'-{4-[(2R)-3,3,3-trifluoro-2-hydroxy-2-phenylpropanoyl]piperazin-1-yl}biphenyl-4-carboxamide | Calc'd 546.2, found 546.4 |

Example 5-1 tert-butyl-4-(5-{3-chloro-4-[(2-hydroxyethyl)(methyl)carbamoyl]phenyl}-3-cyanopyridin-2-yl)piperazine-1-carboxylate A mixture of tert-butyl 4-(5-bromo-3-cyanopyridin-2-yl)piperazine-1-carboxylate (1.0 g, 2.7 mmol, 1.0 eq), 3-chloro-4-(methoxycarbonyl)phenyl boronic acid (0.70 g, 3.3 mmol, 1.2 eq) and 2 M aqueous sodium carbonate solution (1.3 mL, 2.7 mmol, 1.0 eq) in acetonitrile (15 mL) was degassed with nitrogen for 15 minutes prior to the addition of bis(triphenylphosphine) palladium (II) chloride (0.096 g, 0.14 mmol, 0.050 eq). The resulting reaction was heated at reflux under nitrogen for 16 hours. The reaction mixture was concentrated and the residue was partitioned between dichloromethane (150 mL) and water (50 ml). The organic layer was separated, dried over sodium sulfate and concentrated. The residue was purified by silica gel chromatography (0-100% ethyl acetate/hexanes) to yield tert-butyl 4-{5-[3-chloro-4-(methoxycarbonyl)phenyl]-3-cyanopyridin-2-yl}piperazine-1-carboxylate. $^1$H NMR (500 MHz, CDCl$_3$): δ 8.58 (d, J=2.5 Hz, 1H); 7.99 (d, J=2.5 Hz, 1H); 7.95 (d, 1H, J=8 Hz); 7.59 (d, J=1.5 Hz, 1H); 7.43 (dd, J=1.5, 8.0 Hz, 1H); 3.96 (s, 3H); 3.80 (m, 4H); 3.61 (m, 4H); 1.50 (s, 9H). LRMS m/z (M+H) 457.3 found, 457.2 required.

To a solution of tert-butyl 4-{5-[3-chloro-4-(methoxycarbonyl)phenyl]-3-cyanopyridin-2-yl}piperazine-1-carboxylate (0.10 g, 0.22 mmol, 1.0 eq) in methanol (2.0 mL) was added 1 N aqueous sodium hydroxide solution (0.24 mL, 0.24 mmol, 1.1 eq) and the resulting reaction was stirred at 23° C. for 16 hours. The reaction mixture was neutralized with the addition of 1 N aqueous hydrochloric acid solution (0.24 ml, 0.24 mmol, 1.1 eq) and the resulting solution was concentrated. The residue was dissolved in ethyl acetate and filtered. The filtrate was concentrated under reduced pressure to give 4-{6-[4-(tert-butoxycarbonyl)piperazin-1-yl]-5-cyanopyridin-3-yl}-2-chlorobenzoic acid. LRMS m/z (M+H-Boc) 343.1 found, 343.1 required.

To a solution of 4-{6-[4-(tert-butoxycarbonyl)piperazin-1-yl]-5-cyanopyridin-3-yl}-2-chlorobenzoic acid (0.025 g, 0.056 mmol, 1.0 eq) and N,N-diisopropylethylamine (0.039 mL, 0.023 mmol, 4.0 eq) in dimethylformamide (0.56 mL) was added 2-(methylamino)ethanol (0.0069 mL, 0.085 mmol, 1.5 eq) followed by HATU (0.032 g, 0.085 mmol, 1.5 eq) and the resulting reaction was stirred at 23° C. for 16 hours. The reaction mixture was diluted with ethyl acetate and the organic phase was washed consecutively with 10% aqueous citric acid solution, saturated aqueous sodium bicarbonate solution, and brine. The organic phase was then dried over sodium sulfate and concentrated. The resulting residue was dissolved in DMSO and purified by reverse phase liquid chromatography (Gemini-NX C18, 5 μm, 30×100 mm column; 0-100% CH$_3$CN/H$_2$O gradient w/0.10% TFA present) to yield tert-butyl 4-(5-{3-chloro-4-[(2-hydroxyethyl)(methyl)carbamoyl]phenyl}-3-cyanopyridin-2-yl)piperazine-1-carboxylate. $^1$H NMR (500 MHz, CDCl$_3$): δ 8.57-8.54 (m, 1H); 7.98-7.95 (m, 1H); 7.54 (d, J=10.9 Hz, 1H); 7.47-7.41 (m, 2H); 4.13 (dd, J=14.3, 7.1 Hz, 2H); 3.99-3.94 (m, 2H); 3.83-3.77 (m, 4H); 3.64-3.60 (m, 4H); 3.00 (s, 3H); 1.51 (s, 9H). LRMS m/z (M+H) 500.3 found, 500.2 required.

The following examples were prepared according to the procedure in example 5-1 using the appropriate amine.

TABLE 5

| Example | Structure | IUPAC Name | Exact Mass [M + H]+ |
|---|---|---|---|
| 5-2 | 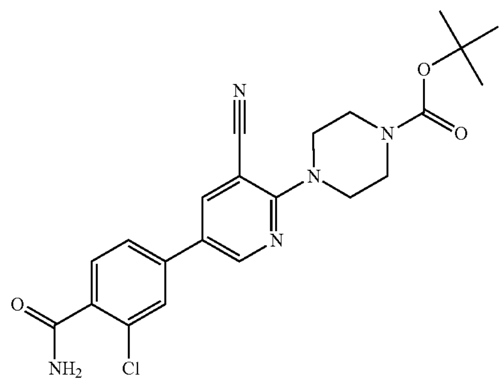 [SMILES: CC(C)(C)OC(=O)N1CCN(c2ncc(-c3ccc(C(N)=O)c(Cl)c3)cc2C#N)CC1] | tert-butyl 4-[5-(4-carbamoyl-3-chlorophenyl)-3-cyanopyridin-2-yl]piperazine-1-carboxylate | Calc'd 442.2, found 442.1 |
| 5-3 | 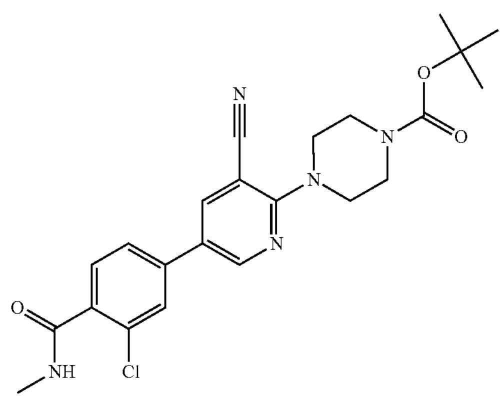 [SMILES: CNC(=O)c1ccc(-c2cnc(N3CCN(C(=O)OC(C)(C)C)CC3)c(C#N)c2)cc1Cl] | tert-butyl 4-{5-[3-chloro-4-(methylcarbamoyl)phenyl]-3-cyanopyridin-2-yl}piperazine-1-carboxylate | Calc'd 456.2, found 456.1 |
| 5-4 | 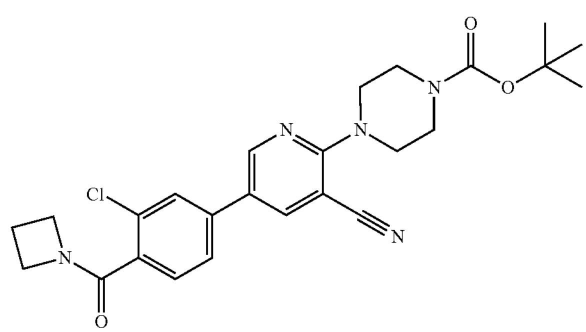 [SMILES: CC(C)(C)OC(=O)N1CCN(c2ncc(-c3ccc(C(=O)N4CCC4)c(Cl)c3)cc2C#N)CC1] | tert-butyl 4-{5-[4-(azetidin-1-ylcarbonyl)-3-chlorophenyl]-3-cyanopyridin-2-yl}piperazine-1-carboxylate | Calc'd 482.2, found 482.1953 |
| 5-5 | 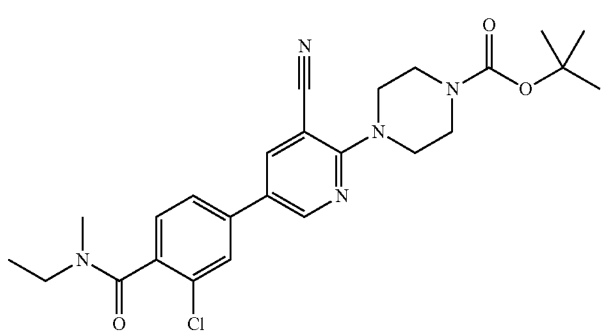 [SMILES: CCN(C)C(=O)c1ccc(-c2cnc(N3CCN(C(=O)OC(C)(C)C)CC3)c(C#N)c2)cc1Cl] | tert-butyl 4-(5-{3-chloro-4-[ethyl(methyl)carbamoyl]phenyl}-3-cyanopyridin-2-yl)piperazine-1-carboxylate | Calc'd 484.2, found 484.2098 |

TABLE 5-continued

| Example | Structure | IUPAC Name | Exact Mass [M + H]+ |
|---|---|---|---|
| 5-6 | 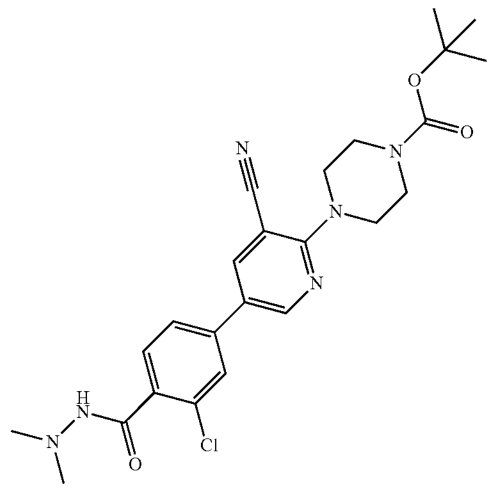 [SMILES: CN(C)NC(=O)c1ccc(-c2cnc(N3CCN(C(=O)OC(C)(C)C)CC3)c(C#N)c2)cc1Cl] | tert-butyl 4-(5-{3-chloro-4-[(2,2-dimethylhydrazino)carbonyl]phenyl}-3-cyanopyridin-2-yl)piperazine-1-carboxylate | Calc'd 485.2, found 485.2065 |
| 5-7 | 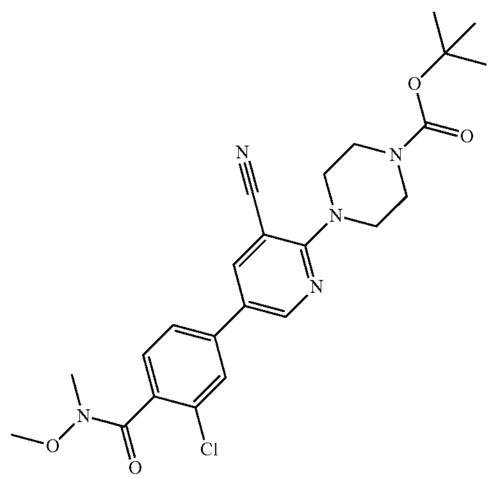 [SMILES: CON(C)C(=O)c1ccc(-c2cnc(N3CCN(C(=O)OC(C)(C)C)CC3)c(C#N)c2)cc1Cl] | tert-butyl 4-(5-{3-chloro-4-[methoxy(methyl)carbamoyl]phenyl}-3-cyanopyridin-2-yl)piperazine-1-carboxylate | Calc'd 486.2, found 486.1900 |
| 5-8 | 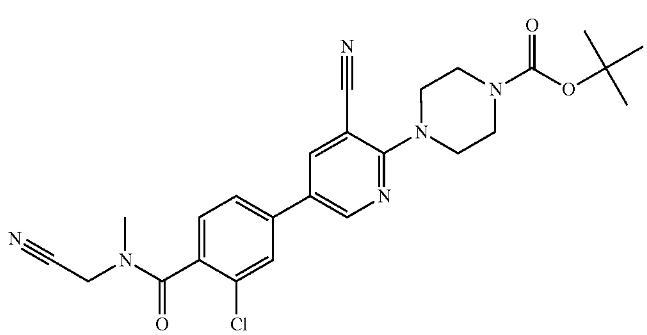 [SMILES: CN(CC#N)C(=O)c1ccc(-c2cnc(N3CCN(C(=O)OC(C)(C)C)CC3)c(C#N)c2)cc1Cl] | tert-butyl 4-(5-{3-chloro-4-[(cyanomethyl)(methyl)carbamoyl]phenyl}-3-cyanopyridin-2-yl)piperazine-1-carboxylate | Calc'd 495.2, found 495.1906 |

TABLE 5-continued

| Example | Structure | IUPAC Name | Exact Mass [M + H]+ |
|---|---|---|---|
| 5-9 | 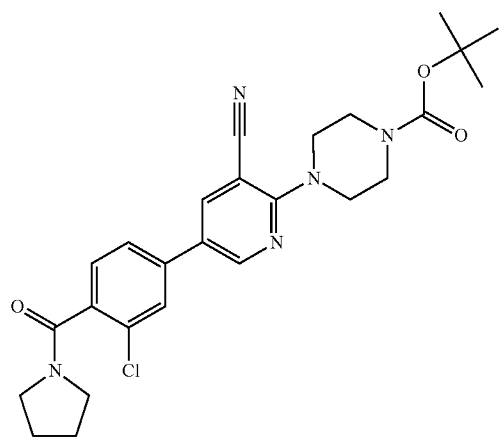 [SMILES: CC(C)(C)OC(=O)N1CCN(c2ncc(-c3ccc(C(=O)N4CCCC4)c(Cl)c3)cc2C#N)CC1] | tert-butyl 4-{5-[3-chloro-4-(pyrrolidin-1-ylcarbonyl)phenyl]-3-cyanopyridin-2-yl}piperazine-1-carboxylate | Calc'd 496.2, found 496.1 |
| 5-10 | 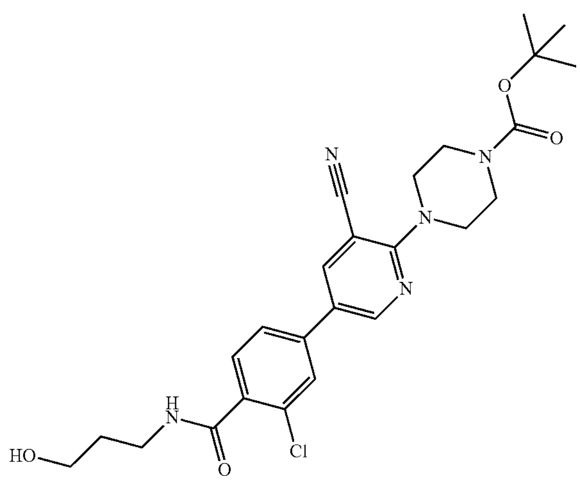 [SMILES: CC(C)(C)OC(=O)N1CCN(c2ncc(-c3ccc(C(=O)NCCCO)c(Cl)c3)cc2C#N)CC1] | tert-butyl 4-(5-{3-chloro-4-[(3-hydroxypropyl)carbamoyl]phenyl}-3-cyanopyridin-2-yl)piperazine-1-carboxylate | Calc'd 500.2, found 500.2052 |
| 5-11 | 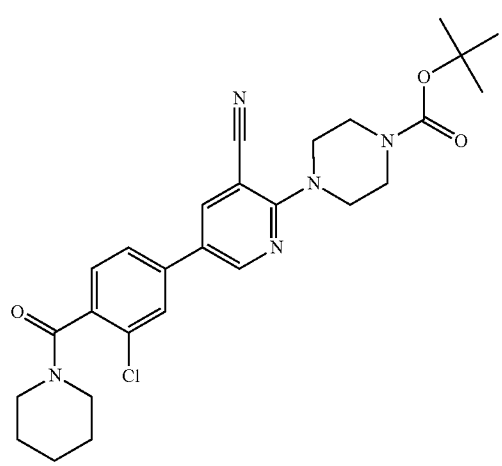 [SMILES: CC(C)(C)OC(=O)N1CCN(c2ncc(-c3ccc(C(=O)N4CCCCC4)c(Cl)c3)cc2C#N)CC1] | tert-butyl 4-{5-[3-chloro-4-(piperidin-1-ylcarbonyl)phenyl]-3-cyanopyridin-2-yl}piperazine-1-carboxylate | Calc'd 510.2, found 510.2 |

TABLE 5-continued

| Example | Structure | IUPAC Name | Exact Mass [M + H]+ |
|---------|-----------|------------|---------------------|
| 5-12 | 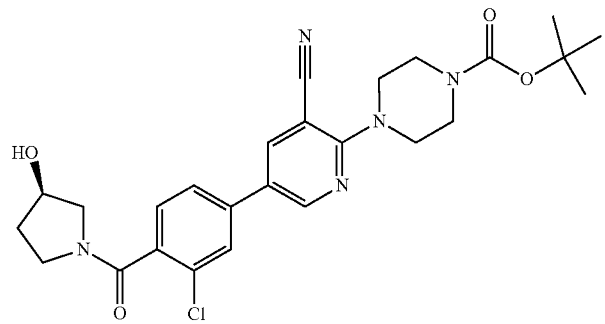 [SMILES: CC(C)(C)OC(=O)N1CCN(c2ncc(-c3ccc(C(=O)N4CC[C@@H](O)C4)c(Cl)c3)cc2C#N)CC1] | tert-butyl 4-[5-(3-chloro-4-{[(3R)-3-hydroxypyrrolidin-1-yl]carbonyl}phenyl)-3-cyanopyridin-2-yl]piperazine-1-carboxylate | Calc'd 512.2, found 512.2052 |
| 5-13 | 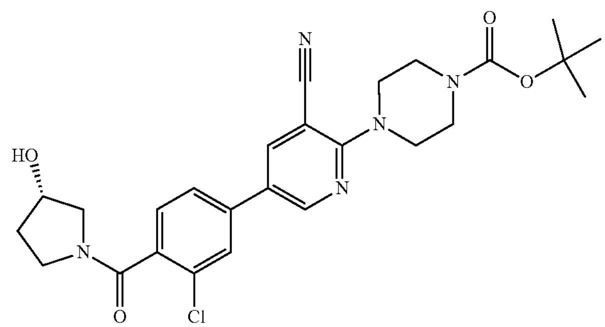 [SMILES: CC(C)(C)OC(=O)N1CCN(c2ncc(-c3ccc(C(=O)N4CC[C@H](O)C4)c(Cl)c3)cc2C#N)CC1] | tert-butyl 4-[5-(3-chloro-4-{[(3S)-3-hydroxypyrrolidin-1-yl]carbonyl}phenyl)-3-cyanopyridin-2-yl]piperazine-1-carboxylate | Calc'd 512.2, found 512.2054 |
| 5-14 | 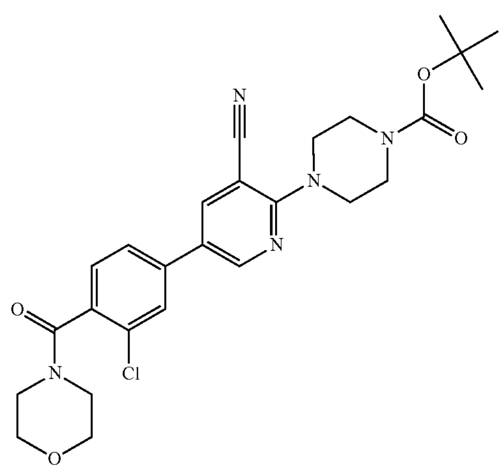 [SMILES: CC(C)(C)OC(=O)N1CCN(c2ncc(-c3ccc(C(=O)N4CCOCC4)c(Cl)c3)cc2C#N)CC1] | tert-butyl 4-{5-[3-chloro-4-(morpholin-4-ylcarbonyl)phenyl]-3-cyanopyridin-2-yl}piperazine-1-carboxylate | Calc'd 512.2, found 512.1 |
| 5-15 | 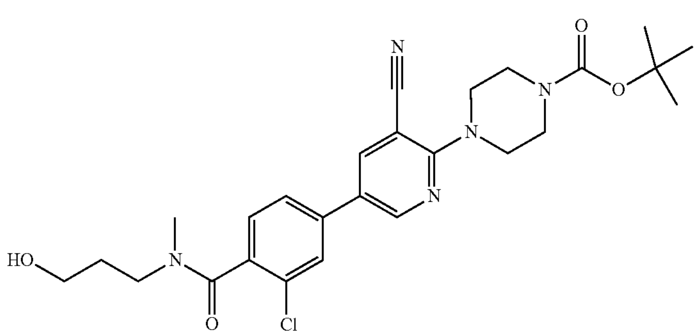 [SMILES: CN(CCCO)C(=O)c1ccc(-c2cnc(N3CCN(C(=O)OC(C)(C)C)CC3)c(C#N)c2)cc1Cl] | tert-butyl 4-(5-{3-chloro-4-[(3-hydroxypropyl)(methyl)carbamoyl]phenyl}-3-cyanopyridin-2-yl)piperazine-1-carboxylate | Calc'd 514.2, found 514.2203 |

TABLE 5-continued

| Example | Structure | IUPAC Name | Exact Mass [M + H]+ |
|---|---|---|---|
| 5-16 | 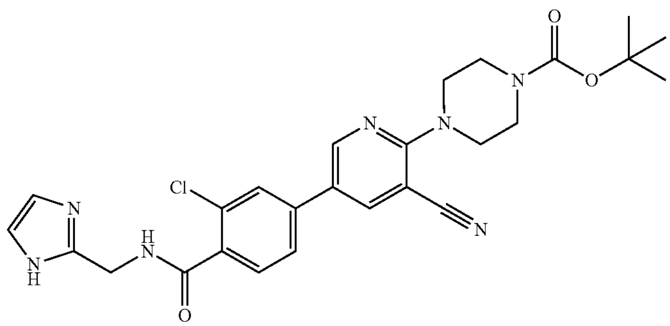 [SMILES: CC(C)(C)OC(=O)N1CCN(c2ncc(-c3ccc(C(=O)NCc4ncc[nH]4)c(Cl)c3)cc2C#N)CC1] | tert-butyl 4-(5-{3-chloro-4-[(1H-imidazol-2-ylmethyl)carbamoyl]phenyl}-3-cyanopyridin-2-yl)piperazine-1-carboxylate | Calc'd 522.2, found 522.2024 |
| 5-17 | 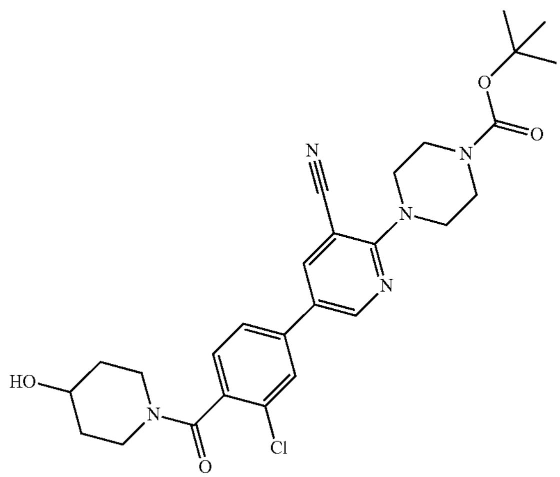 [SMILES: CC(C)(C)OC(=O)N1CCN(c2ncc(-c3ccc(C(=O)N4CCC(O)CC4)c(Cl)c3)cc2C#N)CC1] | tert-butyl 4-(5-{3-chloro-4-[(4-hydroxypiperidin-1-yl)carbonyl]phenyl}-3-cyanopyridin-2-yl)piperazine-1-carboxylate | Calc'd 526.2, found 526.2217 |
| 5-18 | 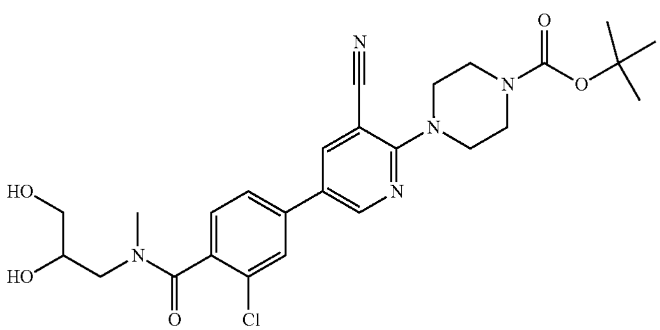 [SMILES: CN(CC(O)CO)C(=O)c1ccc(-c2cnc(N3CCN(C(=O)OC(C)(C)C)CC3)c(C#N)c2)cc1Cl] | tert-butyl 4-(5-{3-chloro-4-[(2,3-dihydroxypropyl)(methyl)carbamoyl]phenyl}-3-cyanopyridin-2-yl)piperazine-1-carboxylate | Calc'd 530.2, found 530.2157 |
| 5-19 | 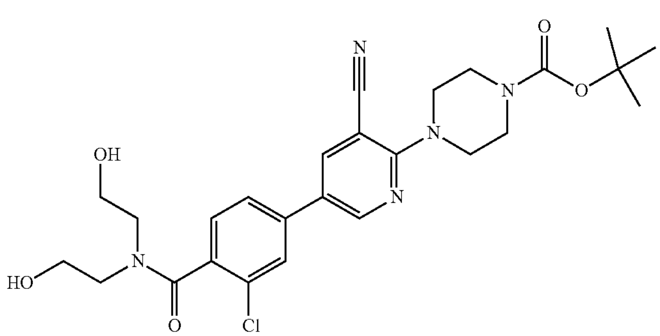 [SMILES: CC(C)(C)OC(=O)N1CCN(c2ncc(-c3ccc(C(=O)N(CCO)CCO)c(Cl)c3)cc2C#N)CC1] | tert-butyl 4-(5-{4-[bis(2-hydroxyethyl)carbamoyl]-3-chlorophenyl}-3-cyanopyridin-2-yl)piperazine-1-carboxylate | Calc'd 530.2, found 530.2158 |

TABLE 5-continued

| Example | Structure | IUPAC Name | Exact Mass [M + H]+ |
|---|---|---|---|
| 5-20 | 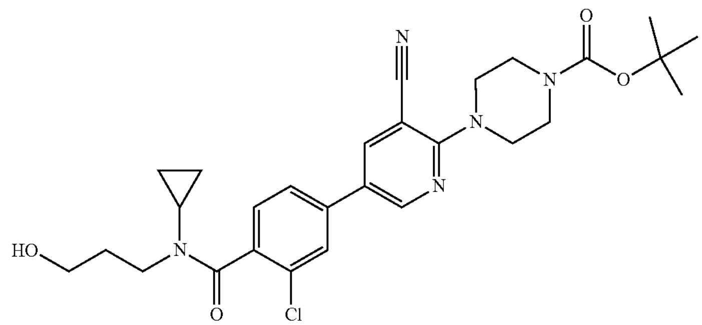 [SMILES: CC(C)(C)OC(=O)N1CCN(c2ncc(-c3ccc(C(=O)N(CCCO)C4CC4)c(Cl)c3)cc2C#N)CC1] | tert-butyl 4-(5-{3-chloro-4-[cyclopropyl(3-hydroxypropyl)carbamoyl]phenyl}-3-cyanopyridin-2-yl)piperazine-1-carboxylate | Calc'd 540.2, found 540.2378 |
| 5-21 | 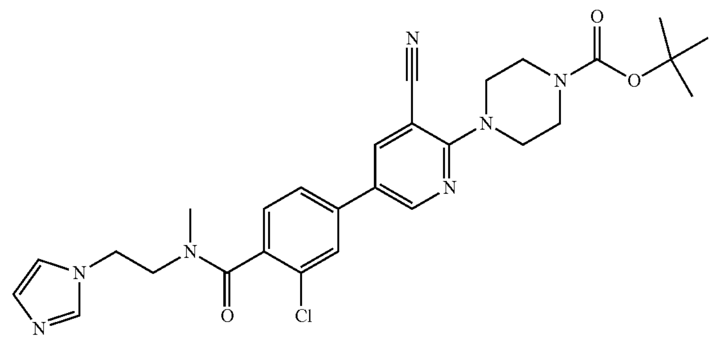 [SMILES: CN(CCn1ccnc1)C(=O)c1ccc(-c2cnc(N3CCN(C(=O)OC(C)(C)C)CC3)c(C#N)c2)cc1Cl] | tert-butyl 4-[5-(3-chloro-4-{[2-(1H-imidazol-1-yl)ethyl](methyl)carbamoyl}phenyl)-3-cyanopyridin-2-yl]piperazine-1-carboxylate | Calc'd 550.2, found 550.2323 |
| 5-22 | 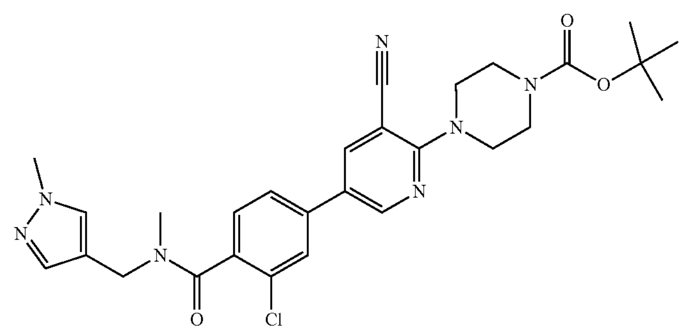 [SMILES: CN(Cc1cnn(C)c1)C(=O)c1ccc(-c2cnc(N3CCN(C(=O)OC(C)(C)C)CC3)c(C#N)c2)cc1Cl] | tert-butyl 4-[5-(3-chloro-4-{methyl[(1-methyl-1H-pyrazol-4-yl)methyl]carbamoyl}phenyl)-3-cyanopyridin-2-yl]piperazine-1-carboxylate | Calc'd 550.2, found 550.2325 |
| 5-23 | 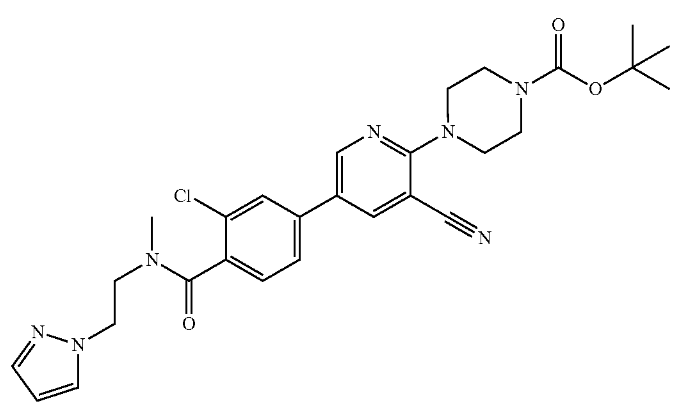 [SMILES: CN(CCn1cccn1)C(=O)c1ccc(-c2cnc(N3CCN(C(=O)OC(C)(C)C)CC3)c(C#N)c2)cc1Cl] | tert-butyl 4-[5-(3-chloro-4-{methyl[2-(1H-pyrazol-1-yl)ethyl]carbamoyl}phenyl)-3-cyanopyridin-2-yl]piperazine-1-carboxylate | Calc'd 550.2, found 550.2333 |

TABLE 5-continued

| Example | Structure | IUPAC Name | Exact Mass [M + H]+ |
|---|---|---|---|
| 5-24 | 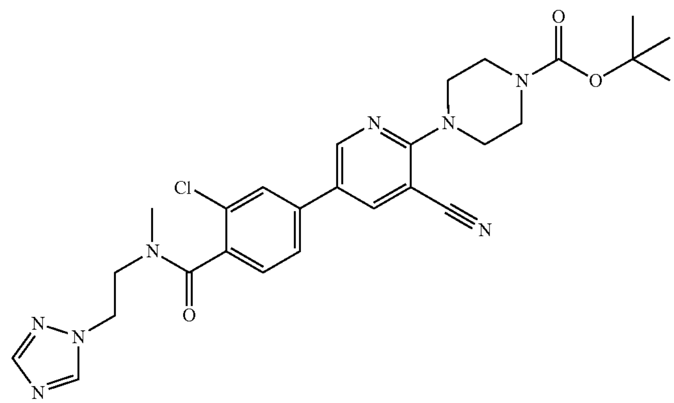 [SMILES: CN(CCn1cncn1)C(=O)c1ccc(-c2cnc(N3CCN(C(=O)OC(C)(C)C)CC3)c(C#N)c2)cc1Cl] | tert-butyl 4-[5-(3-chloro-4-{methyl[2-(1H-1,2,4-triazol-1-yl)ethyl]carbamoyl}phenyl)-3-cyanopyridin-2-yl]piperazine-1-carboxylate | Calc'd 551.2, found 551.2289 |
| 5-25 | 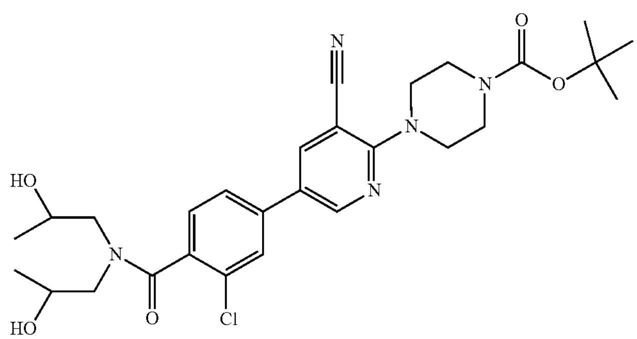 [SMILES: CC(O)CN(CC(C)O)C(=O)c1ccc(-c2cnc(N3CCN(C(=O)OC(C)(C)C)CC3)c(C#N)c2)cc1Cl] | tert-butyl 4-(5-{4-[bis(2-hydroxypropyl)carbamoyl]-3-chlorophenyl}-3-cyanopyridin-2-yl)piperazine-1-carboxylate | Calc'd 558.2, found 558.2465 |
| 5-26 | 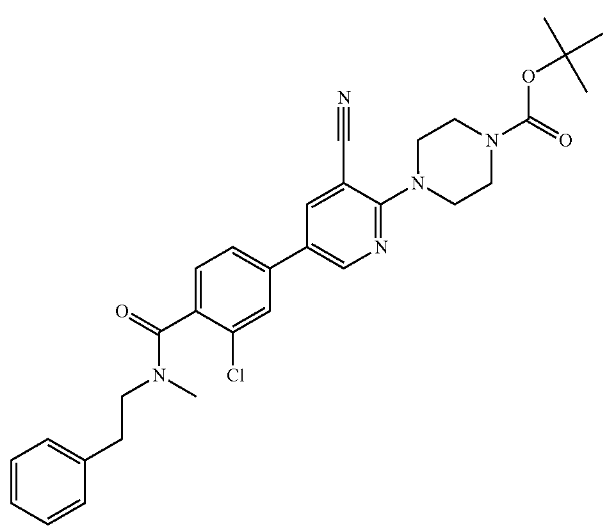 [SMILES: CN(CCc1ccccc1)C(=O)c1ccc(-c2cnc(N3CCN(C(=O)OC(C)(C)C)CC3)c(C#N)c2)cc1Cl] | tert-butyl 4-(5-{3-chloro-4-[methyl(2-phenylethyl)carbamoyl]phenyl}-3-cyanopyridin-2-yl)piperazine-1-carboxylate | Calc'd 560.2, found 560.2 |

TABLE 5-continued

| Example | Structure | IUPAC Name | Exact Mass [M + H]+ |
|---|---|---|---|
| 5-27 | 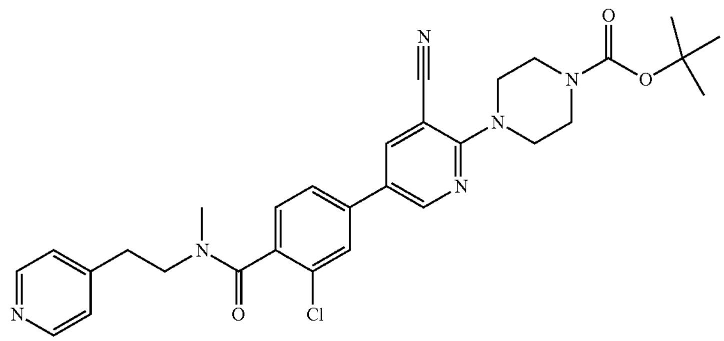 [SMILES: CN(CCc1ccncc1)C(=O)c1ccc(-c2cnc(N3CCN(C(=O)OC(C)(C)C)CC3)c(C#N)c2)cc1Cl] | tert-butyl 4-(5-{3-chloro-4-[methyl(2-pyridin-4-ylethyl)carbamoyl]phenyl}-3-cyanopyridin-2-yl)piperazine-1-carboxylate | Calc'd 561.2, found 561.2374 |
| 5-28 | 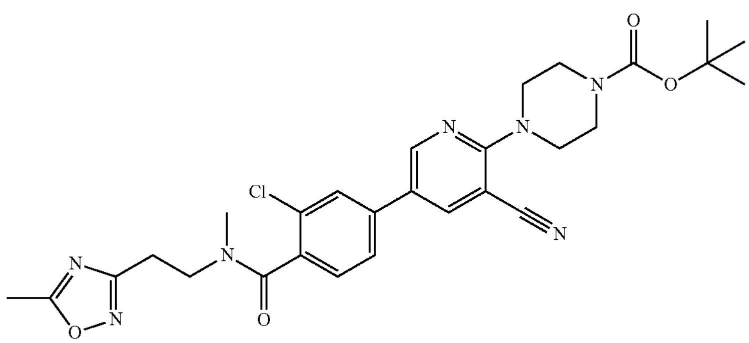 [SMILES: Cc1nc(CCN(C)C(=O)c2ccc(-c3cnc(N4CCN(C(=O)OC(C)(C)C)CC4)c(C#N)c3)cc2Cl)no1] | tert-butyl 4-[5-(3-chloro-4-{methyl[2-(5-methyl-1,2,4-oxadiazol-3-yl)ethyl]carbamoyl}phenyl)-3-cyanopyridin-2-yl]piperazine-1-carboxylate | Calc'd 566.2, found 566.2294 |
| 5-29 | 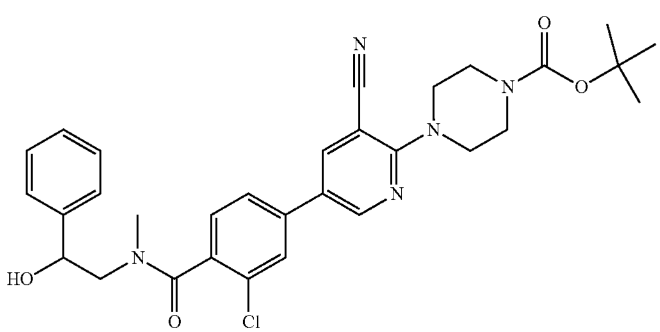 [SMILES: CN(CC(O)c1ccccc1)C(=O)c1ccc(-c2cnc(N3CCN(C(=O)OC(C)(C)C)CC3)c(C#N)c2)cc1Cl] | tert-butyl 4-(5-{3-chloro-4-[(2-hydroxy-2-phenylethyl)(methyl)carbamoyl]phenyl}-3-cyanopyridin-2-yl)piperazine-1-carboxylate | Calc'd 576.2, found 576.2362 |
| 5-30 | 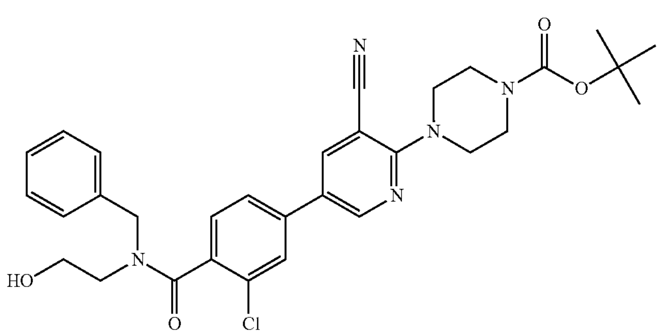 [SMILES: CC(C)(C)OC(=O)N1CCN(c2ncc(-c3ccc(C(=O)N(CCO)Cc4ccccc4)c(Cl)c3)cc2C#N)CC1] | tert-butyl 4-(5-{4-[benzyl(2-hydroxyethyl)carbamoyl]-3-chlorophenyl}-3-cyanopyridin-2-yl)piperazine-1-carboxylate | Calc'd 576.2, found 576.2365 |

TABLE 5-continued

| Example | Structure | IUPAC Name | Exact Mass [M + H]+ |
|---|---|---|---|
| 5-31 | 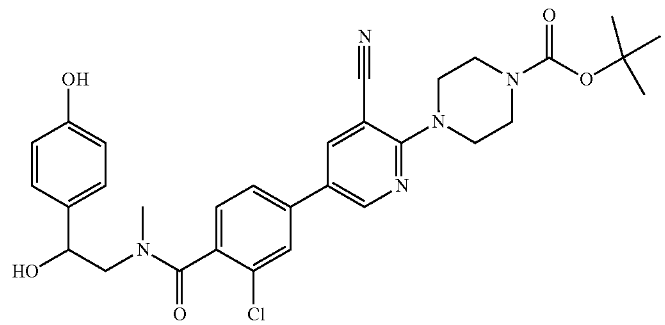 [SMILES: CN(CC(O)c1ccc(O)cc1)C(=O)c1ccc(-c2cnc(N3CCN(C(=O)OC(C)(C)C)CC3)c(C#N)c2)cc1Cl] | tert-butyl 4-[5-(3-chloro-4-{[2-hydroxy-2-(4-hydroxyphenyl)ethyl](methyl)carbamoyl}phenyl)-3-cyanopyridin-2-yl]piperazine-1-carboxylate | Calc'd 592.2, found 592.2310 |
| 5-32 | 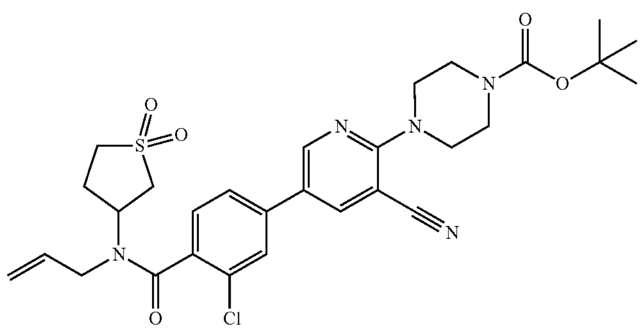 [SMILES: C=CCN(C(=O)c1ccc(-c2cnc(N3CCN(C(=O)OC(C)(C)C)CC3)c(C#N)c2)cc1Cl)C1CCS(=O)(=O)C1] | tert-butyl 4-(5-{3-chloro-4-[(1,1-dioxidotetrahydrothiophen-3-yl)(prop-2-en-1-yl)carbamoyl]phenyl}-3-cyanopyridin-2-yl)piperazine-1-carboxylate | Calc'd 600.2, found 600.2043 |
| 5-33 | 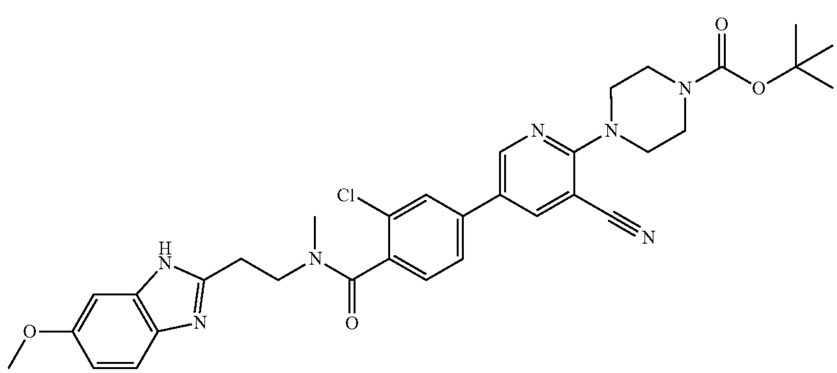 [SMILES: COc1ccc2nc(CCN(C)C(=O)c3ccc(-c4cnc(N5CCN(C(=O)OC(C)(C)C)CC5)c(C#N)c4)cc3Cl)[nH]c2c1] | tert-butyl 4-[5-(3-chloro-4-{[2-(6-methoxy-1H-benzimidazol-2-yl)ethyl](methyl)carbamoyl}phenyl)-3-cyanopyridin-2-yl]piperazine-1-carboxylate | Calc'd 630.3, found 630.2595 |

The following examples were prepared using the appropriate amine in step 3 as described in example 5-1 followed by deprotection and carboxylic acid coupling as described in example 2-2.

TABLE 6

| Example | Structure | IUPAC Name | Exact Mass [M + H]+ |
|---|---|---|---|
| 6-1 | 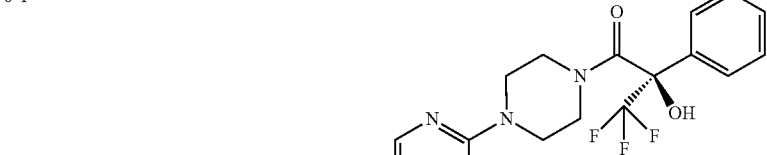 | 2-chloro-4-(5-cyano-6-{4-[(2R)-3,3,3-trifluoro-2-hydroxy-2-phenylpropanoyl]piperazin-1-yl}pyridin-3-yl)-N-methyl-N-[2-(1H-1,2,4-triazol-1-yl)ethyl]benzamide | Calc'd 653.2, found 653.2013 |
| 6-2 | 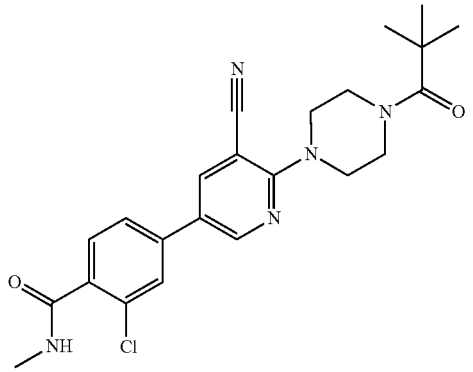 [SMILES: CNC(=O)c1ccc(-c2cnc(N3CCN(C(=O)C(C)(C)C)CC3)c(C#N)c2)cc1Cl] | 2-chloro-4-{5-cyano-6-[4-(2,2-dimethylpropanoyl)piperazin-1-yl]pyridin-3-yl}-N-methylbenzamide | Calc'd 440.2, found 440.1 |
| 6-3 | 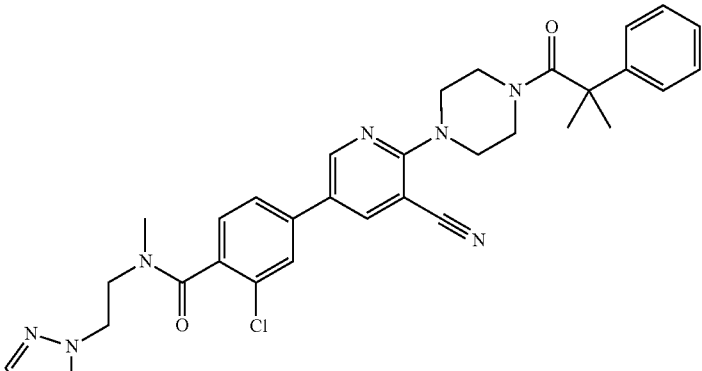 | 2-chloro-4-{5-cyano-6-[4-(2-methyl-2-phenylpropanoyl)piperazin-1-yl]pyridin-3-yl}-N-methyl-N-[2-(1H-1,2,4-triazol-1-yl)ethyl]benzamide | Calc'd 597.2, found 597.2504 |

Example 7-1

2,6-dichloro-4-(5-cyano-6-{4-[(2R)-3,3,3-trifluoro-2-hydroxy-2-phenylpropanoyl]piperazin-1-yl}pyridin-3-yl)-N,N-dimethylbenzamide

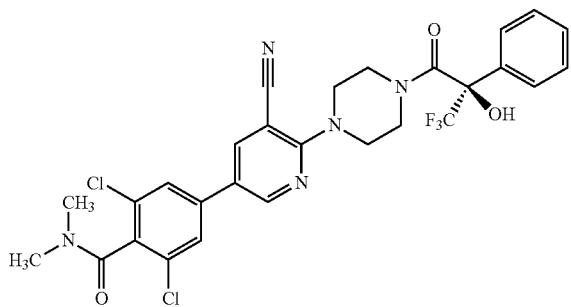 [SMILES: CN(C)C(=O)c1c(Cl)cc(-c2cnc(N3CCN(C(=O)[C@](O)(c4ccccc4)C(F)(F)F)CC3)c(C#N)c2)cc1Cl]

To a solution of 4-bromo-2,6-dichlorobenzoic acid (1.0 g, 3.7 mmol, 1.0 eq) and diisopropylethyl amine (2.6 mL, 15 mmol, 4.0 eq) in dichloromethane (30 mL) was added dimethylamine hydrochloride (0.38 g, 4.6 mmol, 1.2 eq) followed by HBTU (2.1 g, 5.6 mmol, 1.5 eq) and the resulting reaction was stirred at 23° C. for 16 hours. The reaction mixture was purified by silica gel chromatography (0-100% ethyl acetate/hexanes) to yield 4-bromo-2,6-dichloro-N,N-dimethylbenzamide. $^1$H NMR (400 MHz, CDCl$_3$): δ 7.51 (s, 2H); 3.16 (s, 3H); 2.87 (s, 3H). LRMS m/z (M+H) 295.9 found, 295.1 required.

A mixture of tert-butyl 4-(5-bromo-3-cyanopyridin-2-yl)piperazine-1-carboxylate (2.0 g, 5.4 mmol, 1.0 eq), bispinacolatodiboron (1.7 g, 6.5 mmol, 1.2 eq), X-phos (0.11 g, 0.24 mmol, 0.044 eq) and potassium acetate (1.1 g, 10.9 mmol, 2.0 eq) in dimethylacetamide (50 mL) was degassed with nitrogen for 15 minutes prior to the addition of palladium acetate (0.024 g, 0.11 mmol, 0.020 eq). The resulting reaction was heated at 110° C. under nitrogen for 16 hours. The reaction mixture was diluted with water and extracted with ethyl acetate (3×100 mL). The combined organic extracts were washed with brine (50 mL), dried over sodium sulfate, and concentrated. The residue was purified by silica gel chromatography (0-100% ethyl acetate/hexanes) to yield tert-butyl 4-[3-cyano-5-(4,4,5,5-tetramethyl-1,3,2-dioxaborolan-2-yl)pyridin-2-yl]piperazine-1-carboxylate. $^1$H NMR (400 MHz, DMSO): δ 8.47 (d, J=1.9 Hz, 1H); 8.03 (d, J=1.9 Hz, 1H); 3.72-3.66 (m, 4H); 3.45-3.39 (m, 4H); 1.37 (s, 9H); 1.24 (s, 12H). LRMS m/z (M+H-Boc) 315.3 found, 315.2 required.

A mixture of 4-bromo-2,6-dichloro-N,N-dimethylbenzamide (0.57 g, 1.9 mmol, 1.0 eq), tert-butyl 4-[3-cyano-5-(4,4,5,5-tetramethyl-1,3,2-dioxaborolan-2-yl)pyridin-2-yl]piperazine-1-carboxylate (0.78 g, 1.9 mmol, 1.0 eq) and 2 M aqueous sodium carbonate solution (1.9 mL, 3.7 mmol, 2.0 eq) in acetonitrile (20 mL) was degassed with nitrogen for 15 minutes prior to the addition of bis(triphenylphosphine) palladium (II) chloride (0.066 g, 0.094 mmol, 0.050 eq). The resulting reaction was heated at reflux under nitrogen for 16 hours. The reaction mixture was concentrated and the residue was purified by silica gel chromatography (0-100% ethyl acetate/hexanes) to yield tert-butyl 4-{3-cyano-5-[3,5-dichloro-4-(dimethylcarbamoyl)phenyl]pyridin-2-yl}piperazine-1-carboxylate. $^1$H NMR (400 MHz, CDCl$_3$): δ 8.52 (d, J=2.6 Hz, 1H); 7.93 (d, J=2.6 Hz, 1H); 7.44 (s, 2H); 3.83-3.78 (m, 4H); 3.63-3.58 (m, 4H); 3.19 (s, 3H); 2.93 (s, 3H); 1.50 (s, 9H). LRMS m/z (M+H) 504.2 found, 504.2 required.

To a solution of tert-butyl 4-{3-cyano-5-[3,5-dichloro-4-(dimethylcarbamoyl)phenyl]pyridin-2-yl}piperazine-1-carboxylate (0.66 g, 1.3 mmol, 1.0 eq) in methanol (30 mL) was added 4 M hydrochloric acid in dioxane (0.66 mL, 2.6 mmol, 2.0 eq) and the resulting reaction mixture was stirred at 23° C. for 30 minutes. The reaction mixture was concentrated under reduced pressure to give the bis HCl salt 2,6-dichloro-4-[5-cyano-6-(piperazin-1-yl)pyridin-3-yl]-N,N-dimethylbenzamide. LRMS m/z (M+H) 404.1 found, 404.1 required.

To a solution of the bis hydrochloride salt of 2,6-dichloro-4-[5-cyano-6-(piperazin-1-yl)pyridin-3-yl]-N,N-dimethylbenzamide (0.10 g, 0.21 mmol, 1.0 eq) and N,N-diisopropylethylamine (0.15 mL, 0.84 mmol, 4.0 eq) in dichloromethane (2.5 mL) was added (2R)-3,3,3-trifluoro-2-hydroxy-2-phenylpropanoic acid (0.051 g, 0.023 mmol, 1.1 eq) followed by HBTU (0.12 g, 0.31 mmol, 1.5 eq) and the resulting reaction was stirred at 23° C. for 16 hours. The reaction mixture was concentrated and the residue was dissolved in DMSO and purified by reverse phase liquid chromatography (Gemini-NX C18, 5 μm, 30×100 mm column; 0-100% CH$_3$CN/H$_2$O gradient w/0.10% TFA present) to yield purified by silica gel chromatography (0-100% ethyl acetate/hexanes) to yield 2,6-dichloro-4-(5-cyano-6-{4-[(2R)-3,3,3-trifluoro-2-hydroxy-2-phenylpropanoyl]piperazin-1-yl}pyridin-3-yl)-N,N-dimethylbenzamide. $^1$H NMR (400 MHz, CD$_3$OD): δ 8.63 (d, J=2.5 Hz, 1H); 8.25 (d, J=2.5 Hz, 1H); 7.73 (s, 2H); 7.59 (d, J=7.0 Hz, 3H); 7.46-7.43 (m, 3H); 3.88 (d, J=11.3 Hz, 2H); 3.70-3.42 (m, 6H); 3.14 (s, 3H); 2.92 (s, 3H). LRMS m/z (M+H) 606.2 found, 606.2 required.

The following examples were prepared according to the procedure in example 7-1 using the appropriate piperizine intermediates A-3.

TABLE 7

| Example | Structure | IUPAC Name | Exact Mass [M + H]+ |
|---|---|---|---|
| 7-2 | 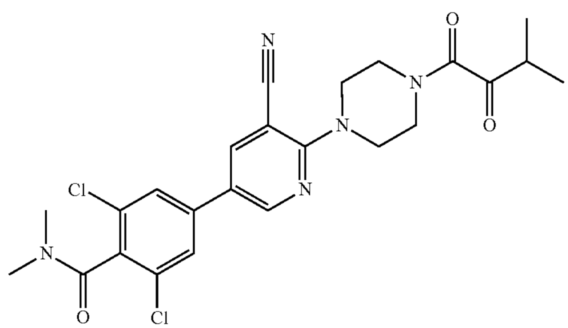 [SMILES: CC(C)C(=O)C(=O)N1CCN(c2ncc(-c3cc(Cl)c(C(=O)N(C)C)c(Cl)c3)cc2C#N)CC1] | 2,6-dichloro-4-{5-cyano-6-[4-(3-methyl-2-oxobutanoyl)piperazin-1-yl]pyridin-3-yl}1-N,N-dimethylbenzamide | Calc'd 502.1, found 502.2 |
| 7-3 | 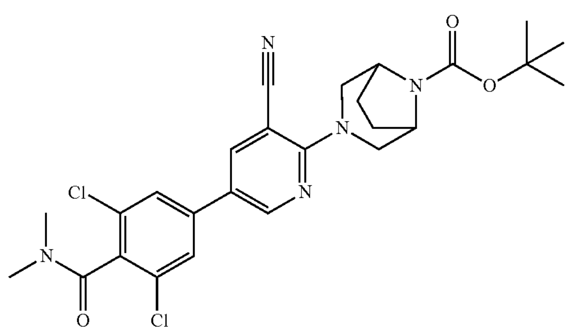 [SMILES: CN(C)C(=O)c1c(Cl)cc(-c2cnc(N3CC4CCC(C3)N4C(=O)OC(C)(C)C)c(C#N)c2)cc1Cl] | tert-butyl 3-(3-cyano-5-(3,5-dichloro-4-(dimethylcarbamoyl)phenyl)pyridin-2-yl)-3,8-diazabicyclo[3.2.1]octane-8-carboxylate | Calc'd 530.2, found 530.2 |
| 7-4 | 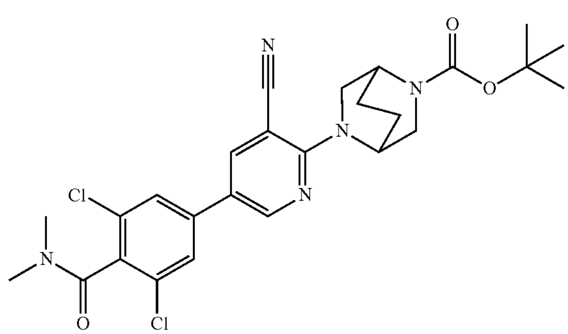 [SMILES: CN(C)C(=O)c1c(Cl)cc(-c2cnc(N3CC4CCC3CN4C(=O)OC(C)(C)C)c(C#N)c2)cc1Cl] | tert-butyl 5-(3-cyano-5-(3,5-dichloro-4-(dimethylcarbamoyl)phenyl)pyridin-2-yl)-2,5-diazabicyclo[2.2.2]octane-2-carboxylate | Calc'd 530.2, found 530.2 |
| 7-5 | 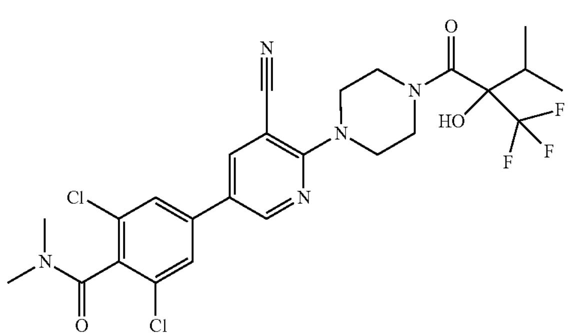 [SMILES: CC(C)C(O)(C(=O)N1CCN(c2ncc(-c3cc(Cl)c(C(=O)N(C)C)c(Cl)c3)cc2C#N)CC1)C(F)(F)F] | 2,6-dichloro-4-(5-cyano-6-{4-[2-hydroxy-3-methyl-2-(trifluoromethyl)butanoyl]piperazin-1-yl}pyridin-3-yl)-N,N-dimethylbenzamide | Calc'd 572.1, found 572.2 |

TABLE 7-continued

| Example | Structure | IUPAC Name | Exact Mass [M + H]+ |
|---|---|---|---|
| 7-6 | 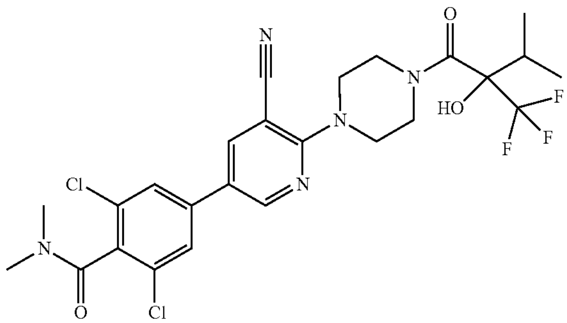 [SMILES: CC(C)C(O)(C(=O)N1CCN(c2ncc(-c3cc(Cl)c(C(=O)N(C)C)c(Cl)c3)cc2C#N)CC1)C(F)(F)F] | 2,6-dichloro-4-(5-cyano-6-{4-[2-hydroxy-3-methyl-2-(trifluoromethyl)butanoyl]piperazin-1-yl}pyridin-3-yl)-N,N-dimethylbenzamide | Calc'd 572.1, found 572.1 |

Example 8-1 tert-butyl 4-[3'-chloro-4'-(dimethylcarbamoyl)biphenyl-4-yl]-1,4-diazepane-1-carboxylate

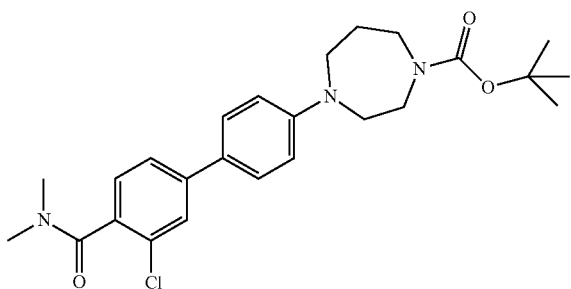 [SMILES: CN(C)C(=O)c1ccc(-c2ccc(N3CCCN(C(=O)OC(C)(C)C)CC3)cc2)cc1Cl]

tert-butyl 4-[3'-chloro-4'-(dimethylcarbamoyl)biphenyl-4-yl]-1,4-diazepane-1-carboxylate was prepared according to the procedure described in example 4-1 starting with commercially available tert-butyl 4-(5-bromo-3-cyanopyridin-2-yl)-1,4-diazepane-1-carboxylate in place of tert-butyl 4-[4-(4,4,5,5-tetramethyl-1,3,2-dioxaborolan-2-yl)phenyl]piperazine-1-carboxylate and omitting the final step. HRMS m/z (M+H) 458.2209 found, 458.2210 required.

Example 8-2 tert-butyl 4-{3-cyano-5-[4-(dimethylcarbamoyl)-3-methoxyphenyl]pyridin-2-yl}piperazine-1-carboxylate

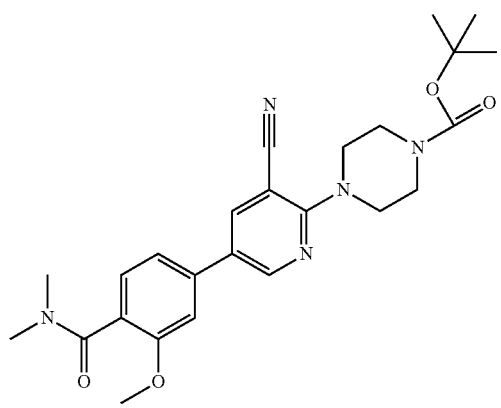 [SMILES: COc1cc(-c2cnc(N3CCN(C(=O)OC(C)(C)C)CC3)c(C#N)c2)ccc1C(=O)N(C)C]

tert-butyl 4-{3-cyano-5-[4-(dimethylcarbamoyl)-3-methoxyphenyl]pyridin-2-yl}piperazine-1-carboxylate was prepared according to example 7-1 using 4-bromo-2-methoxy-N,N-dimethylbenzamide in place of 4-bromo-2,6-dichloro-N,N-dimethylbenzamide in step 3. HRMS m/z (M+H) 466.2447 found, 458.2454 required.

Example 8-3 tert-butyl 3-[3'-chloro-4'-(dimethylcarbamoyl)biphenyl-4-yl]-3,8-diazabicyclo[3.2.1]octane-8-carboxylate

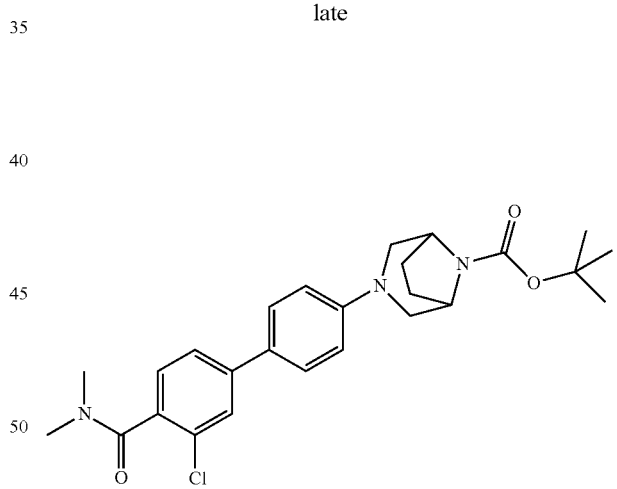

tert-butyl 3-[3'-chloro-4'-(dimethylcarbamoyl)biphenyl-4-yl]-3,8-diazabicyclo[3.2.1]octane-8-carboxylate was prepared according to example 4-3 starting with tert-butyl 3,8-diazabicyclo[3.2.1]octane-8-carboxylate in place of tert-butyl 2,5-diazabicyclo[2.2.2]octane-2-carboxylate in step 1 and omitting the last step. HRMS m/z (M+H) 470.2205 found, 470.2210 required.

Example 8-4 tert-butyl 5-[3'-chloro-4'-(dimethylcarbamoyl)biphenyl-4-yl]-2,5-diazabicyclo[2.2.2]octane-2-carboxylate

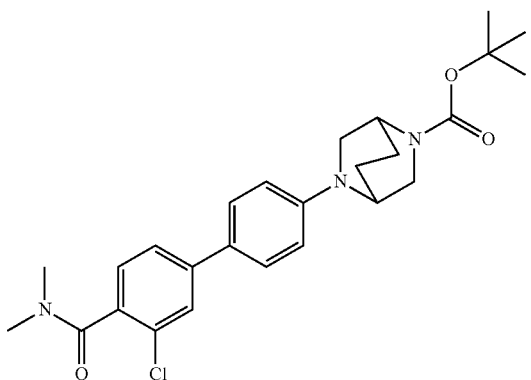 [SMILES: CN(C)C(=O)c1ccc(-c2ccc(N3CC4CCC3CN4C(=O)OC(C)(C)C)cc2)cc1Cl]

tert-butyl 5-[3'-chloro-4'-(dimethylcarbamoyl)biphenyl-4-yl]-2,5-diazabicyclo[2.2.2]octane-2-carboxylate was prepared according to example 4-3 omitting the last step. HRMS m/z (M+H) 470.2204 found, 470.2210 required.

Example 8-9 tert-butyl 4-{3-cyano-5-[4-(dimethylcarbamoyl)-3-(trifluoromethyl)phenyl]pyridin-2-yl}piperazine-1-carboxylate

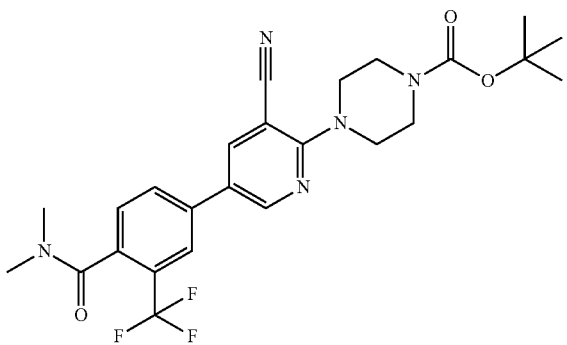 [SMILES: CN(C)C(=O)c1ccc(-c2cnc(N3CCN(C(=O)OC(C)(C)C)CC3)c(C#N)c2)cc1C(F)(F)F]

tert-butyl 4-{3-cyano-5-[4-(dimethylcarbamoyl)-3-(trifluoromethyl)phenyl]pyridin-2-yl}piperazine-1-carboxylate was prepared according to example 7-1 using 4-bromo-2-trifluoromethyl-N,N-dimethylbenzamide in place of 4-bromo-2,6-dichloro-N,N-dimethylbenzamide in step 3. LRMS m/z (M+H) 504.4 found, 504.2 required.

Example 8-10 tert-butyl 3-[3,3'-dichloro-4'-(dimethylcarbamoyl)biphenyl-4-yl]-3,8-diazabicyclo[3.2.1]octane-8-carboxylate

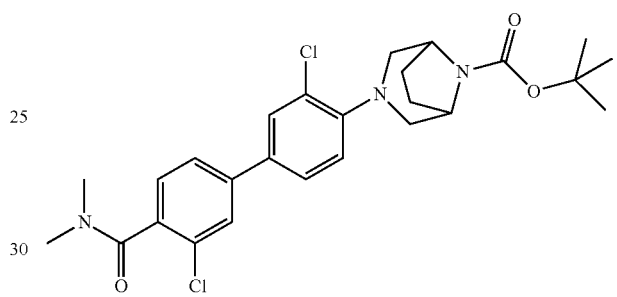

tert-butyl 3-[3,3'-dichloro-4'-(dimethylcarbamoyl)biphenyl-4-yl]-3,8-diazabicyclo[3.2.1]octane-8-carboxylate was prepared according to example 4-3 starting with tert-butyl 3,8-diazabicyclo[3.2.1]octane-8-carboxylate in place of tert-butyl 2,5-diazabicyclo[2.2.2]octane-2-carboxylate in step 1. HRMS m/z (M+H) 504.1815 found, 504.1821 required.

The following examples were prepared according to procedures described in example 1-1 using the appropriate intermediate A-3 in place of tert-butyl 4-(5-bromo-3-cyanopyridin-2-yl)piperazine-1-carboxylate.

TABLE 8

| Example | Structure | IUPAC Name | Exact Mass [M + H]+ |
|---|---|---|---|
| 8-5 | 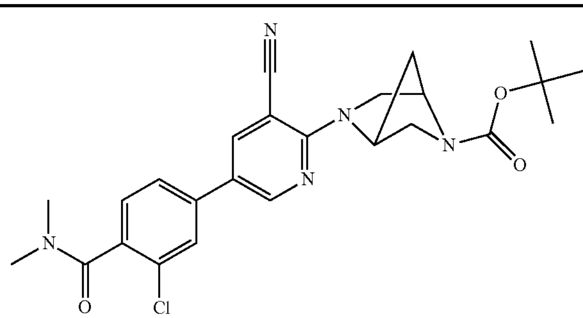 | tert-butyl 5-{5-[3-chloro-4-(dimethylcarbamoyl)phenyl]-3-cyanopyridin-2-yl}-2,5-diazabicyclo[2.2.1]heptane-2-carboxylate | Calc'd 482.2, found 482.1956 |

TABLE 8-continued

| Example | Structure | IUPAC Name | Exact Mass [M + H]+ |
|---|---|---|---|
| 8-6 | 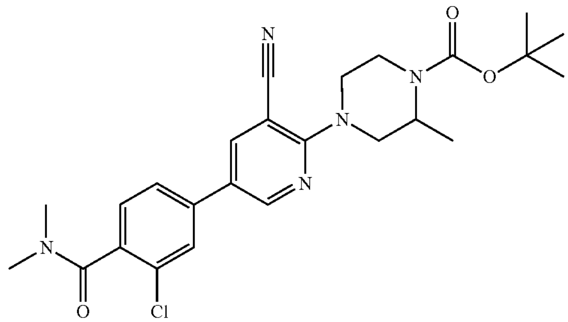 [SMILES: CC1CN(c2ncc(-c3ccc(C(=O)N(C)C)c(Cl)c3)cc2C#N)CCN1C(=O)OC(C)(C)C] | tert-butyl 4-{5-[3-chloro-4-(dimethylcarbamoyl)phenyl]-3-cyanopyridin-2-yl}-2-methylpiperazine-1-carboxylate | Calc'd 484.2, found 484.4 |
| 8-7 | 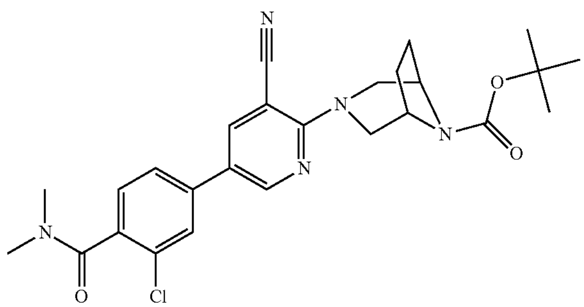 [SMILES: CN(C)C(=O)c1ccc(-c2cnc(N3CC4CCC(C3)N4C(=O)OC(C)(C)C)c(C#N)c2)cc1Cl] | tert-butyl 3-{5-[3-chloro-4-(dimethylcarbamoyl)phenyl]-3-cyanopyridin-2-yl}-3,8-diazabicyclo[3.2.1]octane-8-carboxylate | Calc'd 496.2, found |
| 8-8 | 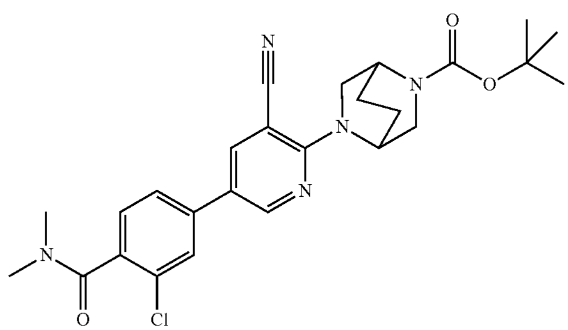 [SMILES: CN(C)C(=O)c1ccc(-c2cnc(N3CC4CCC3CN4C(=O)OC(C)(C)C)c(C#N)c2)cc1Cl] | tert-butyl 5-{5-[3-chloro-4-(dimethylcarbamoyl)phenyl]-3-cyanopyridin-2-yl}-2,5-diazabicyclo[2.2.2]octane-2-carboxylate | Calc'd 496.2, found |
| 8-11 | 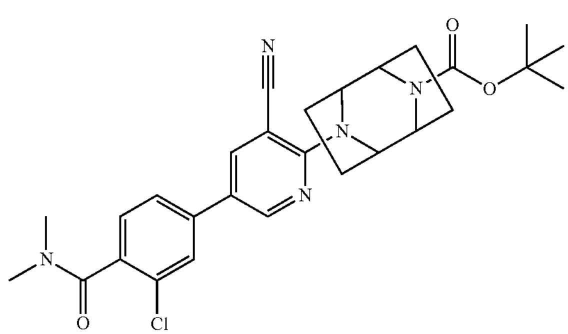 [SMILES: CN(C)C(=O)c1ccc(-c2cnc(N3C4CCC3C3CCC4N3C(=O)OC(C)(C)C)c(C#N)c2)cc1Cl] | tert-butyl 10-{5-[3-chloro-4-(dimethylcarbamoyl)phenyl]-3-cyanopyridin-2-yl}-9,10-diazatricyclo[4.2.1.1~2,5~]decane-9-carboxylate | Calc'd 522.2, found 522.4 |

TABLE 8-continued

| Example | Structure | IUPAC Name | Exact Mass [M + H]+ |
|---|---|---|---|
| 8-12 | 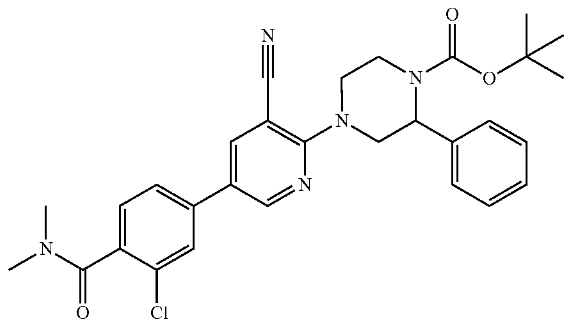 [SMILES: CN(C)C(=O)c1ccc(-c2cnc(N3CCN(C(=O)OC(C)(C)C)C(c4ccccc4)C3)c(C#N)c2)cc1Cl] | tert-butyl 4-{5-[3-chloro-4-(dimethylcarbamoyl)phenyl]-3-cyanopyridin-2-yl}-2-phenylpiperazine-1-carboxylate | Calc'd 546.2, found 546.4 |
| 8-13 | 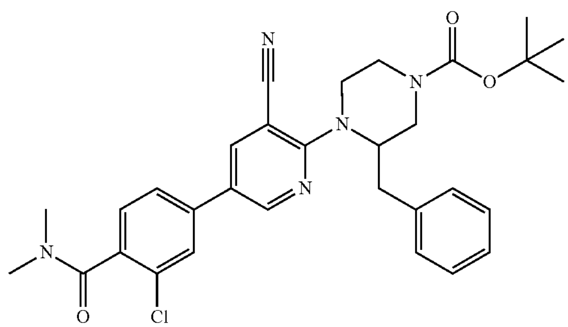 [SMILES: CN(C)C(=O)c1ccc(-c2cnc(N3CCN(C(=O)OC(C)(C)C)CC3Cc3ccccc3)c(C#N)c2)cc1Cl] | tert-butyl 3-benzyl-4-{5-[3-chloro-4-(dimethylcarbamoyl)phenyl]-3-cyanopyridin-2-yl}piperazine-1-carboxylate | Calc'd 560.2, found 560.4 |

Example 8-14

3-chloro-4'-{8-[(2,6-dichlorophenyl)sulfonyl]-3,8-diazabicyclo[3.2.1]oct-3-yl}-N,N-dimethylbiphenyl-4-carboxamide

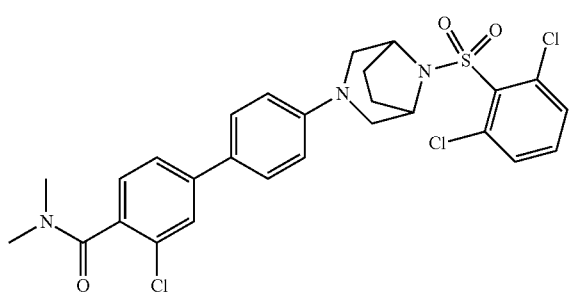 [SMILES: CN(C)C(=O)c1ccc(-c2ccc(N3CC4CCC(C3)N4S(=O)(=O)c3c(Cl)cccc3Cl)cc2)cc1Cl]

tert-butyl 3-[3'-chloro-4'-(dimethylcarbamoyl)biphenyl-4-yl]-3,8-diazabicyclo[3.2.1]octane-8-carboxylate (example 8-3) was deprotected and reacted with 2,6-dichlorobenzenesulfonyl chloride according to the procedure in example 1-1. HRMS m/z (M+H) 578.0827 found, 578.0839 required.

Example 8-15 tert-butyl 4-[3'-chloro-3-cyano-4'-(dimethylcarbamoyl)biphenyl-4-yl]piperazine-1-carboxylate

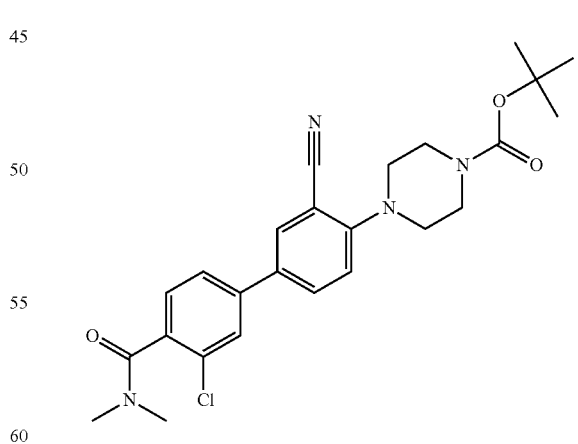

tert-butyl 4-[3'-chloro-3-cyano-4'-(dimethylcarbamoyl)biphenyl-4-yl]piperazine-1-carboxylate was prepared according to the procedures in example 1-1, step 1 using commercially available tert-butyl 4-(4-bromo-2-cyanophenyl)piperazine-1-carboxylate. LRMS m/z (M+H) 469.2 found, 469.1 required.

Example 8-16

3,3'-dichloro-4'-{8-[(2,6-dichlorophenyl)sulfonyl]-3,8-diazabicyclo[3.2.1]oct-3-yl}-N,N-dimethylbiphenyl-4-carboxamide

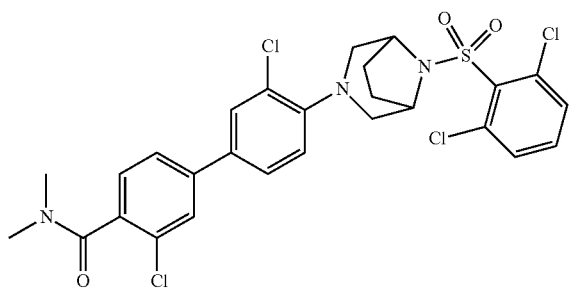 [SMILES: CN(C)C(=O)c1ccc(-c2ccc(N3CC4CCC(C3)N4S(=O)(=O)c3c(Cl)cccc3Cl)c(Cl)c2)cc1Cl]

tert-butyl 3-[3,3'-dichloro-4'-(dimethylcarbamoyl)biphenyl-4-yl]-3,8-diazabicyclo[3.2.1]octane-8-carboxylate (example 8-10) was deprotected and reacted with 2,6-dichlorobenzenesulfonyl chloride according to the procedure in example 1-1. HRMS m/z (M+H) 612.0441 found, 612.0449 required.

Example 8-17 tert-butyl 4-{3-cyano-5-[4-(dimethylcarbamoyl)-3-ethylphenyl]pyridin-2-yl}piperazine-1-carboxylate

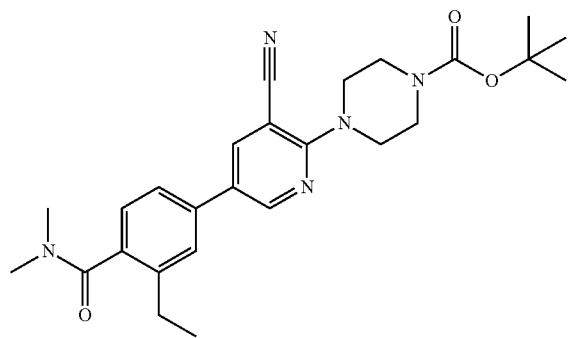 [SMILES: CCc1cc(-c2cnc(N3CCN(C(=O)OC(C)(C)C)CC3)c(C#N)c2)ccc1C(=O)N(C)C]

tert-butyl 4-{3-cyano-5-[4-(dimethylcarbamoyl)-3-ethylphenyl]pyridin-2-yl}piperazine-1-carboxylate was prepared according to the procedure in example 9-4 using potassium ethyltrifluoroborate in place of cyclopropylboronic acid-MIDA ester. HRMS m/z (M+H) 464.2658 found, 464.2662 required.

Example 9-1 tert-butyl 4-(3-chloro-5-(3-chloro-4-(dimethylcarbamoyl)phenyl)pyridin-2-yl)piperazine-1-carboxylate

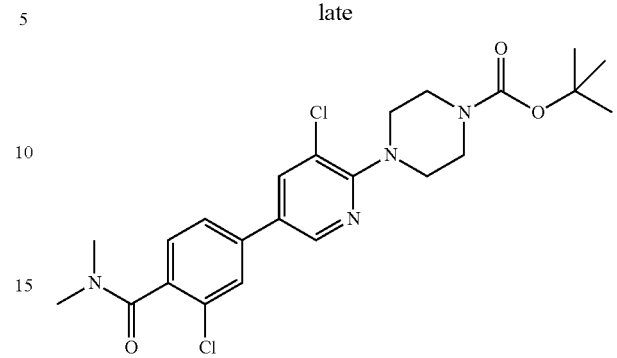

To a solution of 2,3-dichloro-5-bromopyridine (1 g, 4.4 mmol) in ACN (5 mL) was added DIEA (0.92 mL, 5.29 mmol) and tert-butyl piperazine-1-carboxylate (0.9 g, 4.85 mmol). The mixture was then heated to 200 C under microwave irradiation for 25 min. The reaction was then diluted with EtOAc (10 mL) and the formed solid was removed by filtration. The filtrate was then concentrated in vacuo and purified by silica gel chromatography (gradient elution, 0-20% EtOAc/hexanes) to yield tert-butyl 4-(5-bromo-3-chloropyridin-2-yl)piperazine-1-carboxylate. $^1$H NMR (400 MHz, CDCl$_3$): δ 8.20 (d, J=2.0 Hz, 1H), 7.73 (d, J=2.4 Hz, 1H), 3.56 (m, 4H), 3.28 (m, 4H), 1.40 (s, 9H). LRMS m/z (M+H) 376.0422 found, 376.0425.

To a solution of tert-butyl 4-(5-bromo-3-chloropyridin-2-yl)piperazine-1-carboxylate (640 mg, 1.7 mmol) in ACN (8.5 mL) was added sodium carbonate (2.12 mL, 2M, 4.25 mmol) and (3-chloro-4-(dimethylcarbamoyl)phenyl)boronic acid (464 mg, 2.0 mmol). Nitrogen was then bubbled through the solution for 15 min and (Ph$_3$P)$_2$PdCl$_2$ (47 mg, 0.068 mmol) was added. The reaction was then heated to 80 C for 5 h, cooled to r.t., diluted with EtOAc, filtered through celite, and the solvent was removed in vacuo. The crude material purified by silica gel chromatography (gradient elution, 0-80% EtOAc/hexanes) to yield intermediate tert-butyl 4-(3-chloro-5-(3-chloro-4-(dimethylcarbamoyl)phenyl)pyridin-2-yl)piperazine-1-carboxylate. $^1$H NMR (400 MHz, CDCl$_3$): δ 8.30 (d, J=2.4 Hz, 1H), 7.79 (d, J=2.4 Hz, 1H), 7.54 (d, J=2.0 Hz, 1H), 7.4 (m, 1H), 7.3 (m, 1H), 3.6 (m, 4H), 3.38 (m, 4H), 3.16 (s, 3H), 2.91 (s, 3H), 1.49 (s, 9H). LRMS m/z (M+H) 479.1611 found, 479.1610.

Example 9-2 tert-butyl 4-{5-[3-chloro-4-(dimethylcarbamoyl)phenyl]-3-ethenylpyridin-2-yl}piperazine-1-carboxylate

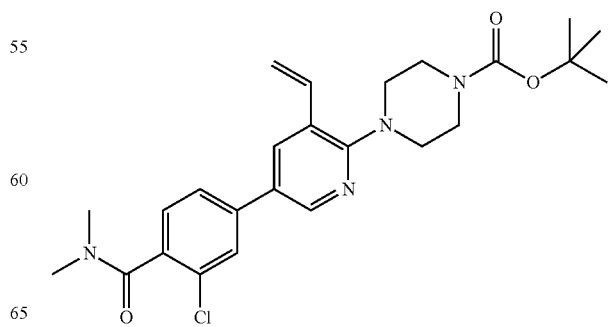

To a solution of intermediate tert-butyl 4-(3-chloro-5-(3-chloro-4-(dimethylcarbamoyl)phenyl)pyridin-2-yl)piperazine-1-carboxylate (50 mg, 0.1 mmol) under nitrogen in dioxane (1.1. mL) was added CsF (35 mg, 0.23 mmol), vinyltri-n-butyltin (46 uL, 0.16 mmol), and bis-triphenylphosphine-palladium (2.7 mg, 0.005 mmol). The mixture was heated to 70 C under nitrogen for 48 h, concentrated in vacuo, and the crude material was purified by silica gel chromotography (gradient elution, 0-100% EtOAc/hexanes) to yield a mixture of mono- and bis-vinylated products. This mixture was then purified by reverse phase chromatography (20-95% ACN/water with 0.1% TFA) to yield the bis-vinylated side product and tert-butyl 4-{5-[3-chloro-4-(dimethylcarbamoyl)phenyl]-3-ethenylpyridine-2-yl}piperazine-1-carboxylate as the free base after extraction from EtOAc/NaHCO$_3$. 1H NMR (400 MHz, CDCl$_3$): δ 8.39 (d, J=2.4 Hz, 1H), 7.82 (d, J=2.4 Hz, 1H), 7.54 (d, J=1.6 Hz, 1H), 7.5 (m, 1H), 7.37 (m, 1H), 6.8 (m, 1H), 5.8 (dd, J=17.8, 0.8 Hz, 1H), 5.4 (dd, J=11.0, 0.8 Hz, 1H), 3.65 (m, 2H), 3.58 (m, 2H), 3.43 (m, 2H), 3.26 (m, 2H), 3.16 (s, 3H), 2.93 (s, 3H), 1.49 (s, 9H).

LRMS m/z (M+H) 463.2704 found, 463.2696.

Example 9-3 tert-butyl 4-{5-[3-chloro-4-(dimethylcarbamoyl)phenyl]-3-(hydroxymethyl)pyridin-2-yl}piperazine-1-carboxylate

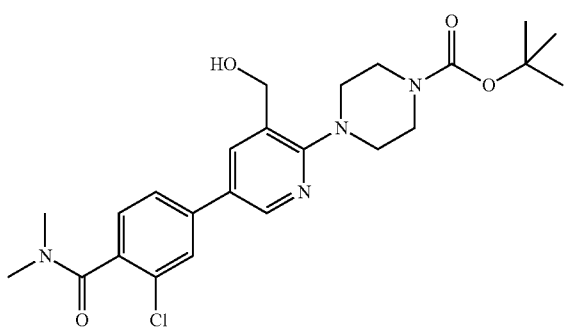 [SMILES: CN(C)C(=O)c1ccc(-c2cnc(N3CCN(C(=O)OC(C)(C)C)CC3)c(CO)c2)cc1Cl]

tert-butyl 4-(5-(3-chloro-4-(dimethylcarbamoyl)phenyl)-3-formylpyridine-2-yl)piperazine-1-carboxylate was prepared according to the procedure in example 1-1 using 5-bromo-2-chloronicotinaldehyde. LRMS m/z (M+H) 473.1950 found, 473.1949.

To a solution of tert-butyl 4-(5-(3-chloro-4-(dimethylcarbamoyl)phenyl)-3-formylpyridine-2-yl)piperazine-1-carboxylate (25 mg, 0.05 mmol) in EtOH (0.5 mL) was added sodium borohydride (2 mg, 0.05 mmol) at r.t. After 45 min, the reaction was diluted with EtOAc and extracted with 5% KHSO$_4$. The organic layer was dried over MgSO$_4$ and the solvent was removed in vacuo. The crude material was purified on silica (gradient elution, 0-100% EtOAc/hexanes) to yield the title compound. $^1$H NMR (400 MHz, CDCl$_3$): δ 8.46 (d, J=2.4 Hz, 1H), 7.85 (d, J=2.4 Hz, 1H), 7.58 (d, J=1.6 Hz, 1H), 7.48 (m, 1H), 7.38 (d, J=8 Hz, 1H), 4.80 (s, 2H), 3.61 (m, 4H), 3.18 (m, 4H), 3.16 (s, 3H), 2.92 (s, 3H), 1.49 (s, 9H). LRMS m/z (M+H) 475.2107 found, 475.2104.

Example 9-4 tert-butyl 4-{3-cyano-5-[3-cyclopropyl-4-(dimethylcarbamoyl)phenyl]pyridin-2-yl}piperazine-1-carboxylate

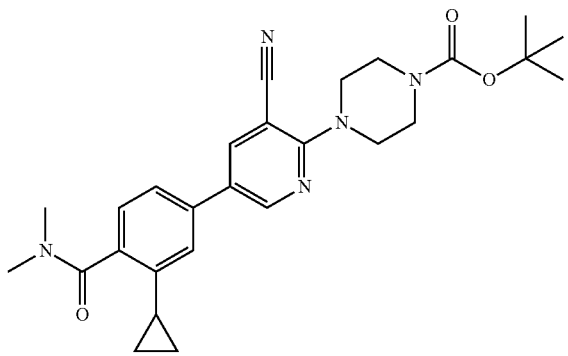 [SMILES: CN(C)C(=O)c1ccc(-c2cnc(N3CCN(C(=O)OC(C)(C)C)CC3)c(C#N)c2)cc1C1CC1]

To a solution of tert-butyl 4-{5-[3-chloro-4-(dimethylcarbamoyl)phenyl]-3-cyanopyridin-2-yl}piperazine-1-carboxylate (50 mg, 0.1 mmol) in dioxane (1.5 mL) was added cyclopropylboronic acid-MIDA ester (25 mg, 0.13 mmol) and degassed potassium phosphate (0.56 mL, 0.8 mmol, 30 wt % in water) and bis-tri(t-butylphosphine)palladium (2.7 mg, 0.005 mmol). The mixture was then sealed and heated to 95 C overnight (16 h), and then diluted with EtOAc and extracted with 5% KHSO$_4$. The organic layer was dried over MgSO$_4$ and the solvent was removed in vacuo. The crude product was purified on silica (gradient elution, 0-80% EtOAc/hexanes) to yield the title compound. $^1$H NMR (400 MHz, CDCl$_3$): δ 8.53 (br s, 1H), 7.93 (br s, 1H), 7.3 (m, 2H), 6.96 (s, 1H), 3.73 (m, 4H), 3.61 (m, 4H), 3.17 (s, 3H), 2.93 (s, 3H), 1.94 (m, 1H), 1.49 (s, 9H), 1.25 (m, 2H), 1.0 (m, 2H). LRMS m/z (M+H) 476.2656 found, 476.2663.

Example 9-5 tert-butyl 4-{3-cyano-5-[3-cyclopropyl-4-(dimethylcarbamoyl)phenyl]pyridin-2-yl}piperazine-1-carboxylate

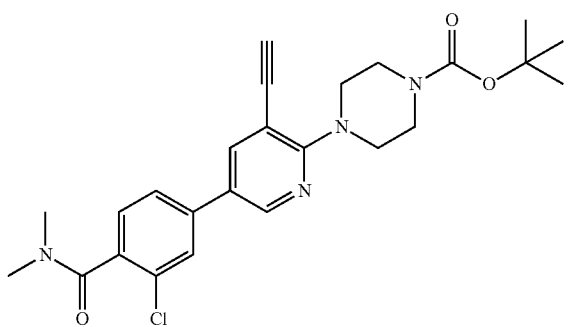 [SMILES: C#Cc1cc(-c2ccc(C(=O)N(C)C)c(Cl)c2)cnc1N1CCN(C(=O)OC(C)(C)C)CC1]

To a solution of tert-butyl 4-(5-(3-chloro-4-(dimethylcarbamoyl)phenyl)-3-formylpyridin-2-yl)piperazine-1-carboxylate (29 mg, 0.06 mmol) in MeOH (1 mL) was added potassium carbonate (17 mg, 0.12 mmol) and dimethyl (1-diazo-2-oxopropyl)phosphonate (14 mg, 0.07 mmol) at r.t. After stirring overnight, the MeOH was removed in vacuo and the solids were taken up in EtOAc and extracted with water. The water layer was then washed with EtOAc and the combined organic layers were dried over $MgSO_4$ and the solvent was removed in vacuo. The crude material was purified on silica (gradient elution, 0-100% EtOAc/hexanes) to yield the title compound. $^1$H NMR (400 MHz, $CDCl_3$): δ 8.40 (d, J=2.4 Hz, 1H), 7.87 (d, J=2.4 Hz, 1H), 7.54 (s, 1H), 7.38 (m, 1H), 7.36 (m, 1H), 3.64 (m, 4H), 3.57 (m, 4H), 3.16 (s, 3H), 2.92 (s, 3H), 2.0 (s, 1H), 1.49 (s, 9H). LRMS m/z (M+H) 469.2001 found, 469.2014.

Potency (Inflection Point, IP) and efficacy (Emax) are evaluated via compound-induced co-activator recruitment to glutathione-S-transferase (GST) tagged LXRbeta and LXRalpha LBD (ligand binding domain) proteins in relation to reference dual agonist compound T1317 using the LanthaScreen™ TR-FRET Liver X Receptor Coactivator Assays according to manufacturer's instructions (Invitrogen catalog number pv4658.pps and pv4655). While running the LanthaScreen™ TR-FRET Liver X Receptor Coactivator Assay, LXR alpha-LBD or LXR beta-LBD was added to ligand test compounds followed by addition of a mixture of a fluorescein-labelled coactivator peptide and terbium-conjugated anti-GST antibody. After an incubation period at room temperature, TR-FRET (time-resolved fluorescence resonance energy transfer) was measured using a filter-based instrument capable of TR-FRET, e.g. PerkinElmer Envision. When the terbium label on the anti-GST antibody was excited at 340 nm, energy was transferred to the fluorescein label on the coactivator peptide and detected as emission at 520 nm, providing an indication of ligand binding that enables ligand-dependent recruitment of coactivator peptide, and the ratio of 520 nm:495 nm is calculated and is used to determine the ligands potencies and efficacies from appropriate dose response curves of the compound. IP and % Emax values for compounds of the invention are provided below in the Table 1 below.

TABLE 1

| Example | LXR beta IP (nM) | LXR beta activity at max dose (%) (Emax) | LXR alpha IP (nM) | LXR alpha activity at max dose (%) (Emax) |
|---|---|---|---|---|
| 1-1 | 7 | 124 | 690 | 55 |
| 1-2 | 543 | 68 | 22530 | 37 |
| 1-3 | 200 | 93 | 10450 | 52 |
| 1-4 | 279 | 81 | 49010 | 44 |
| 1-5 | 939 | 85 | 60490 | 31 |
| 1-6 | 31 | 77 | 6844 | 23 |
| 1-7 | 337 | 79 | 14210 | 39 |
| 1-8 | 17 | 89 | 12060 | 34 |
| 1-9 | 22 | 123 | 618 | 46 |
| 1-10 | 162 | 65 | 733 | 18 |
| 1-11 | 8 | 108 | 3411 | 51 |
| 1-12 | 28 | 97 | 7405 | 27 |
| 1-13 | 11 | 127 | 1002 | 60 |
| 1-14 | 20 | 99 | 1054 | 37 |
| 1-15 | 437 | 86 | 19480 | 43 |
| 1-16 | 144 | 69 | 50530 | 63 |
| 1-17 | 43 | 98 | 4839 | 36 |
| 1-18 | 151 | 126 | 1670 | 62 |
| 2-1 | 212 | 40 | 8855 | 23 |
| 2-2 | 1 | 102 | 617 | 61 |
| 2-3 | 56 | 105 | 4812 | 67 |
| 2-4 | 95 | 79 | 12840 | 44 |
| 2-5 | 109 | 97 | 11100 | 62 |
| 2-6 | 1563 | 49 | No IP | 16 |
| 2-7 | 50 | 102 | 6790 | 54 |
| 2-8 | 4173 | 46 | No IP | 5 |
| 2-9 | 245 | 99 | 16570 | 42 |
| 2-10 | 2331 | 63 | No IP | 10 |
| 2-11 | 1059 | 77 | 27950 | 30 |
| 2-12 | 27 | 79 | 1748 | 43 |
| 2-13 | 57 | 108 | 8053 | 50 |
| 2-14 | 1347 | 77 | No IP | 23 |
| 2-15 | 171 | 101 | 13100 | 58 |
| 2-16 | 242 | 94 | 12980 | 58 |
| 2-17 | 27 | 95 | 4360 | 27 |
| 2-18 | 15 | 99 | 16360 | 43 |
| 2-19 | 27 | 77 | 60230 | 27 |
| 2-20 | 138 | 102 | 6071 | 60 |
| 2-21 | 147 | 59 | 6286 | 41 |
| 2-22 | 186 | 83 | 29970 | 54 |
| 2-23 | 43 | 97 | 1138 | 47 |
| 2-24 | 463 | 104 | 29570 | 42 |
| 2-25 | 94 | 100 | 4153 | 53 |
| 2-26 | 43 | 84 | 1988 | 25 |
| 2-27 | 226 | 80 | No IP | 14 |
| 2-28 | 12 | 98 | 1926 | 30 |
| 2-29 | 15 | 93 | 4233 | 57 |
| 2-30 | 6 | 125 | 5294 | 66 |
| 2-31 | 307 | 68 | 7290 | 12 |
| 2-32 | 4 | 98 | 3053 | 37 |
| 2-33 | 162 | 115 | 3294 | 27 |
| 2-34 | 25 | 88 | 12740 | 49 |
| 2-35 | 75 | 70 | 54110 | 62 |
| 2-36 | 205 | 81 | 5134 | 36 |
| 2-37 | 735 | 58 | 97630 | 55 |
| 2-38 | 13 | 69 | 292 | 18 |
| 3-1 | 12 | 119 | 2313 | 60 |
| 3-2 | 1563 | 41 | No IP | 19 |
| 3-3 | 217 | 62 | 19840 | 42 |
| 3-4 | 87 | 86 | 2820 | 122 |
| 3-5 | 56 | 97 | 1338 | 57 |
| 3-6 | 21 | 92 | 6609 | 50 |
| 3-7 | 36 | 85 | 8585 | 41 |
| 3-8 | 210 | 65 | 24610 | 65 |
| 3-9 | 155 | 84 | 8905 | 39 |
| 3-10 | 68 | 75 | 23460 | 79 |
| 3-11 | 79 | 96 | 1195 | 39 |
| 3-12 | 39 | 55 | 4326 | 30 |
| 3-13 | 105 | 31 | No IP | 16 |
| 3-14 | 57 | 74 | 4834 | 26 |
| 4-1 | 833 | 90 | | |
| 4-2 | 2325 | 93 | No IP | 24 |
| 4-3 | 39 | 87 | 1572 | 79 |
| 4-4 | 98 | 75 | 1306 | 44 |
| 4-5 | 39 | 88 | 618 | 63 |
| 4-6 | 188 | 39 | 1599 | 16 |
| 4-7 | 106 | 83 | 1277 | 64 |
| 4-8 | 2818 | 101 | 10530 | 38 |
| 4-9 | 597 | 96 | 4133 | 51 |
| 4-10 | 94 | 77 | 1264 | 30 |
| 4-11 | 238 | 82 | 5471 | 55 |
| 4-12 | 881 | 83 | No IP | 20 |
| 4-13 | 380 | 97 | 5727 | 29 |
| 4-14 | 549 | 88 | 9809 | 25 |
| 4-15 | 1673 | 85 | No IP | 16 |
| 4-16 | 4160 | 77 | No IP | 19 |
| 4-17 | 1389 | 80 | No IP | 9 |
| 4-18 | 259 | 65 | 1290 | 20 |
| 4-19 | 1267 | 93 | 16940 | 20 |
| 5-1 | 40 | 80 | 1260 | 68 |
| 5-2 | 94 | 94 | 2025 | 66 |
| 5-3 | 176 | 82 | 33730 | 76 |
| 5-4 | 1517 | 71 | 21160 | 39 |
| 5-5 | 88 | 76 | 2675 | 54 |
| 5-6 | 435 | 77 | 8778 | 43 |
| 5-7 | 82 | 69 | 2656 | 39 |
| 5-8 | 170 | 91 | 14920 | 58 |
| 5-9 | 274 | 71 | 14310 | 48 |
| 5-10 | 1086 | 63 | 2714 | 37 |
| 5-11 | 300 | 59 | 11730 | 89 |
| 5-12 | 481 | 60 | 8437 | 37 |
| 5-13 | 262 | 62 | 6898 | 44 |
| 5-14 | 332 | 63 | 12560 | 38 |
| 5-15 | 261 | 70 | 6870 | 42 |

TABLE 1-continued

| Example | LXR beta IP (nM) | LXR beta activity at max dose (%) (Emax) | LXR alpha IP (nM) | LXR alpha activity at max dose (%) (Emax) |
|---|---|---|---|---|
| 5-16 | 43 | 91 | 1457 | 68 |
| 5-17 | 415 | 47 | No IP | 17 |
| 5-18 | 301 | 70 | 8604 | 40 |
| 5-19 | 102 | 93 | 2977 | 68 |
| 5-20 | 565 | 55 | 4072 | 31 |
| 5-21 | 931 | 81 | 9244 | 37 |
| 5-22 | 382 | 65 | 9698 | 34 |
| 5-23 | 282 | 74 | 19310 | 46 |
| 5-24 | 118 | 71 | 8458 | 52 |
| 5-25 | 741 | 56 | 7894 | 36 |
| 5-26 | 4268 | 74 | 25950 | 48 |
| 5-27 | 705 | 76 | No IP | 17 |
| 5-28 | 164 | 84 | 3713 | 71 |
| 5-29 | 1172 | 75 | 6577 | 30 |
| 5-30 | 1186 | 73 | 10050 | 57 |
| 5-31 | 1859 | 67 | 8534 | 27 |
| 5-32 | 2208 | 78 | 23930 | 44 |
| 5-33 | 703 | 78 | 4827 | 52 |
| 6-1 | 2 | 101 | 1169 | 33 |
| 6-2 | 329 | 98 | 11250 | 34 |
| 6-3 | 30 | 113 | 2423 | 33 |
| 7-1 | 3 | 73 | 186 | 53 |
| 7-2 | 32 | 88 | 2039 | 30 |
| 7-3 | 13 | 67 | 151 | 21 |
| 7-4 | 49 | 62 | 671 | 11 |
| 7-5 | 12 | 93 | 929 | 41 |
| 7-6 | 34 | 79 | 760 | 28 |
| 8-1 | 63 | 86 | 936 | 55 |
| 8-2 | 846 | 73 | 25840 | 28 |
| 8-3 | 189 | 87 | 11730 | 64 |
| 8-4 | 32 | 78 | 1502 | 73 |
| 8-5 | 252 | 53 | 16800 | 37 |
| 8-6 | 57 | 78 | 12740 | 68 |
| 8-7 | 31 | 71 | 1637 | 52 |
| 8-8 | 64 | 68 | 882 | 38 |
| 8-9 | 1660 | 73 | 10850 | 30 |
| 8-10 | 70 | 63 | 660 | 64 |
| 8-11 | 1052 | 57 | 10880 | 41 |
| 8-12 | 6 | 70 | 954 | 40 |
| 8-13 | 18 | 120 | 538 | 78 |
| 8-14 | 76 | 118 | 3471 | 37 |
| 8-15 | 177 | 81 | 3890 | 54 |
| 8-16 | 37 | 82 | 569 | 79 |
| 8-17 | 424 | 71 | 7466 | 41 |
| 9-1 | 55 | 61 | 1346 | 48 |
| 9-2 | 161 | 49 | 3445 | 38 |
| 9-3 | 730 | 57 | 30090 | 34 |
| 9-4 | 676 | 68 | 4632 | 39 |
| 9-5 | 62 | 59 | 2361 | 49 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

We claim:

1. A compound having the structural Formula (I):

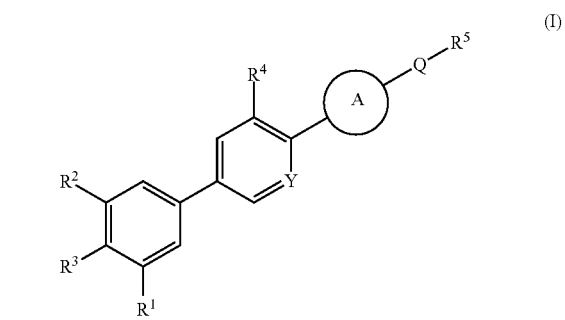

or a pharmaceutically acceptable salt thereof, wherein:
the moiety

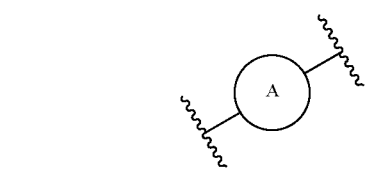

is a divalent moiety selected from the group consisting of

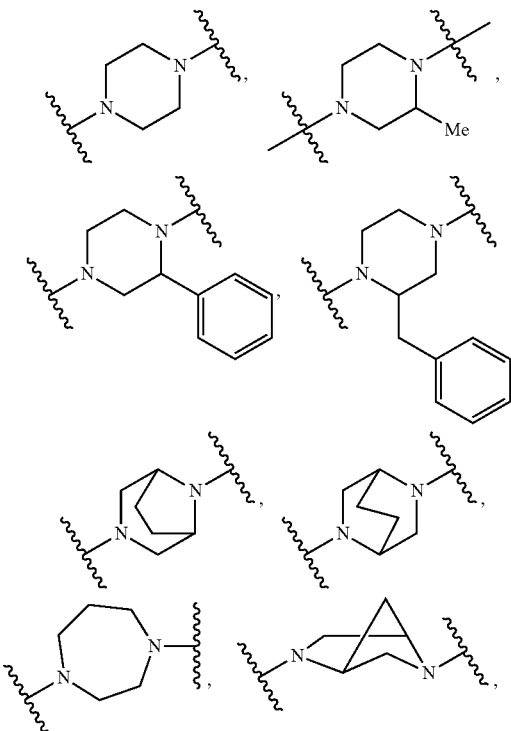

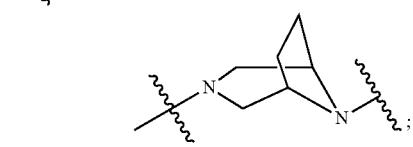

Y is selected from the group consisting of C(H), C(F), C(Cl), and N,

R$^1$ is selected from the group consisting of halogen, CN, OH, —(C$_3$-C$_6$)cycloalkyl, —(C$_1$-C$_4$)alkyl, —(C$_1$-C$_4$)haloalkyl, and —(C$_1$-C$_4$)alkoxy;

R$^2$ is selected from the group consisting of H and halogen;

R$^3$ is a moiety selected from the group consisting of:
—C(O)N(R$^{N1}$)(R$^{N2}$),
wherein R$^{N1}$ and R$^{N2}$ are each independently selected from the group consisting of H, —NH2, —NH(C$_1$-C$_4$alkyl), —N(C$_1$-C$_4$alkyl)$_2$, —(C$_1$-C$_4$alkyl), —(C$_2$-C$_6$)alkenyl, —(C$_1$-C$_4$)alkoxy, —(C$_3$-C$_6$)cycloalkyl, —CH$_2$(C$_3$-C$_6$)cycloalkyl, phenyl, —(C$_1$-C$_4$)alkyl-phenyl, heterocycloalkyl, —(C$_1$-C$_4$)alkylheterocycloalkyl, heteroaryl, and —(C$_1$-C$_4$)alkylheteroaryl, wherein said —(C$_1$-C$_4$)alkyl, —(C$_1$-C$_4$)alkoxy, phenyl, —(C$_3$-C$_6$)cycloalkyl, heterocycloalkyl, and heteroaryl portions of said R$^{N1}$ and R$^{N2}$ are unsubstituted or substituted with one, two, or three groups independently selected from the group consisting of OH, CN, halogen, —NH$_2$, —N(C$_1$-C$_4$alkyl)$_2$, —NH(C$_1$-C$_4$alkyl), —(C$_1$-C$_4$)alkoxy, optionally substituted phenyl, and optionally substituted heteroaryl, wherein said optional substituents on said phenyl are 1 to 3 groups independently selected from OH, CN, —(C$_1$-C$_4$)alkyl, —(C$_1$-C$_4$)alkoxy, and wherein said optional substituents on said heteroaryl are 1 to 3 groups independently selected from —(C$_1$-C$_4$)alkyl, and —(C$_1$-C$_4$)alkoxyl, or, alternatively, R$^{N1}$ and R$^{N2}$, together with the nitrogen atom to which they are shown attached, form a 4-, 5-, or 6-membered heteroaryl or partially unsaturated or fully saturated heterocyclic ring comprising (including said nitrogen atom) 1, 2, or 3 ring heteroatoms independently selected from the group consisting of N, O, and S, wherein said heterocyclic ring is unsubstituted or substituted with one, two, or three substitutents independently selected from the group consisting of halo, OH, CN, —(C$_1$-C$_4$)alkyl, amino-substituted —(C$_1$-C$_4$)alkyl, wherein said amino is one, two, or three groups independently selected from the group consisting of —NH$_2$, —N(C$_1$-C$_4$alkyl)$_2$, and —NH(C$_1$-C$_4$alkyl), —(C$_1$-C$_4$)haloalkyl, —(C$_1$-C$_4$)alkyl-OH, phenyl, benzyl, heteroaryl, and —(C$_1$-C$_4$)alkylheteroaryl;

R$^4$ is selected from the group consisting of H, —CN, halogen, —(C$_1$-C$_4$)alkyl, —(C$_2$-C$_4$)alkenyl, and —(C$_2$-C$_4$)alkynyl, wherein said —(C$_1$-C$_4$)alkyl is optionally substituted with hydroxyl;

Q is selected from the group consisting of —S(O)$_2$—, —C(O)—, —C(O)O—, and —C(O)C(O)—; and R$^5$ is selected from the group consisting of
—(C$_1$-C$_8$)alkyl, —(C$_1$-C$_8$)haloalkyl, —C(OH)(R$^{5A}$)$_2$, —C(OCH$_3$)(R$^{5A}$)$_2$, phenyl, —(C$_1$-C$_4$)alkyl-phenyl, cycloalkyl, —(C$_1$-C$_4$)alkyl-cycloalkyl, heterocycloalkyl, —(C$_1$-C$_4$)alkylheterocycloalkyl, heteroaryl, and —(C$_1$-C$_4$)alkyl-heteroaryl,
wherein each said phenyl, cycloalkyl, and heteroaryl portion of R$^5$ is unsubstituted or substituted with one, two, or three groups independently selected from the group consisting of halogen, CN, —(C$_1$-C$_6$)alkyl, —(C$_1$-C$_4$)haloalkyl, —O(C$_1$-C$_6$)alkyl, —O(C$_1$-C$_4$)haloalkyl, and
wherein each R$^{5A}$ is independently selected from the group consisting of —(C$_1$-C$_8$)alkyl, —(C$_1$-C$_8$)haloalkyl, phenyl, —(C$_1$-C$_4$)alkyl-phenyl, and cycloalkyl, wherein said phenyl and said cycloalkyl portion of R$^{5A}$ is unsubstituted or substituted with one, two, or three groups independently selected from the group consisting of halogen, CN, —(C$_1$-C$_6$)alkyl, —(C$_1$-C$_4$)haloalkyl, —O(C$_1$-C$_6$)alkyl, and —O(C$_1$-C$_4$)haloalkyl.

2. The compound of claim 1, wherein:
Y is selected from the group consisting of CH, C(F), C(Cl); and
the moiety

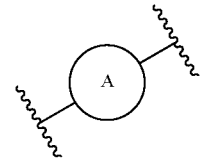

is selected from the group consisting of

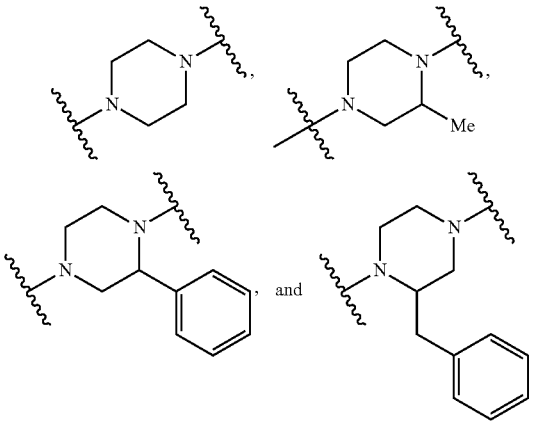

3. The compound of claim 1, wherein:
Y is selected from the group consisting of CH, C(F), C(Cl); and
the moiety

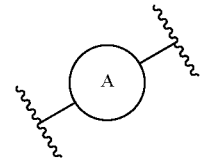

is selected from the group consisting of

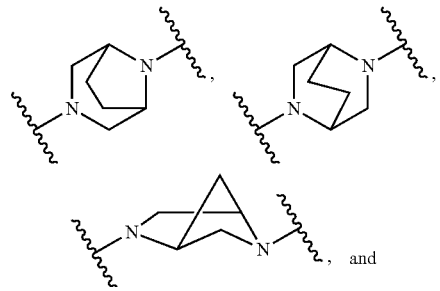

-continued

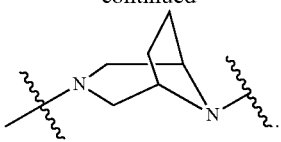

4. The compound according to claim 1, wherein:
Y is selected from the group consisting of CH, C(F), C(Cl); and
the moiety

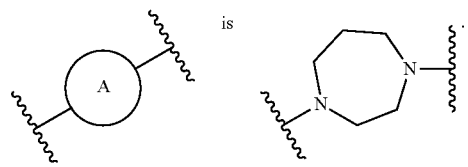

5. The compound of claim 1, wherein:
Y is N; and
the moiety

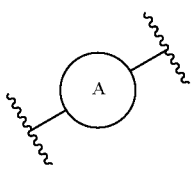

is selected from the group consisting of

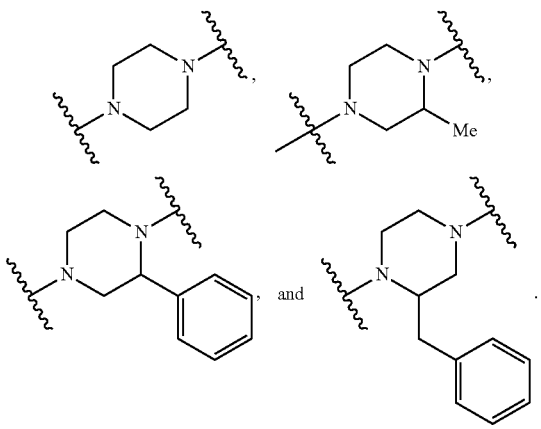

6. The compound according to claim 1, wherein:
Y is N; and
the moiety

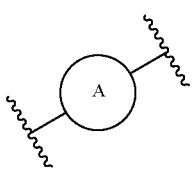

is selected from the group consisting of

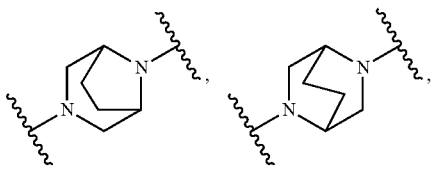

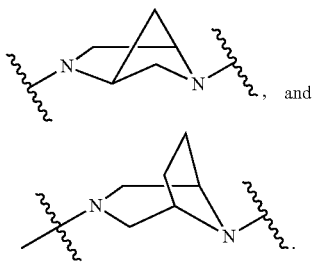

7. The compound according to claim 1, wherein:
Y is N; and
the moiety

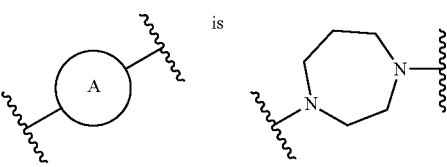

8. The compound according to claim 1, wherein:
$R^{N1}$ is selected from the group consisting of H, $CH_3$, and cyclopropyl; and
$R^{N2}$ is selected from the group consisting of —$NH_2$, —NH($C_1$-$C_4$alkyl), —N($C_1$-$C_4$alkyl)$_2$, —($C_1$-$C_4$)alkyl, —($C_1$-$C_4$)alkenyl, —($C_1$-$C_4$)alkoxyl, and heterocycloalkyl, wherein said —($C_1$-$C_4$)alkyl of $R^{N2}$ is unsubstituted or substituted with from 1 to 3 groups independently selected from CN, OH, optionally substituted phenyl, and optionally substituted heteroaryl, wherein said optional substituents on said phenyl are 1 to 3 groups independently selected from OH, CN, —($C_1$-$C_4$)alkyl, —($C_1$-$C_4$)alkoxyl, and wherein said optional substituents on said heteroaryl are 1 to 3 groups independently selected from —($C_1$-$C_4$)alkyl, and —($C_1$-$C_4$)alkoxyl.

9. The compound according to claim 1, wherein:
$R^{N1}$ and $R^{N2}$, together with the nitrogen atom to which they are shown attached, form a 4-, 5-, or 6-membered heteroaryl or partially unsaturated or fully saturated heterocyclic ring comprising (including said nitrogen atom) 1, 2 or 3 ring heteroatoms independently selected from the group consisting of N, O, and S, wherein said heteroaryl and said heterocyclic ring is unsubstituted or substituted with one, two, or three substitutents independently selected from the group consisting of halo, OH, CN, —($C_1$-$C_4$)alkyl, amino-substituted —($C_1$-$C_4$)alkyl, wherein said amino is one, two, or three groups independently selected from the group consisting of —$NH_2$, —N($C_1$-$C_4$alkyl)$_2$, and —NH($C_1$-$C_4$alkyl), —($C_1$-$C_4$)haloalkyl, —($C_1$-$C_4$)alkyl-OH, phenyl, benzyl, heteroaryl, and —($C_1$-$C_4$)alkylheteroaryl.

10. The compound according to claim 1, or a pharmaceutically acceptable salt thereof, wherein said compound is selected from the group consisting of:

141  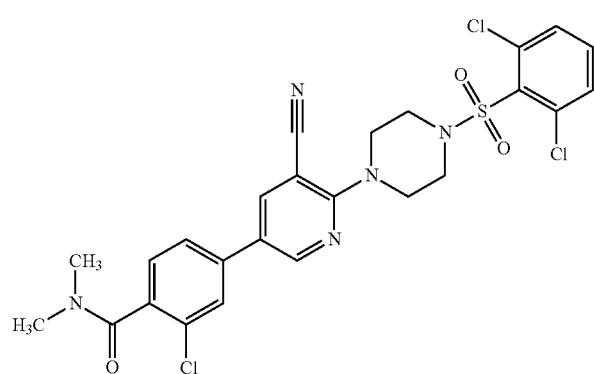  142  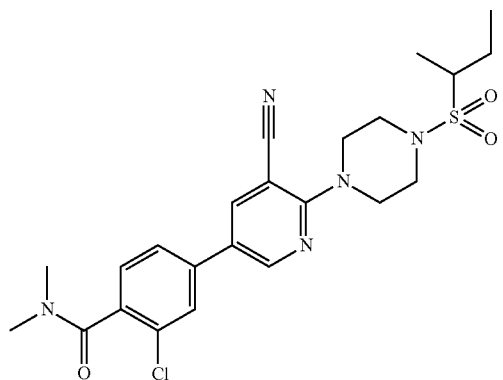
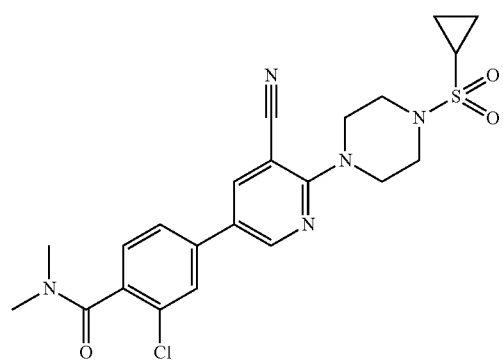  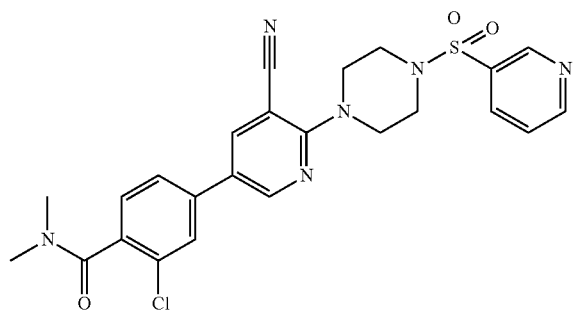
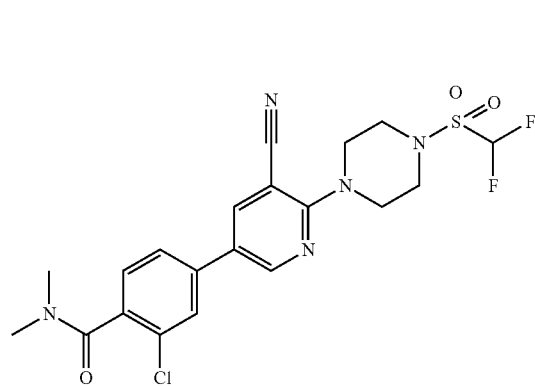  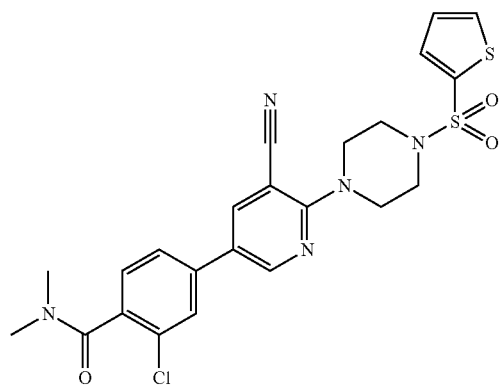
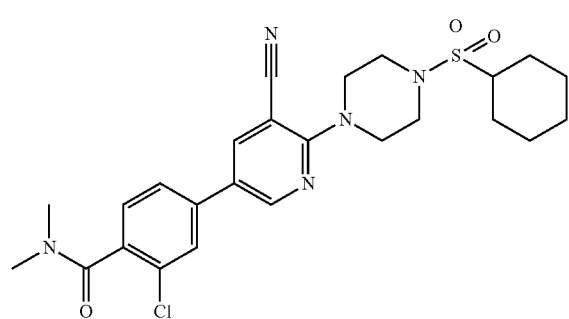  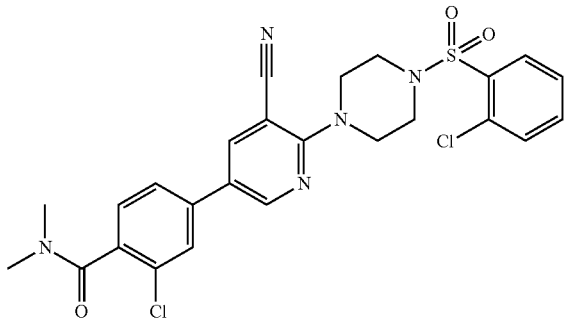

-continued
143
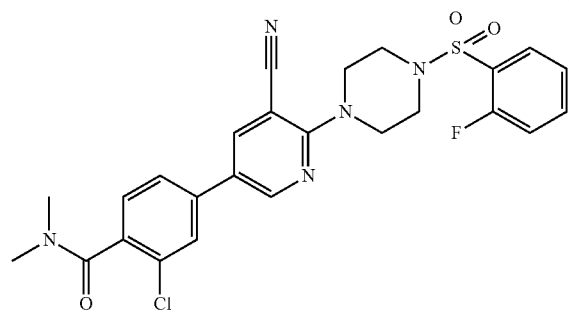
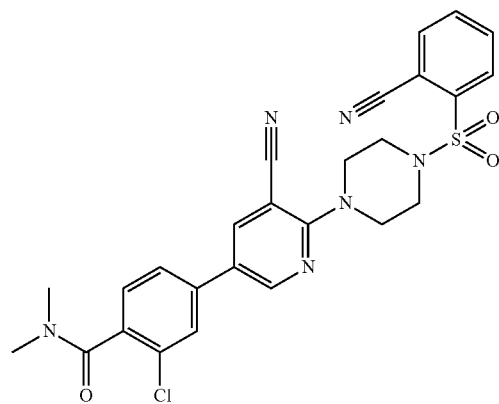
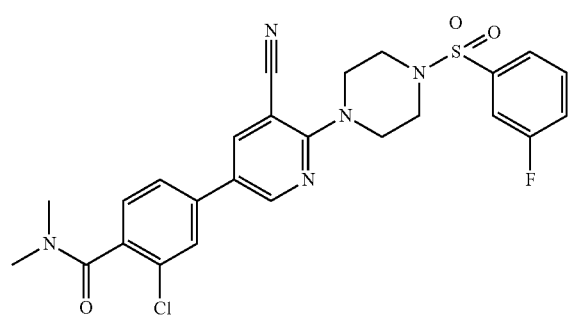
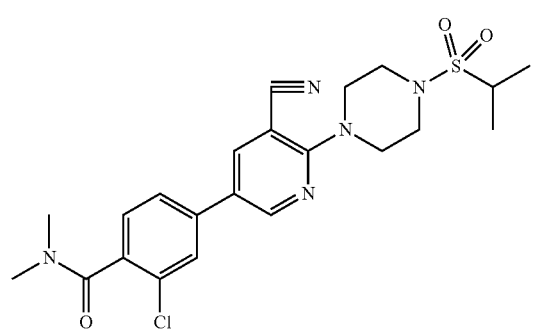
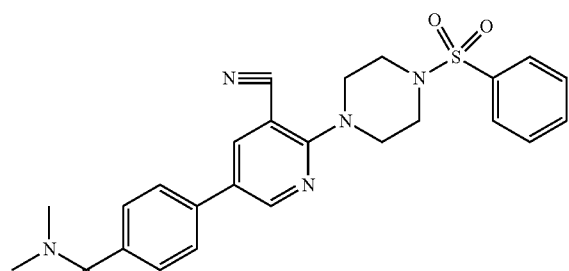
144
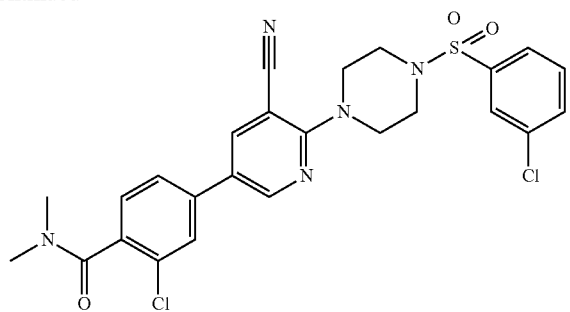
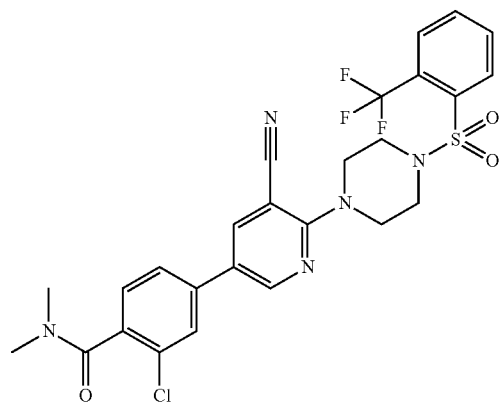
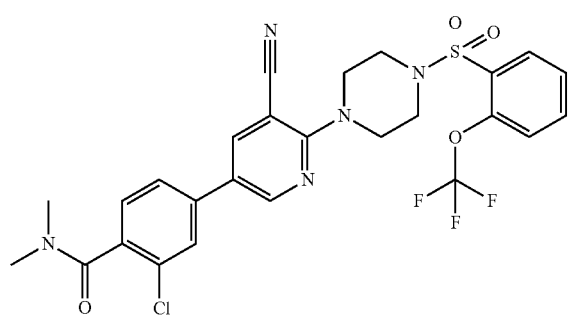
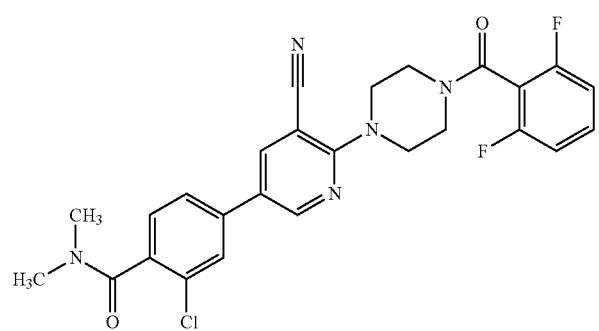
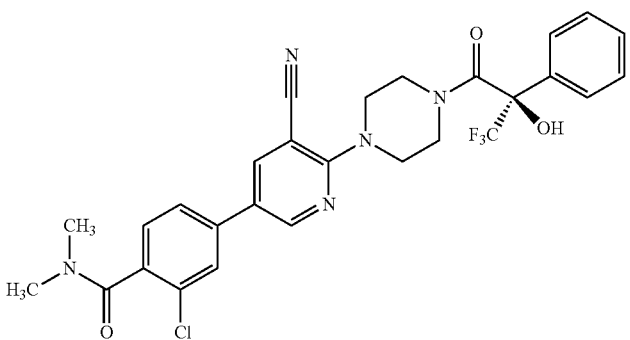

-continued
145
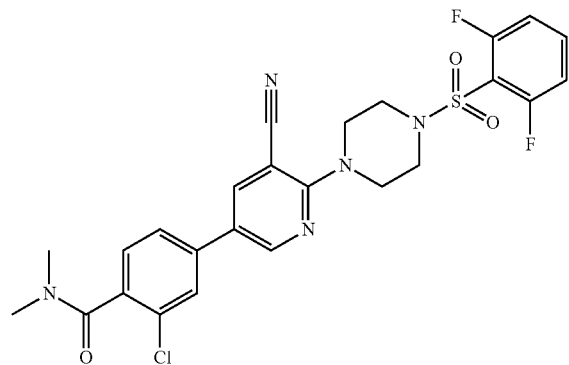
146
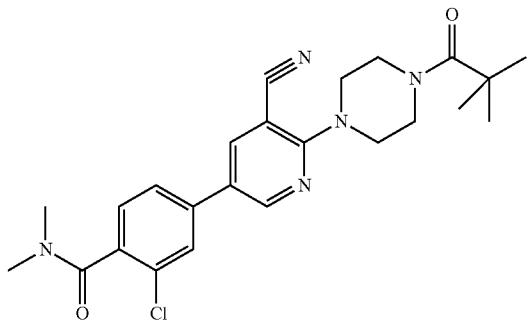
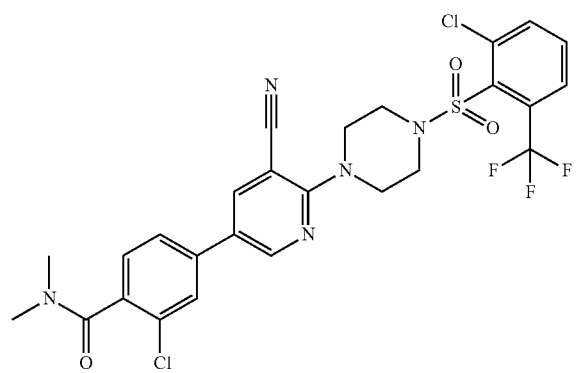
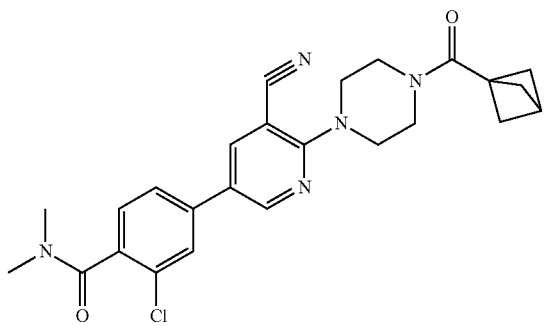
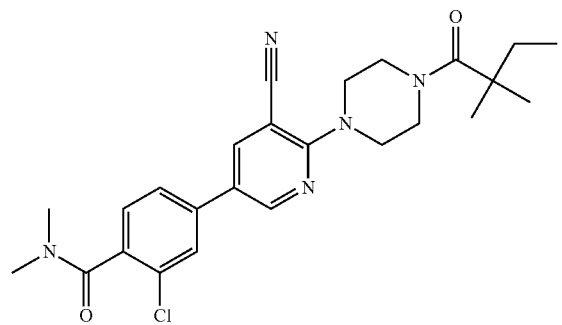
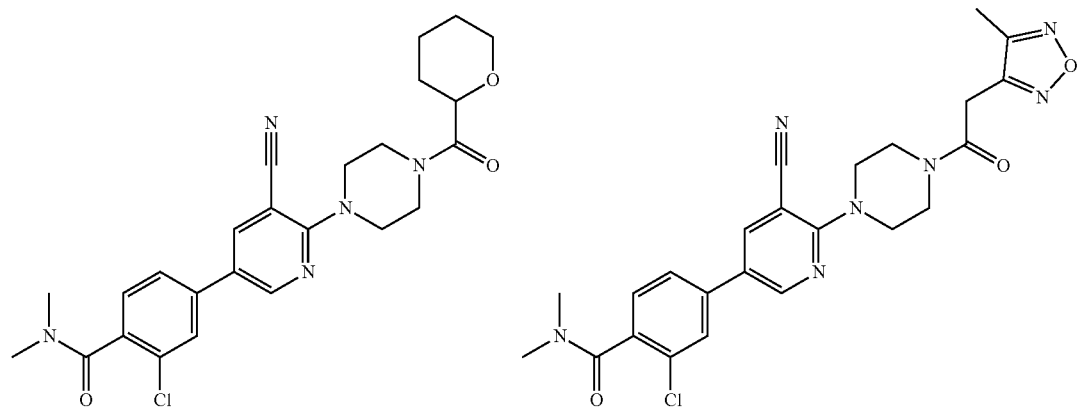

147
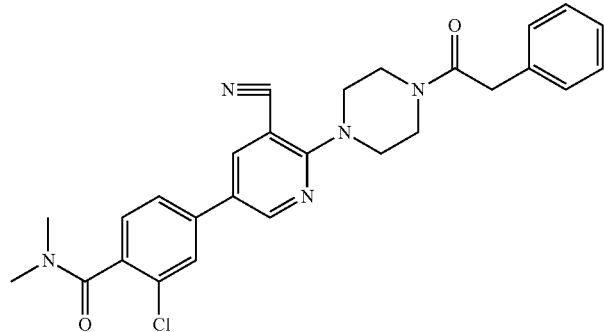
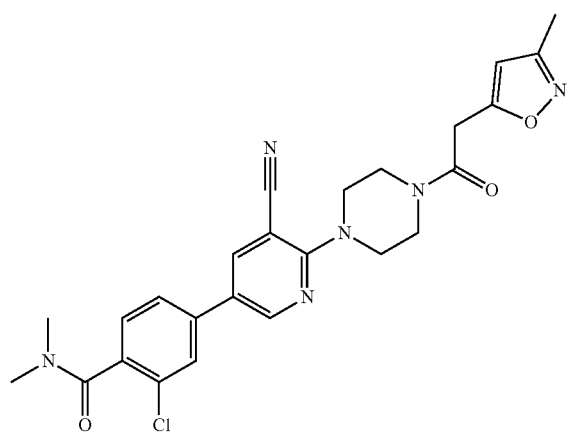
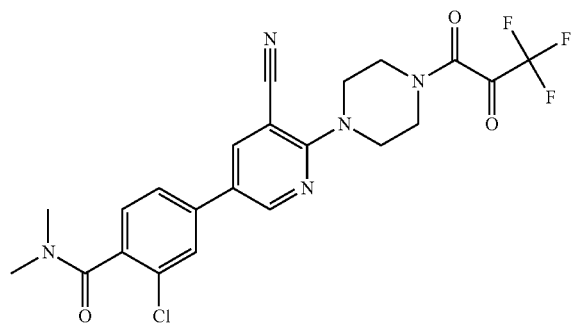
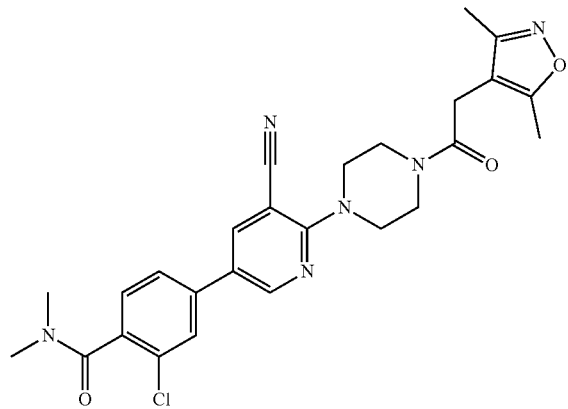
148
-continued
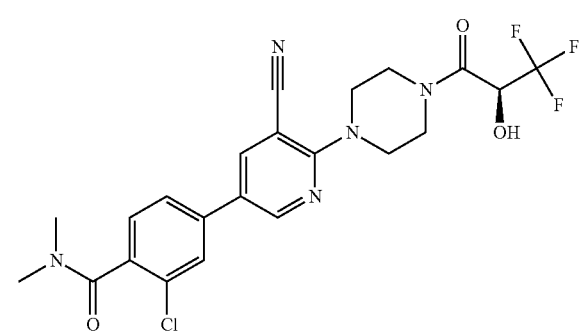
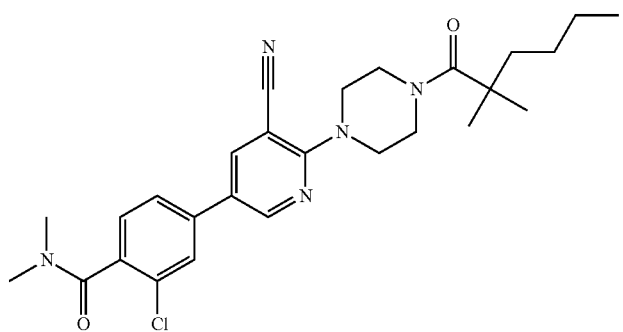
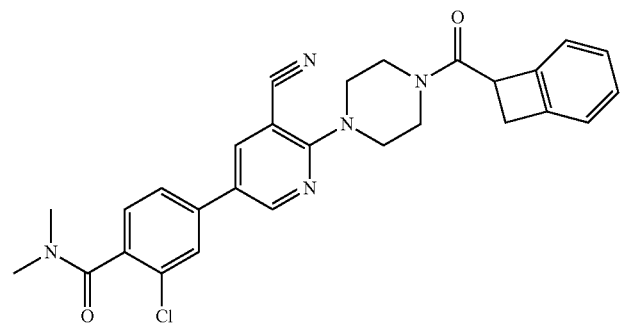
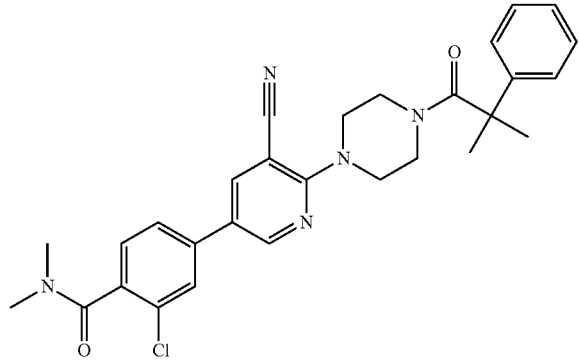

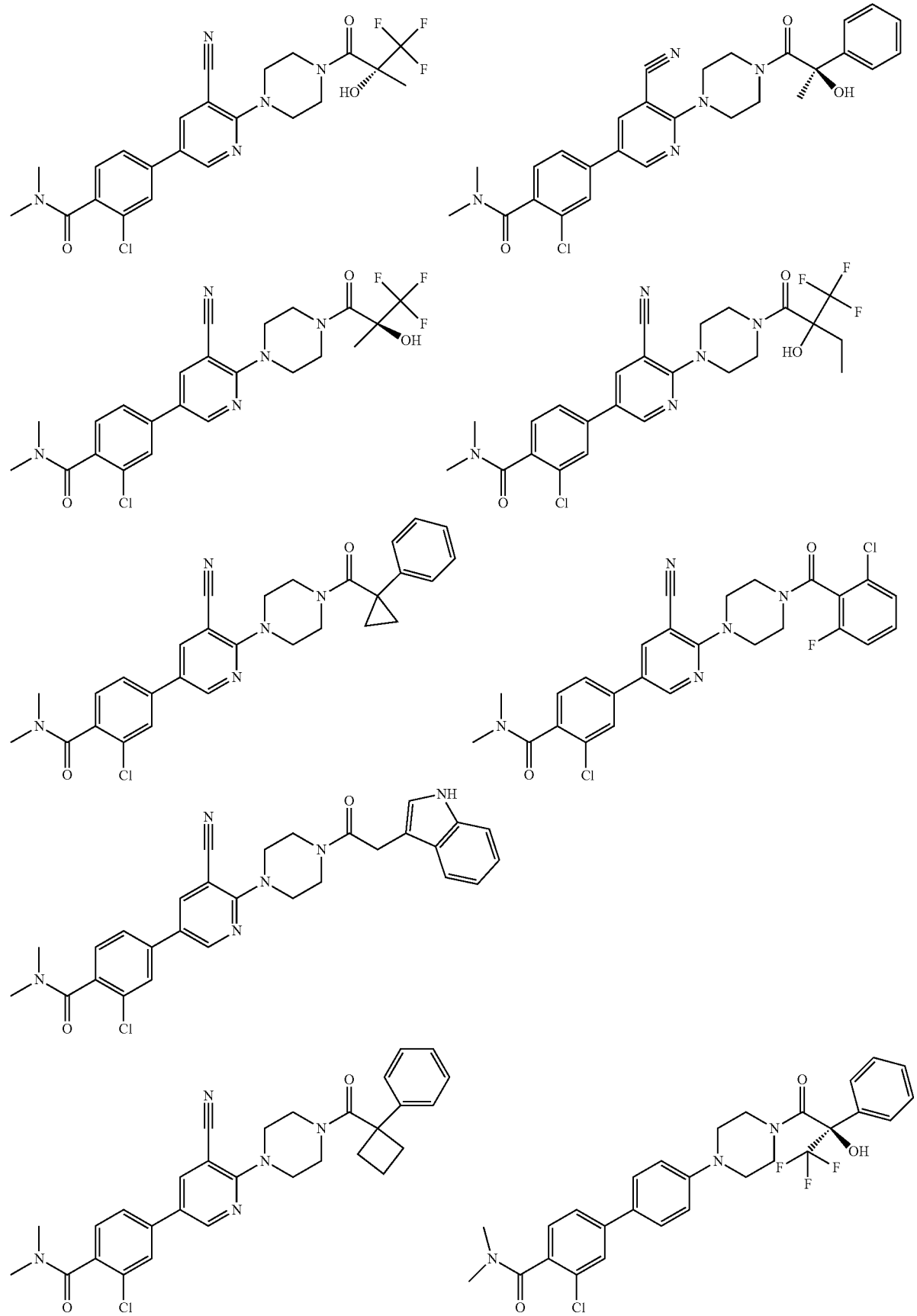

151 152 -continued
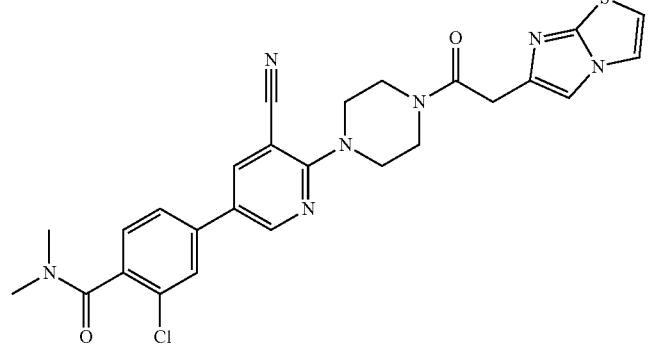
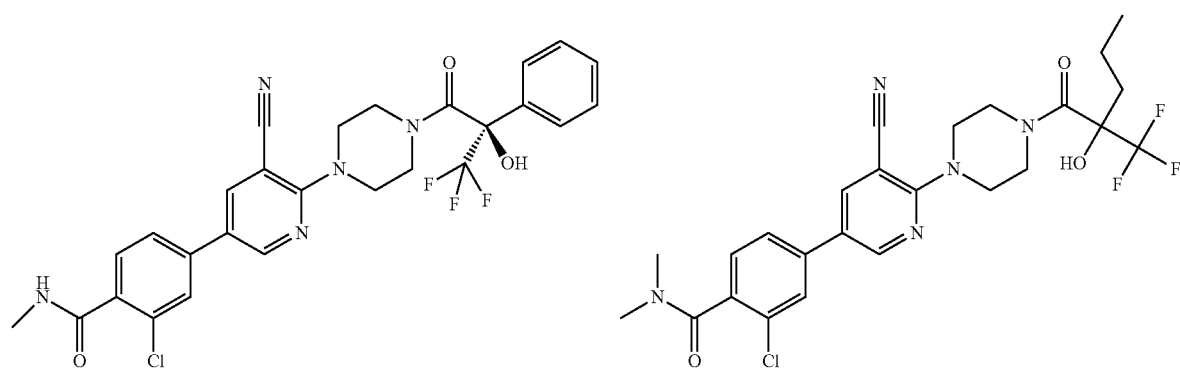
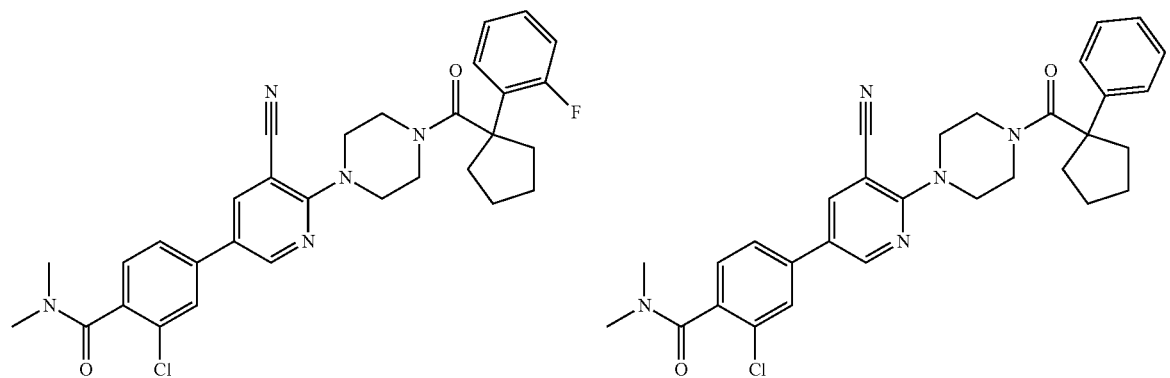
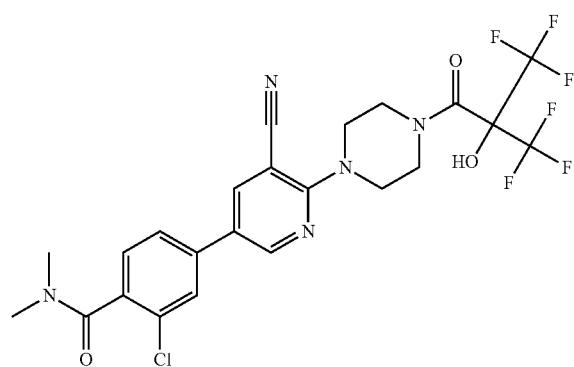

-continued
| 153 | 154 |
|---|---|
| 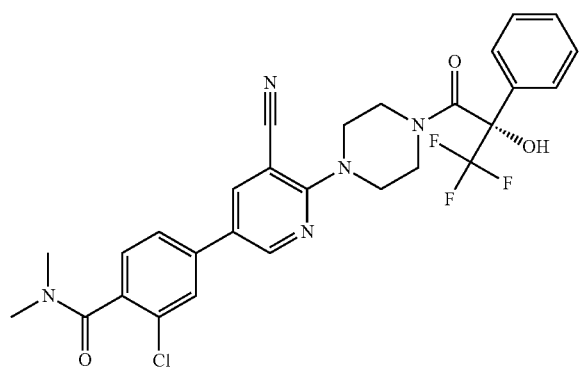 | 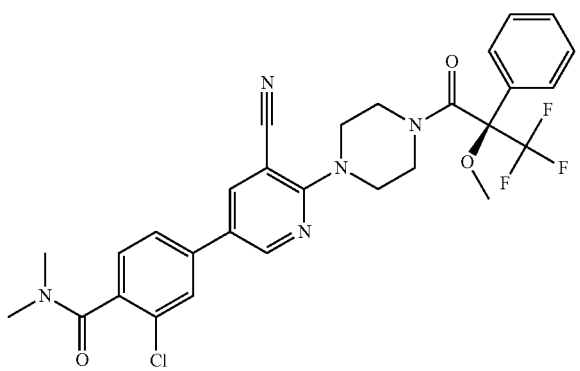 |
| 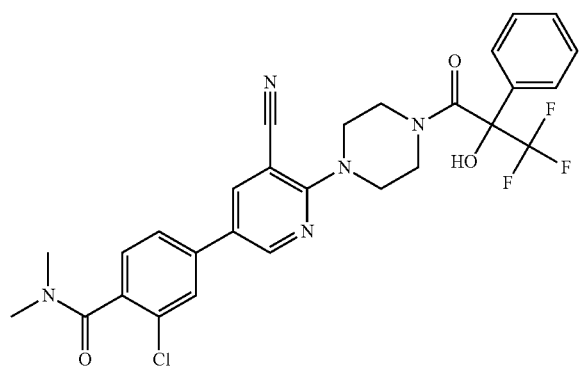 | 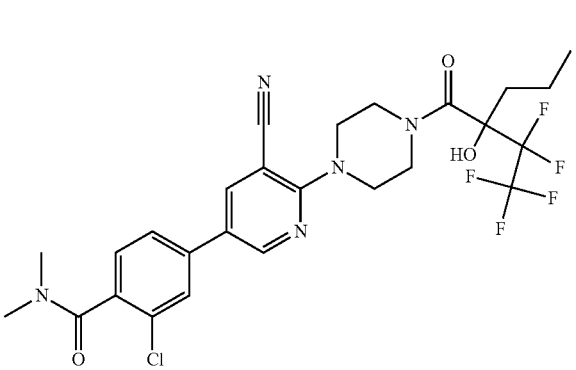 |
| 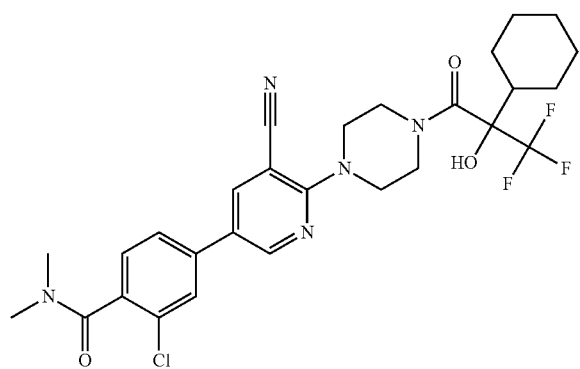 | 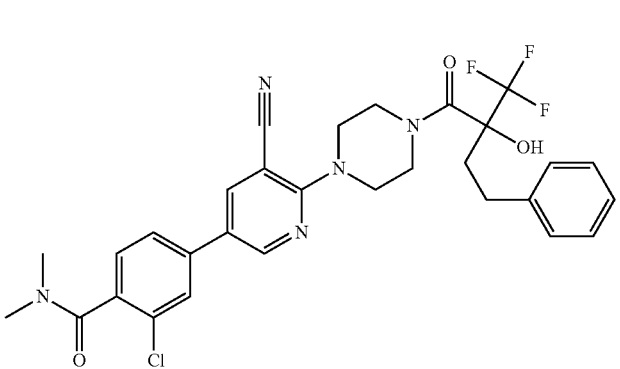 |
| 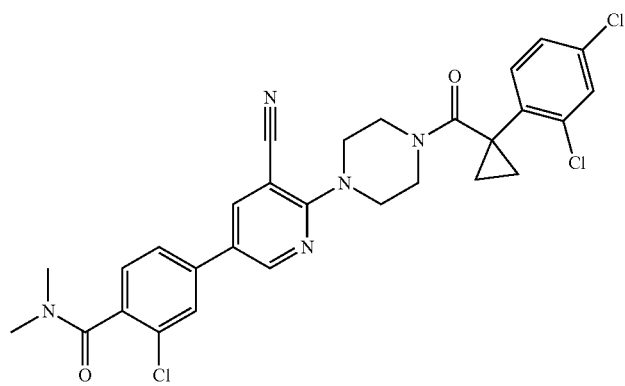 | |

-continued
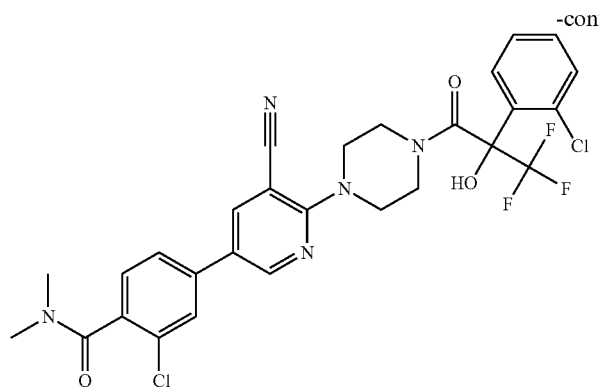
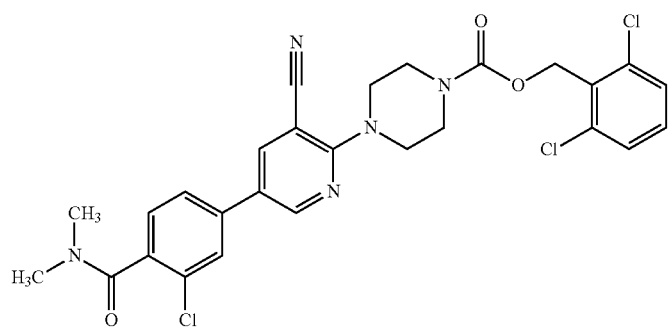
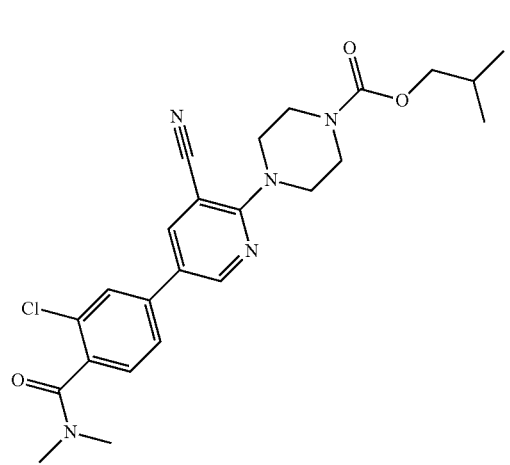
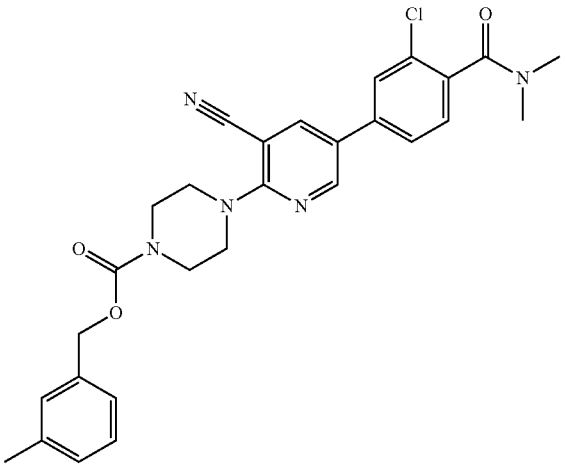
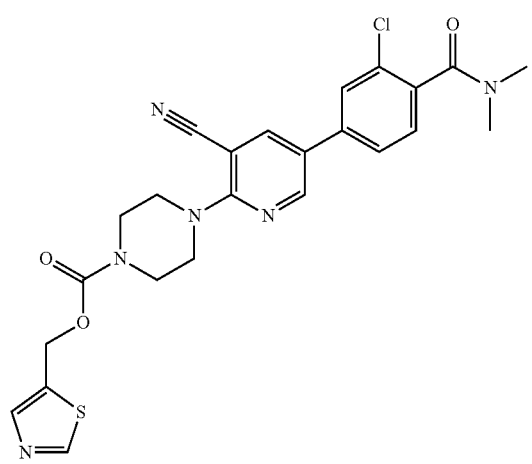
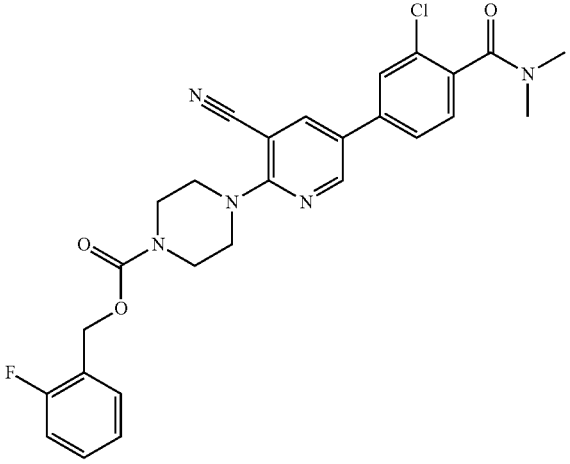

157
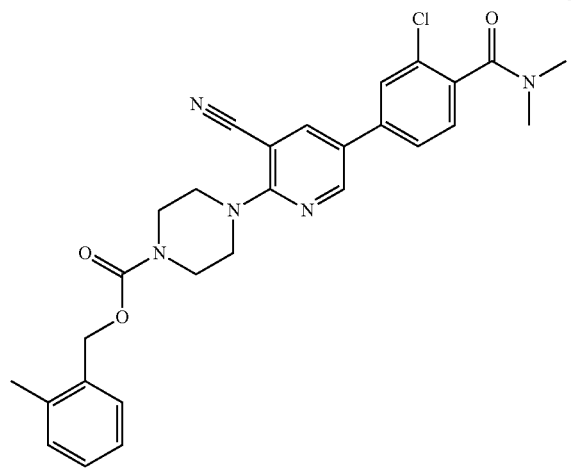
158
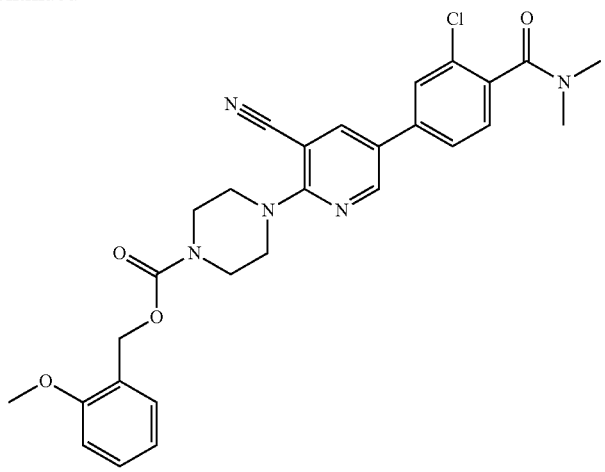
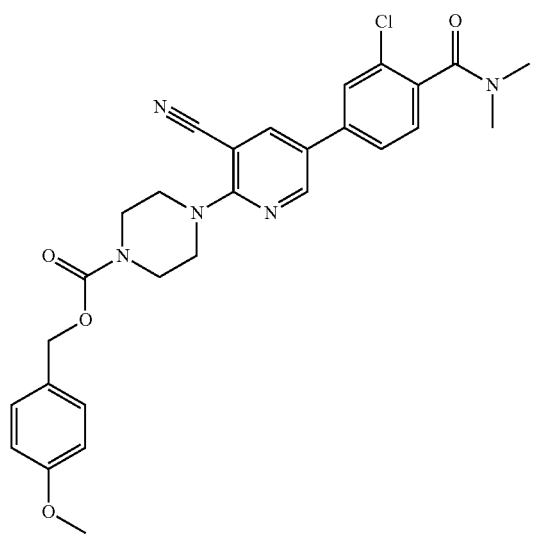
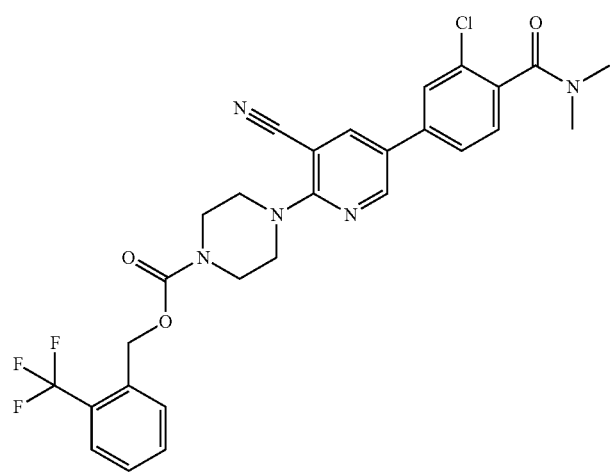
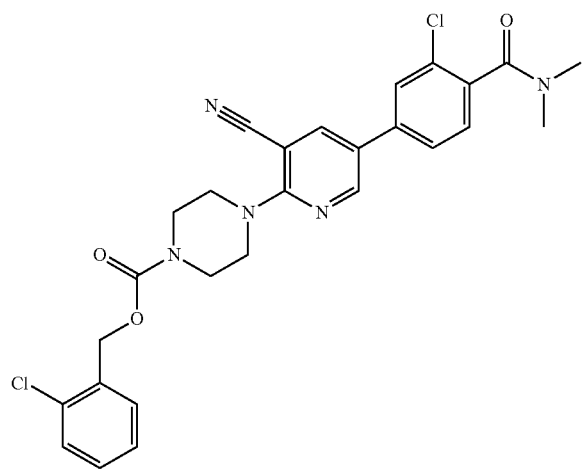
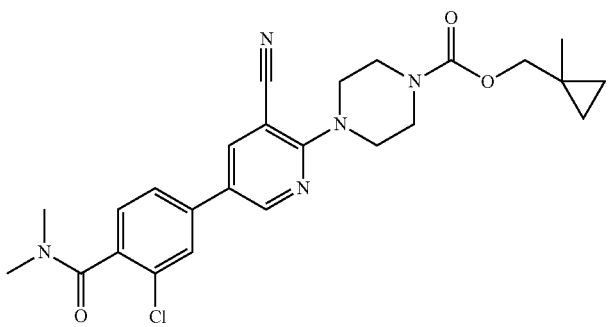

-continued
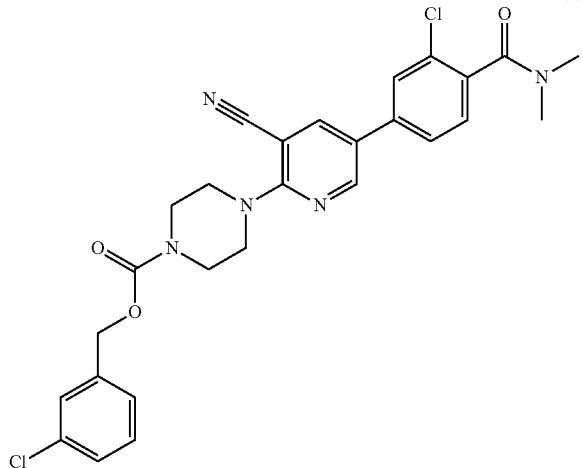
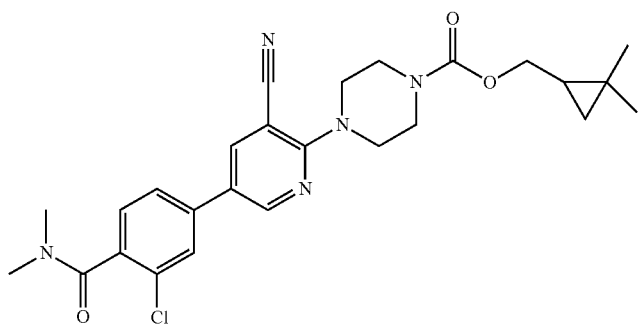
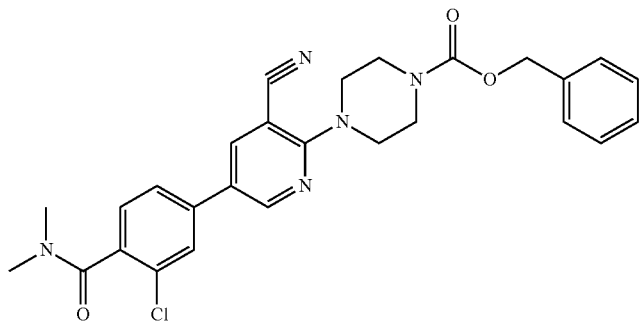
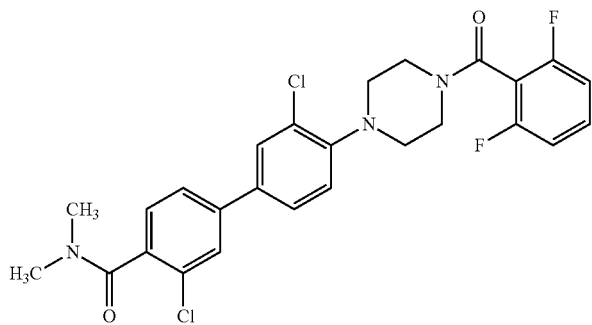

161
-continued
162
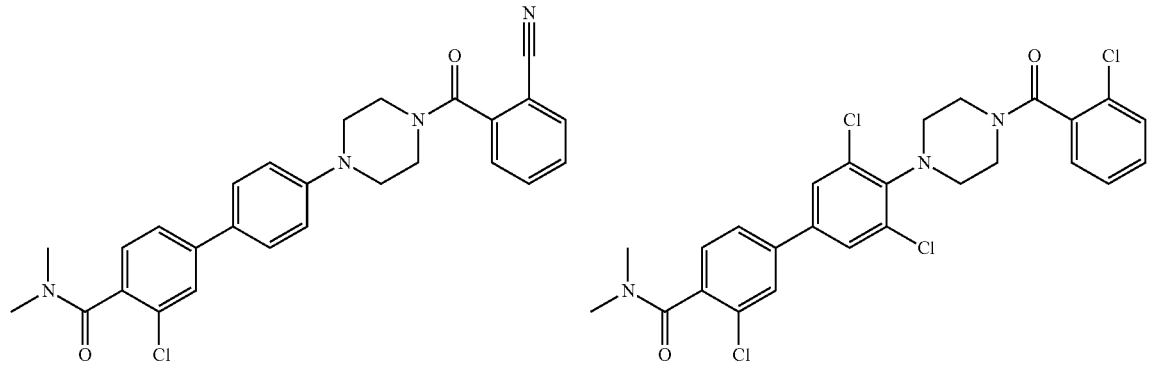
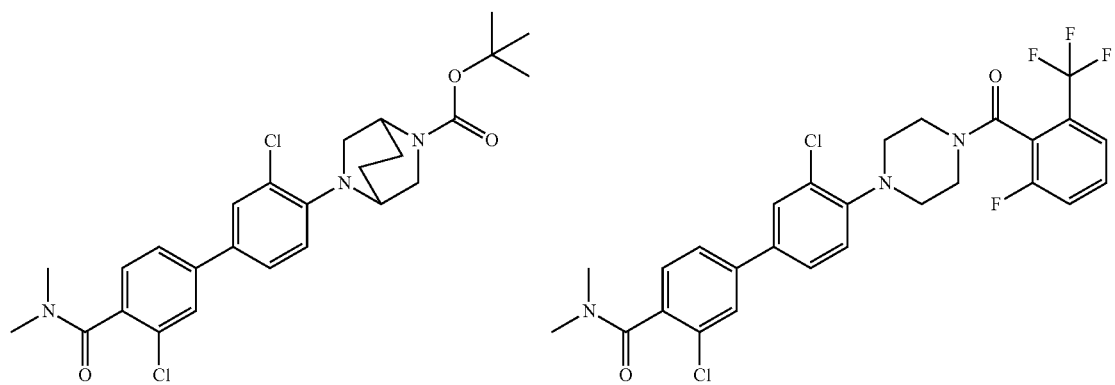
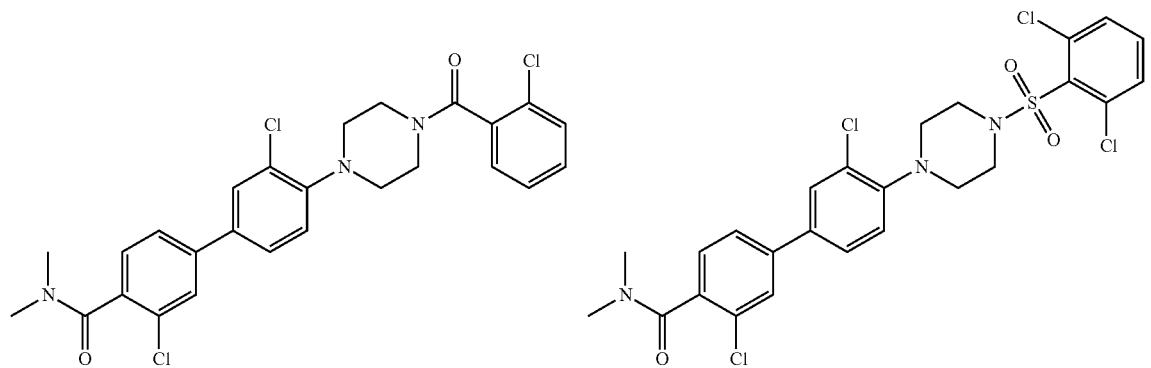
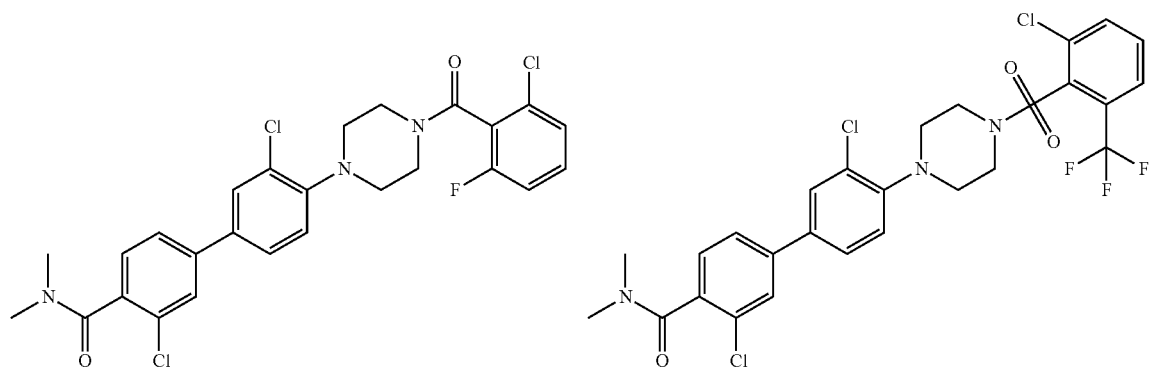

-continued
163
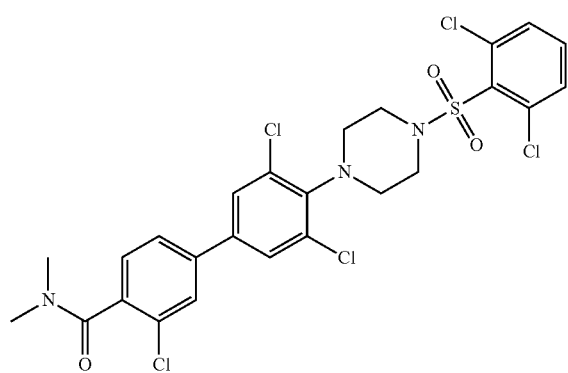
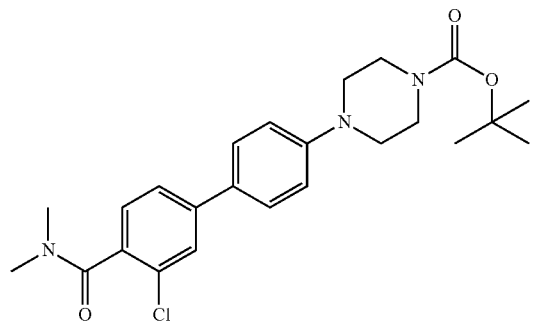
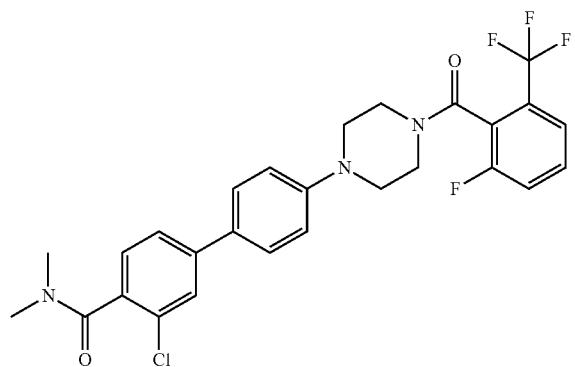
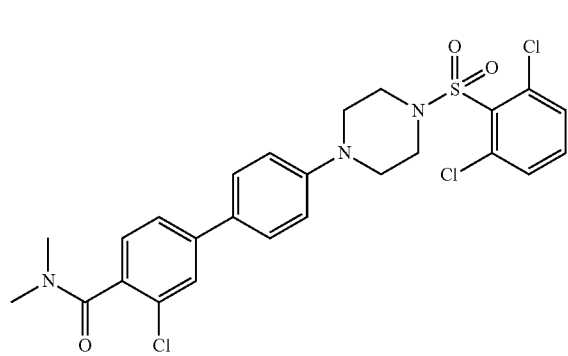
164
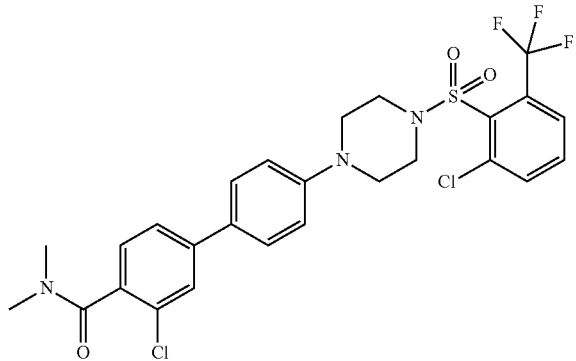
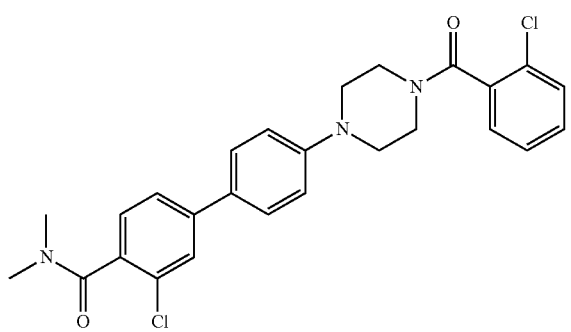
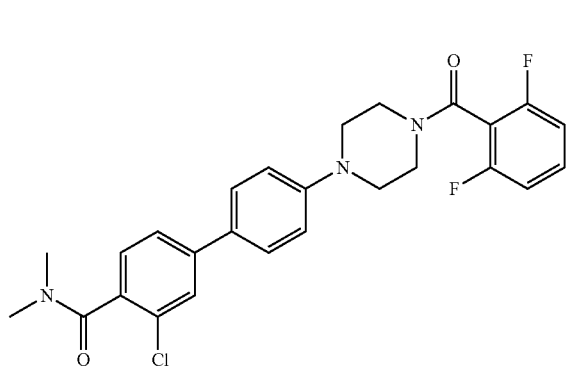
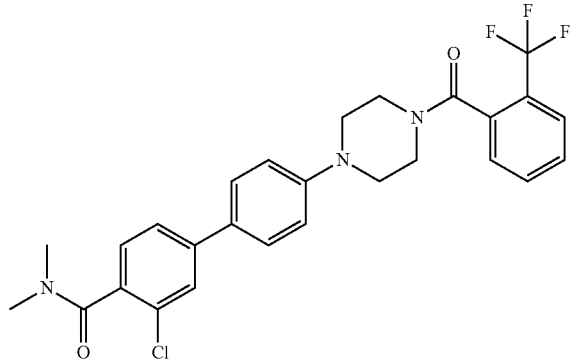

-continued
165 166
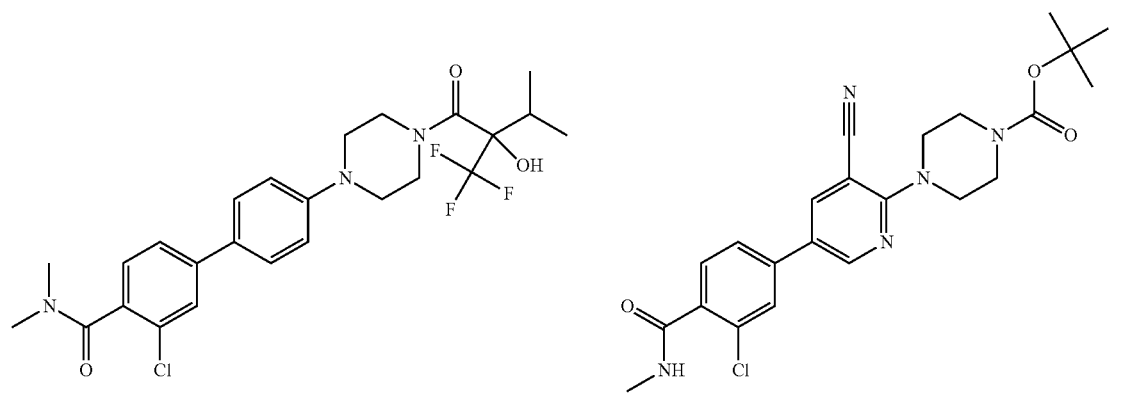
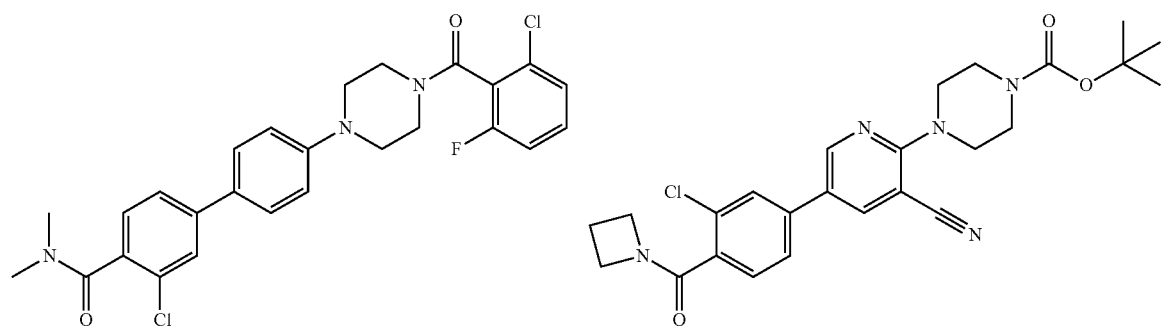
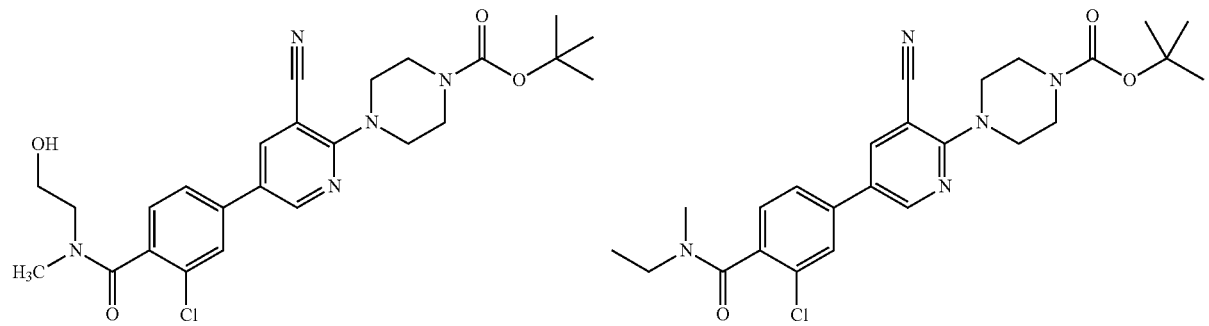
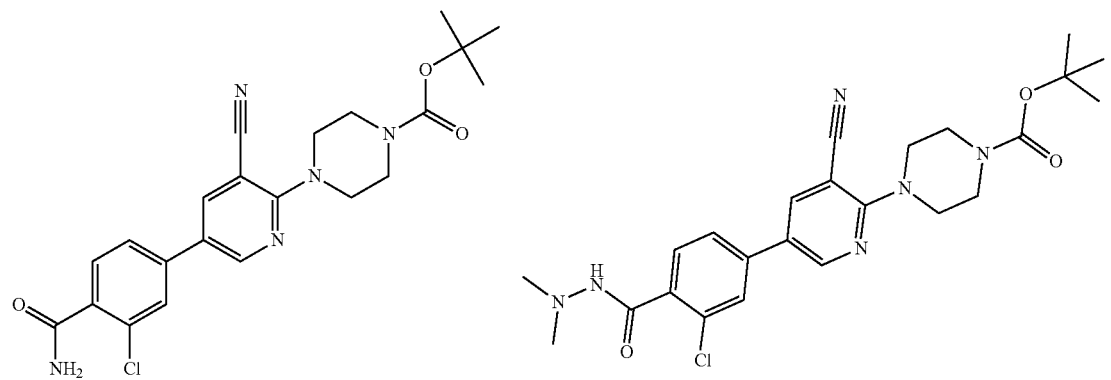

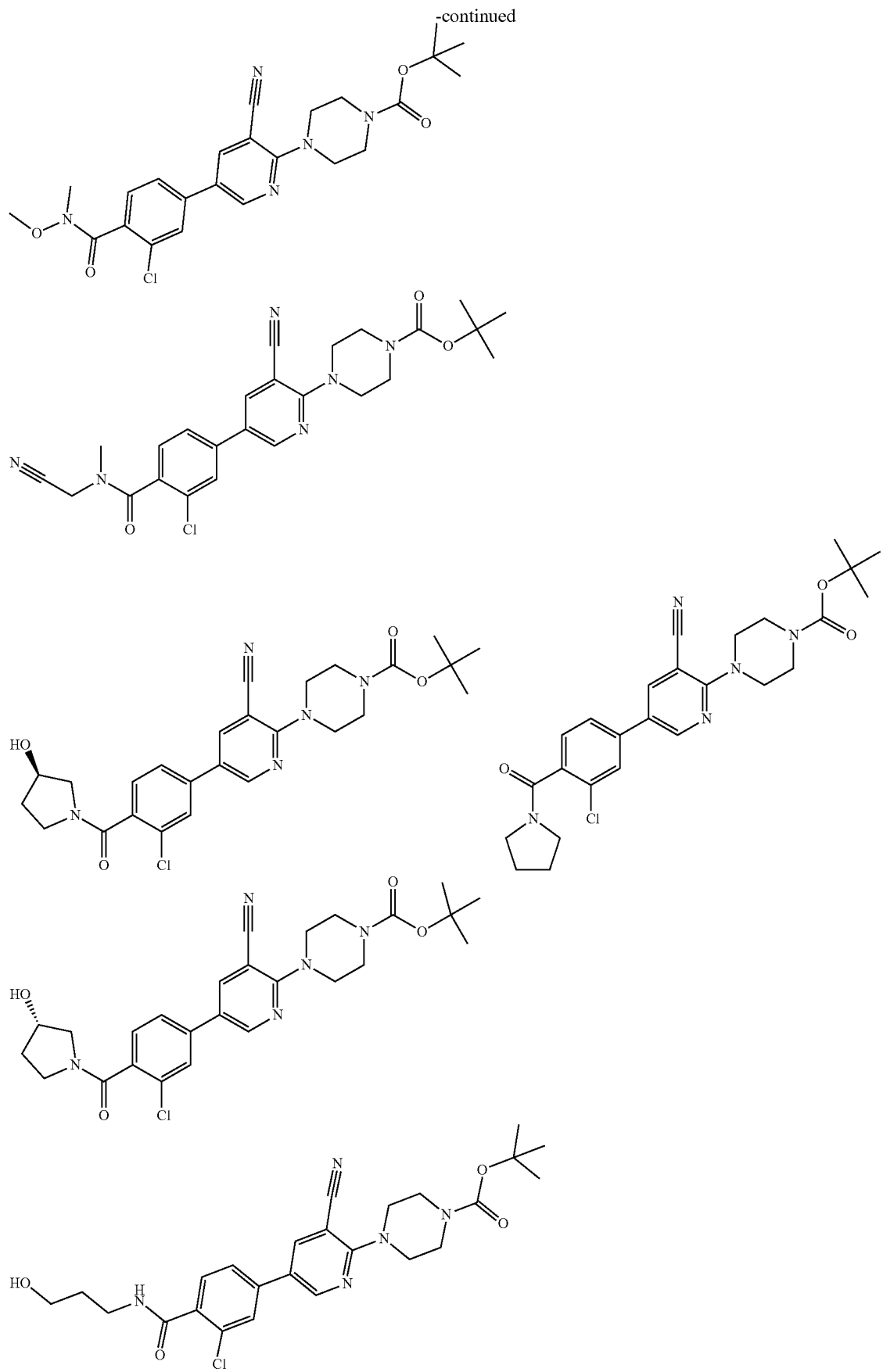

-continued
169
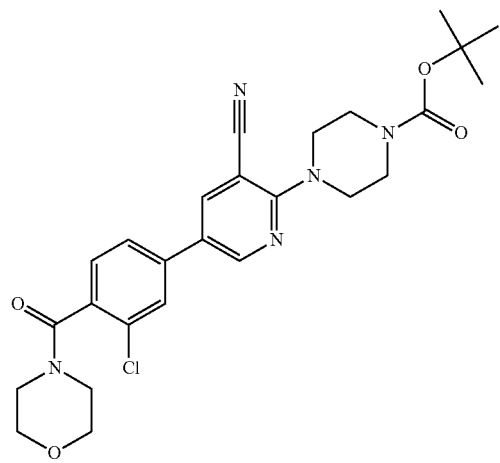
170
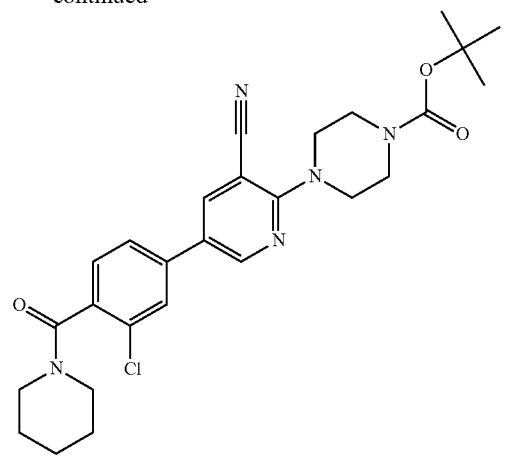
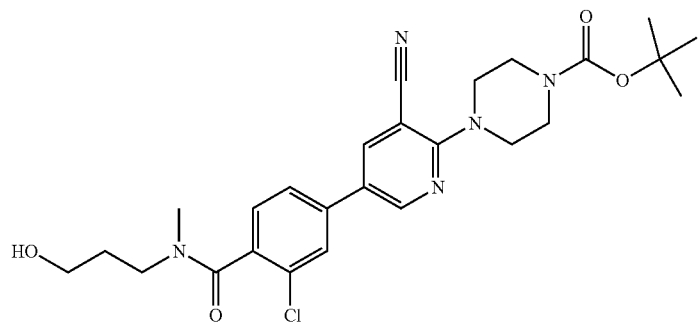
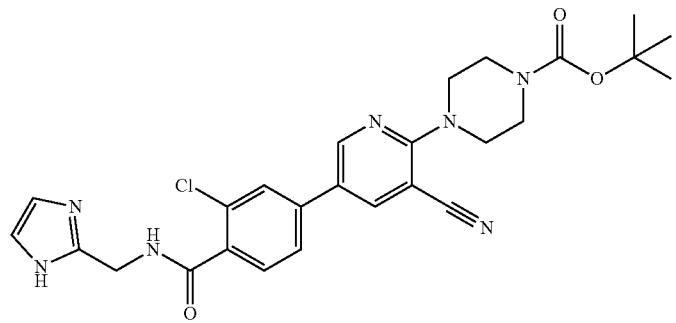
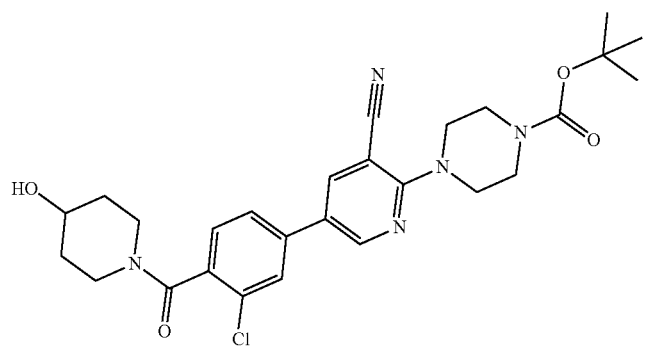

-continued
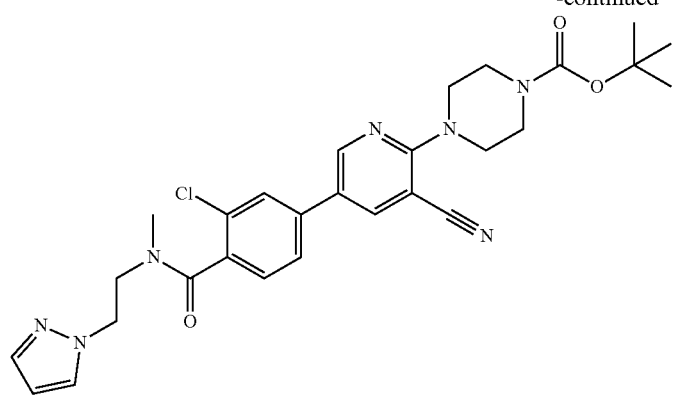
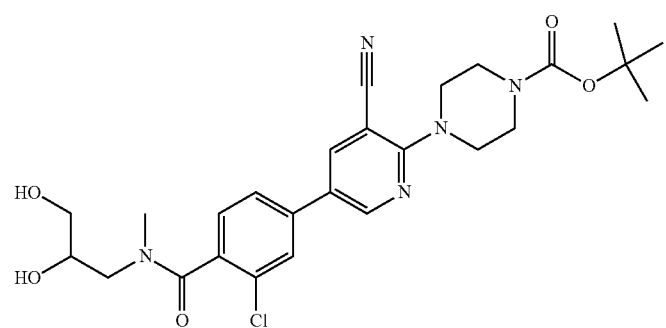
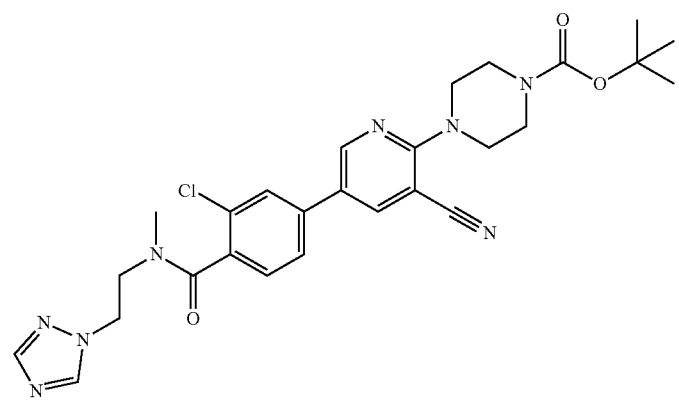
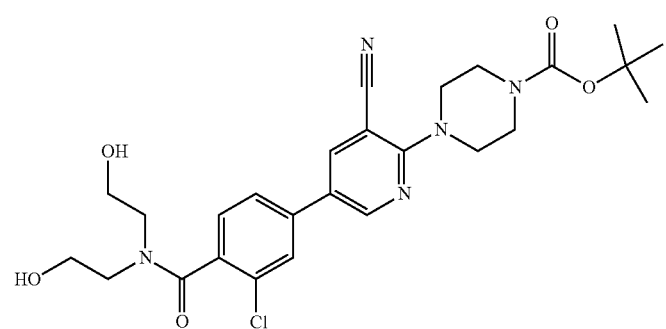

-continued
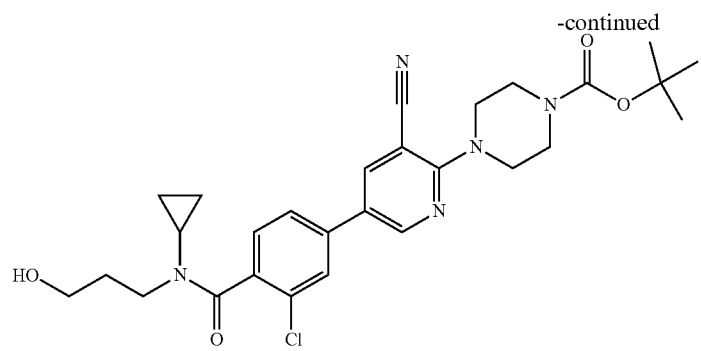
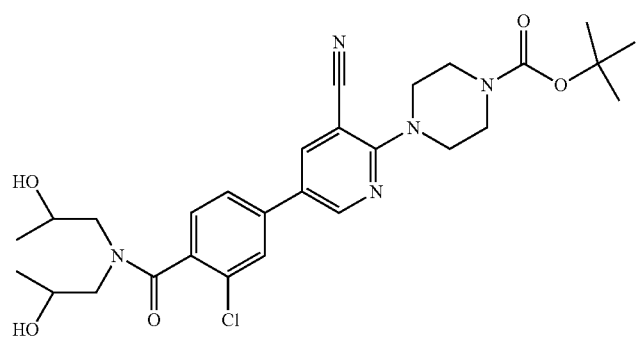
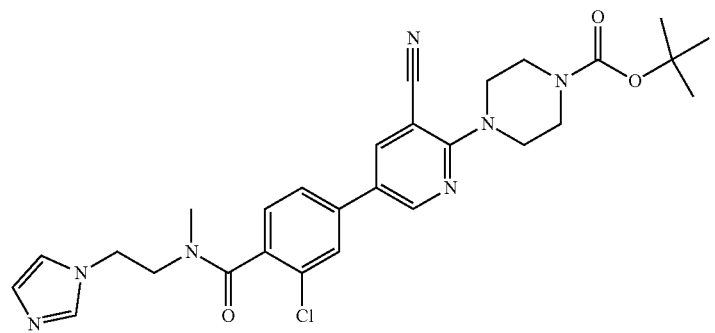
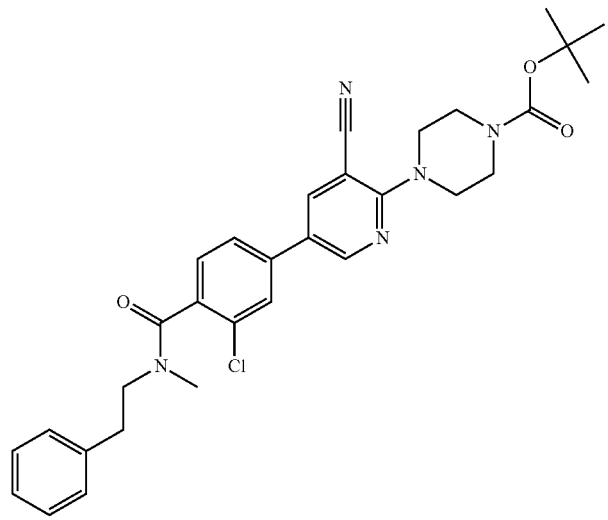

-continued
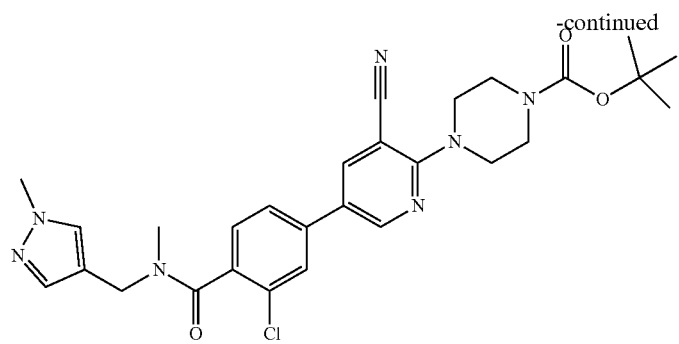
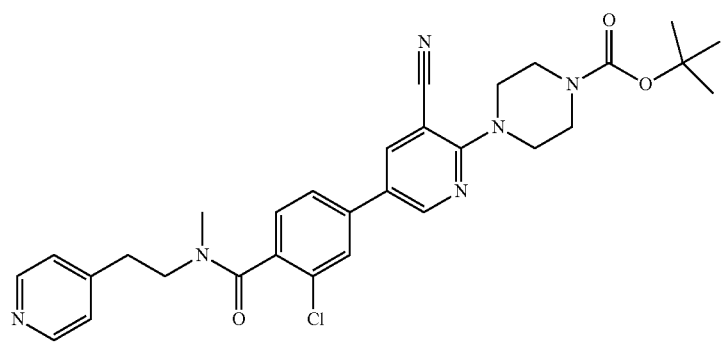
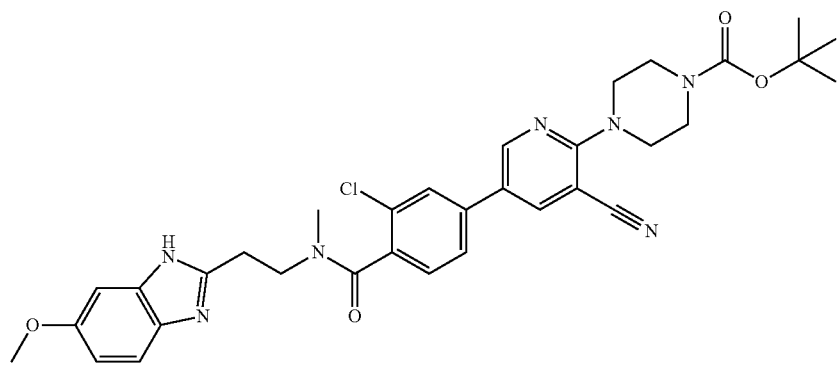
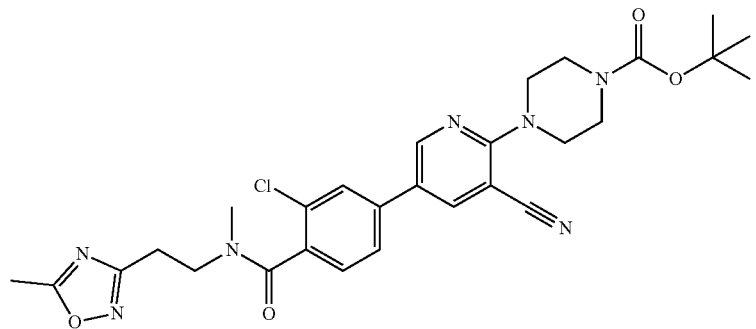

177 178
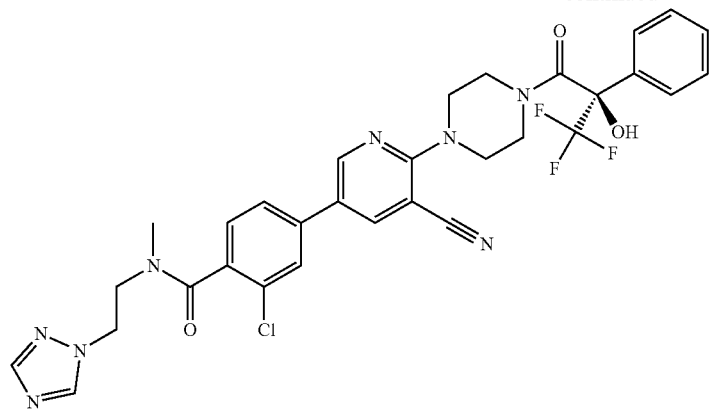
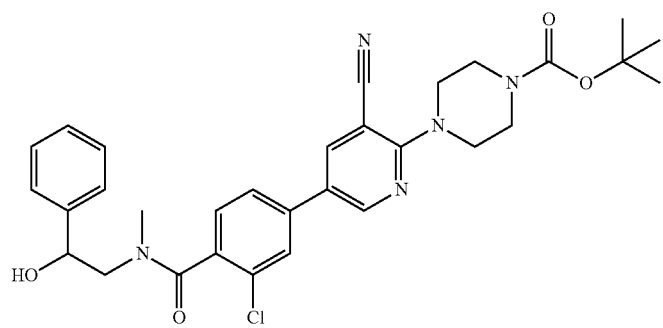
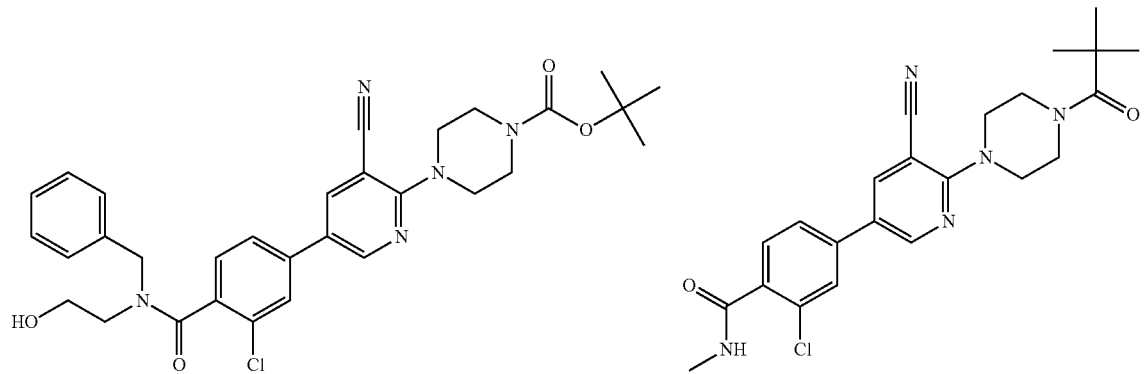
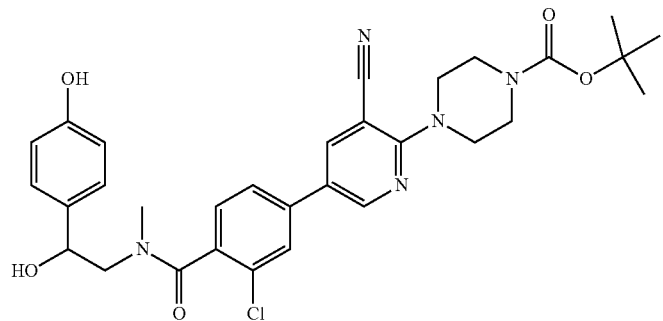

-continued
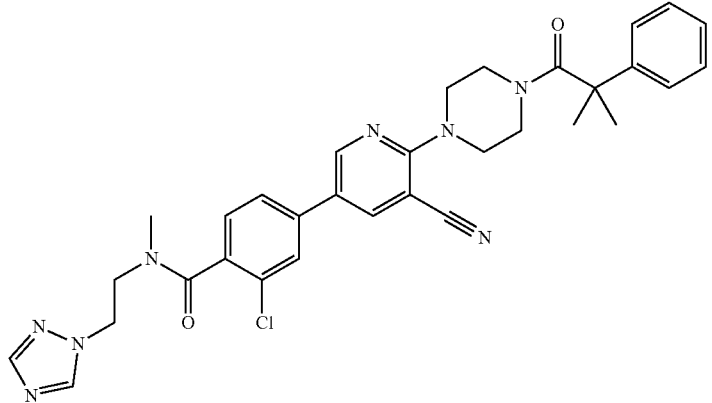
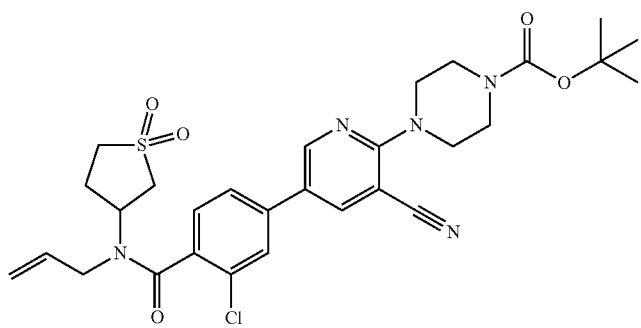
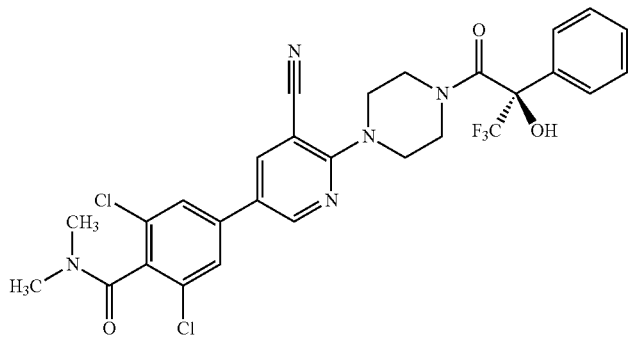
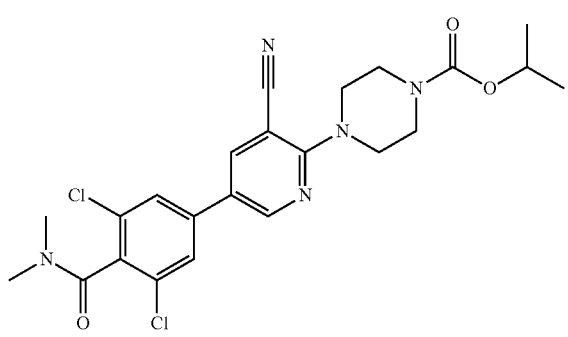
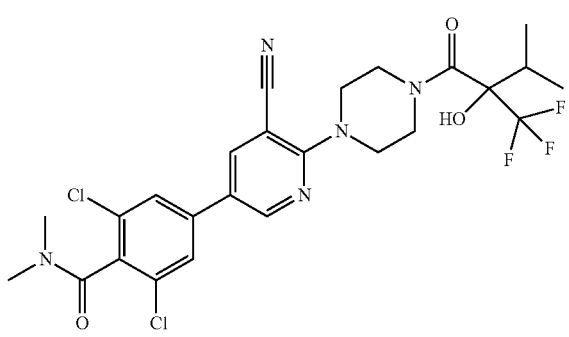
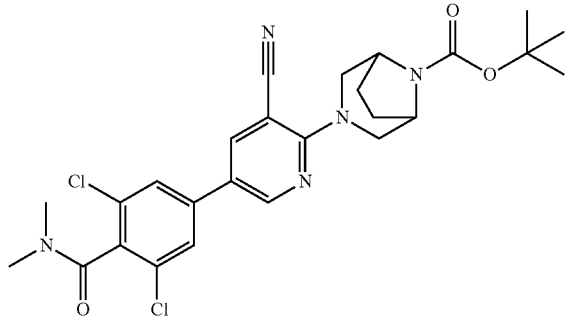
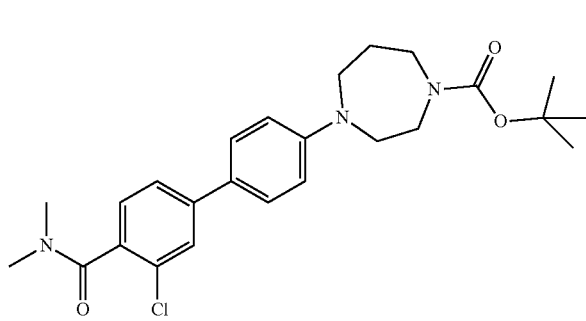

-continued
| 181 | 182 |
|---|---|
| 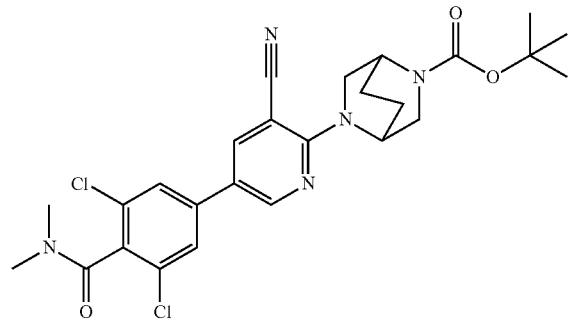 | 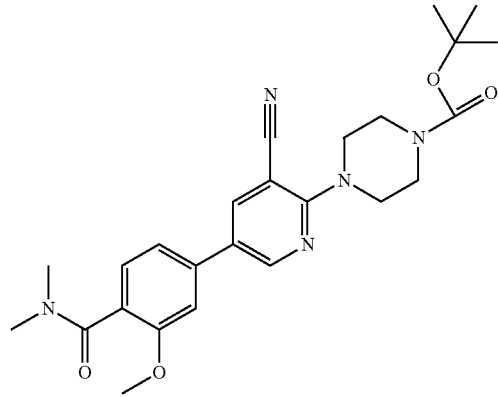 |
| 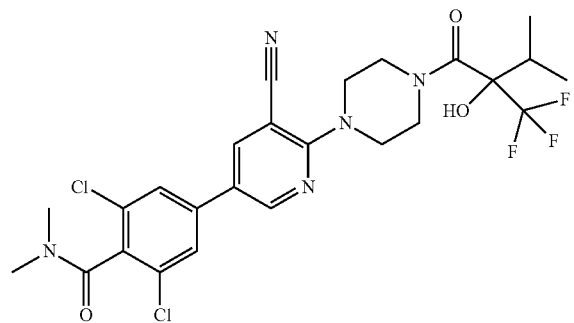 | 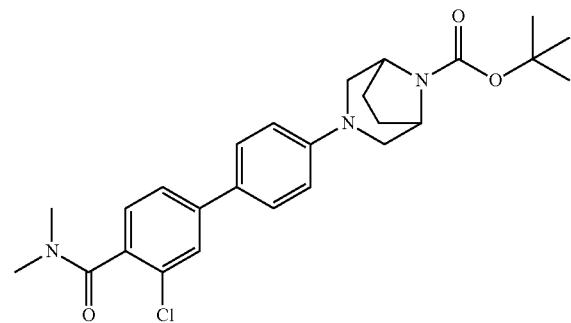 |
| 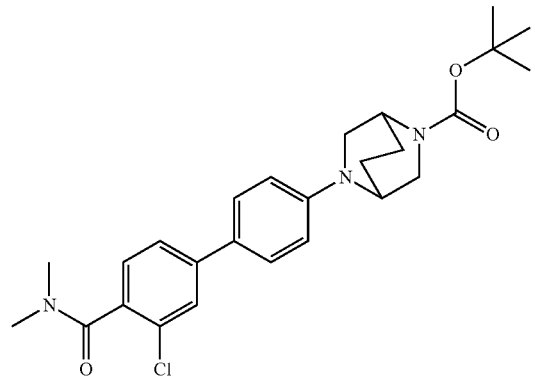 | 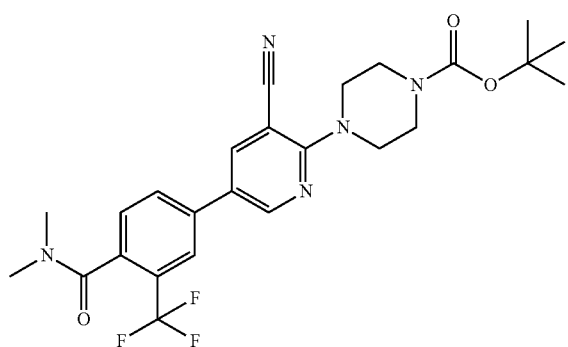 |
| 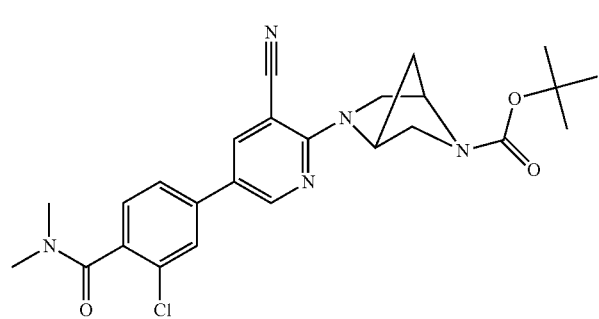 | 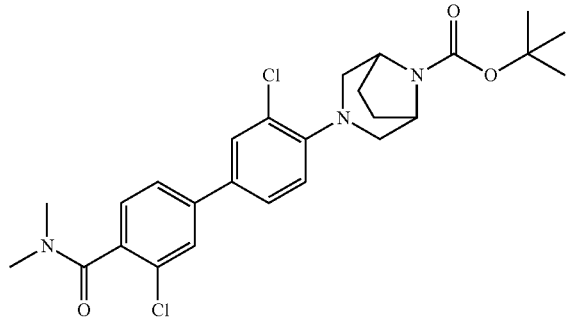 |

-continued
| 183 | 184 |
|---|---|
| 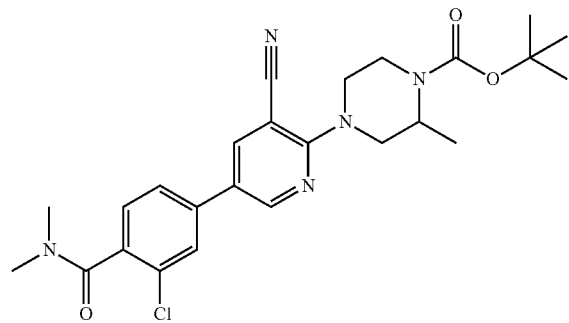 | 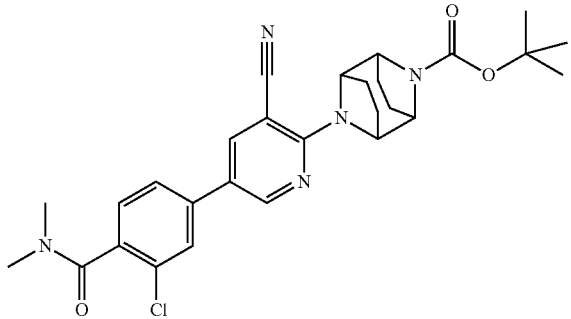 |
| 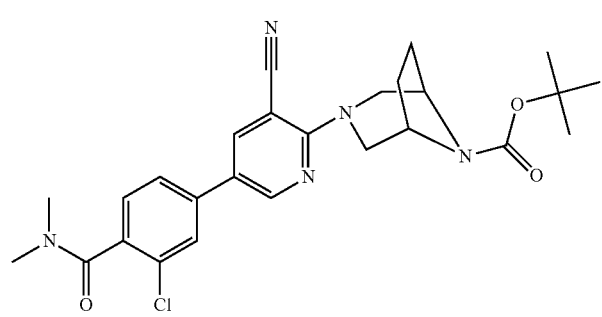 | 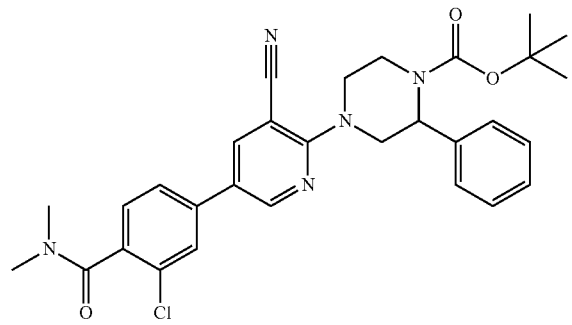 |
| 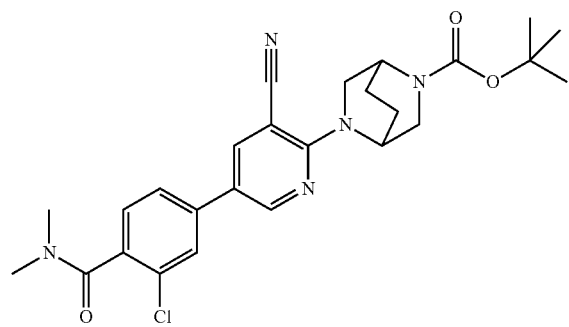 | 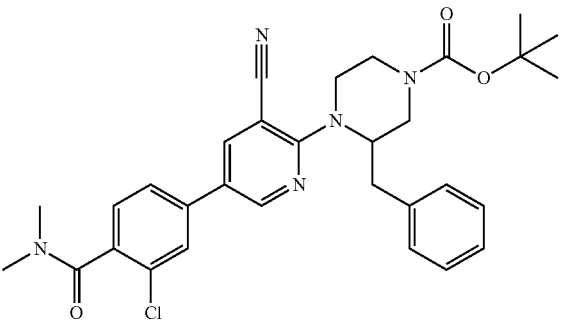 |
| 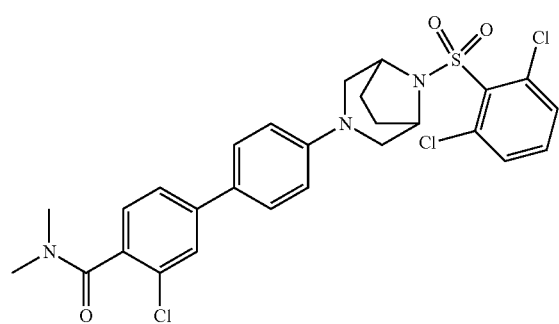 | 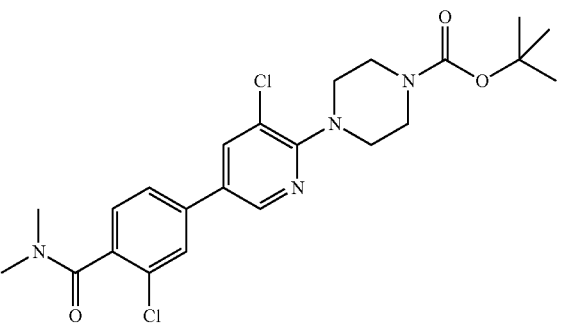 |
| 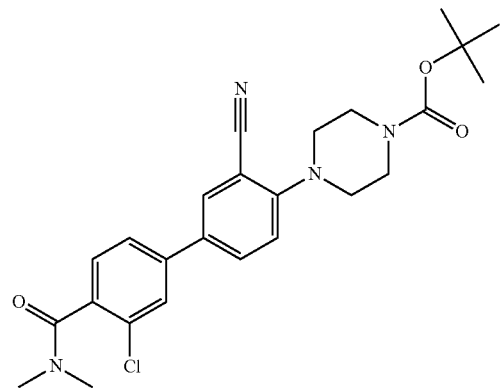 | 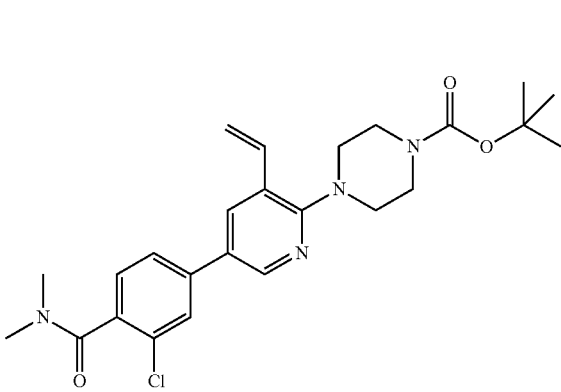 |

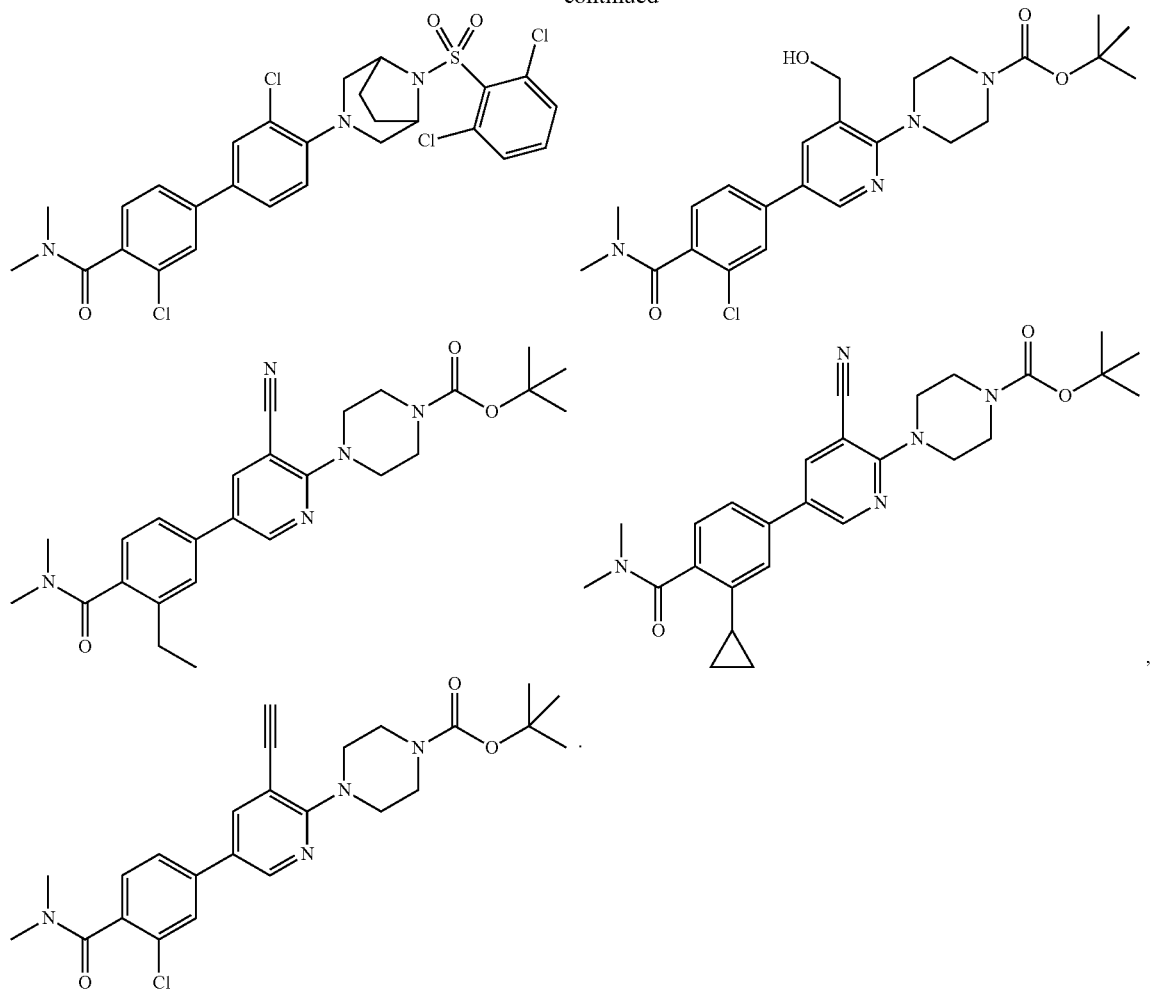

11. A pharmaceutical composition comprising a compound according to claim 1, a pharmaceutically acceptable salt thereof, and a pharmaceutically acceptable carrier or diluent.

12. A method for the treatment of Alzheimer's Disease, Neimann-Pick disease type C1, Parkinson's Disease, amyotrophic lateral sclerosis, stroke, age-related macular degeneration, schizophrenia, depression, cardiovascular disease, obesity or diabetes, said method comprising administering an effective amount of a compound according to claim 1 to a patient in need thereof.

13. The method of claim 12, wherein said treatment is Alzheimer's disease.

* * * * *